(12) United States Patent
Bergeron et al.

(10) Patent No.: US 7,544,702 B2
(45) Date of Patent: Jun. 9, 2009

(54) BISARYL-SULFONAMIDES

(75) Inventors: Philippe Bergeron, San Mateo, CA (US); Christopher N. Farthing, London (GB); Stuart D. Jones, Prestbury (GB); John W. Liebeschuetz, Macclesfield (GB); Sarah E. Lively, San Carlos, CA (US); Lawrence R. McGee, Pacifica, CA (US); Sharon McKendry, Glasgow (GB); David Sheppard, Macclesfield (GB); Stephen C. Young, Stockport (GB)

(73) Assignee: Amgen Inc., Thousand Oaks, CA (US)

( * ) Notice: Subject to any disclaimer, the term of this patent is extended or adjusted under 35 U.S.C. 154(b) by 559 days.

(21) Appl. No.: 11/203,006

(22) Filed: Aug. 11, 2005

(65) Prior Publication Data

US 2006/0084802 A1 Apr. 20, 2006

Related U.S. Application Data

(60) Provisional application No. 60/601,578, filed on Aug. 12, 2004.

(51) Int. Cl.
C07D 417/02 (2006.01)
C07D 413/02 (2006.01)
C07D 403/02 (2006.01)
A61K 31/4427 (2006.01)

(52) U.S. Cl. ............... 514/333; 514/335; 514/336; 514/349; 546/256; 546/261; 546/262; 546/266

(58) Field of Classification Search ............ 546/256, 546/261, 262, 266; 514/333, 335, 336, 349
See application file for complete search history.

(56) References Cited

U.S. PATENT DOCUMENTS

| | | | | |
|---|---|---|---|---|
| 4,096,264 A | * | 6/1978 | Bochis et al. | 514/300 |
| 5,403,816 A | * | 4/1995 | Takabe et al. | 504/243 |
| 5,902,726 A | | 5/1999 | Kliewer et al. | |
| 6,506,781 B1 | | 1/2003 | Cobb et al. | |
| 6,602,901 B2 | | 8/2003 | Jeppesen et al. | |
| 6,646,008 B1 | | 11/2003 | Evans et al. | |
| 6,756,399 B2 | | 6/2004 | Mulshine et al. | |
| 6,762,171 B1 | | 7/2004 | Murakami et al. | |
| 6,770,648 B2 | | 8/2004 | McGee et al. | |
| 6,869,967 B2 | | 3/2005 | Jeppesen et al. | |
| 6,869,975 B2 | | 3/2005 | Abe et al. | |
| 2003/0088103 A1 | | 5/2003 | Houze et al. | |
| 2004/0209929 A1 | | 10/2004 | Sklitzky et al. | |
| 2005/0009871 A1 | | 1/2005 | Ramesh et al. | |

FOREIGN PATENT DOCUMENTS

| | | |
|---|---|---|
| EP | 0 173 361 | 3/1986 |
| EP | 0 355 586 | 2/1990 |
| JP | 10114744 A * | 5/1998 |
| JP | 2001083656 | 3/2001 |
| JP | 2001089412 A * | 4/2001 |
| WO | WO 99/38845 | 8/1999 |
| WO | WO01/00579 | 1/2001 |
| WO | WO 02/00633 | 1/2002 |
| WO | WO 02/28434 | 4/2002 |
| WO | WO 03/059893 | 7/2003 |
| WO | PCT/US2005/028673 | 12/2006 |

OTHER PUBLICATIONS

Hamdouchi et al. Journal of Medicinal Chemistry (1999), 42(11), 50-59.*
Oliver, et al., 2001 "A Selective Peroxisome Proliferator-Activated Receptor δ Agonist Promotes Reverse Cholesterol Transport", *Proc. Natl. Acad. Sci. USA* 98(9): 5306-5311.
He, et al. 1999 "PPAR Delta is an APC-Regulated Target of Nonsteroidal Anti-Inflammatory Drugs" *Cell* 99: 335-345.
Jiang, et al. 1998 "PPAR-Gamma Agonist Inhibit Production of Monocyte Inflammatory Cytokines", *Nature*, 391: 82-86.
Lehmann, et al. 1995 "An Antidiabetic Thiazolidinedione is a High Affinity Ligand for Peroxisome Proliferator-Activated Receptor Gamma (PPAR gamma)." J. Biol. Chem. 270(12): 12953-12956.
Ricote, et al. 1998 "The Peroxisome Proliferator-Activated Receptor-Gamma is a Negative Regulator of Macrophage Activation", *Nature* 391: 79-82.
CAS Registry No. 329784-15-8, "Benzenesulfonamide, 3-[(4-bromophenyl)sulfonyl]-N-[4-[4-(4-morpholinylsulfonyl)phenoxy]phenyl]," entered STN: Apr. 3, 2001.
CAS Registry No. 507465-91-0, "Benzenesulfonamide, 2,5-dichloro-N-[4-[4-(4-morpholinylsulfonyl)phenoxy]phenyl]," entered STN: Apr. 30, 2003.
CAS Registry No. 663927-90-0, "Benzamide, N-(4-bromophenyl)-3-[[[4-[4-(4-morpholinylsulfonyl)phenoxy]phenyl]amino]sulfonyl]," entered STN: Mar. 17, 2004.
CAS Registry No. 331766-85-9, "Carbamic acid, diethyl-, 4-[[[4-[[6-[(tribromomethyl)sulfonyl]-3-pyridinyl]sulfonyl]phenyl]amino]sulfonyl]phenyl ester (9CI)," entered STN: Apr. 18, 2001.

(Continued)

*Primary Examiner*—Kahsay T Habte
(74) *Attorney, Agent, or Firm*—Jones Day

(57) ABSTRACT

Bisaryl-sulfonamide compounds having the formula

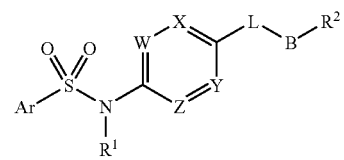

wherein Ar, $R^1$, $R^2$, L, B, W, X, Y, and Z, compositions and methods are provided that are useful in the treatment or prevention of a condition or disorder mediated by PPARγ or PPARδ. In particular, the compounds of the invention modulate the function of PPARγ or PPARδ. The subject methods are particularly useful in the treatment and/or prevention of diabetes, obesity, hypercholesterolemia, rheumatoid arthritis and atherosclerosis.

66 Claims, 49 Drawing Sheets

OTHER PUBLICATIONS

CAS Registry No. 320368-50-1, "Benzenesulfonamide, 4-chloro-N-[4-[4-(4-morpholinylsulfony)phenoxy]phenyl]," entered STN: Feb. 6, 2001.

CAS Registry No. 128647-93-8, "Benzenesulfonic acid, 2-[[4-chloro-6-[[5-[[9, 10-dihydro-4-[[(4-mehtylphenyl)sulfonyl]amino]-9, 10-dioxo-1-anthracenyl]thio]-2-sulfophenyl]amino]-1,3,5-triazin-2-yl]amino]-4-[[2-(sulfooxy)ethyl]sulfonyl]," entered STN: Aug. 3, 1990.

CAS Registry No. 104497-86-1, "Benzenesulfonamide, 4-[4-[[[3-[[1-[3-[4-(hexadecyloxy)phenyl]-1,4,5,6,7,8-hexahydro-1,4-dioxo-2-naphthalenyl]ethyl]sulfonyl]phenyl]sulfonyl]amino]phenoxy]N-[3-[[[8-hydroxy-5-[[2-(methylsufonyl)-4-nitrophenyl]azo]-1-naphthalenyl]amino]sulfonyl]phenyl]- (9CI)," entered STN: Oct. 4, 1986.

* cited by examiner

Figure 2-8
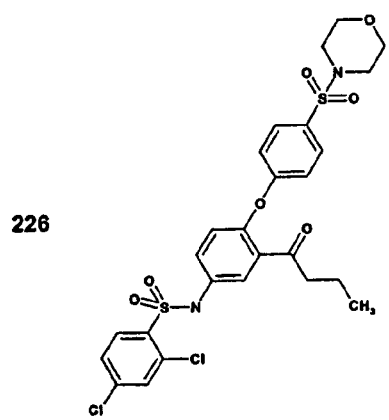
226
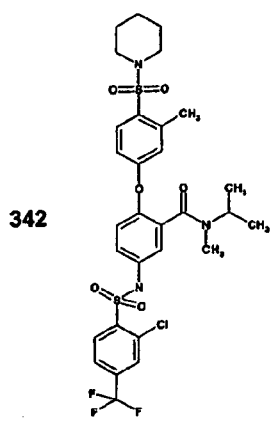
342
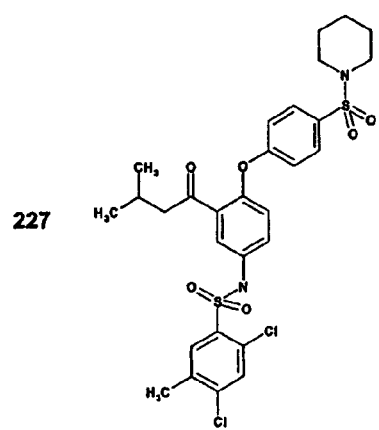
227
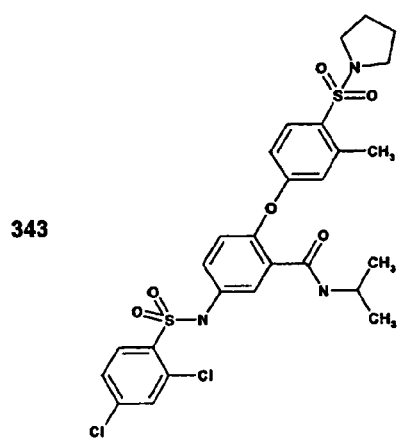
343
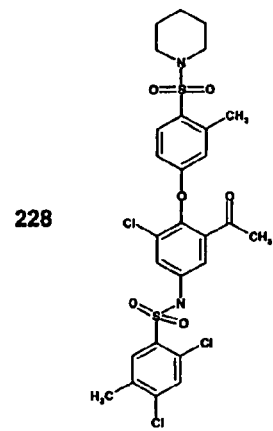
228
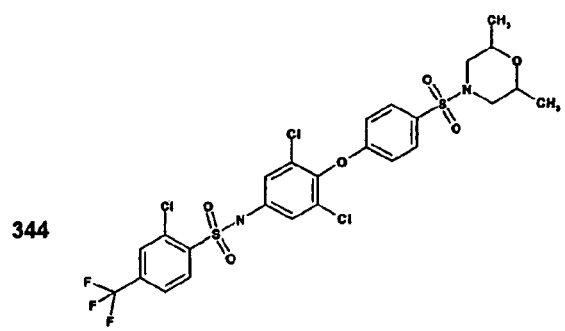
344

Figure 2-21
261 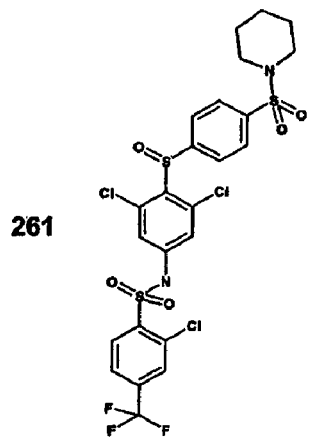
381 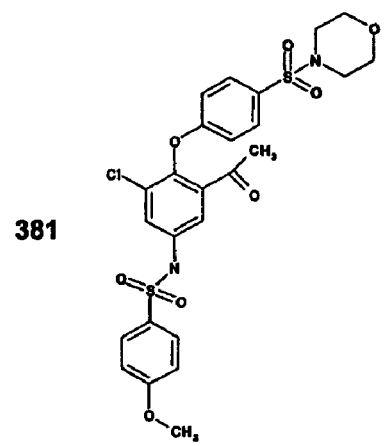
262 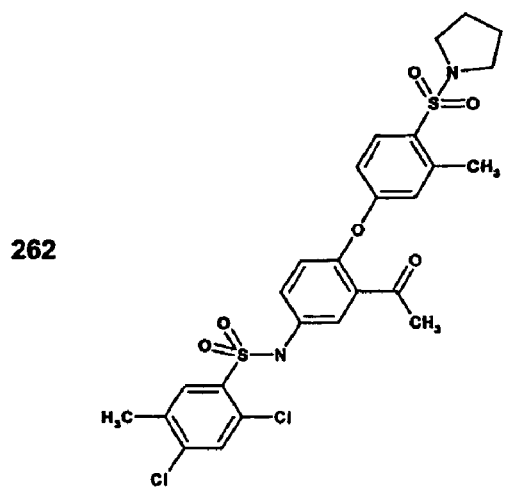
382 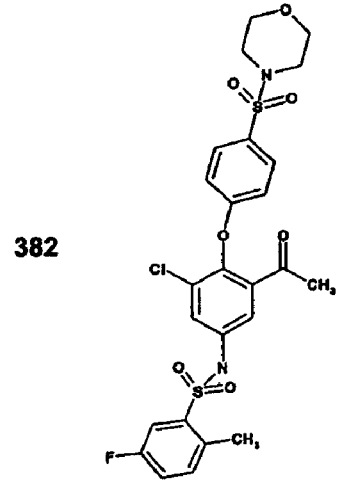
263 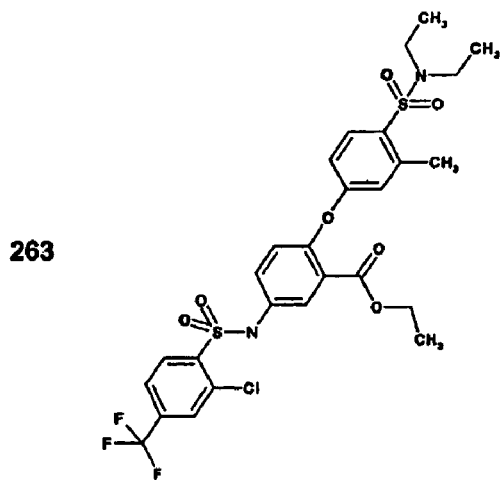
383 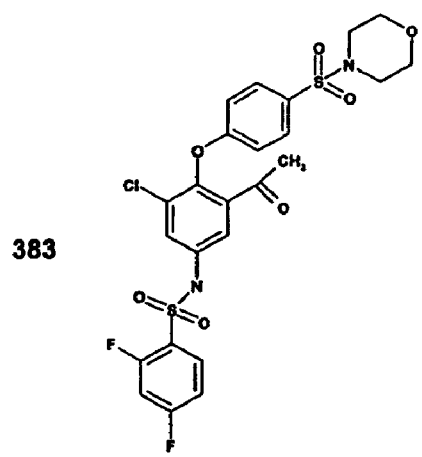

Figure 2-22
264 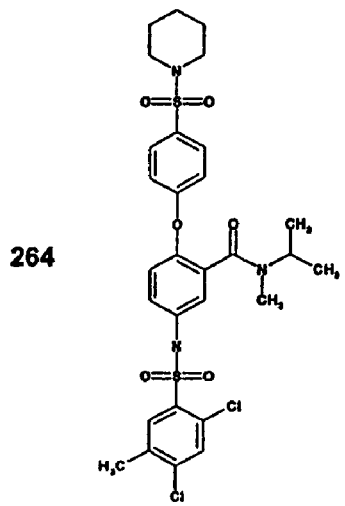
384 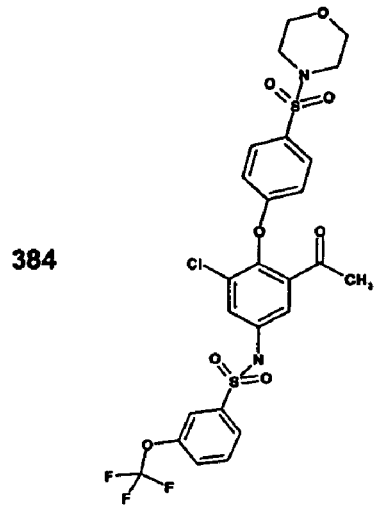
265 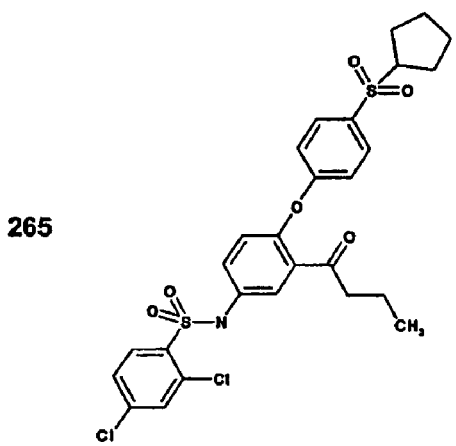
385 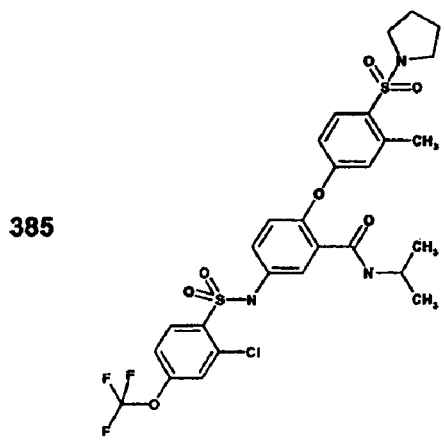
266 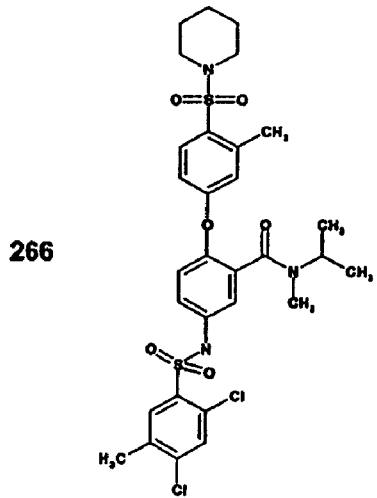
386 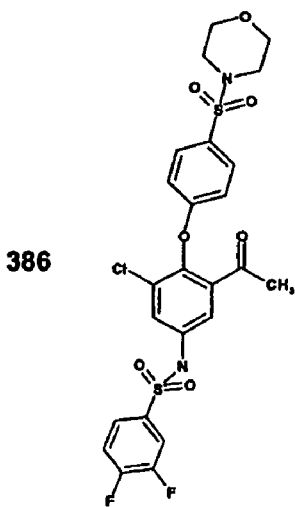

Figure 2-24
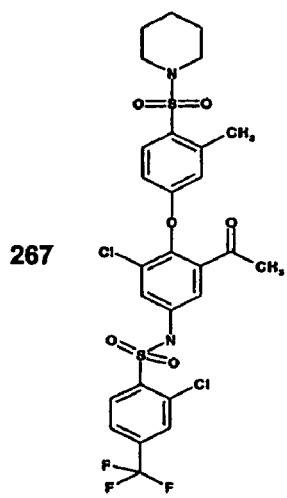
267
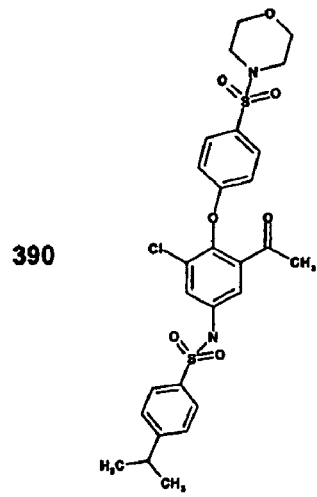
390
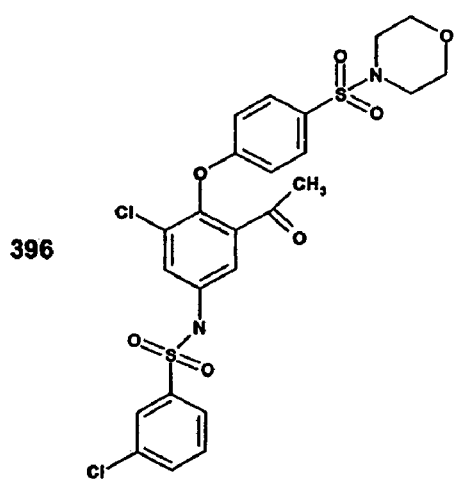
396
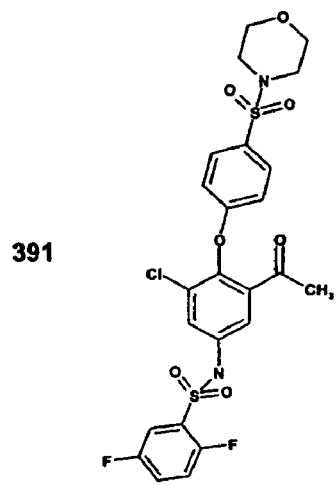
391
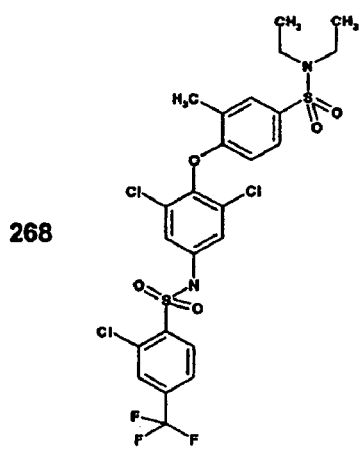
268
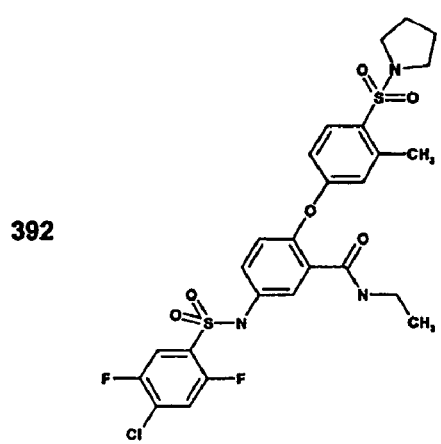
392

BISARYL-SULFONAMIDES

CROSS-REFERENCE TO RELATED APPLICATIONS

This application claims the benefit of U.S. Provisional Application No. 60/601,578, filed Aug. 12, 2004, the content of which is incorporated by reference in its entirety.

FIELD OF THE INVENTION

The present invention relates to compounds that modulate the PPARγ or PPARδ receptor and are useful in the diagnosis and treatment of metabolic disorders, inflammatory disorders, neoplastic diseases and complicaitons thereof.

BACKGROUND OF THE INVENTION

The peroxisome proliferator-activated receptors (PPARs) are transducer proteins belonging to the steroid/thyroid/retinoid receptor superfamily. The PPARs were originally identified as orphan receptors, without known ligands, but were named for their ability to mediate the pleiotropic effects of fatty acid peroxisome proliferators. At least three mammalian PPARs have been isolated: PPARγ, PPARα and PPARδ (PPARβ, NUC1). These receptors function as ligand-regulated transcription factors that control the expression of target genes by binding to their responsive DNA sequence as heterodimers with RXR. The target genes encode enzymes involved in lipid metabolism and differentiation of adipocytes. Accordingly, the discovery of transcription factors involved in controlling lipid metabolism has provided insight into regulation of energy homeostasis in vertebrates, and further provided targets for the development of therapeutic agents for disorders such as obesity, diabetes and dyslipidemia.

PPARγ is one member of the nuclear receptor superfamily of ligand-activated transcription factors and has been shown to be expressed in an adipose tissue-specific manner. Its expression is induced early during the course of differentiation of several preadipocyte cell lines. Additional research has now demonstrated that PPARγ plays a pivotal role in the adipogenic signaling cascade. PPARγ also regulates the ob/leptin gene which is involved in regulating energy homeostasis, and adipocyte differentiation which has been shown to be a critical step to be targeted for anti-obesity and diabetic conditions.

In an effort to understand the role of PPARγ in adipocyte differentiation, several investigators have focused on the identification of PPARγ activators. One class of compounds, the thiazolidinediones, which were known to have adipogenic effects on preadipocyte and mesenchymal stem cells in vitro, and antidiabetic effects in animal models of non-insulin-dependent diabetes mellitus (NIDDM) were also demonstrated to be PPARγ-selective ligands. More recently, compounds that selectively activate murine PPARγ were shown to possess in vivo antidiabetic activity in mice.

Despite the advances made with the thiazolidinedione class of antidiabetes agents, unacceptable side effects have limited their clinical use. Accordingly, there remains a need for potent, selective activators of PPARγ which will be useful for the treatment of NIDDM and other disorders related to lipid metabolism and energy homeostasis. Still further, compounds that block PPARγ activity would be useful for interfering with the maturation of preadipocytes into adipocytes and thus would be useful for the treatment of obesity and related disorders associated with undesirable adipocyte maturation.

Evidence suggests that PPARδ controls the peroxisomal beta-oxidation pathway of fatty acids. Activators of PPARδ have been shown to promote reverse cholesterol transport, which can raise HDL cholesterol levels. See, Oliver et al. (2001) *Proc. Natl. Acad. Sci. USA* 98(9):5306-5311. It has also been shown that PPARδ activators inhibit the formation of the inflammatory mediator's inducible nitric oxide synthase (iNOS) and tumor necrosis factor (TNF). See, U.S. Pat. No. 6,869,975; International Publication No. WO 02/28434 to Buchan et al. Moreover, it has been shown that PPARδ, unlike PPARγ or PPARα, represents a β-catenin/Tcf-4 target with particular importance for chemoprevention (He et al. (1999) *Cell* 99:335-345).

The identification of compounds which modulate PPARδ provides an opportunity to probe PPARδ mediated processes and discover new therapeutic agents for conditions and diseases associated therewith, such as cardiovascular disease, atherosclerosis, diabetes, obesity, syndrome X and malignant diseases.

The present invention provides compounds that are useful as activators as well as antagonists of PPARγ or PPARδ activity, compositions containing them and methods for their use.

BRIEF SUMMARY OF THE INVENTION

In one aspect, the present invention provides methods of treating or preventing a metabolic disorder, an inflammatory condition, a cadivascular disease or a neoplastic disease. The methods typically involve administering to a subject in need thereof a therapeutically effective amount of a compound having the formula (I):

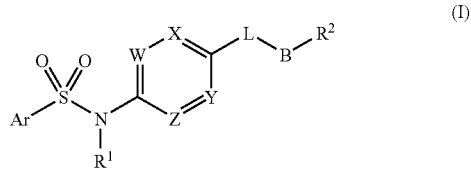

in which the symbol Ar is a member selected from the group consisting of phenyl, naphthyl and pyridyl; each of which is optionally substituted with from one to three $R^8$ substituents, wherein each $R^8$ is a member independently selected from the group consisting of halogen, cyano, nitro, $(C_1-C_8)$alkyl, $(C_1-C_8)$alkoxy, $(C_1-C_8)$haloalkyl, $(C_1-C_8)$haloalkoxy, $(C_2-C_8)$alkenyl, $(C_2-C_8)$ alkynyl, hydroxyl and $NR^{12}R^{13}$.

The letter B represents an aryl or heteroaryl group; each of which is optionally substituted with from one to two $R^9$ substituents, wherein each $R^9$ is a member independently selected from the group consisting of halogen, nitro, $(C_1-C_8)$ alkyl, $(C_1-C_8)$alkoxy and $NR^{12}R^{13}$.

The letter L represents a member selected from the group consisting of O, $S(O)_k$, $CR^aR^b$ and C(O); wherein each $R^a$ or $R^b$ is independently selected from the group consisting of hydrogen, cyano, nitro, and $(C_1-C_8)$ alkyl; and the subscript k represents an integer of from 0 to 2.

The symbol W represents $C(R^3)$ or N; the symbol X represents $C(R^4)$ or N; the symbol Y represents $C(R^5)$ or N; and the symbol Z represents $C(R^6)$ or N, wherein at least one of W, X, Y and Z is N and at least one W, X, Y and Z is other than N; and each $R^3$, $R^4$, $R^5$, or $R^6$ is a member independently selected from the group consisting of hydrogen, hydroxy, halogen, cyano, nitro, $NR^{12}R^{13}$, $(C_1-C_8)$alkyl, halo$(C_1-C_8)$alkyl, hydroxy$(C_1-C_8)$alkyl, $(C_3-C_8)$cycloalkyl, $(C_1-C_8)$alkoxy, ($C_1$-$C_8$)thioalkoxy, ($C_2$-$C_8$)heteroalkyl, aryl, heteroaryl, —C(O)$R^{11}$, —$CO_2R^{11}$, —C(O)N $R^{12}R^{13}$, —C(O)$CH_2$CN, —$X^1Q^1$, $X^2OR^{11}$ and $X^2$ $NR^{12}R^{13}$; or optionally, adjacent $R^3$, $R^4$, $R^5$, or $R^6$ groups can be combined to form an additional 5- or 6-membered fused ring which can be saturated or unsaturated.

The symbol $R^1$ represents a member selected from the group consisting of hydrogen, ($C_1$-$C_8$)alkyl, ($C_2$-$C_8$)heteroalkyl and aryl($C_1$-$C_8$)alkyl; and the symbol $R^2$ represents a member selected from the group consisting of hydrogen, halogen, cyano, nitro, $NR^{12}R^{13}$ and $S(O)_mR^7$.

The symbol $X^1$ represents a member selected from the group consisting of ($C_1$-$C_2$)alkylene and C(O); and the symbol $Q^1$ represents a member independently selected from the group consisting of pyrrolidinyl, piperidinyl, and morpholinyl.

The symbol $R^7$ is selected from the group consisting of ($C_1$-$C_8$)alkyl, ($C_3$-$C_8$)cycloalkyl, ($C_1$-$C_8$)haloalkyl, aryl, $NR^{12}R^{13}$, ($C_3$-$C_8$)heterocycloalkyl, $X^2$—C(O)$OR^{15}$, $X^2$—C(O)N($R^{15}$)$_2$, and —$X^2$—$NR^{12}R^{13}$; wherein each symbol $X^2$ represents ($C_1$-$C_8$)alkylene.

The symbol $R^{11}$ represents a member independently selected from the group consisting of hydrogen, ($C_1$-$C_8$)alkyl, ($C_2$-$C_8$)alkenyl, ($C_3$-$C_8$)cycloalkyl, ($C_2$-$C_8$)heteroalkyl, aryl, heteroaryl, heteroaryl($C_1$-$C_8$)alkyl, ($C_3$-$C_8$)heterocycloalkyl and aryl($C_1$-$C_8$)alkyl; and the symbols $R^{12}$ and $R^{13}$ each represent a member independently selected from the group consisting of hydrogen, ($C_1$-$C_8$)alkyl, ($C_2$-$C_8$)alkenyl, ($C_3$-$C_8$)cycloalkyl, ($C_2$-$C_8$)heteroalkyl, ($C_1$-$C_8$)alkoxy, aryl and aryl($C_1$-$C_8$)alkyl; optionally, $R^{12}$ and $R^{13}$ are combined with the nitrogen to which each is attached to form a 3-, 4-, 5-, 6- or 7-membered ring which can be saturated or unsaturated and contain 0 to 2 additional heteroatoms selected from N, O and S; wherein said ring is optionally substituted with from one to four substituents selected from the group consisting of hydroxy, oxo, and ($C_1$-$C_8$)alkyl.

Each symbol $R^{15}$ represents a member selected from the group consisting of H, ($C_1$-$C_8$)alkyl, ($C_2$-$C_8$)alkenyl and ($C_3$-$C_8$)cycloalkyl; and the subscript m represents an integer of 0 to 2.

In another aspect, the present invention provides methods of treating or preventing a metabolic disorder or an inflammatory condition. The methods typically involve administering to a subject in need thereof a therapeutically effective amount of a compound having the formula (XIV)

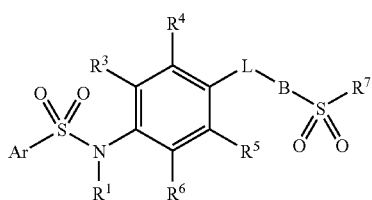

in which Ar is a member selected from the group consisting of phenyl, naphthyl and pyridyl; each of which is optionally substituted with from one to three $R^8$ substituents, wherein each $R^8$ is a member independently selected from the group consisting of halogen, cyano, nitro, ($C_1$-$C_8$)alkyl, ($C_1$-$C_8$)alkoxy, ($C_1$-$C_8$)haloalkyl, ($C_1$-$C_8$)haloalkoxy, ($C_2$-$C_8$) alkenyl, ($C_2$-$C_8$) alkynyl, hydroxyl and $NR^{12}R^{13}$.

The letter B represents an aryl or heteroaryl group; each of which is optionally substituted with from one to two $R^9$ substituents, wherein each $R^9$ is a member independently selected from the group consisting of halogen, nitro, ($C_1$-$C_8$) alkyl, ($C_1$-$C_8$)alkoxy and $NR^{12}R^{13}$.

The letter L represents a member selected from the group consisting of O, $S(O)_k$, $CR^aR^b$ and C(O); wherein each $R^a$ or $R^b$ is independently selected from the group consisting of hydrogen, cyano, nitro, and ($C_1$-$C_8$) alkyl; and the subscript k represents an integer of from 0 to 2.

Each symbol $R^3$, $R^4$, $R^5$, or $R^6$ is a member independently selected from the group consisting of hydrogen, hydroxy, halogen, cyano, nitro, $NR^{12}R^{13}$, ($C_1$-$C_8$)alkyl, halo($C_1$-$C_8$) alkyl, hydroxy($C_1$-$C_8$)alkyl, ($C_3$-$C_8$)cycloalkyl, ($C_1$-$C_8$) alkoxy, ($C_1$-$C_8$)thioalkoxy, ($C_2$-$C_8$)heteroalkyl, aryl, heteroaryl, —C(O)$R^{11}$, —$CO_2R^{11}$, —C(O)N $R^{12}R^{13}$, —C(O) $CH_2$CN, —$X^1Q^1$, $X^2OR^{11}$ and $X^2NR^{12}R^{13}$; or optionally, adjacent $R^3$, $R^4$, $R^5$, or $R^6$ groups can be combined to form an additional 5- or 6-membered fused ring which can be saturated or unsaturated.

The symbol $R^1$ represents a member selected from the group consisting of hydrogen, ($C_1$-$C_8$)alkyl, ($C_2$-$C_8$)heteroalkyl and aryl($C_1$-$C_8$)alkyl; and the symbol $R^2$ represents a member selected from the group consisting of hydrogen, halogen, cyano, nitro, $NR^{12}R^{13}$ and $S(O)_mR^7$.

The symbol $X^1$ represents a member selected from the group consisting of ($C_1$-$C_2$)alkylene and C(O); and the symbol $Q^1$ represents a member independently selected from the group consisting of pyrrolidinyl, piperidinyl, and morpholinyl.

The symbol $R^7$ is selected from the group consisting of ($C_1$-$C_8$)alkyl, ($C_3$-$C_8$)cycloalkyl, ($C_1$-$C_8$)haloalkyl, aryl, $NR^{12}R^{13}$, ($C_3$-$C_8$)heterocycloalkyl, $X^2$—C(O)$OR^{15}$, $X^2$—C(O)N($R^{15}$)$_2$, and —$X^2$—$NR^{12}R^{13}$; wherein each symbol $X^2$ represents ($C_1$-$C_8$)alkylene.

The symbol $R^{11}$ represents a member independently selected from the group consisting of hydrogen, ($C_1$-$C_8$) alkyl, ($C_2$-$C_8$)alkenyl, ($C_3$-$C_8$)cycloalkyl, ($C_2$-$C_8$)heteroalkyl, aryl, heteroaryl, heteroaryl($C_1$-$C_8$)alkyl, ($C_3$-$C_8$)heterocycloalkyl and aryl($C_1$-$C_8$)alkyl; and the symbols $R^{12}$ and $R^{13}$ each represent a member independently selected from the group consisting of hydrogen, ($C_1$-$C_8$)alkyl, ($C_2$-$C_8$) alkenyl, ($C_3$-$C_8$)cycloalkyl, ($C_2$-$C_8$)heteroalkyl, ($C_1$-$C_8$) alkoxy, aryl and aryl($C_1$-$C_8$)alkyl; optionally, $R^{12}$ and $R^{13}$ are combined with the nitrogen to which each is attached to form a 3-, 4-, 5-, 6- or 7-membered ring which can be saturated or unsaturated and contain 0 to 2 additional heteroatoms selected from N, O and S; wherein said ring is optionally substituted with from one to four substituents selected from the group consisting of hydroxy, oxo, and ($C_1$-$C_8$)alkyl.

Each symbol $R^{15}$ represents a member selected from the group consisting of H, ($C_1$-$C_8$)alkyl, ($C_2$-$C_8$)alkenyl and ($C_3$-$C_8$)cycloalkyl; and the subscript m represents an integer of 0 to 2.

In another aspect, the present invention provides methods of treating or preventing a condition or disorder mediated by PPARγ or PPARδ and methods for modulating PPARγ or PPARδ.

In yet another aspect, the present invention provides compounds of formula I and XIV and pharmaceutical compositions containing compounds of formula I and XIV.

DETAILED DESCRIPTION OF THE INVENTION

1. Abbreviations and Definitions

Figure 1:
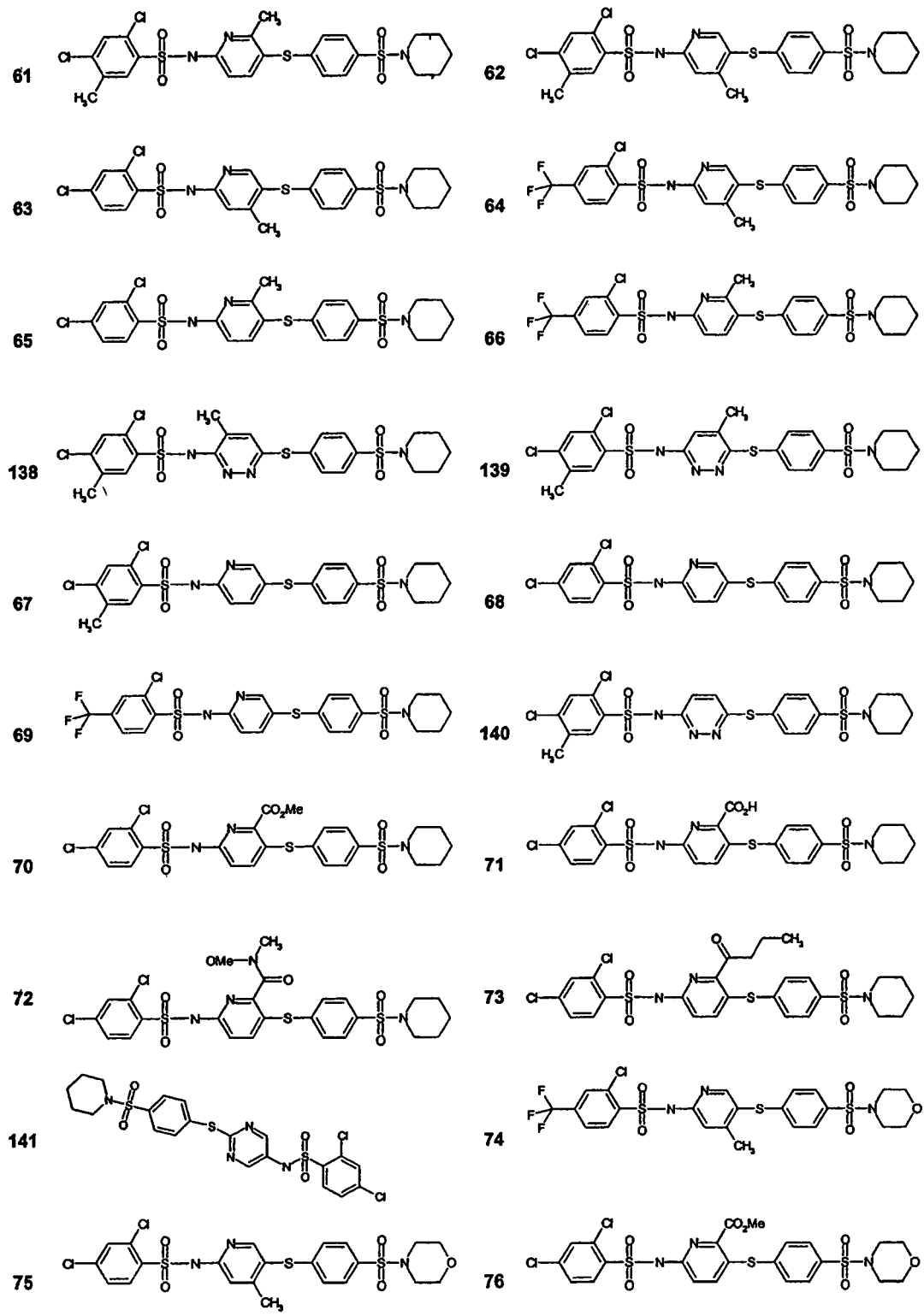
FIG. 1 provides structures for a variety of compounds of the present invention.
Figures 1, 2:
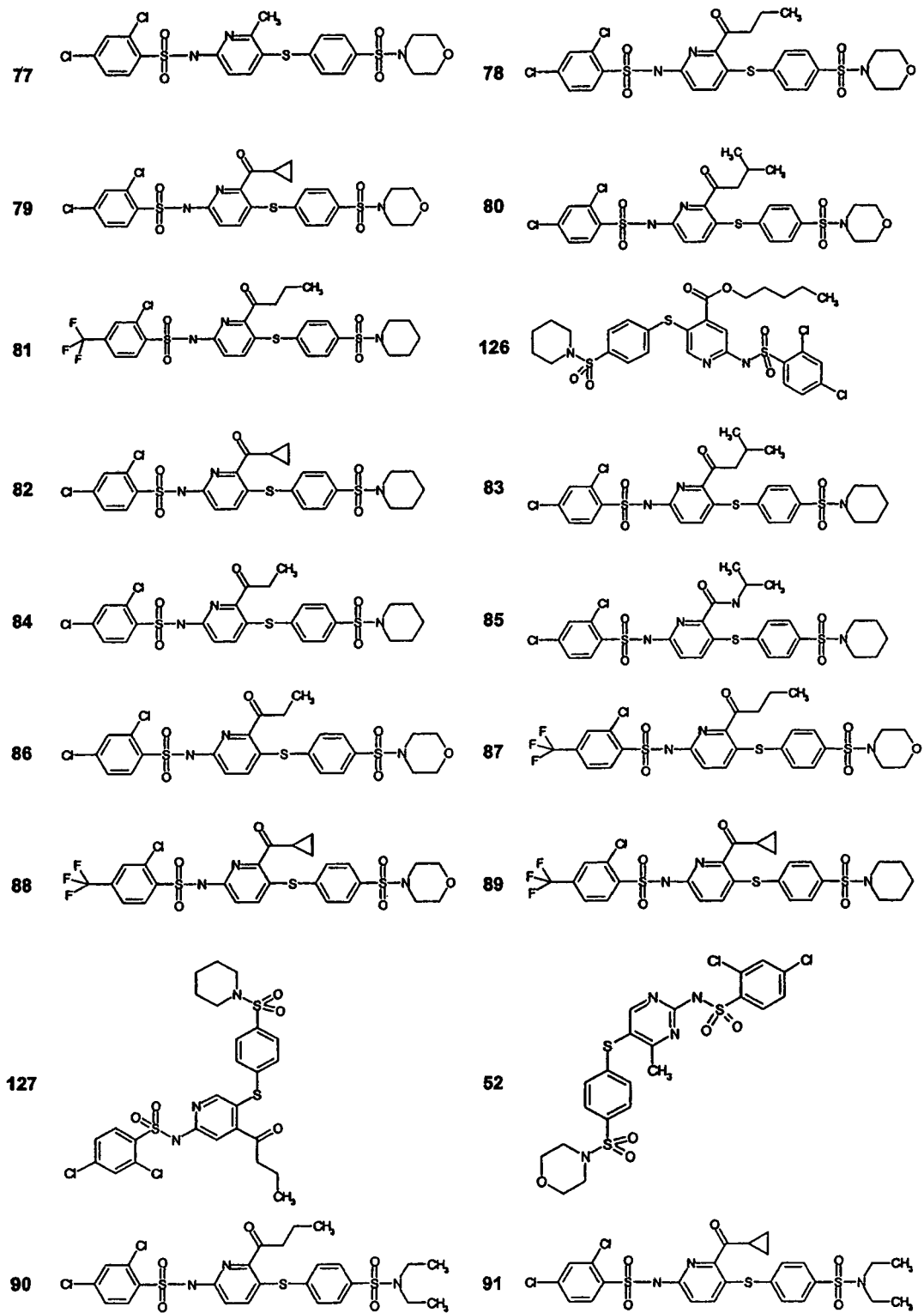
FIG. 2 also provides structures for a variety of compounds of the present invention
Figures 1, 2, 3:
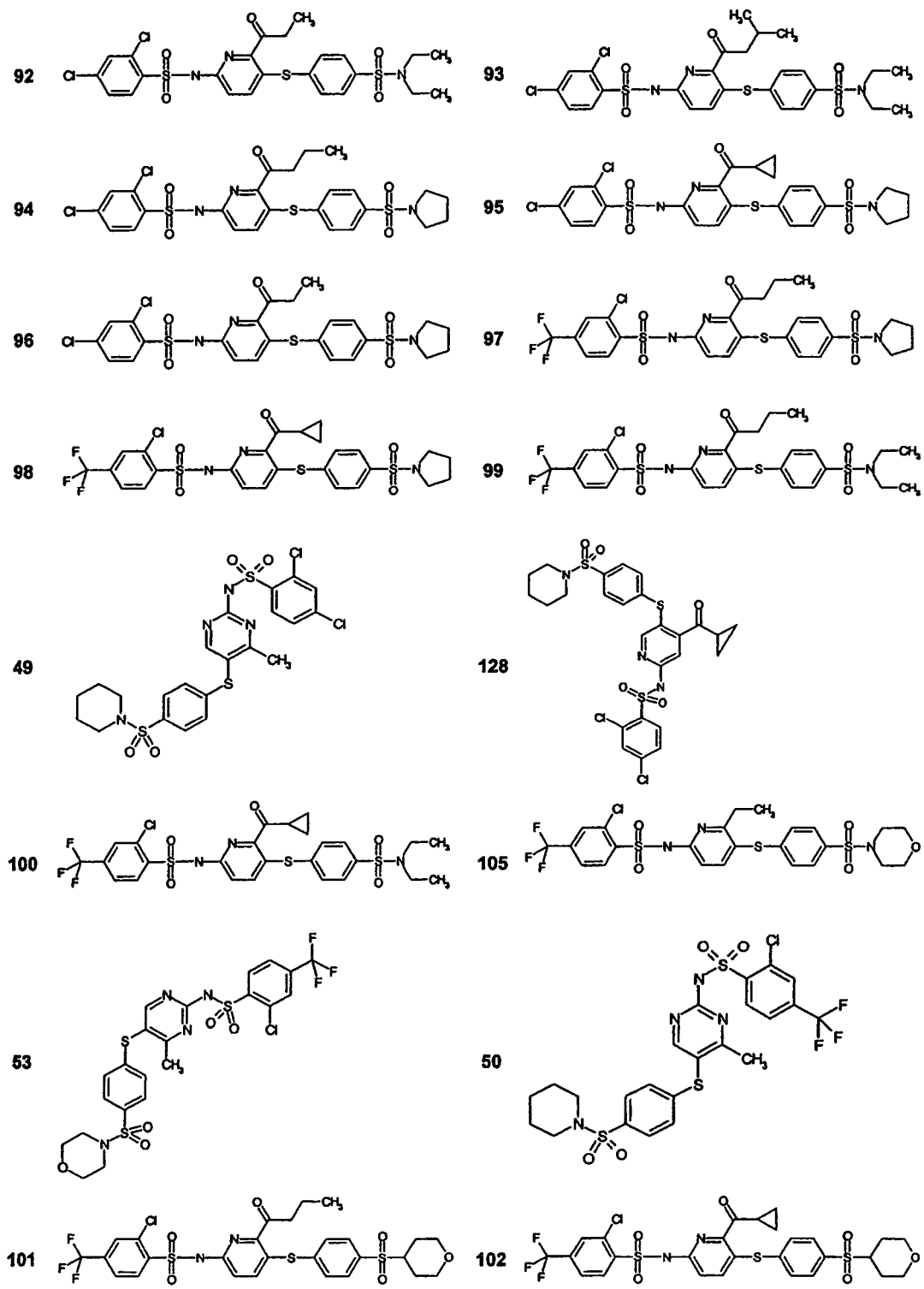
Figures 1, 2, 3, 4:
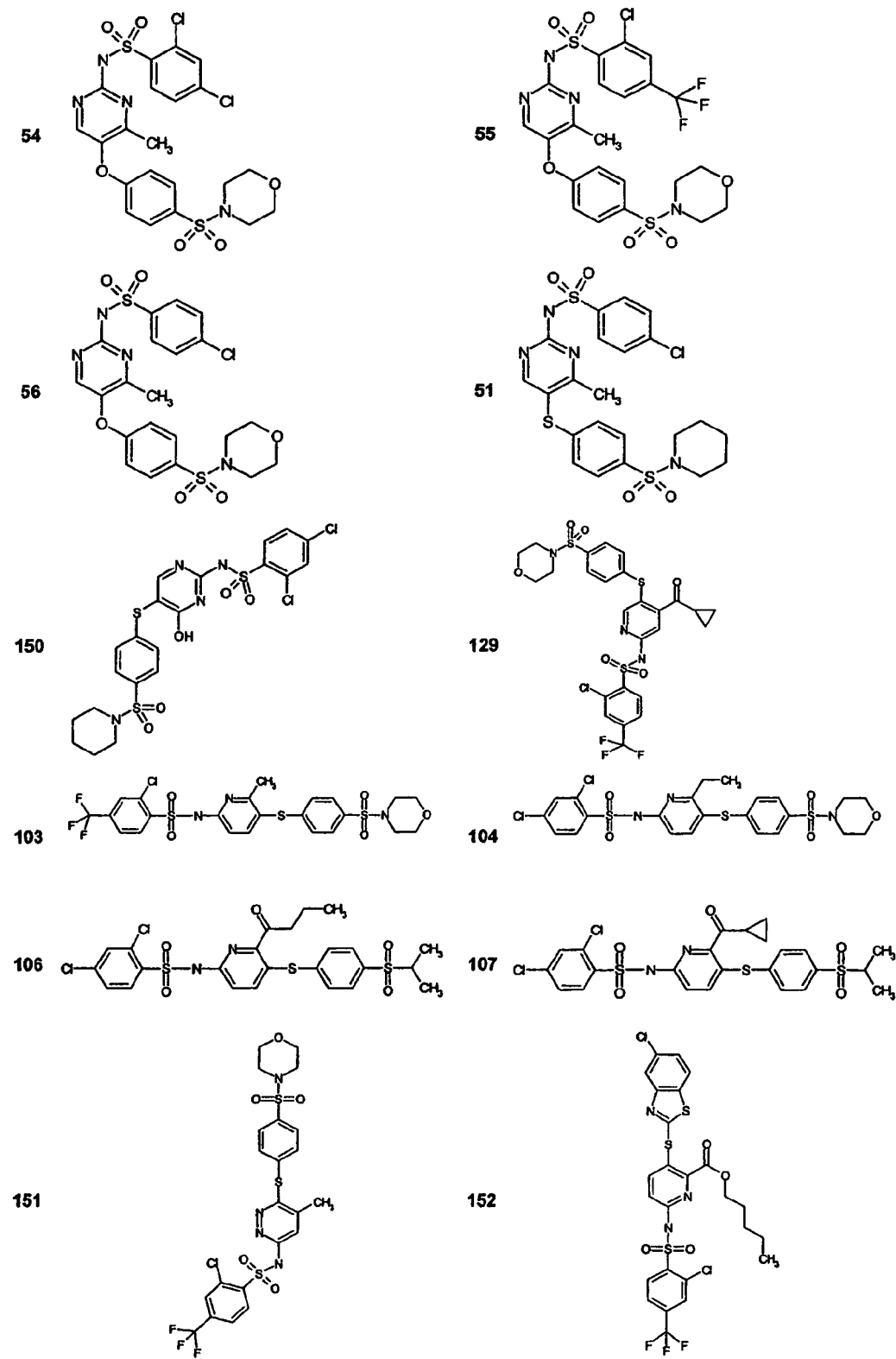
Figures 1, 2, 3, 4, 5:
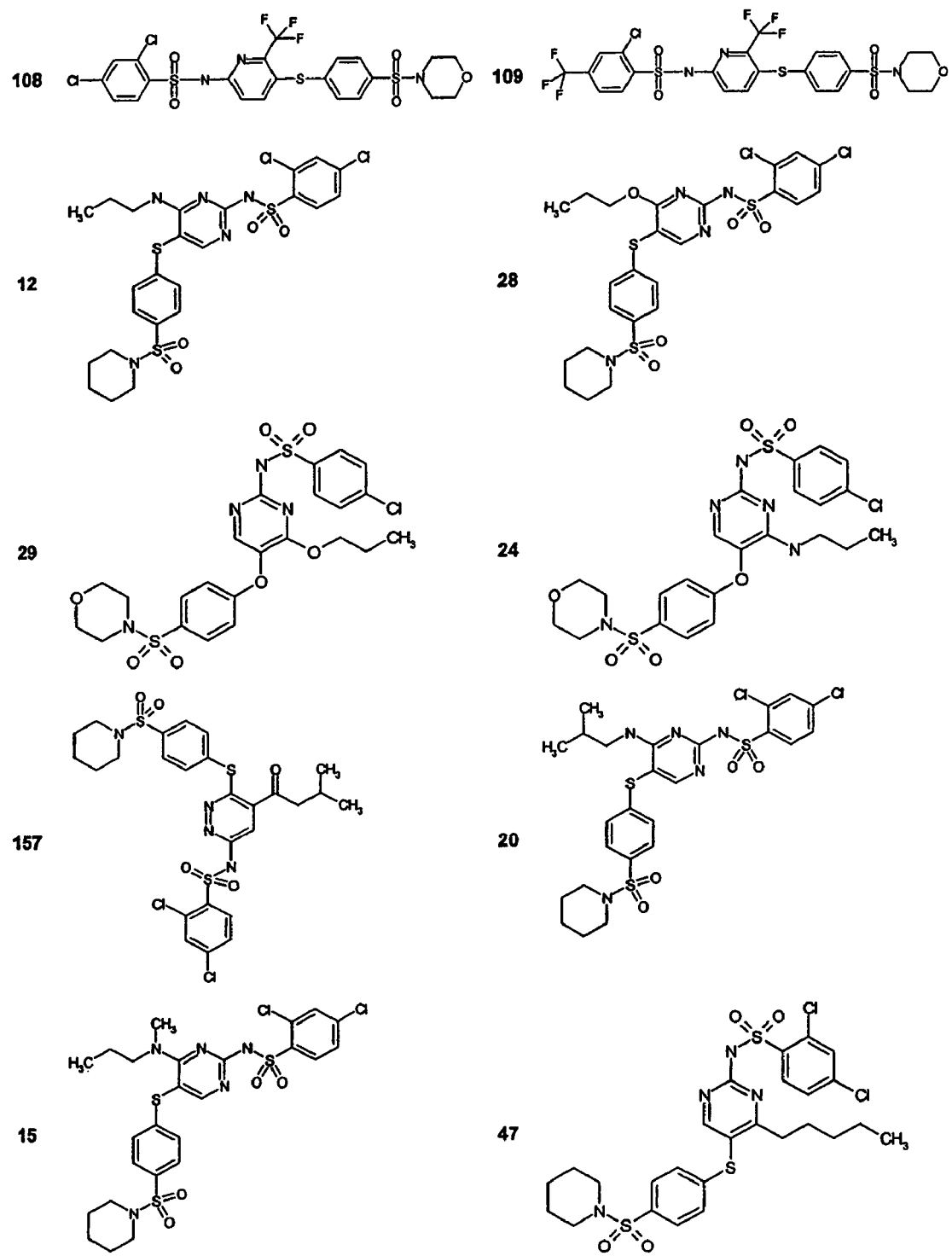
Figures 1, 2, 3, 4, 5, 6:
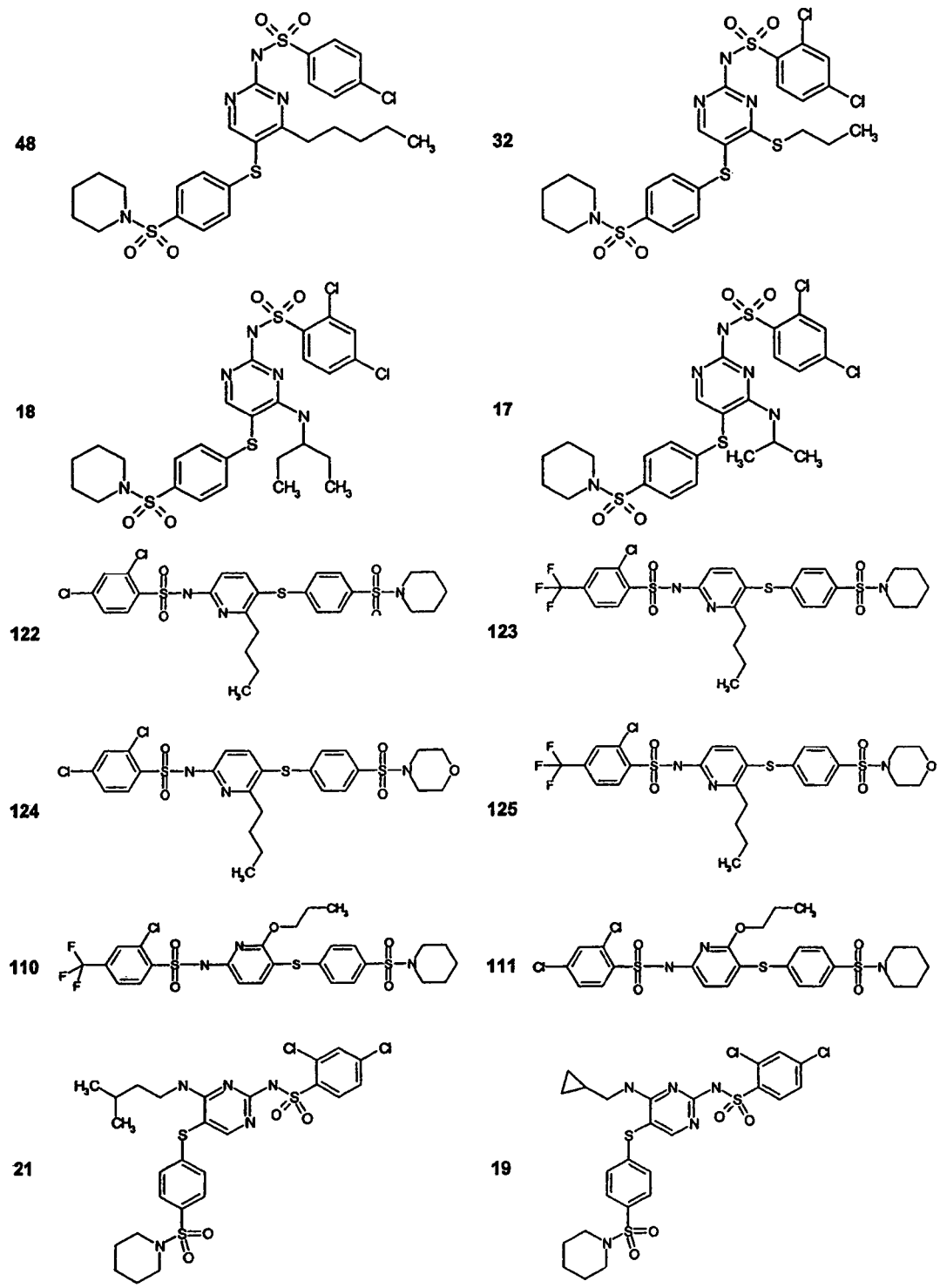
Figures 1, 2, 3, 4, 5, 6, 7:
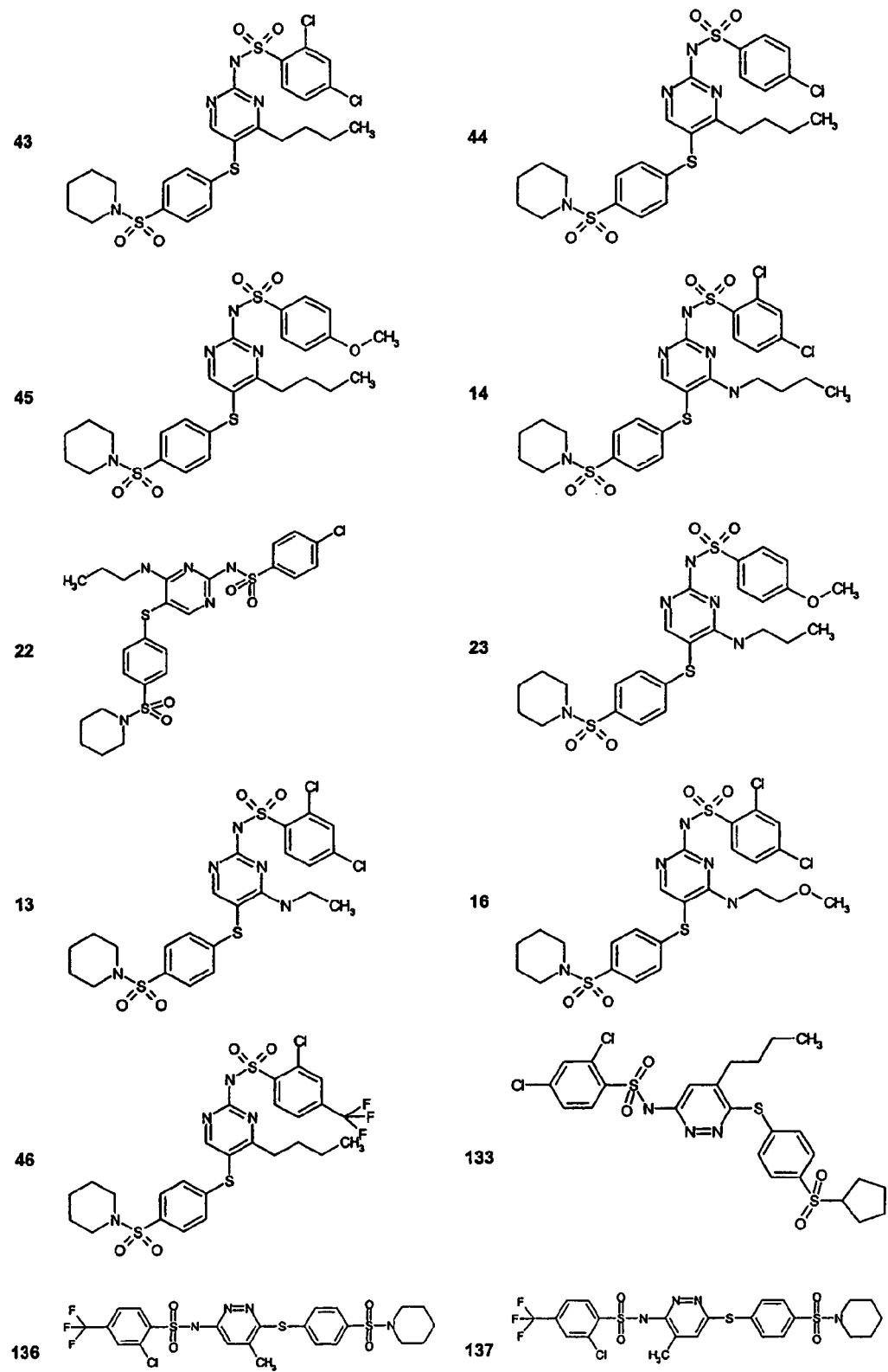
Figures 1, 2, 3, 4, 5, 6, 7, 8:
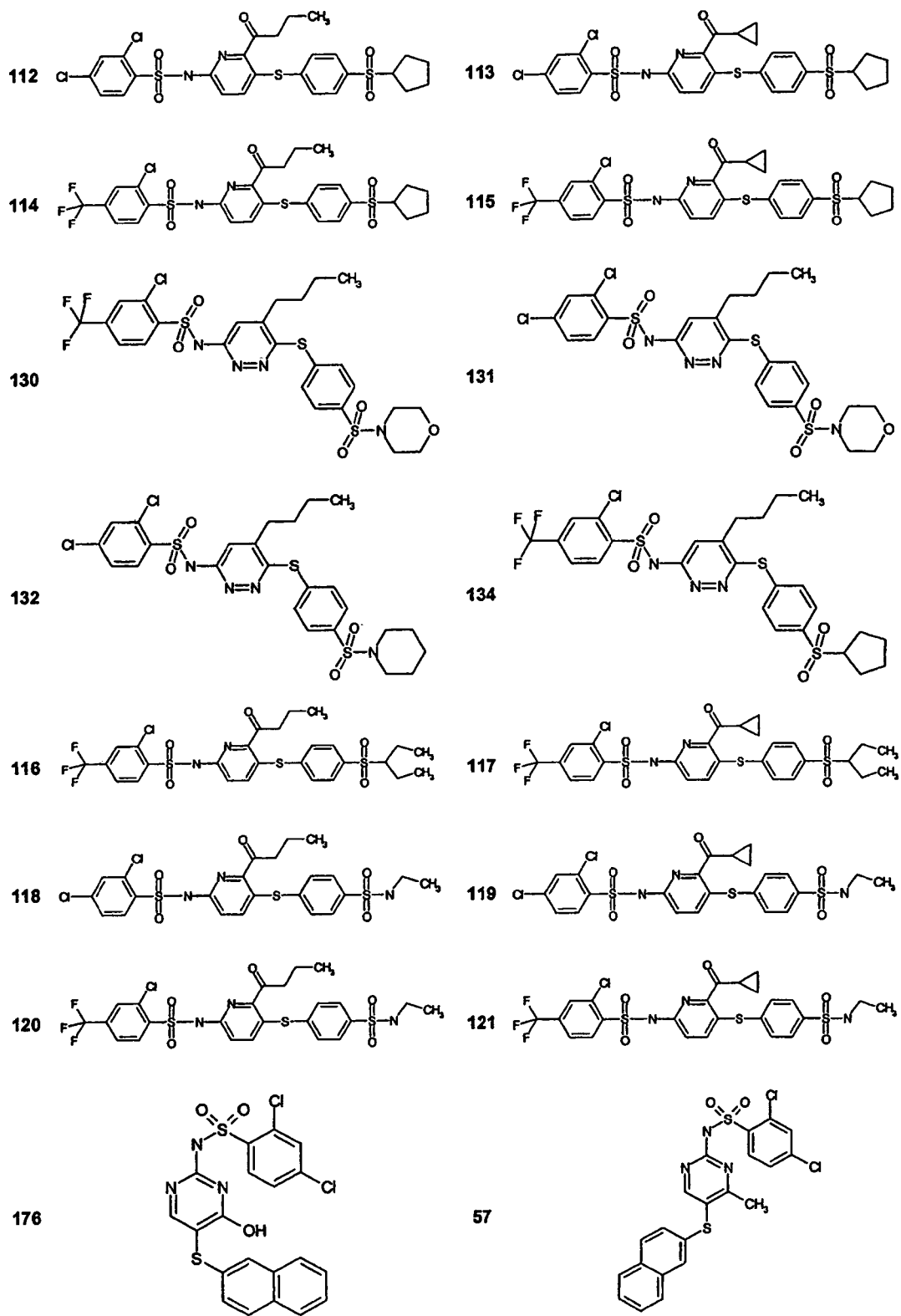
Figures 1, 2, 3, 4, 5, 6, 7, 8, 9:
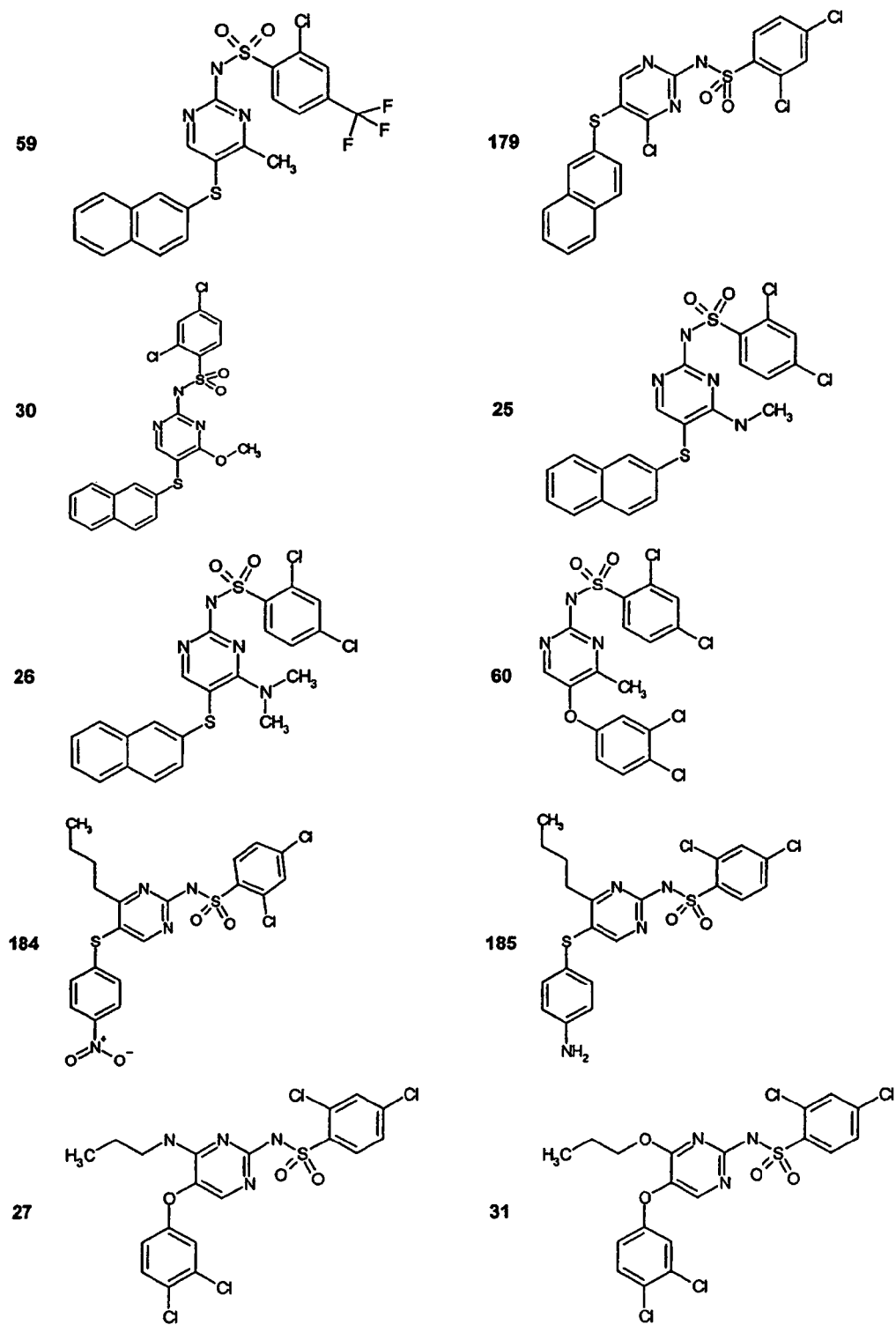
Figures 1, 2, 3, 4, 5, 6, 7, 8, 9, 10:
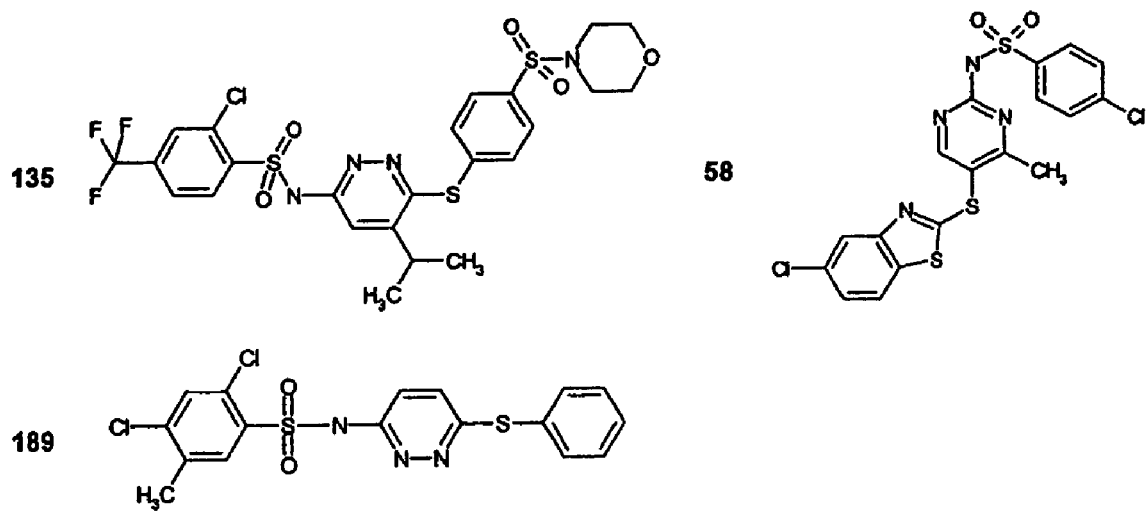
Figures 1, 2:
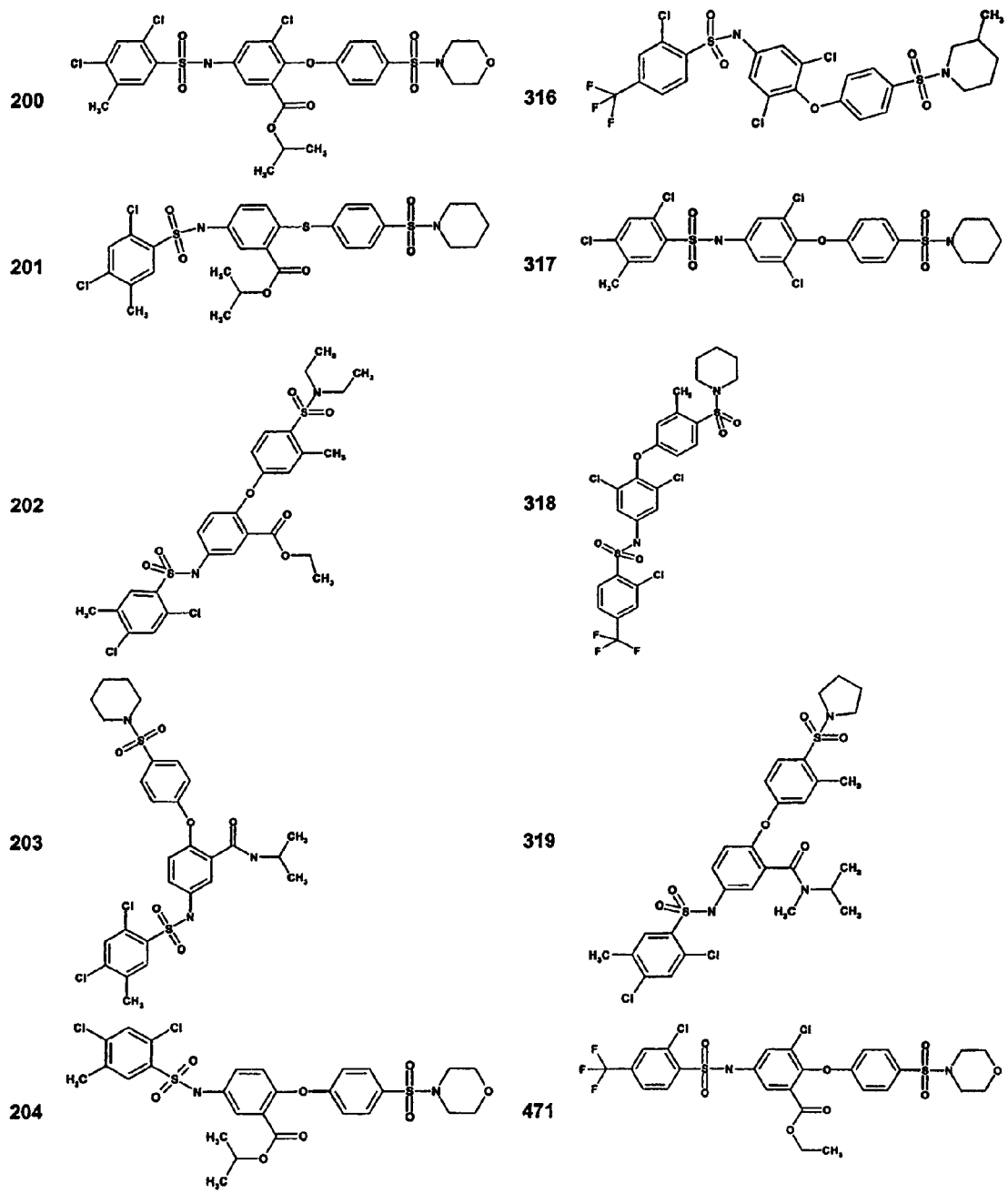
Figure 2:
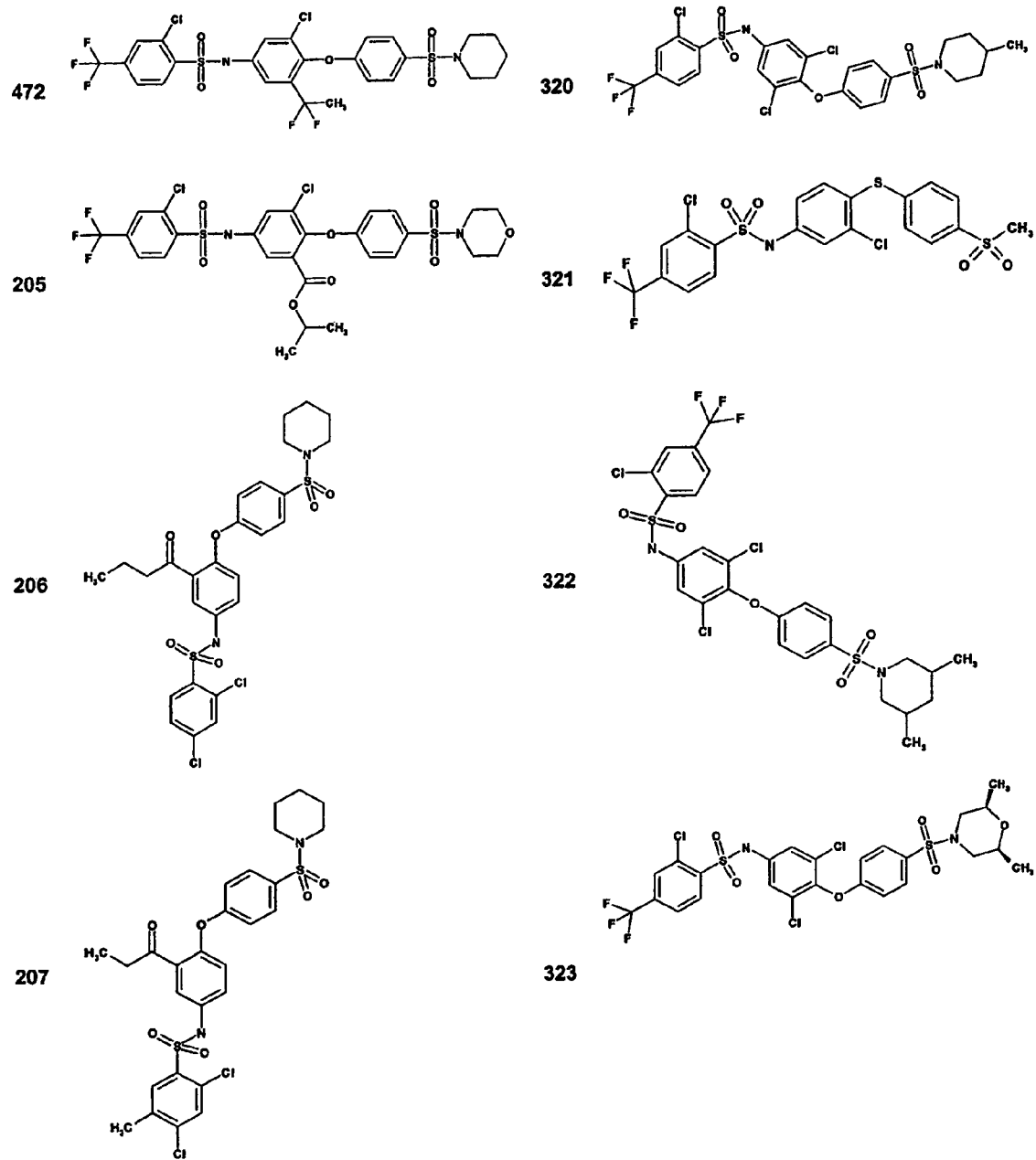
Figures 2, 3:
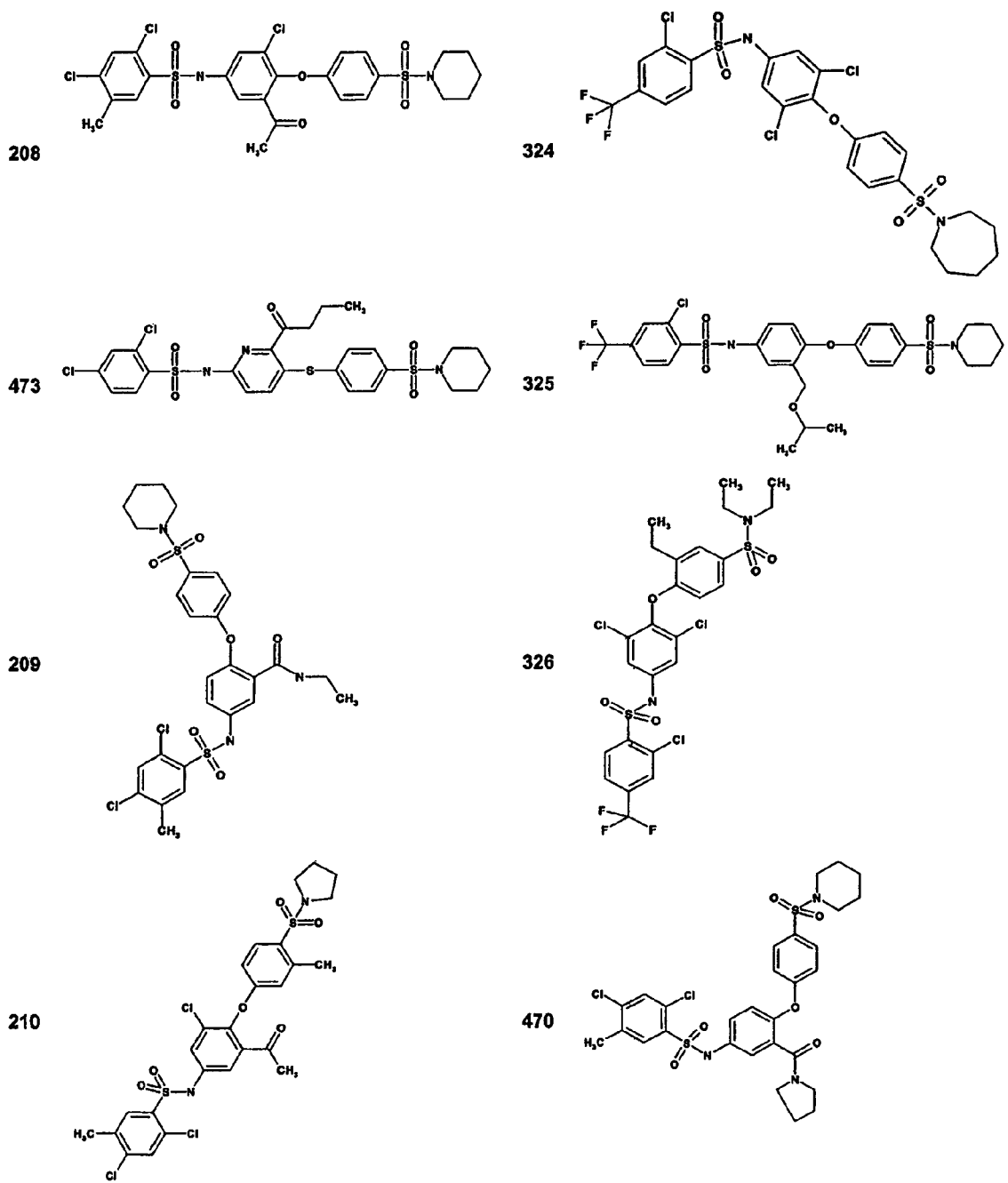
Figures 2, 3, 4:
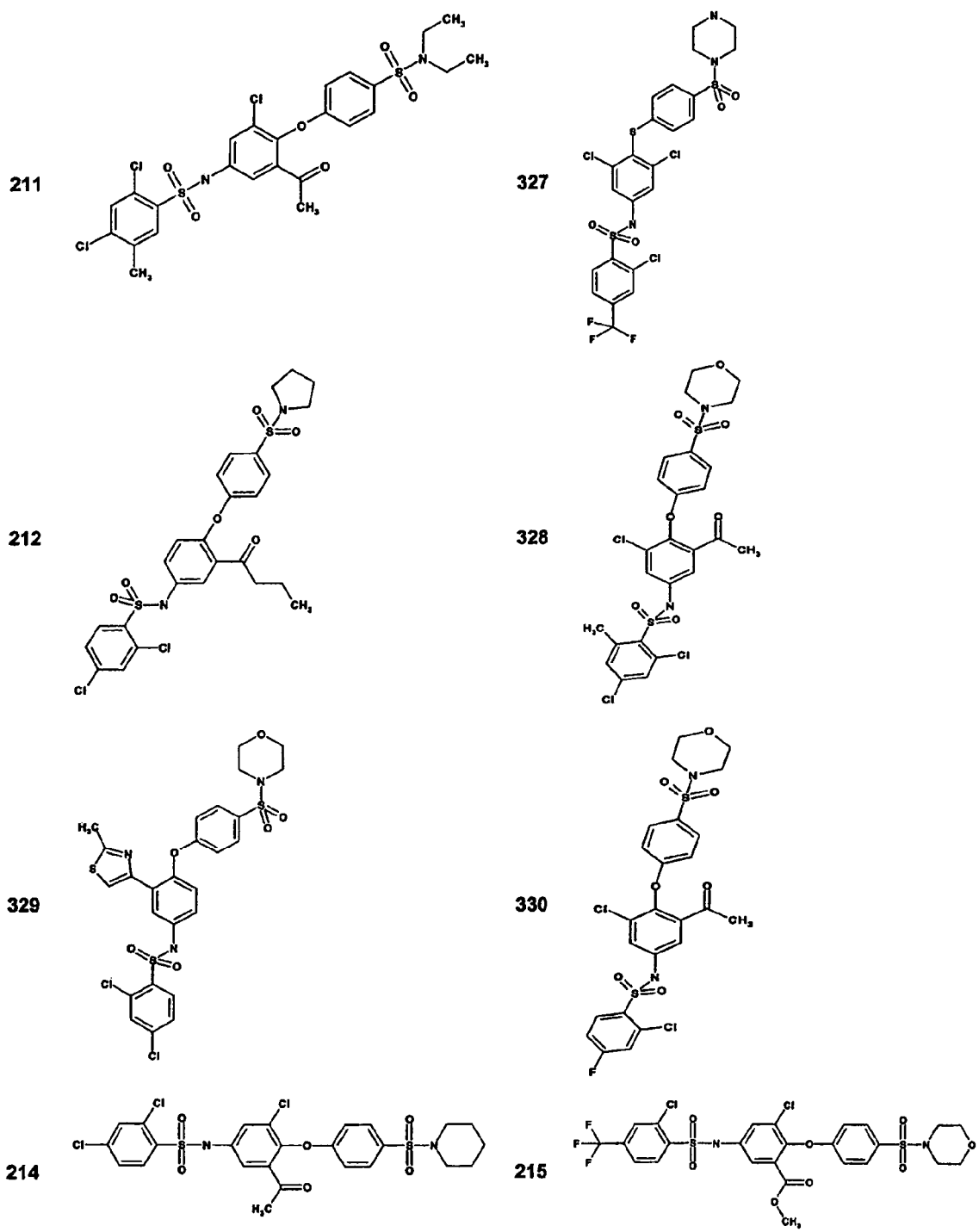
Figures 2, 3, 4, 5:
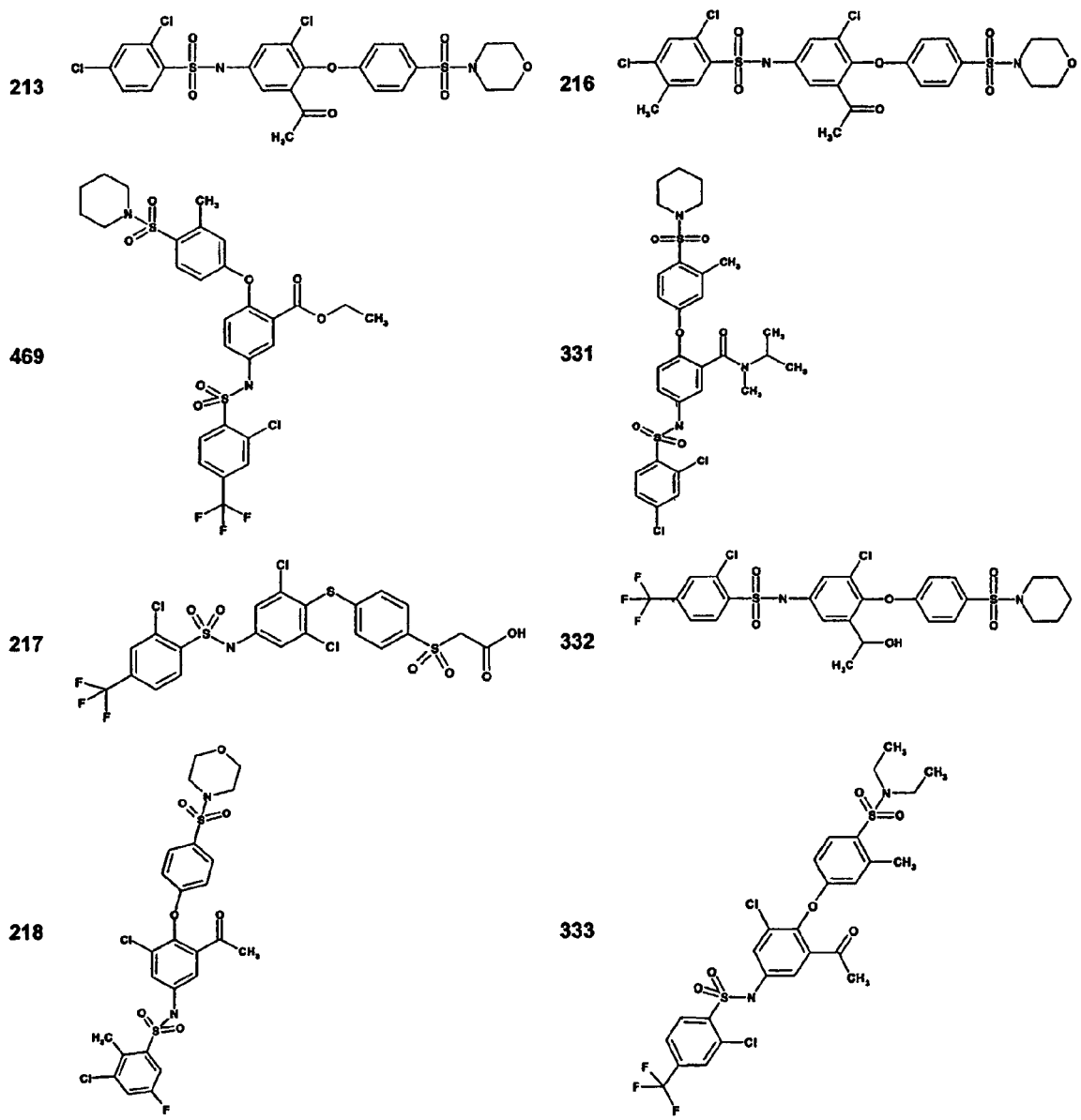
Figures 2, 3, 4, 5, 6:
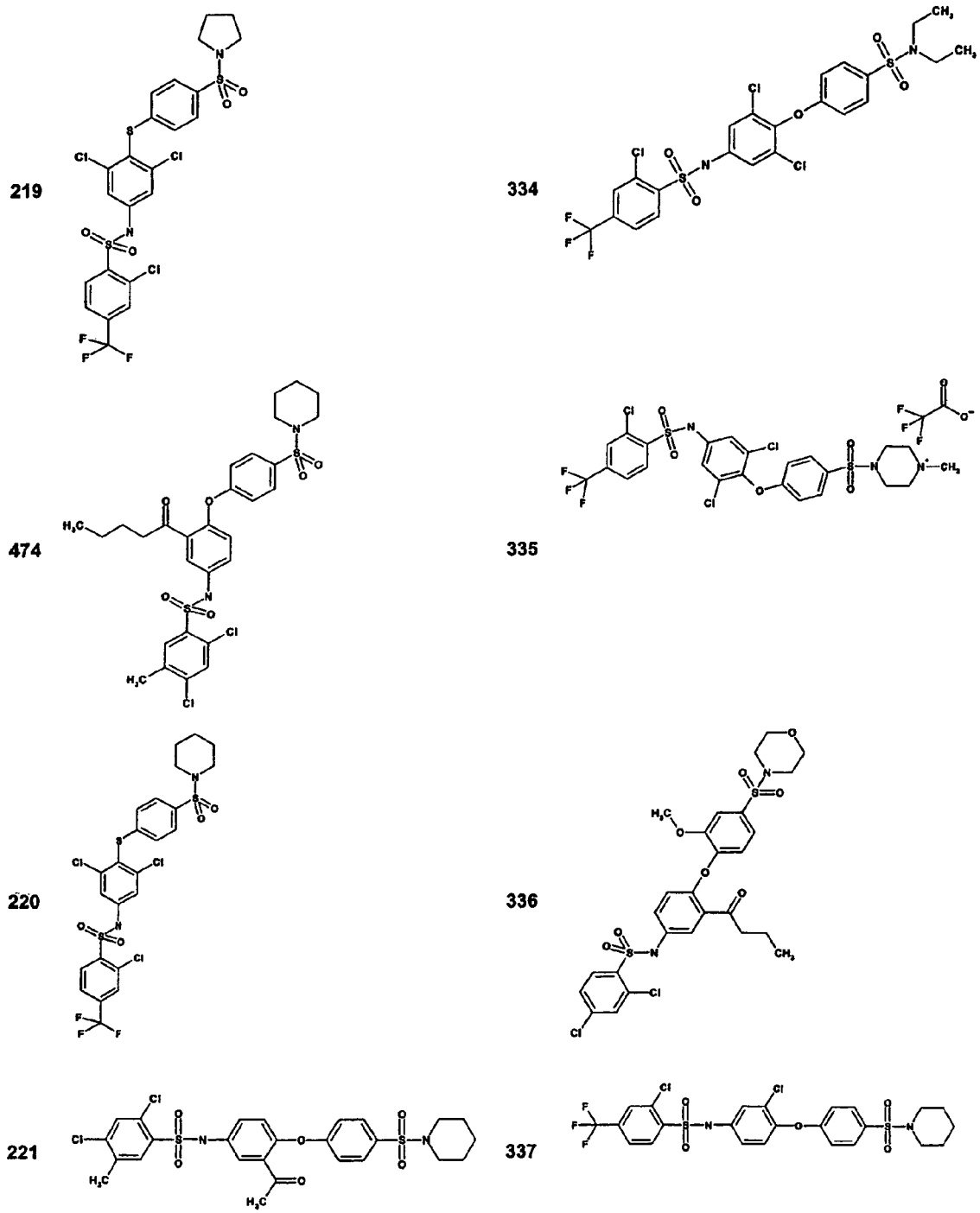
Figures 2, 3, 4, 5, 6, 7:
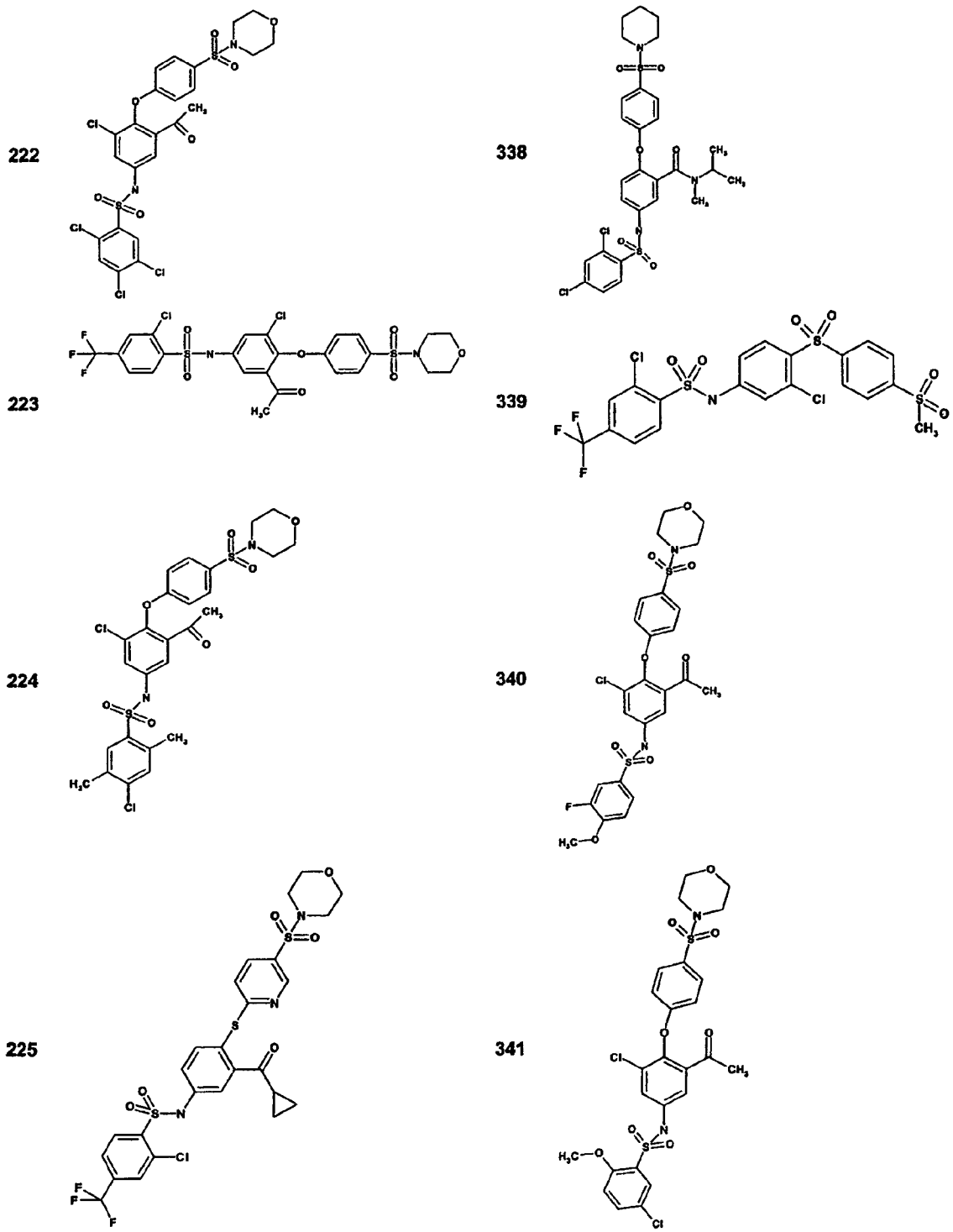
Figures 2, 3, 4, 5, 6, 7, 8, 9:
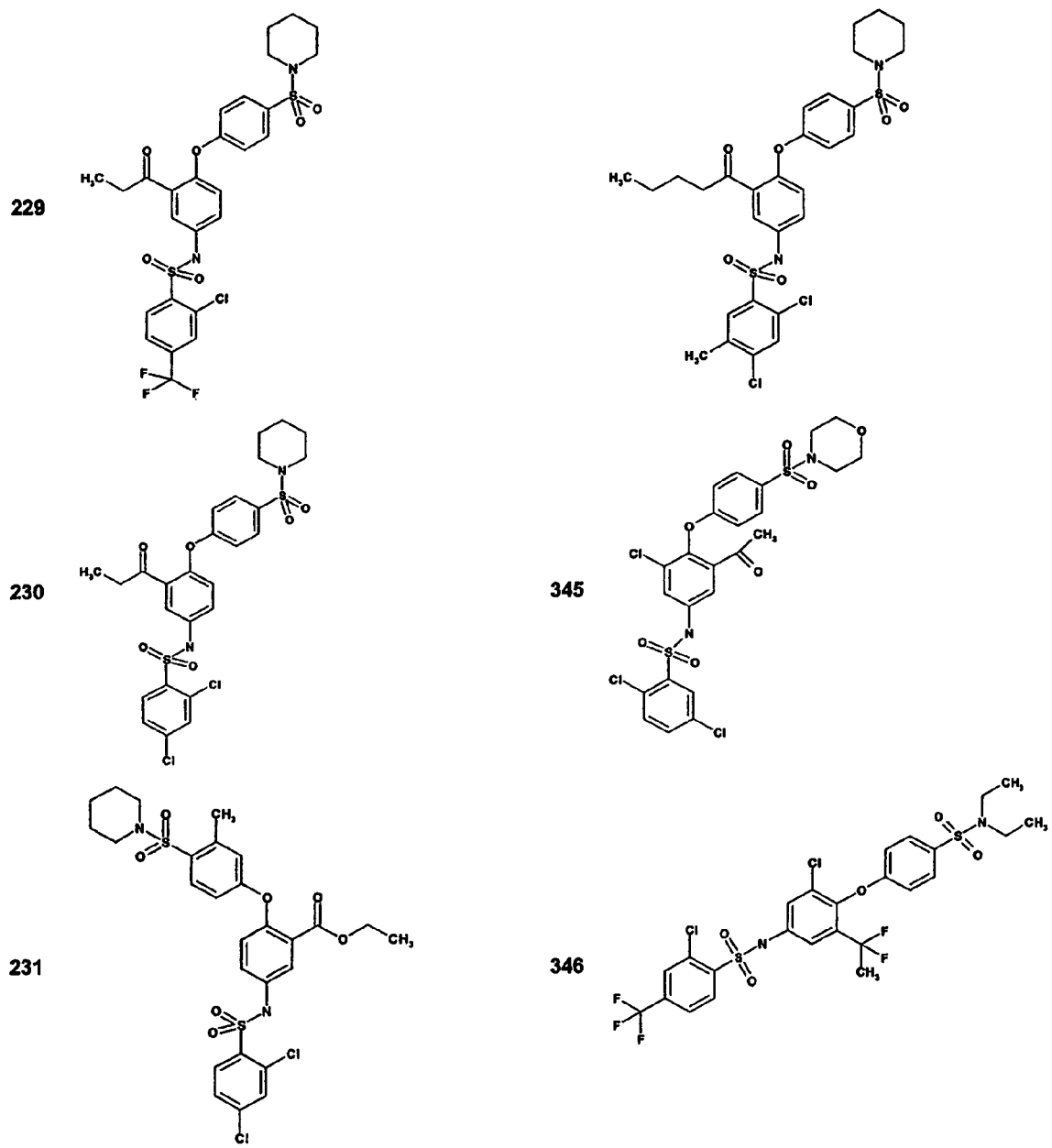
Figures 2, 3, 4, 5, 6, 7, 8, 9, 10:
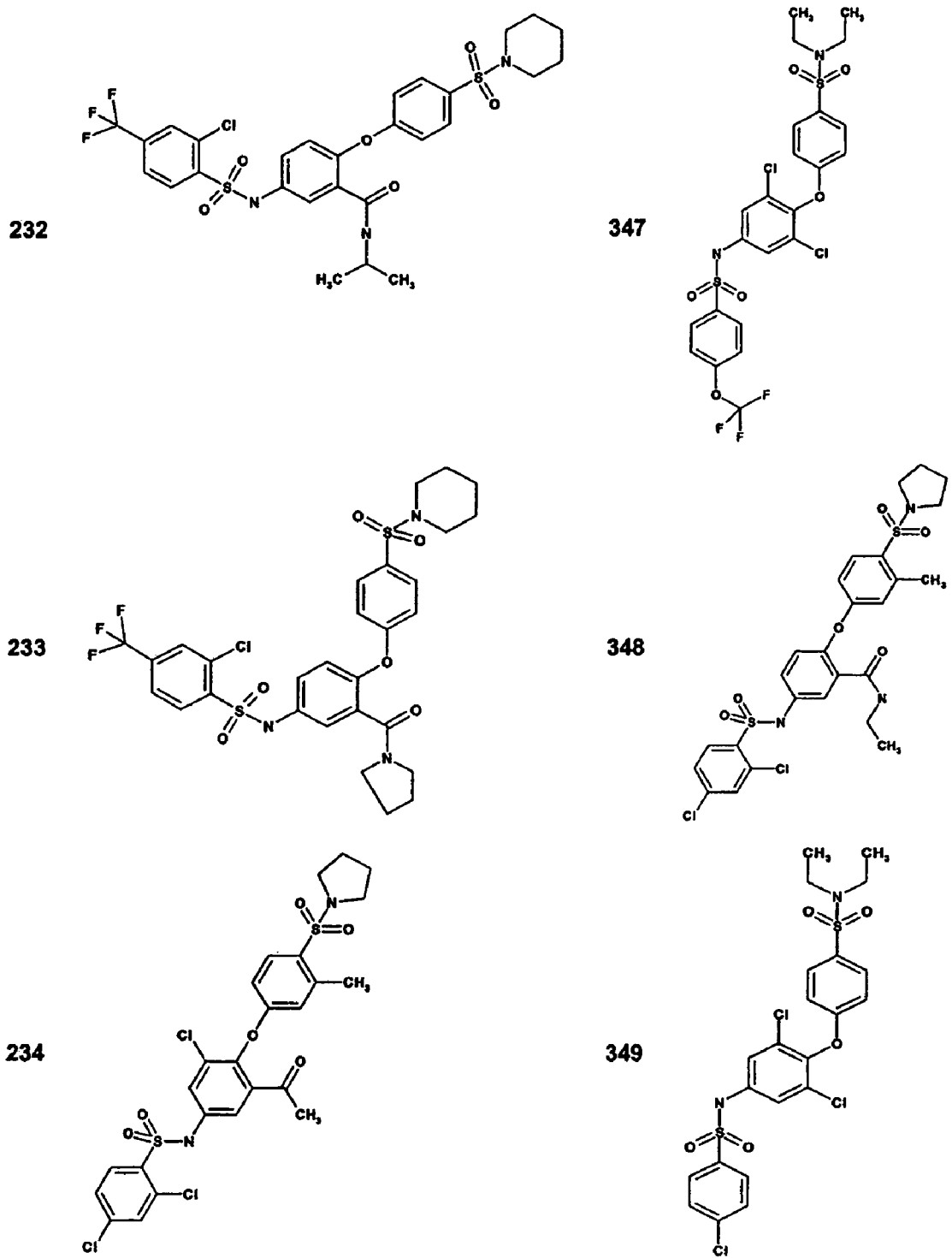
Figures 2, 3, 4, 5, 6, 7, 8, 9, 10, 11:
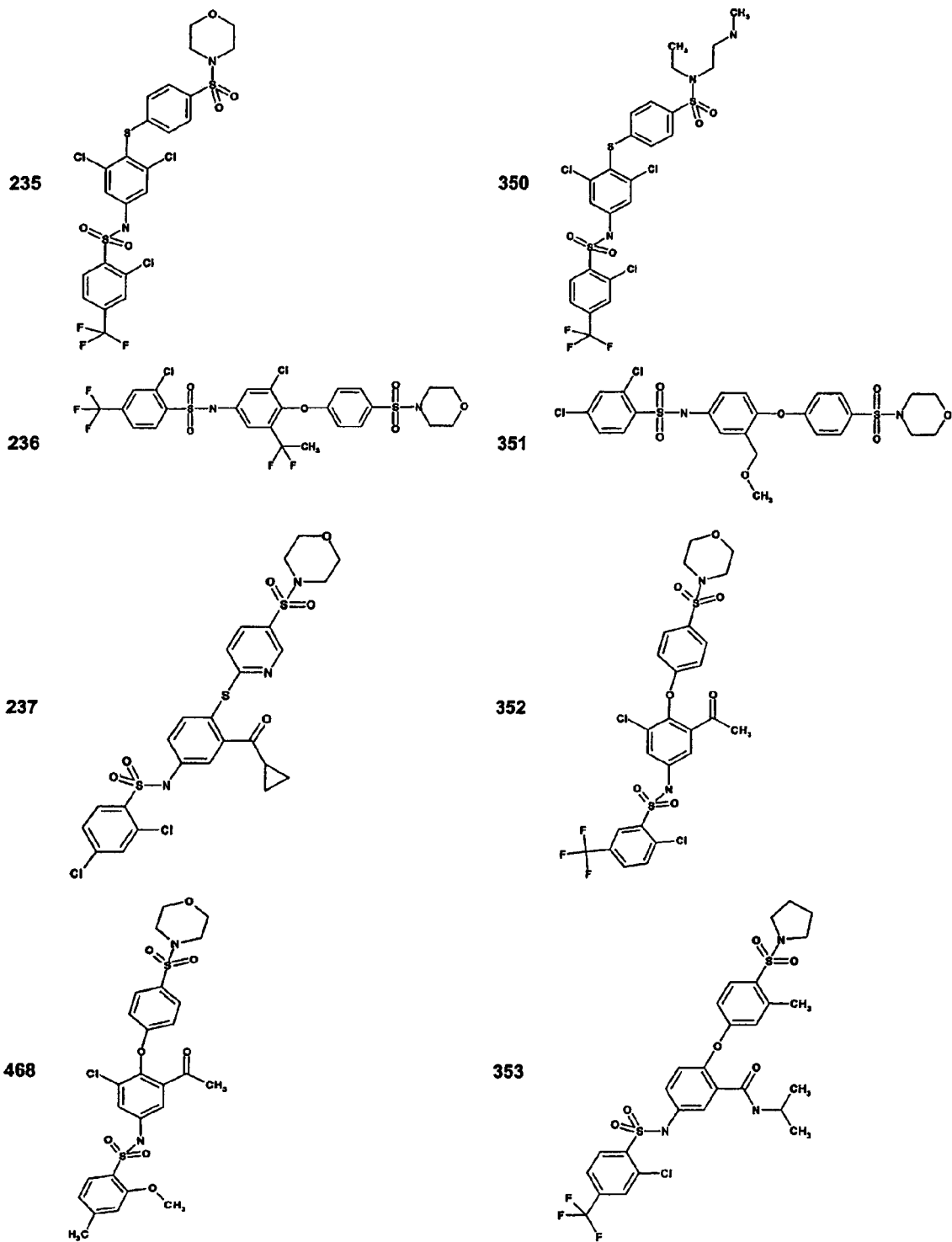
Figures 2, 3, 4, 5, 6, 7, 8, 9, 10, 11, 12:
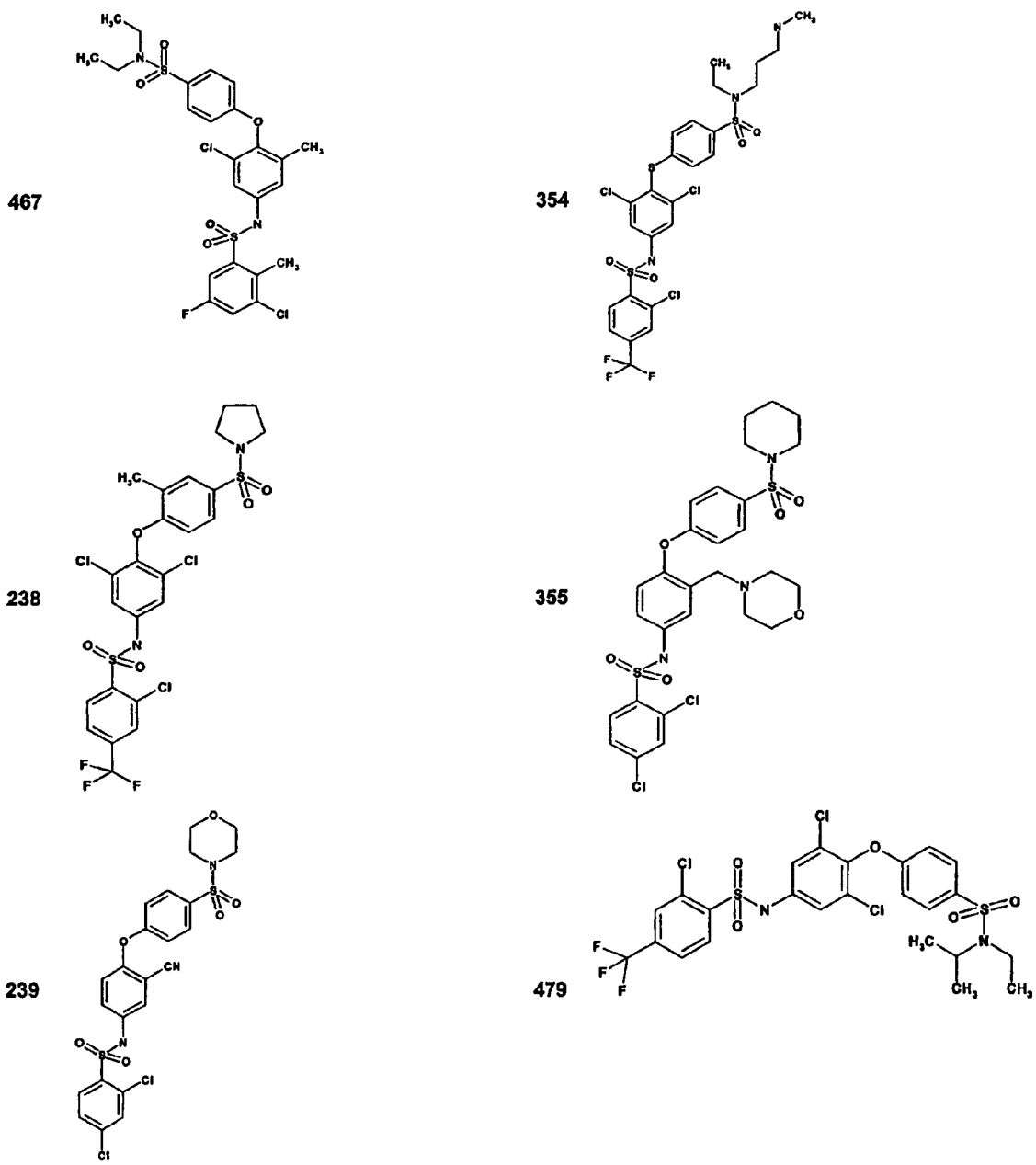
Figures 2, 3, 4, 5, 6, 7, 8, 9, 10, 11, 12, 13:
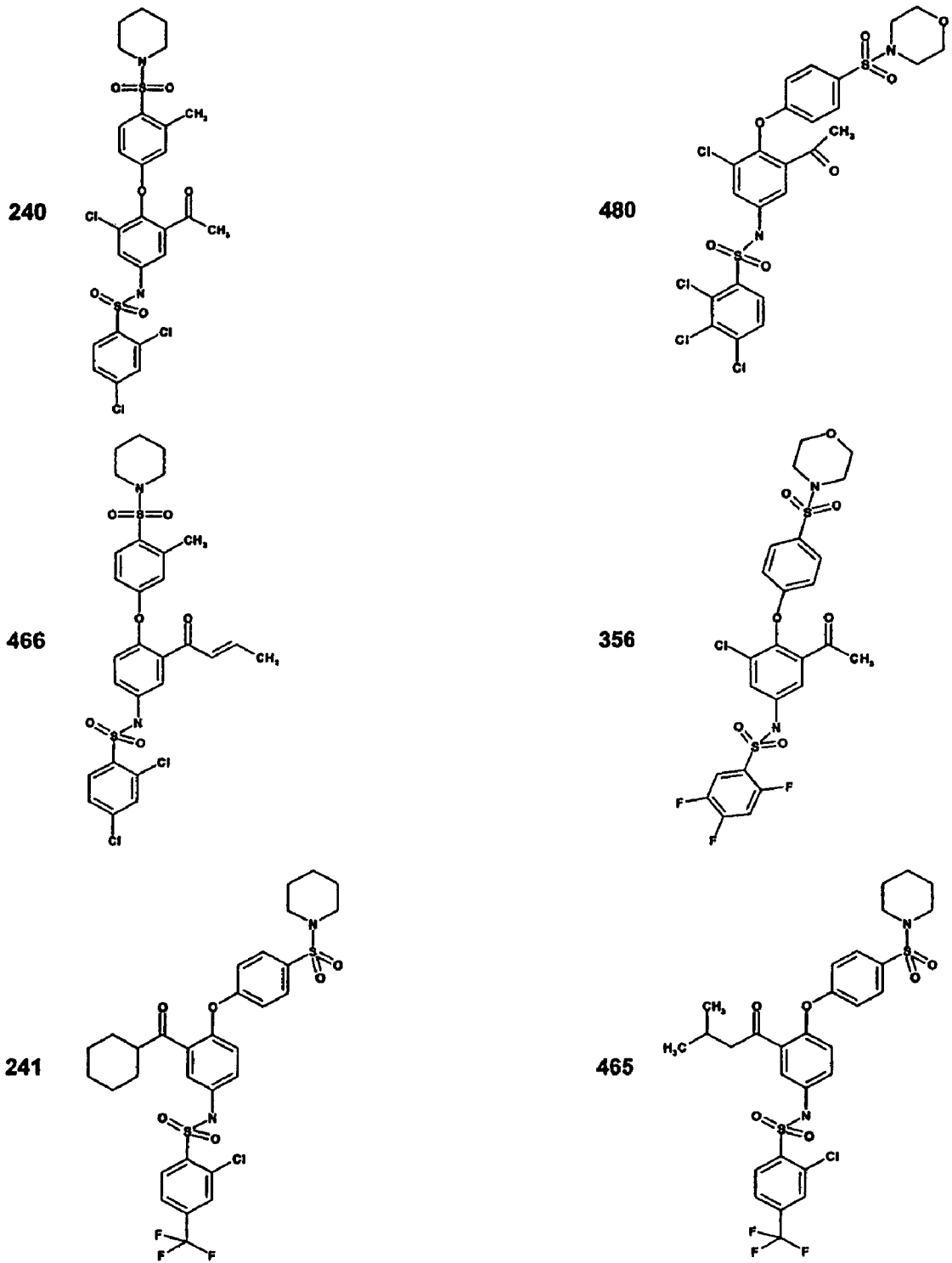
Figures 2, 3, 4, 5, 6, 7, 8, 9, 10, 11, 12, 13, 14:
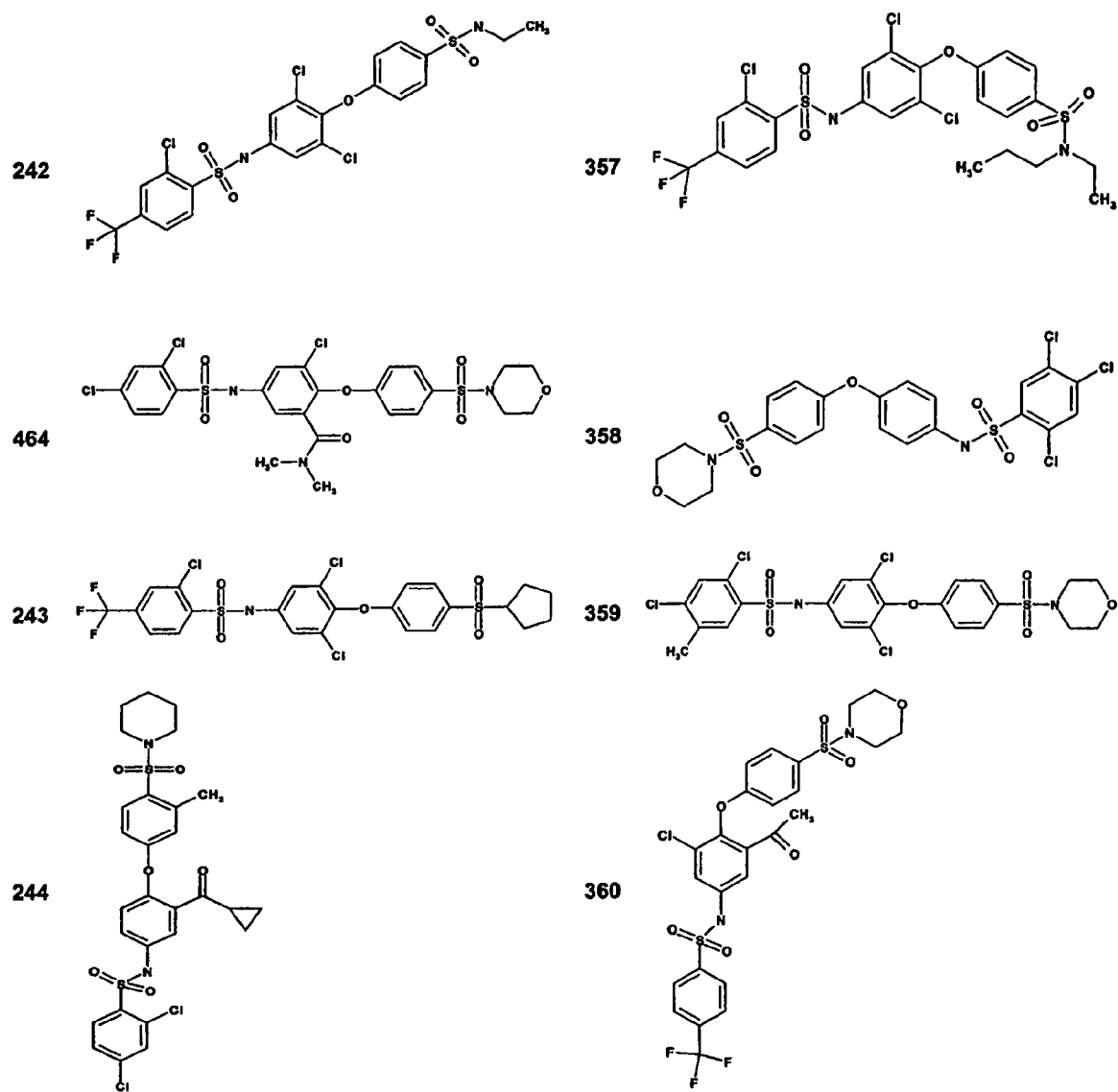
Figures 2, 3, 4, 5, 6, 7, 8, 9, 10, 11, 12, 13, 14, 15:
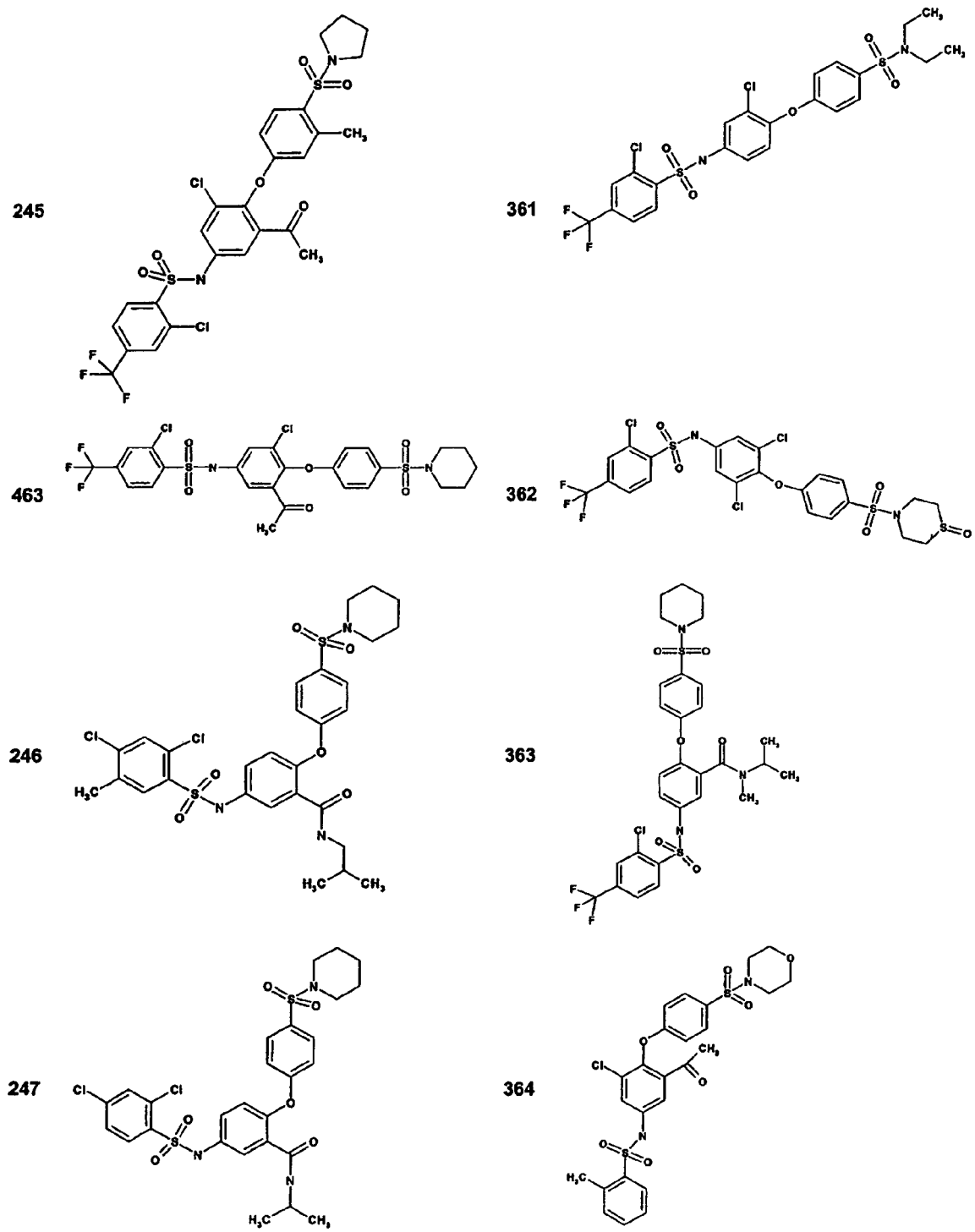
Figures 2, 3, 4, 5, 6, 7, 8, 9, 10, 11, 12, 13, 14, 15, 16:
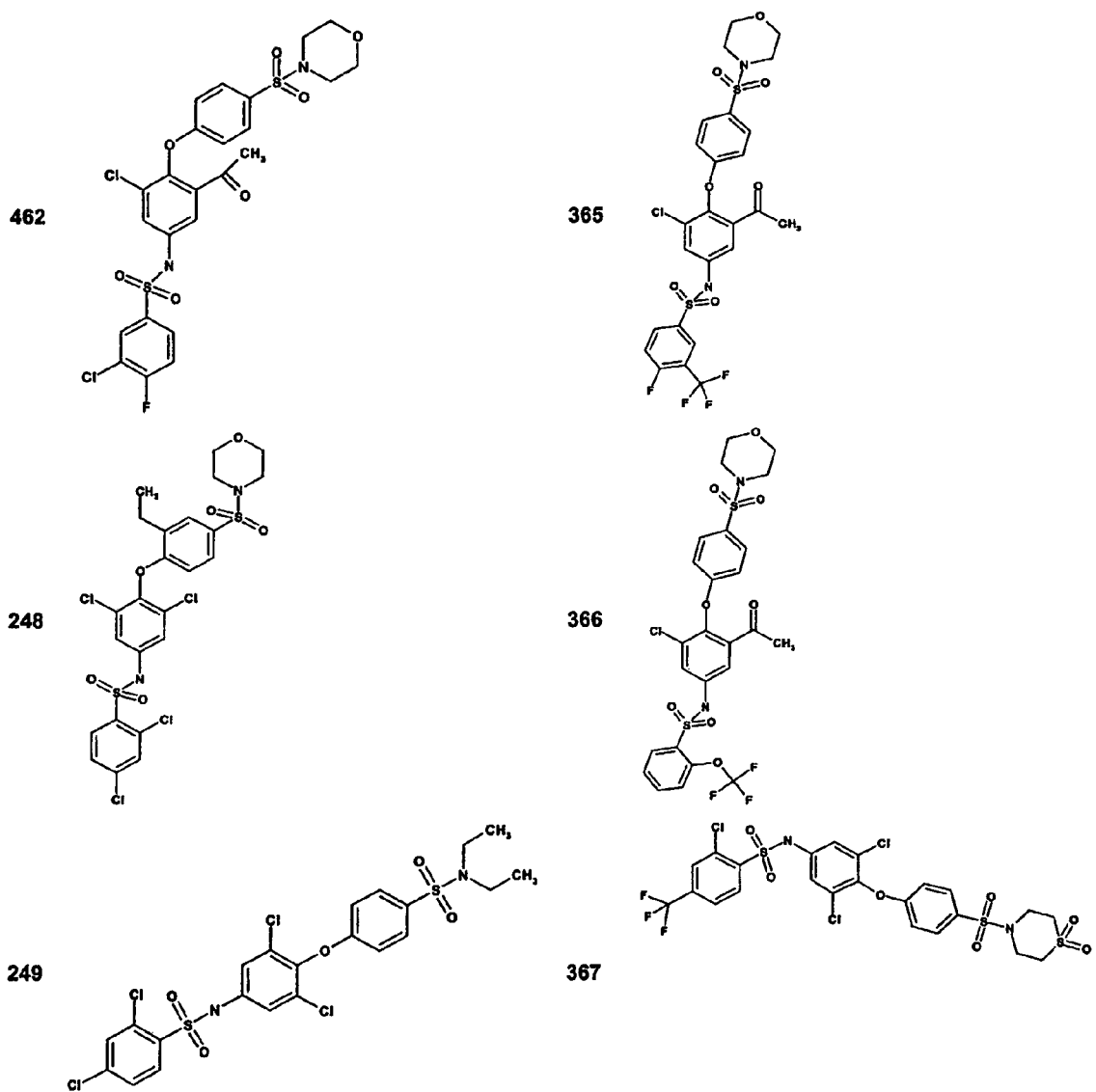
Figures 2, 3, 4, 5, 6, 7, 8, 9, 10, 11, 12, 13, 14, 15, 16, 17:
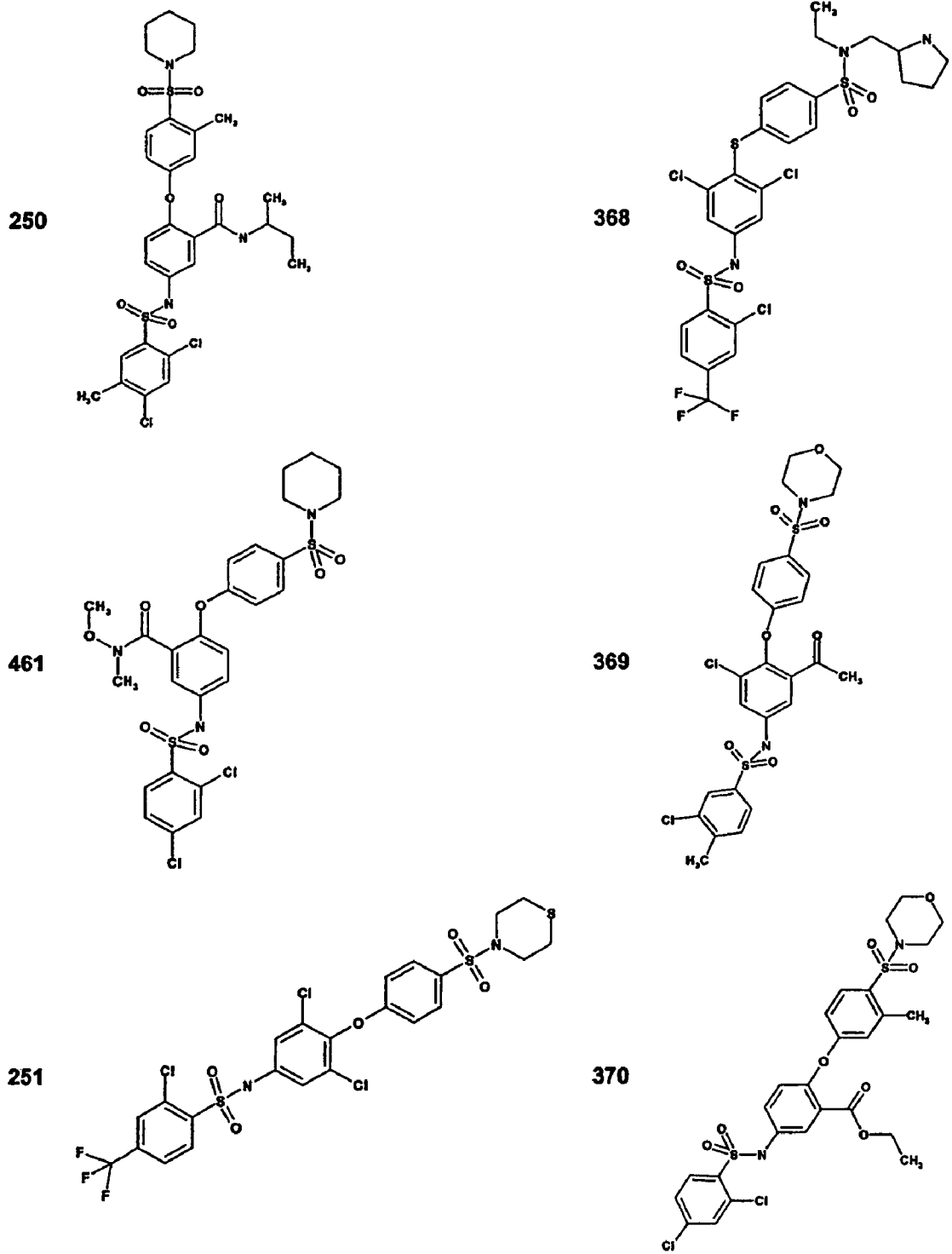
Figures 2, 3, 4, 5, 6, 7, 8, 9, 10, 11, 12, 13, 14, 15, 16, 17, 18:
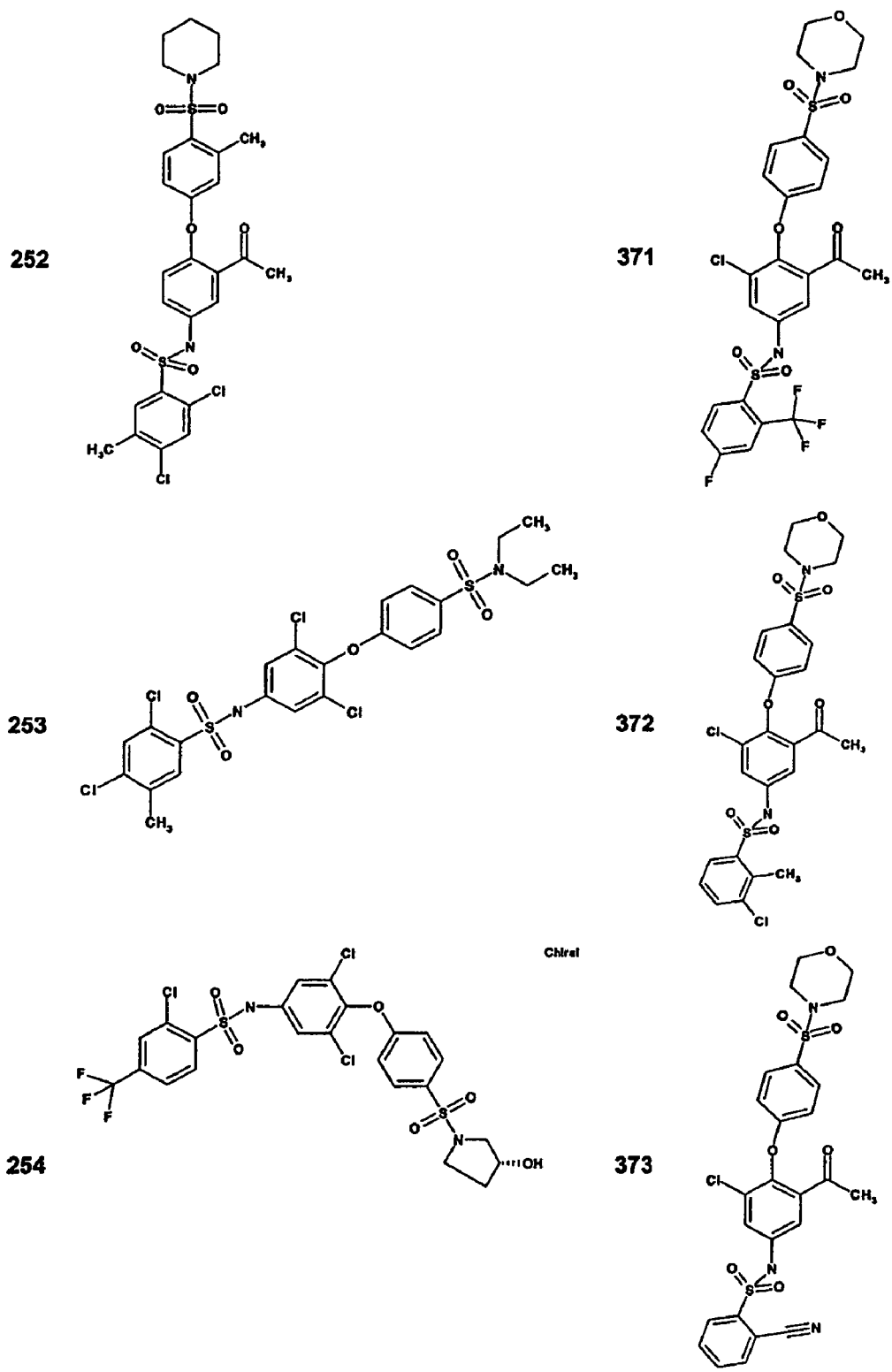
Figures 2, 3, 4, 5, 6, 7, 8, 9, 10, 11, 12, 13, 14, 15, 16, 17, 18, 19:
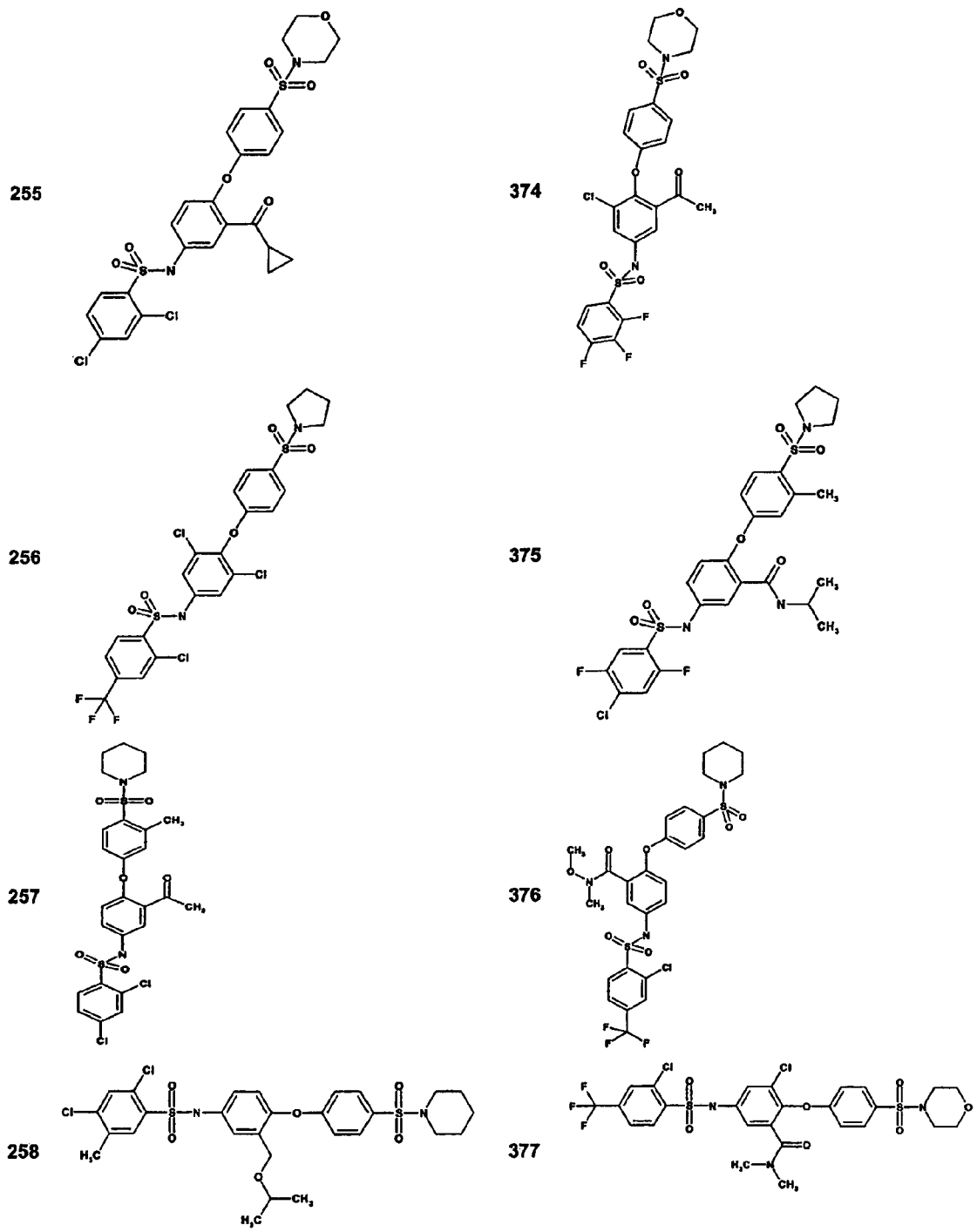
Figures 2, 3, 4, 5, 6, 7, 8, 9, 10, 11, 12, 13, 14, 15, 16, 17, 18, 19, 20:
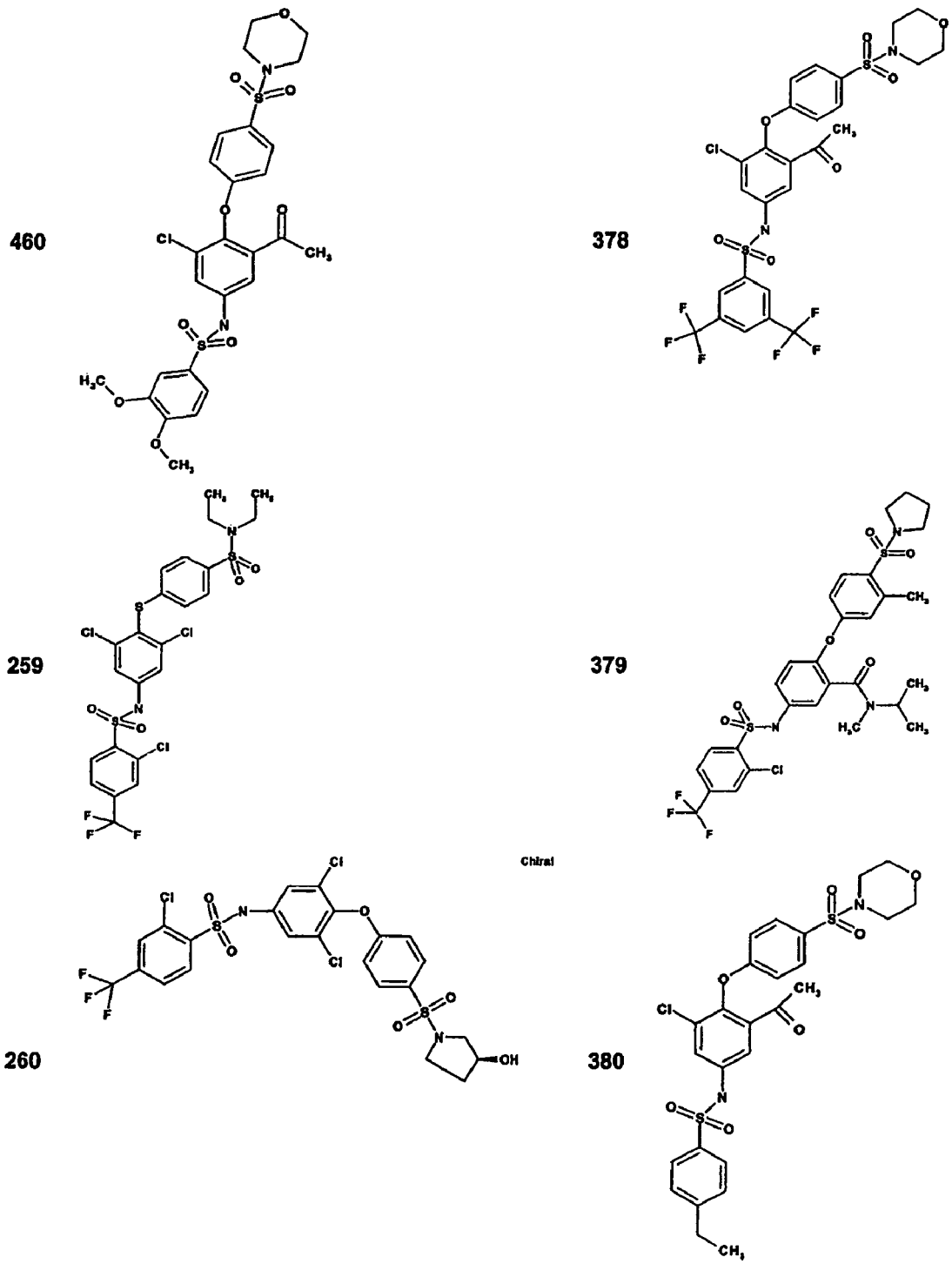
Figures 2, 3, 4, 5, 6, 7, 8, 9, 10, 11, 12, 13, 14, 15, 16, 17, 18, 19, 20, 21, 22, 23:
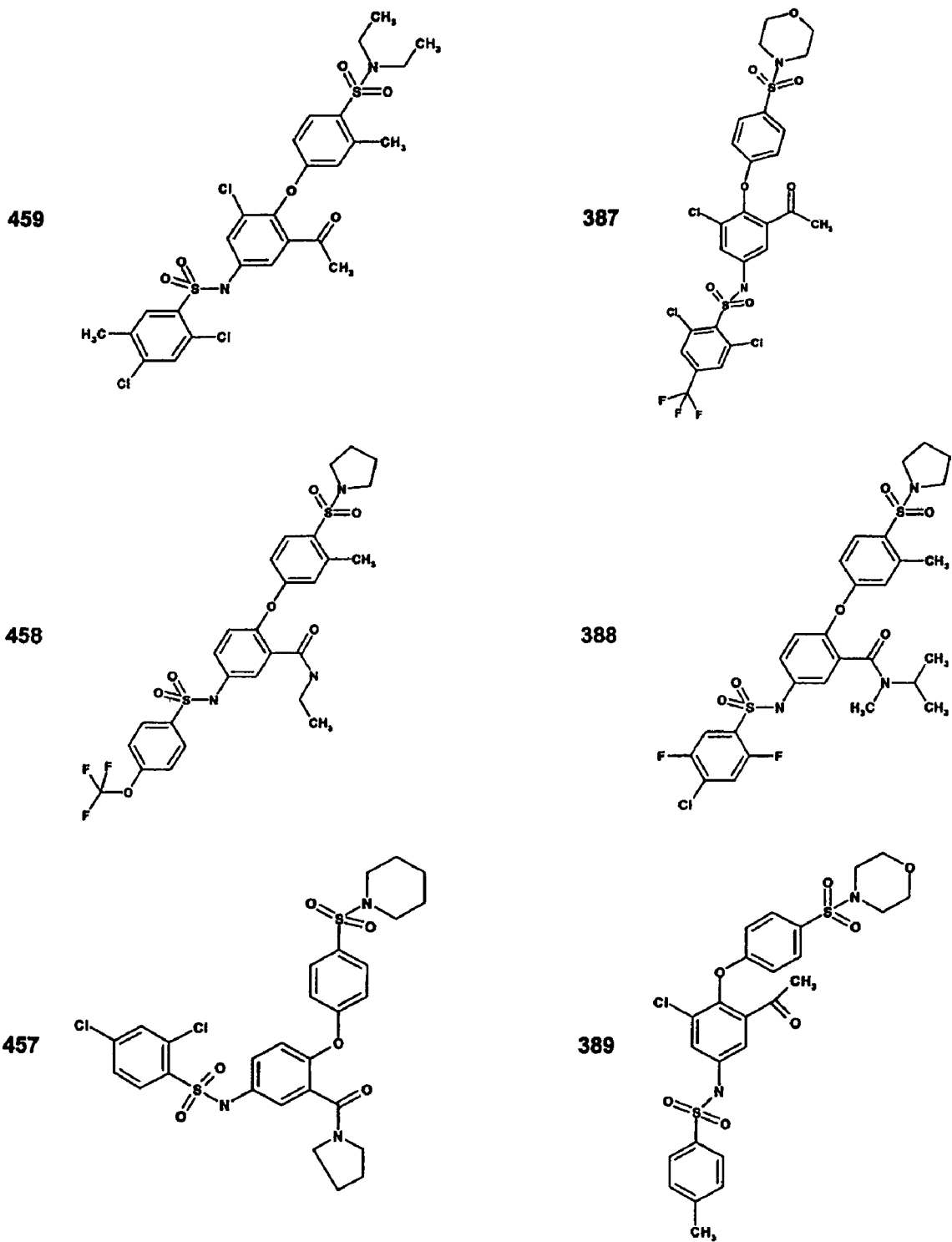
Figures 2, 3, 4, 5, 6, 7, 8, 9, 10, 11, 12, 13, 14, 15, 16, 17, 18, 19, 20, 21, 22, 23, 24, 25:
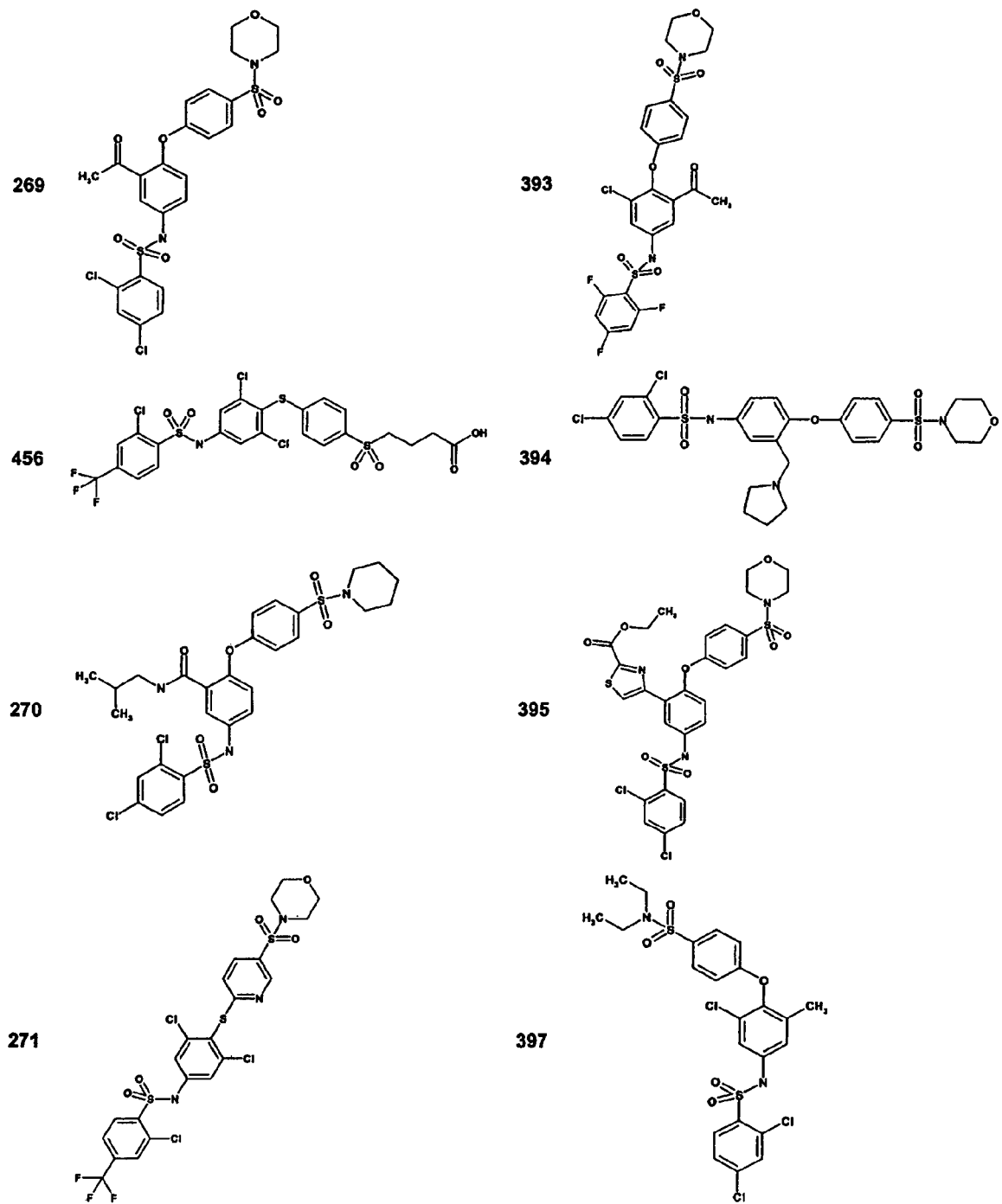
Figures 2, 3, 4, 5, 6, 7, 8, 9, 10, 11, 12, 13, 14, 15, 16, 17, 18, 19, 20, 21, 22, 23, 24, 25, 26:
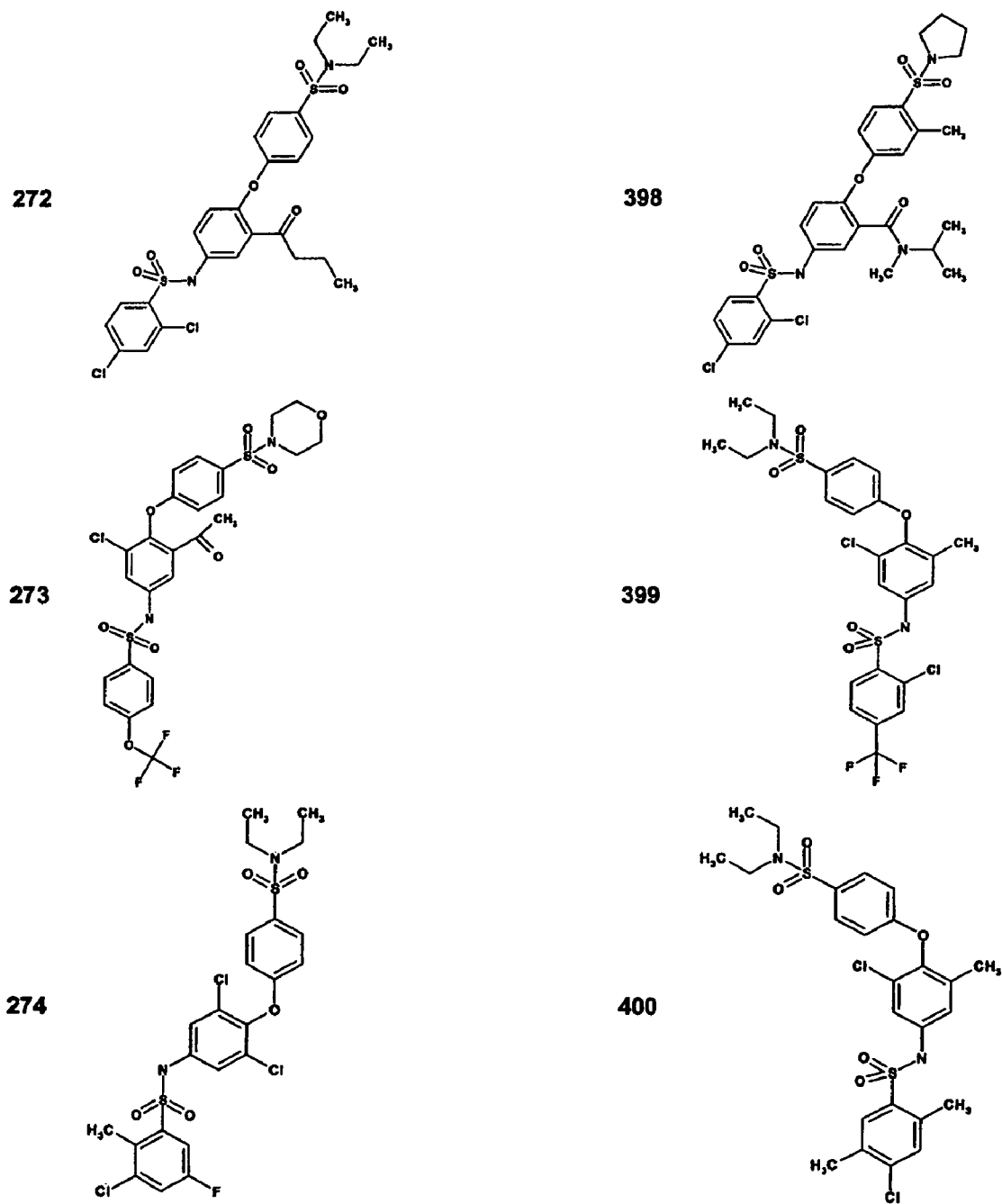
Figures 2, 3, 4, 5, 6, 7, 8, 9, 10, 11, 12, 13, 14, 15, 16, 17, 18, 19, 20, 21, 22, 23, 24, 25, 26, 27:
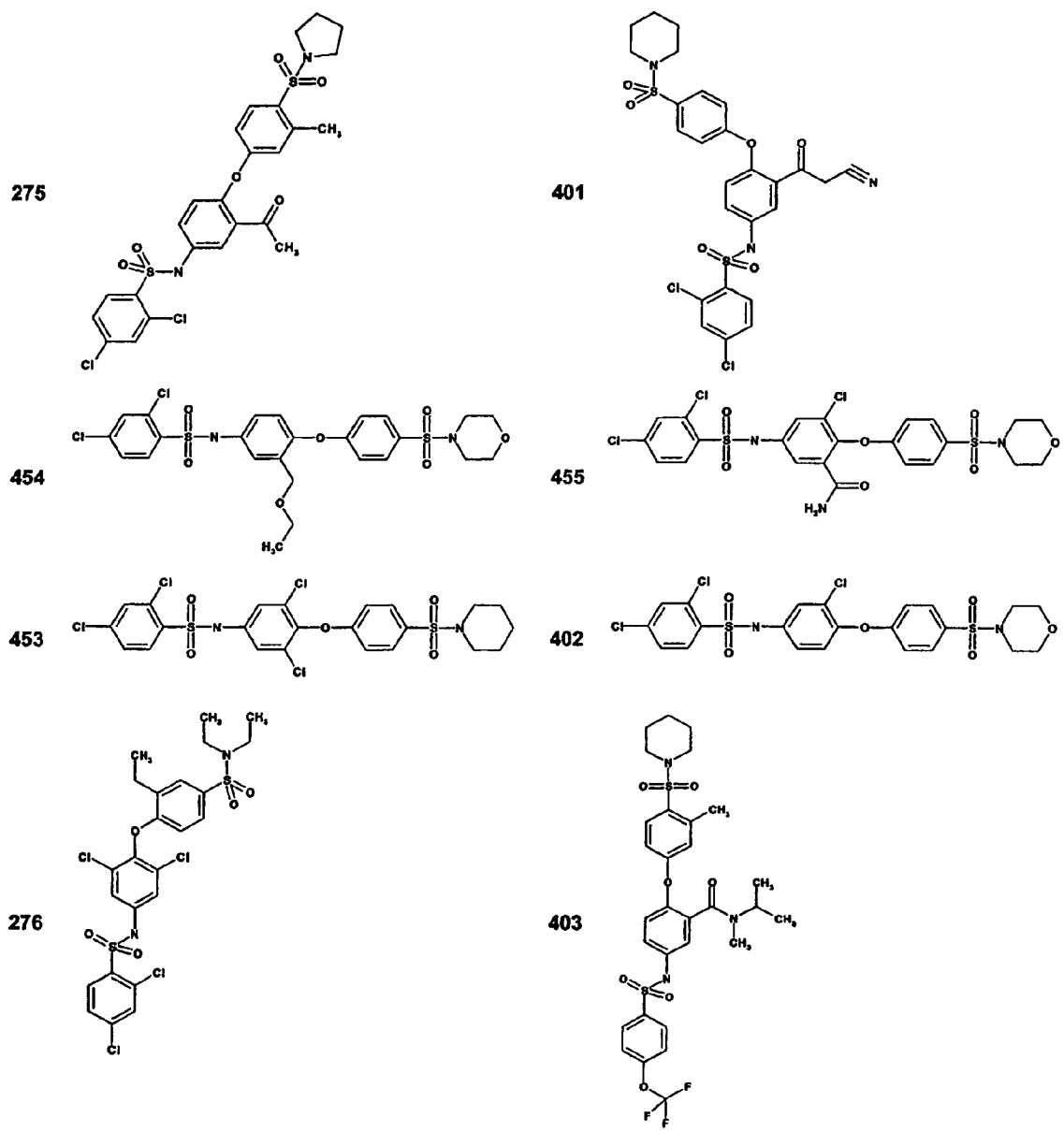
Figures 2, 3, 4, 5, 6, 7, 8, 9, 10, 11, 12, 13, 14, 15, 16, 17, 18, 19, 20, 21, 22, 23, 24, 25, 26, 27, 28:
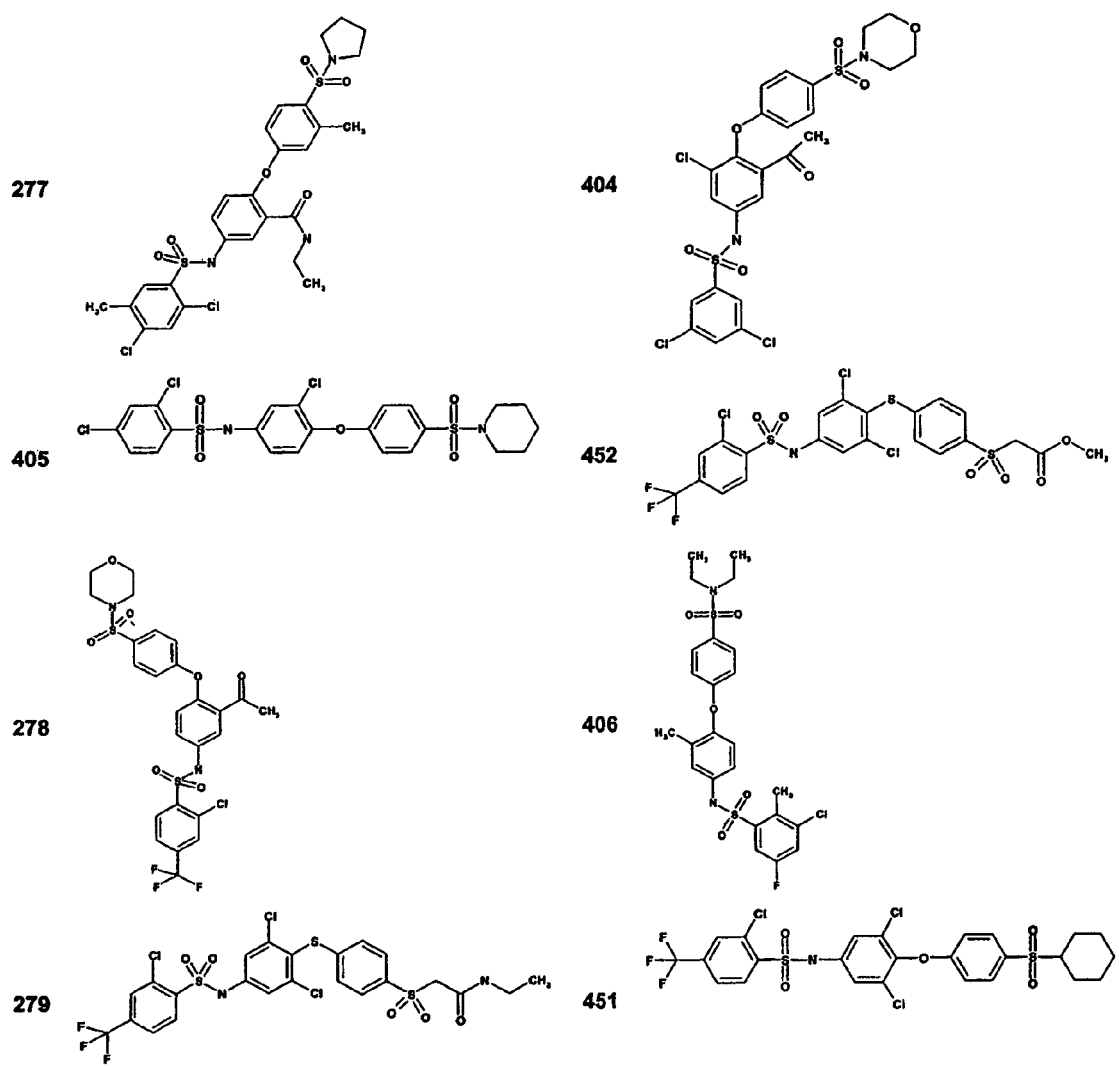
Figures 2, 3, 4, 5, 6, 7, 8, 9, 10, 11, 12, 13, 14, 15, 16, 17, 18, 19, 20, 21, 22, 23, 24, 25, 26, 27, 28, 29:
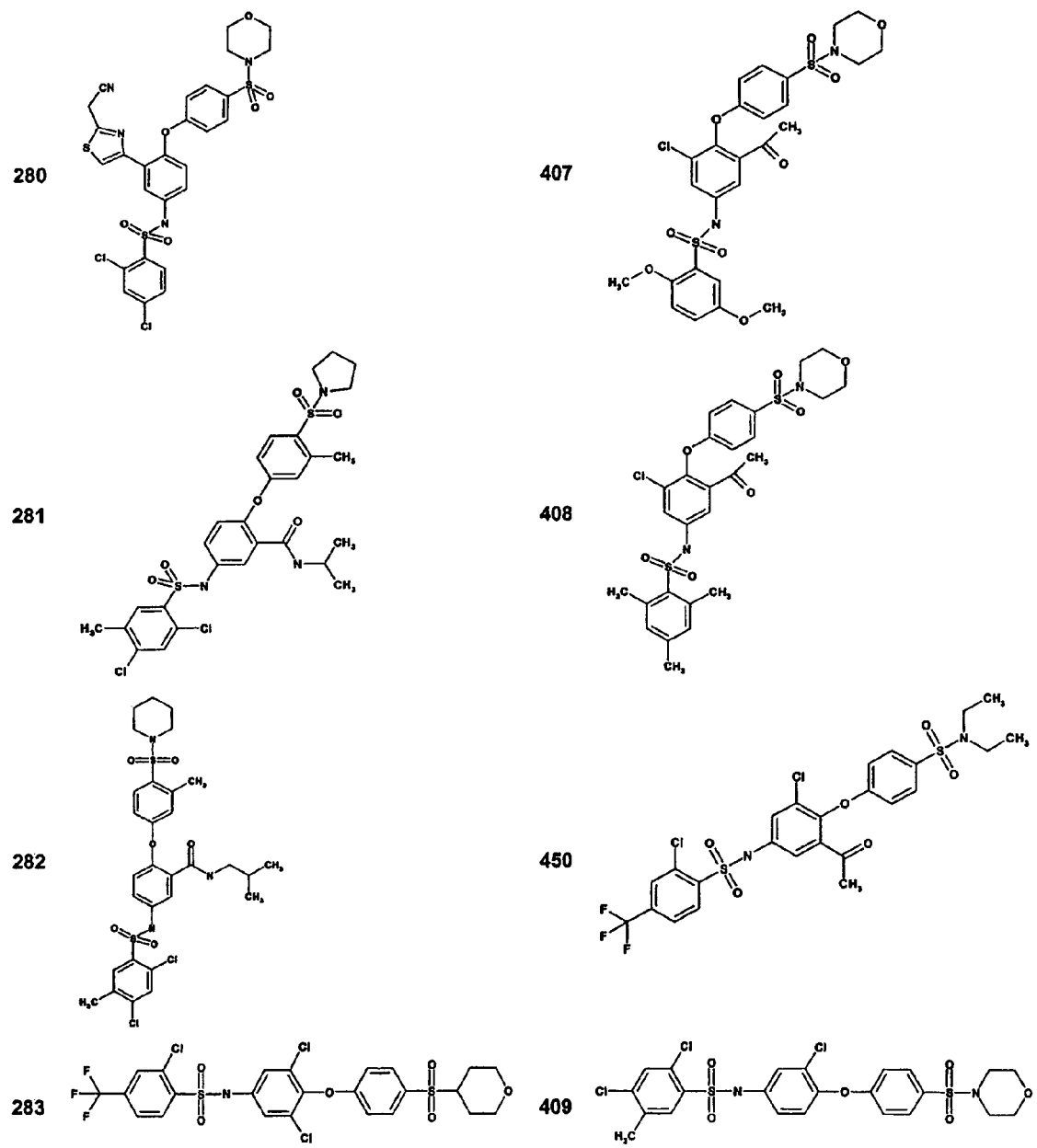
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30:
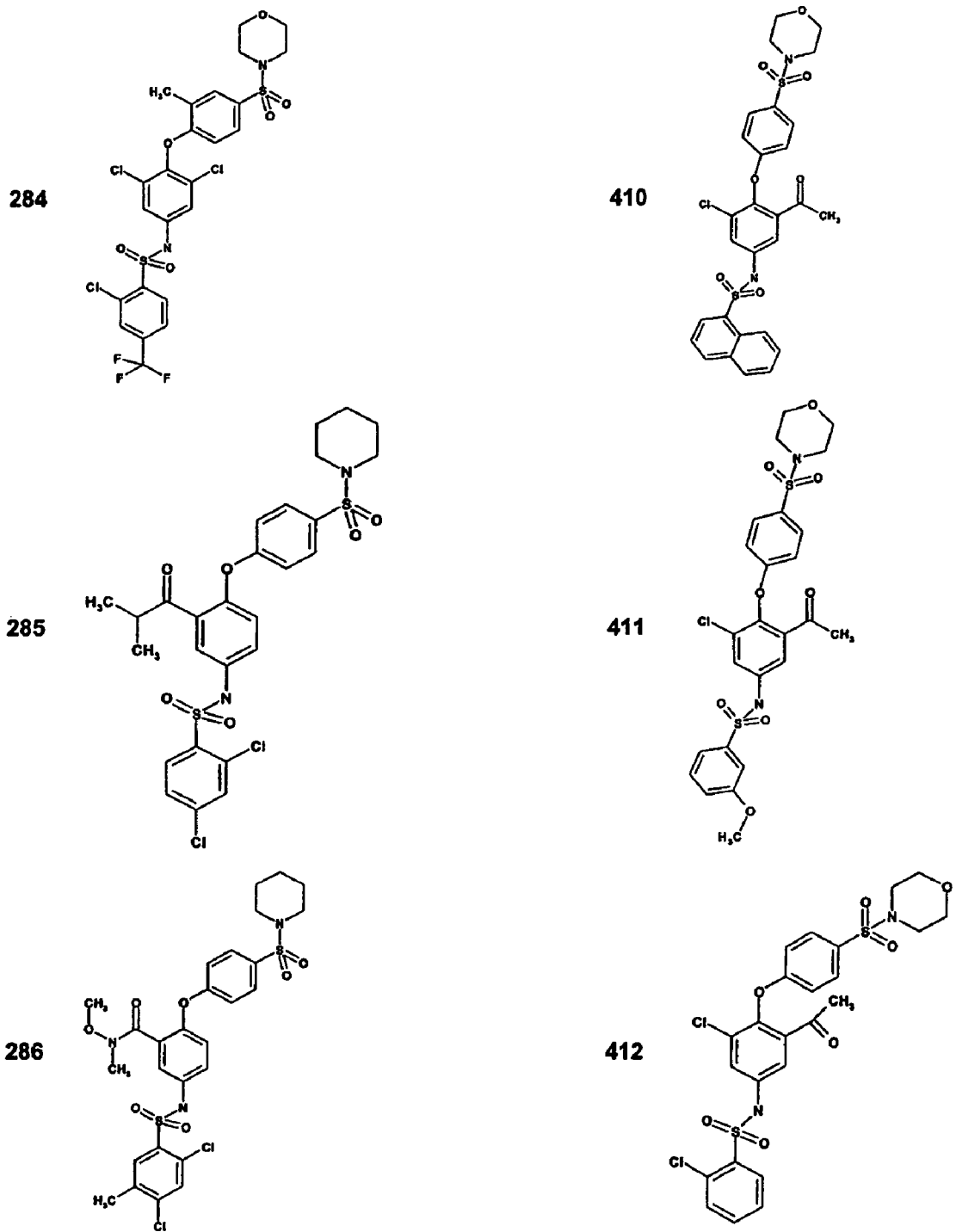
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31:
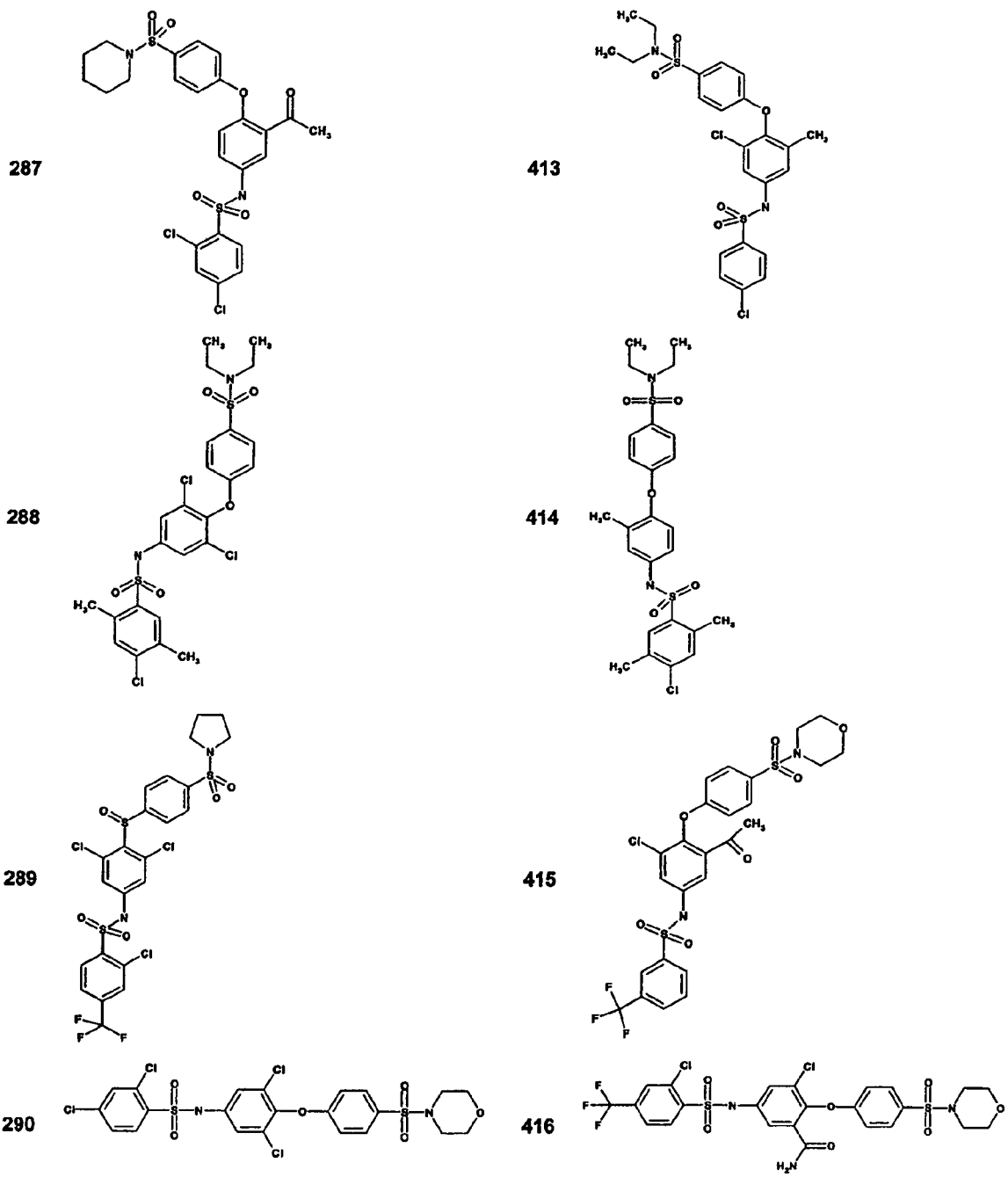
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32:
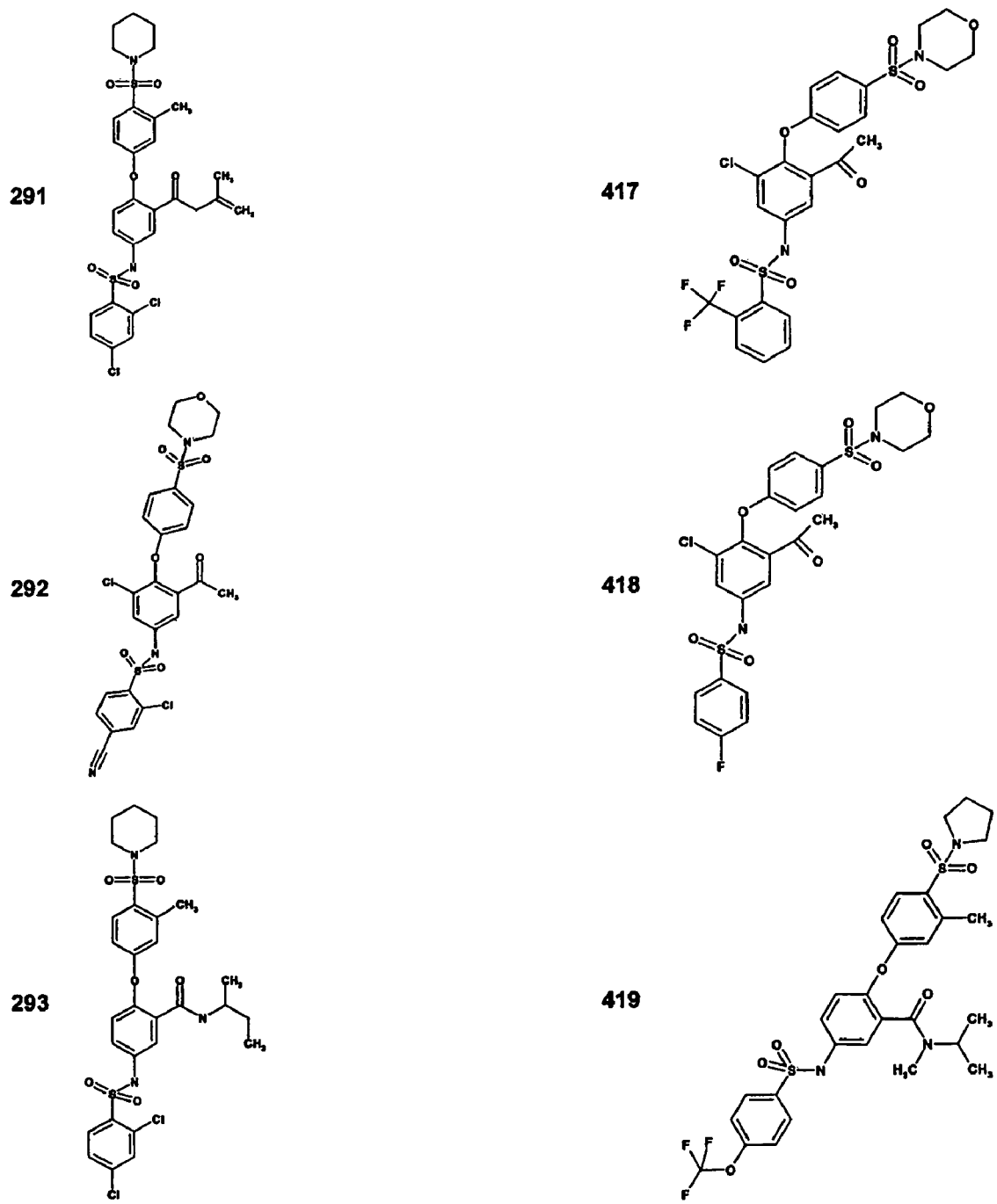
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33:
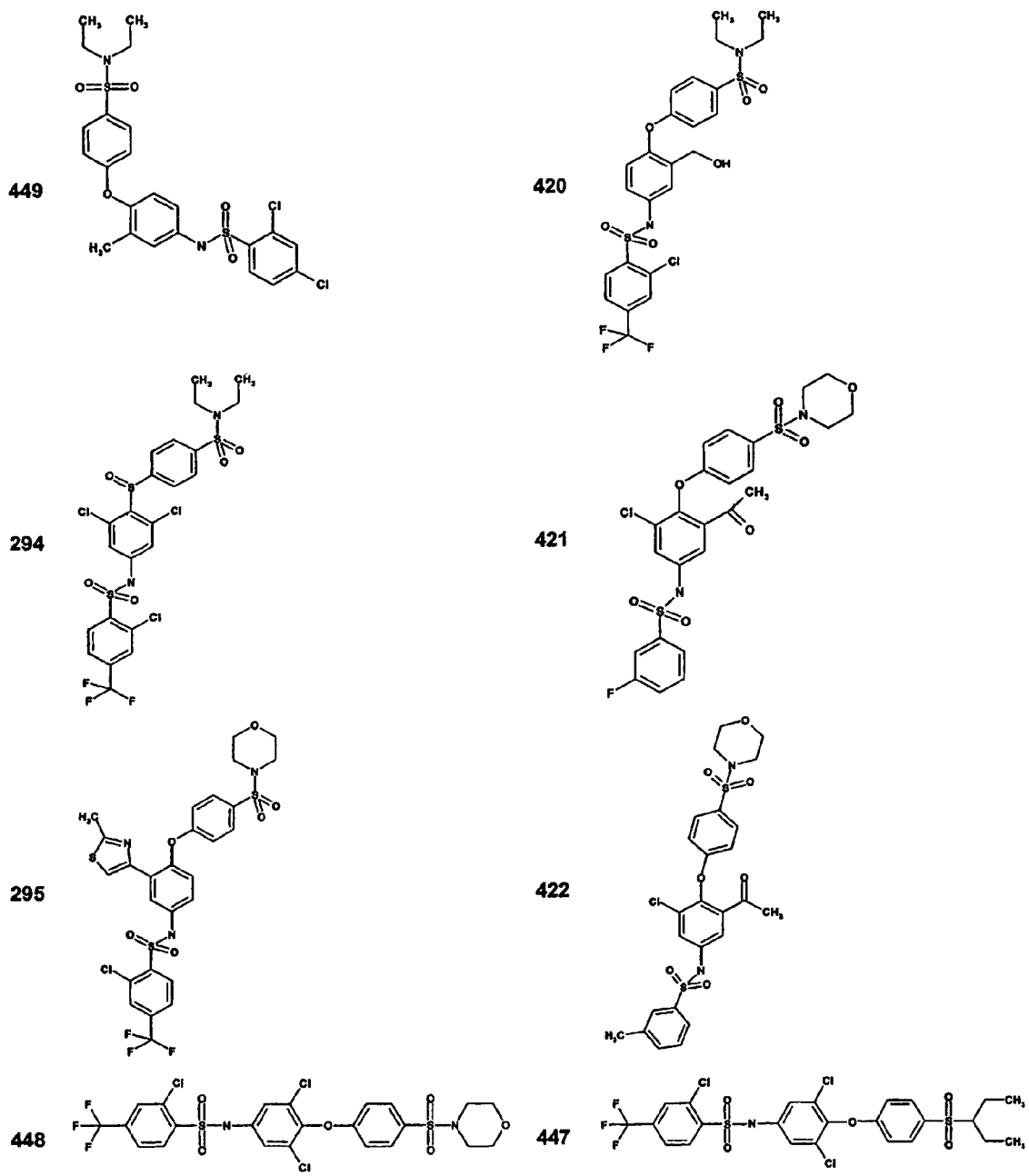
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34:
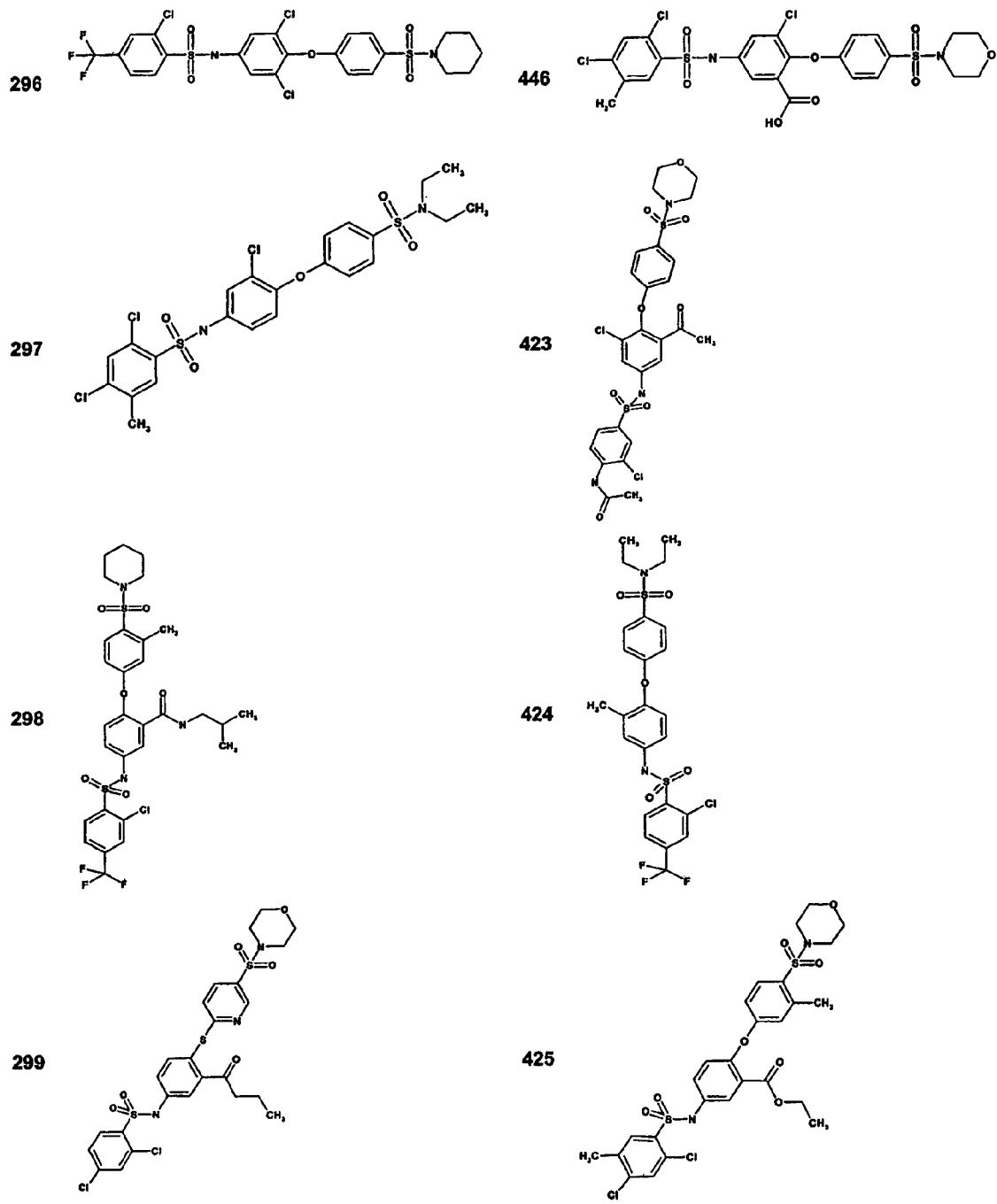
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35:
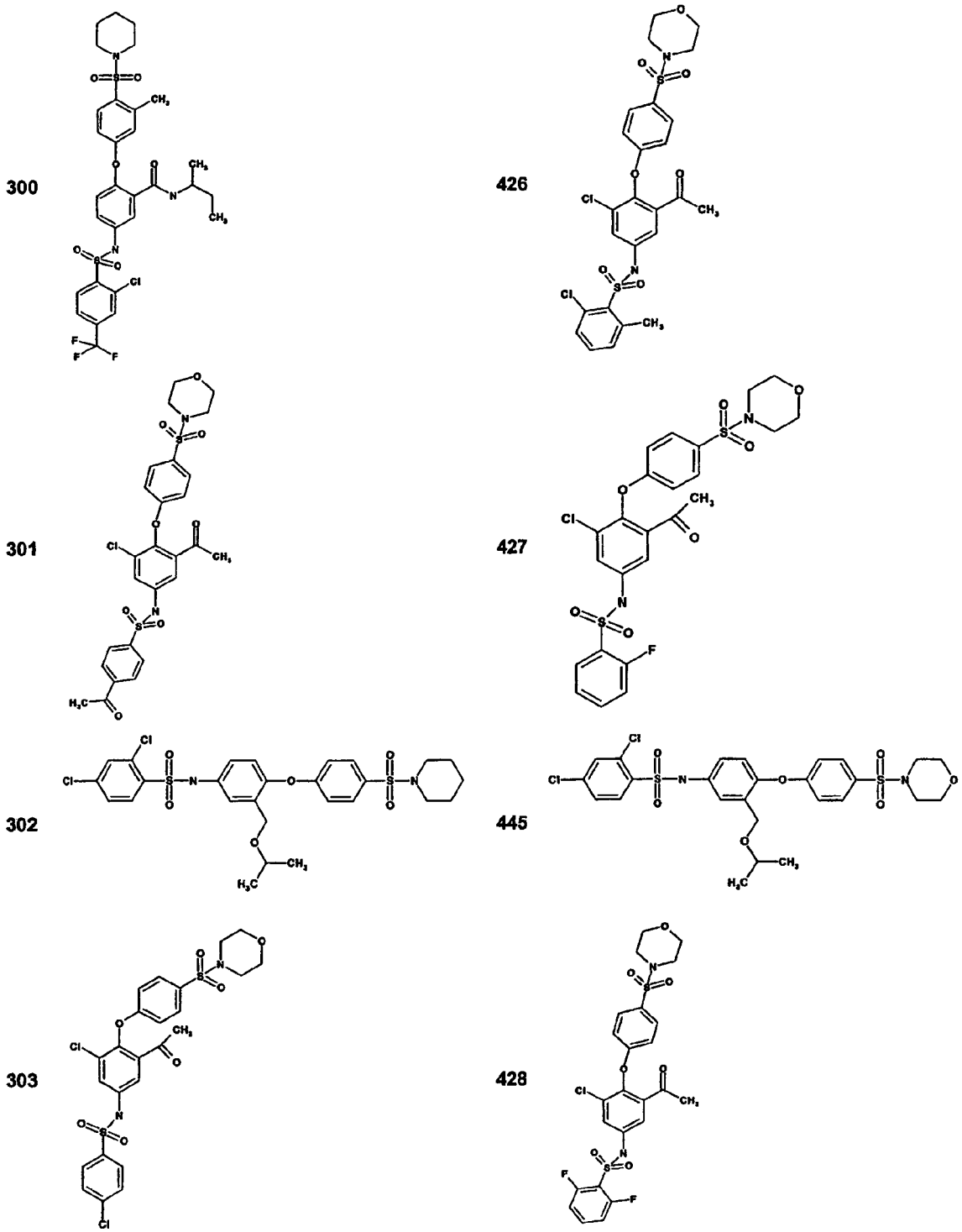
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36:
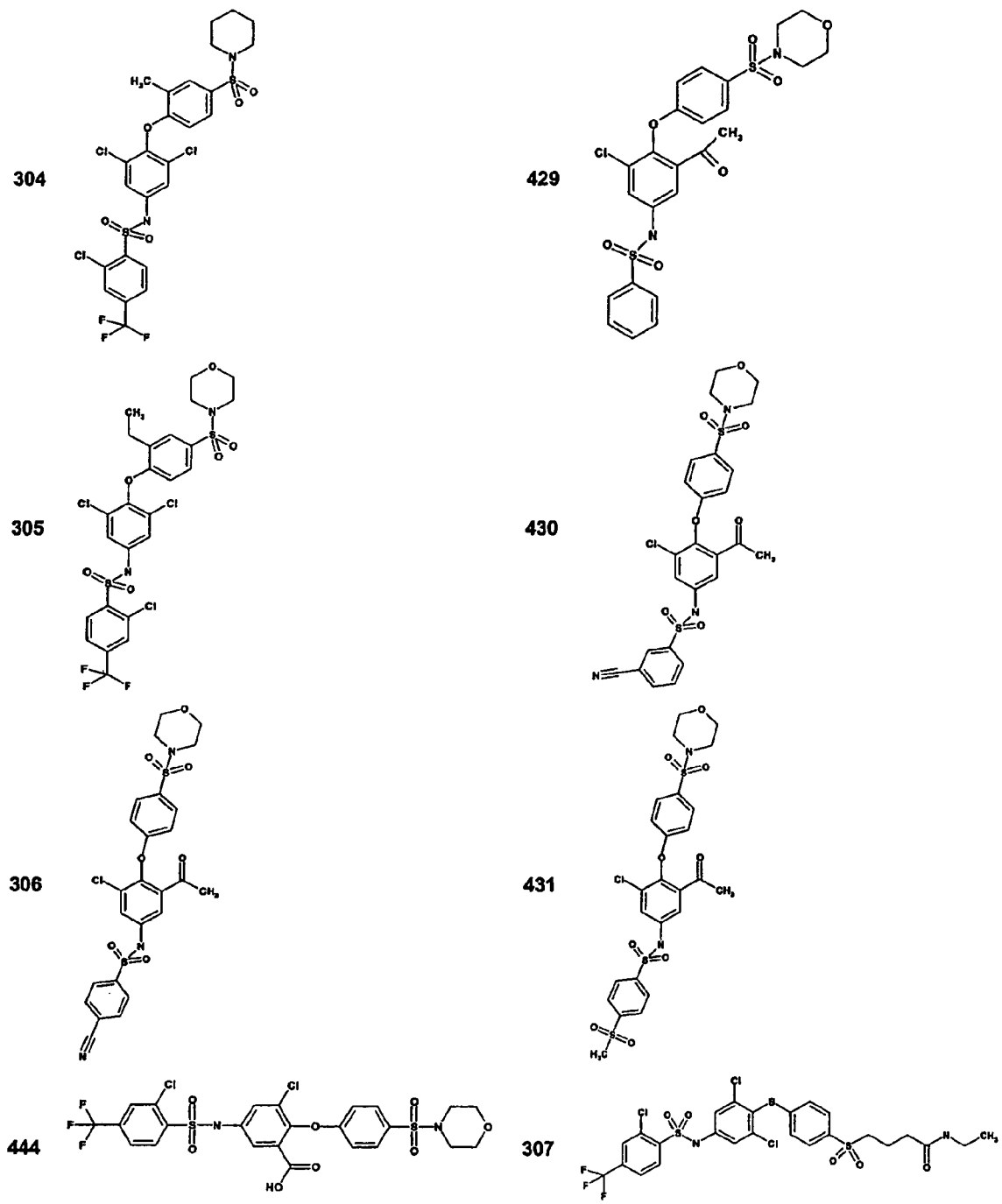
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37:
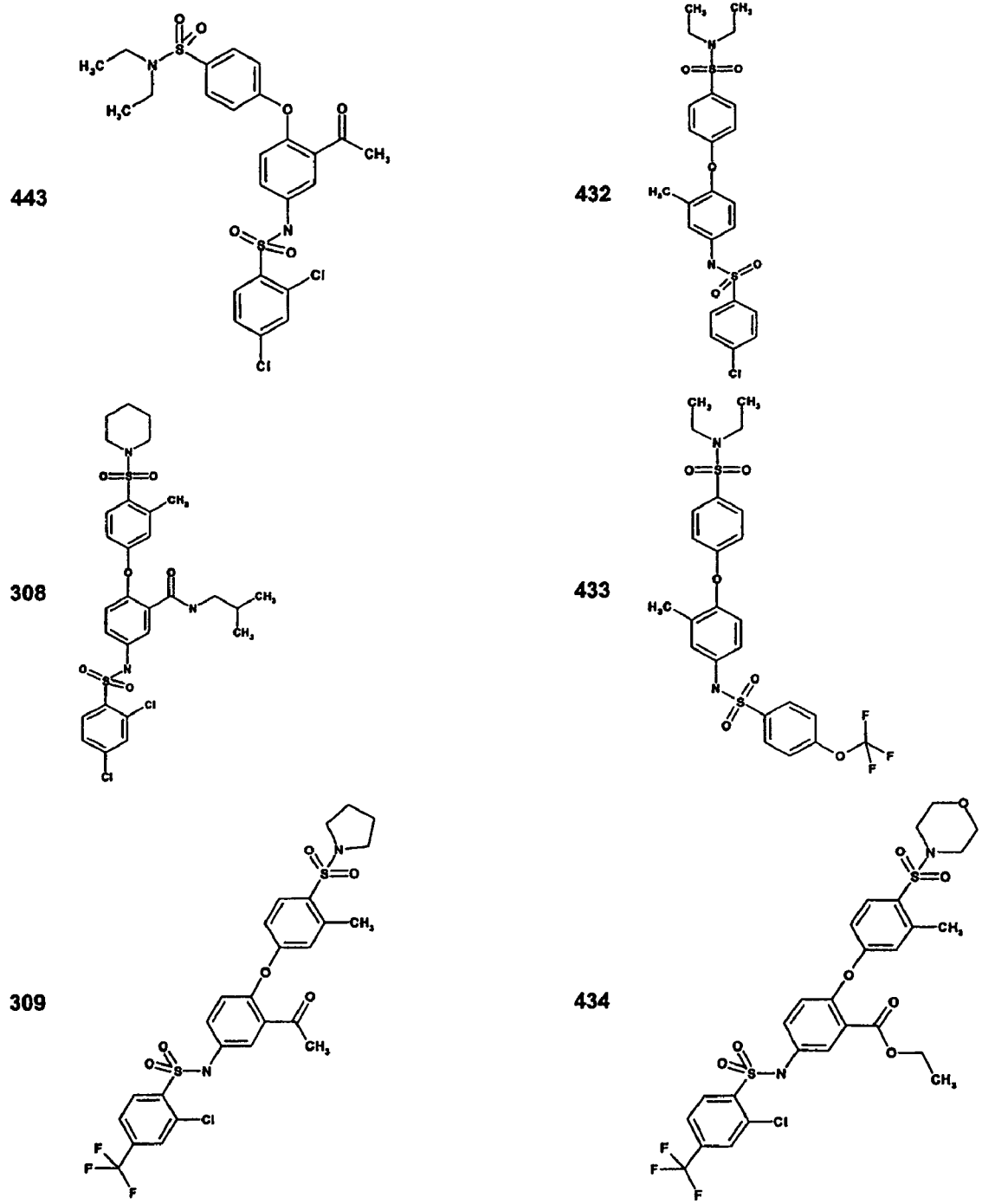
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38:
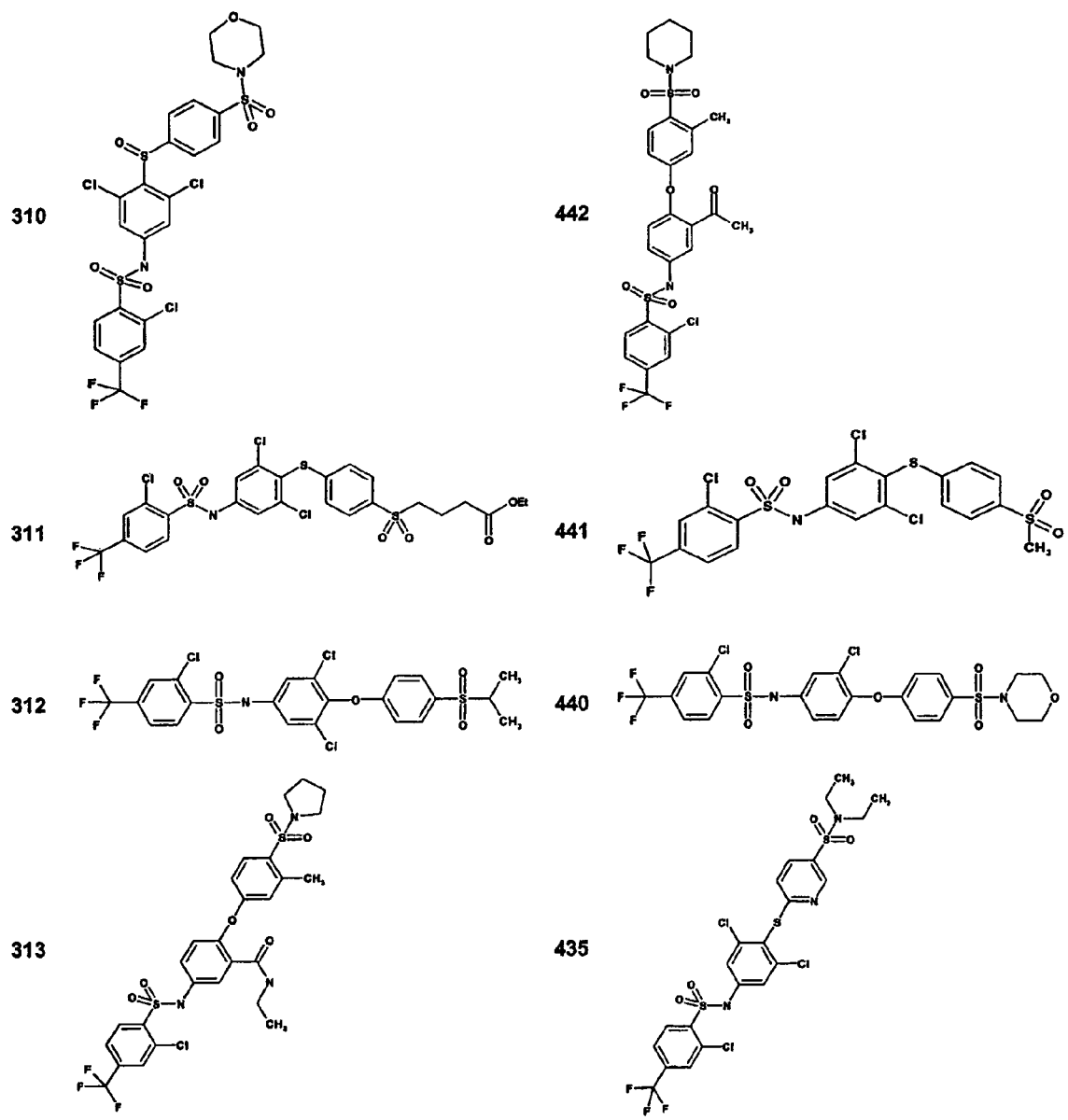
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39:
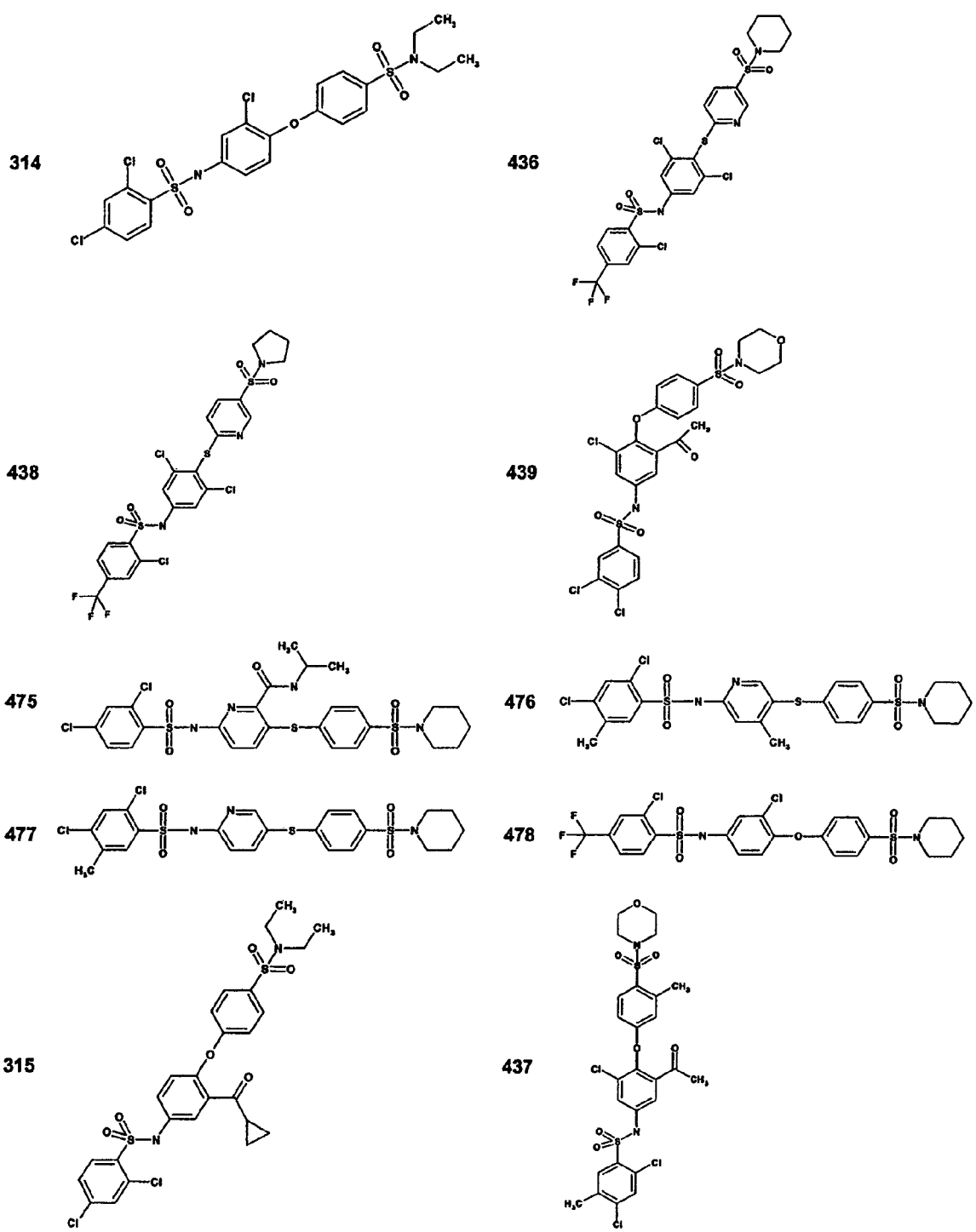

The abbreviations used herein are conventional, unless otherwise defined.

The terms "treat", "treating" and "treatment" refer to a method of alleviating or abrogating a disease and/or its attendant symptoms.

The terms "prevent", "preventing" and "prevention" refer to a method of decreasing the probability or eliminating the possibility that a disease will be contracted.

As used herein, the term "PPARγ-mediated condition or disorder" and the like refers to a condition or disorder characterized by inappropriate, e.g., less than or greater than normal, PPARγ activity. A PPARγ-mediated condition or disorder can be completely or partially mediated by inappropriate PPARγ activity. However, a PPARγ-mediated condition or disorder is one in which modulation of PPARγ results in some effect on the underlying condition or disease (e.g., a PPARγ antagonist results in some improvement in patient well-being in at least some patients). Exemplary PPARγ-mediated conditions and disorders include metabolic disorders, e.g., diabetes, obesity, hyperglycemia, insulin resistance, hyperinsulinemia, hypercholesterolemia, hypertension, hyperlipoproteinemia, hyperlipidemia, hypertriglylceridemia and dyslipidemia, and inflammatory conditions, e.g., rheumatoid arthritis and atherosclerosis.

As used herein, the term "PPARδ-mediated condition or disorder" and related terms and phrases refer to a condition or disorder characterized by inappropriate, e.g., less than or greater than normal, PPARδ activity. Inappropriate PPARδ functional activity might arise as the result of PPARδ expression in cells which normally do not express PPARδ, decreased PPARδ expression (leading to, e.g., metabolic and inflammatory disorders and diseases) or increased PPARδ expression. A PPARδ-mediated condition or disease may be completely or partially mediated by inappropriate PPARδ functional activity. However, a PPARδ-mediated condition or disease is one in which modulation of PPARδ results in some effect on the underlying condition or disorder (e.g., a PPARδ agonist results in some improvement in patient well-being in at least some patients). Exemplary PPARδ-mediated conditions and disorders include metabolic disorders, e.g., diabetes, obesity, hyperglycemia, insulin resistance, hyperinsulinemia, hypercholesterolemia, hypertension, hyperlipoproteinemia, hyperlipidemia, hypertriglylceridemia, dyslipidemia, syndrome X and an easting disorder, inflammatory conditions, e.g., rheumatoid arthritis and atherosclerosis, cardiovascular diseases, e.g., atherosclerosis, neoplastic diseases, e.g., breast cancer, lung cancer colerectal cancer, prostate cancer, kidney cancer, stomach cancer, bladder cancer, ovarian cancer and cancer of the gastrointestinal tract, immune disorders, e.g., arthritis and asthma, shock states, e.g., septic shock, disorders of gastrointestinal motility, e.g., ileus, and diseases of the central nervous systems, e.g., migraine.

As used herein, "diabetes" refers to type I diabetes mellitus (juvenile onset diabetes, insulin dependent-diabetes mellitus or IDDM) or type II diabetes mellitus (non-insulin-dependent diabetes mellitus or NIDDM), preferably, NIDDM.

As used herein, "syndrome X" refers to a collection of abnormalities including hyperinsulinemia, obesity, elevated levels of triglycerides, uric acid, fibrinogen, small dense LDL particles and plasminogen activator inhibitor 1 (PAI-1), and decreased levels of HDL cholesterol. Syndrome X is further meant to include metabolic syndrome.

As used herein, the term "eating disorder" refers to an emotional and/or behavioral disturbance associated with an excessive decrease in body weight and/or inappropriate efforts to avoid weight gain, e.g., fasting, self-induced vomiting, laxative or diuretic abuse. Exemplary eating disorders include anorexia nervosa and bulimia.

As used herein, the term "obesity" refers to the excessive accumulation of body fat. Obesity may have genetic, environmental (e.g., expending less energy than is consumed) and regulatory determinants. Obesity includes exogenous, hyperinsulinar, hyperplasmic, hypothyroid, hypothalamic, symptomatic, infantile, upper body, alimentary, hypogonadal, simple and central obesity, hypophyseal adiposity and hyperphagia. Cardiovascular disorders, such as hypertension and coronary artery disease, and metabolic disorders, such as hyperlidemia and diabetes, are commonly associated with obesity.

The term "modulate" refers to the ability of a compound to increase or decrease the function, or activity of PPARγ or PPARδ. Modulation, as described herein, includes the inhibition or activation of PPARγ or PPARδ, either directly or indirectly. Inhibitors are compounds that, e.g., bind to, partially or totally block stimulation, decrease, prevent, delay activation, inactivate, desensitize, or down regulate signal transduction, e.g., antagonists. Activators are compounds that, e.g., bind to, stimulate, increase, open, activate, facilitate, enhance activation, sensitize or up regulate signal transduction, e.g., agonists.

The term "therapeutically effective amount" refers to that amount of the compound being administered sufficient to prevent development of or alleviate to some extent one or more of the symptoms of the condition or disorder being treated.

The term "subject" is defined herein to include animals such as mammals, including, but not limited to, primates (e.g., humans), cows, sheep, goats, horses, dogs, cats, rabbits, rats, mice and the like. In preferred embodiments, the subject is a human.

The term "alkyl," by itself or as part of another substituent, means, unless otherwise stated, a straight or branched chain, or cyclic hydrocarbon radical, or combination thereof, which can be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)ethyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below as "heteroalkyl," "cycloalkyl" and "alkylene." The term "alkylene" by itself or as part of another substituent means a divalent radical derived from an alkane, as exemplified by —$CH_2CH_2CH_2CH_2$—. Typically, an alkyl group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms are optionally oxidized and the nitrogen heteroatom can optionally be quaternized. The heteroatom(s) O, N and S can be placed at any interior position of the heteroalkyl group. The heteroatom Si can be placed at any position of the heteroalkyl group, including the position at which the alkyl group is attached to the remainder of the molecule. Examples include —O—$CH_3$, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—$S(O)_2$—$CH_3$, —CH=CH—O—$CH_3$, —Si$(CH_3)_3$, —$CH_2$—CH=N—$OCH_3$, and —CH=CH—N($CH_3$)—$CH_3$. Up to two heteroatoms can be consecutive, such as, for example, —CH2-NH—$OCH_3$ and —$CH_2$—O—Si$(CH_3)_3$. Also included in the term "heteroalkyl" are those radicals described in more detail below as "heteroalkylene" and "heterocycloalkyl." The term "heteroalkylene" by itself or as part of another substituent means a divalent radical derived from heteroalkyl, as exemplified by —$CH_2$—$CH_2$—S—$CH_2CH_2$—and —$CH_2$—S—$CH_2$—$CH_2$—NH—$CH_2$—. For heteroalkylene groups, heteroatoms can also occupy either or both of the chain termini. Still further, for alkylene and heteroalkylene linking groups, as well as all other linking group provided in the present invention, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "fluoroalkyl," are meant to include monofluoroalkyl and polyfluoroalkyl.

The term "aryl," employed alone or in combination with other terms (e.g., aryloxy, arylthioxy, arylalkyl) means, unless otherwise stated, an aromatic substituent which can be a single ring or multiple rings (up to three rings) which are fused together or linked covalently. The rings can each contain from zero to four heteroatoms selected from N, O, and S, wherein the nitrogen and sulfur atoms are optionally oxidized, and the nitrogen atom(s) are optionally quaternized. The aryl groups that contain heteroatoms can be referred to as "heteroaryl" and can be attached to the remainder of the molecule through a heteroatom. Non-limiting examples of aryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 2-benzothiazolyl, 5-benzothiazolyl, 2-benzoxazolyl, 5-benzoxazolyl, purinyl, 2-benzimidazolyl, 5-indolyl, 1-isoquinolinyl, 5-isoquinolinyl, 2-quinoxalinyl, 5-quinoxalinyl, 3-quinolinyl, and 6-quinolinyl.

Substituents for each of the above noted aryl ring systems are selected from the group of acceptable substituents described below. The term "arylalkyl" is meant to include those radicals in which an aryl group is attached to an alkyl group (e.g., benzyl, phenethyl, pyridylmethyl and the like) or a heteroalkyl group (e.g., phenoxymethyl, 2-pyridyloxymethyl, 3-(1-naphthyloxy)propyl, and the like).

Each of the above terms (e.g., "alkyl," "heteroalkyl" and "aryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR'R"R'", —OC(O)R', —C(O)R', —CO2R', —CONR'R", —OC(O)NR'R", —NR"C(O)R', —NR'—C(O)NR"R'", —NR"C(O)$_2$R', —NH—C($NH_2$)=NH, —NR'C($NH_2$)=NH, —NH—C($NH_2$)=NR', —S(O)R', —S(O)$_2$R', —S(O)$_2$NR'R", —CN and —$NO_2$ in a number ranging from zero to (2N+1), where N is the total number of carbon atoms in such radical. R', R" and R'" each independently refer to hydrogen, unsubstituted ($C_1$-$C_8$)alkyl and heteroalkyl, unsubstituted aryl, aryl substituted with 1-3 halogens, unsubstituted alkyl, alkoxy or thioalkoxy groups, or aryl-($C_1$-$C_8$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —$CF_3$ and —$CH_2CF_3$) and acyl (e.g., —C(O)$CH_3$, —C(O)$CF_3$, —C(O)$CH_2OCH_3$, and the like). Preferably, the alkyl groups (and related alkoxy, heteroalkyl, etc.) are unsubstituted or have 1 to 3 substituents selected from halogen, —OR', =O, —NR'R", —SR', —OC(O)R', —C(O)R', —CO$_2$R', —CONR'R", —NR"C(O)R', —S(O)$_2$R', —S(O)$_2$NR'R", —CN and —NO$_2$. More preferably, the alkyl and related groups have 0 to 2 substituents selected from halogen, —OR', =O, —NR'R", —SR', —CO$_2$R', —CONR'R", —NR"C(O)R', —CN and —NO$_2$.

Similarly, substituents for the aryl groups are varied and are selected from halogen, —OR', —OC(O)R', —NR'R", —SR', —R', —CN, —NO$_2$—, —CO$_2$R', —CONR'R", —C(O)R', —OC(O)NR'R", —NR"C(O)R', —NR"C(O)$_2$R', —NR'—C(O)NR"R'", —NH—C($NH_2$)=NH, —NR'C($NH_2$)=NH, —NH—C($NH_2$)=NR', —S(O)R', —S(O)$_2$R', —S(O)$_2$NR'R", —$N_3$, —CH(Ph)$_2$, perfluoro($C_1$-$C_8$)alkoxy, and perfluoro($C_1$-$C_8$)alkyl, in a number ranging from zero to the total number of open valences on the aromatic ring system; and where R', R" and R'" are independently selected from hydrogen, ($C_1$-$C_8$)alkyl and heteroalkyl, unsubstituted aryl, (unsubstituted aryl)-($C_1$-$C_8$)alkyl, and (unsubstituted aryl)oxy-($C_1$-$C_8$)alkyl. Preferably, the aryl groups are unsubstituted or have from 1 to 3 substituents selected from halogen, —OR', —OC(O)R', —NR'R", —SR', —R', —CN, —NO$_2$—, —CO2R', —CONR'R", —C(O)R', —NR"C(O)R', —S(O)$_2$R', —S(O)$_2$NR'R", perfluoro($C_1$-$C_8$)alkoxy, and perfluoro($C_1$-$C_8$)alkyl. Still more preferably, the aryl groups have 0 to 2 substituents selected from halogen, —OR', —NR'R", —SR', —R', —CN, —NO$_2$— —CO$_2$R', —CONR'R", —NR"C(O)R', —S(O)$_2$R', —S(O)$_2$NR'R", perfluoro($C_1$-$C_8$)alkoxy, and perfluoro($C_1$-$C_8$)alkyl.

Two of the substituents on adjacent atoms of the aryl ring can optionally be replaced with a substituent of the formula, wherein T and U are independently —NH—, —O—, —CH2- or a single bond, and q is an integer of from 0 to 2. Alternatively, two of the substituents on adjacent atoms of the aryl ring can optionally be replaced with a substituent of the formula -A-$(CH_2)_r$—B—, wherein A and B are independently —$CH_2$—, —O—, —NH—, —S—, —S(O)—, —$S(O)_2$—, —$S(O)_2NR'$— or a single bond, and r is an integer of from 1 to 3. One of the single bonds of the new ring so formed can optionally be replaced with a double bond. Alternatively, two of the substituents on adjacent atoms of the aryl ring can optionally be replaced with a substituent of the formula —$(CH_2)_s$—X—$(CH_2)_t$—, where s and t are independently integers of from 0 to 3, and X is —O—, —NR'—, —S—, —S(O)—, —$S(O)_2$—, or —$S(O)_2NR'$—. The substituent R' in —NR'— and —$S(O)_2NR'$— is selected from hydrogen or unsubstituted ($C_1$-$C_8$)alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are often useful because, in some situations, they can be easier to administer than the parent drug. They can, for instance, be bioavailable by oral administration whereas the parent drug is not. The prodrug can also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the present invention which is administered as an ester (the "prodrug"), but then is metabolically hydrolyzed to the carboxylic acid, the active entity. Additional examples include peptidyl derivatives of a compound of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention can exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention can also contain unnatural proportions of atomic isotopes at one or more of the atoms that constitute such compounds. For example, the compounds can be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

.2. Description of the Embodiments of the Invention

A new class of compounds that modulate PPARγ or PPARδ has now been discovered. Depending on the biological environment (e.g., cell type, pathological condition of the subject, etc.), these compounds of the present invention can activate or inhibit PPARγ or PPARδ activity. Thus, the compounds of the invention are useful in the treatment or prevention of conditions and disorders associated with energy homeostasis, lipid metabolism, adipocyte differentiation and inflammation (see, Ricote et al. (1998) *Nature* 391:79-82 and Jiang et al. (1998) *Nature* 391:82-86). For example, compounds that activate PPARγ or PPARδ are useful in the treatment of metabolic disorders, cardiovascular diseases, inflammatory conditions and neoplastic diseases. Additionally, the compounds of the invention are useful for the prevention and treatment of complications of metabolic disorders, such as diabetes, e.g., neuropathy, retinopathy, glomerulosclerosis and cardiovascular disorders.

In addition to their anti-diabetic activity, many synthetic PPAR ligands also promote increased body weight gain, a situation that can aggravate the diabetic and obese condition. The ligands exemplified herein improve upon this profile by providing effective lowering of serum glucose levels in the absence of such profound increases in body weight.

Related compounds of the more general class have in certain instances been modified to produce pharmacologically active metabolites with exposures and in vivo lifetimes that exceed the parent compounds. In the treatment of certain chronic conditions, such metabolites have been linked to untoward conditions. Some of the compounds contemplated by the present invention avoid the formation of such long-lived metabolites while still maintaining the desirable pharmacological properties of the general class.

.2.1 Compounds

In one embodiment, the present invention provides compounds which are represented by the formula (I):

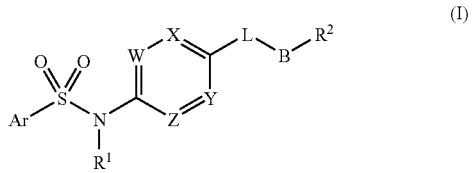

In formula I, the symbol Ar is a member selected from the group consisting of phenyl, naphthyl and pyridyl; each of which is optionally substituted with from one to three $R^8$ substituents, wherein each $R^8$ is a member independently selected from the group consisting of halogen, cyano, nitro, $(C_1-C_8)$alkyl, $(C_1-C_8)$alkoxy, $(C_1-C_8)$haloalkyl, $(C_1-C_8)$haloalkoxy, $(C_2-C_8)$ alkenyl, $(C_2-C_8)$ alkynyl, hydroxyl and $NR^{12}R^{13}$.

The letter B represents an aryl or heteroaryl group; each of which is optionally substituted with from one to two $R^9$ substituents, wherein each $R^9$ is a member independently selected from the group consisting of halogen, nitro, $(C_1-C_8)$alkyl, $(C_1-C_8)$alkoxy and $NR^{12}R^{13}$.

The letter L represents a member selected from the group consisting of O, $S(O)_k$, $CR^aR^b$ and C(O); wherein each $R^a$ or $R^b$ is independently selected from the group consisting of hydrogen, cyano, nitro, and $(C_1-C_8)$ alkyl; and the subscript k represents an integer of from 0 to 2.

The symbol W represents $C(R^3)$ or N; the symbol X represents $C(R^4)$ or N; the symbol Y represents $C(R^5)$ or N; and the symbol Z represents $C(R^6)$ or N, wherein at least one of W, X, Y and Z is N and at least one W, X, Y and Z is other than N; and each $R^3$, $R^4$, $R^5$, or $R^6$ is a member independently selected from the group consisting of hydrogen, hydroxy, halogen, cyano, nitro, $NR^{12}R^{13}$, $(C_1-C_8)$alkyl, halo$(C_1-C_8)$alkyl, hydroxy$(C_1-C_8)$alkyl, $(C_3-C_8)$cycloalkyl, $(C_1-C_8)$alkoxy, $(C_1-C_8)$thioalkoxy, $(C_2-C_8)$heteroalkyl, aryl, heteroaryl, —C(O)$R^{11}$, —CO$_2R^{11}$, —C(O)N $R^{12}R^{13}$, —C(O)CH$_2$CN, —$X^1Q^1$, $X^2OR^{11}$ and $X^2NR^{12}R^{13}$; or optionally, adjacent $R^3$, $R^4$, $R^5$, or $R^6$ groups can be combined to form an additional 5- or 6-membered fused ring which can be saturated or unsaturated.

The symbol $R^1$ represents a member selected from the group consisting of hydrogen, $(C_1-C_8)$alkyl, $(C_2-C_8)$heteroalkyl and aryl$(C_1-C_8)$alkyl; and the symbol $R^2$ represents a member selected from the group consisting of hydrogen, halogen, cyano, nitro, $NR^{12}R^{13}$ and $S(O)_mR^7$.

The symbol $X^1$ represents a member selected from the group consisting of $(C_1-C_2)$alkylene and C(O); and the symbol $Q^1$ represents a member independently selected from the group consisting of pyrrolidinyl, piperidinyl, and morpholinyl.

The symbol $R^7$ is selected from the group consisting of $(C_1-C_8)$alkyl, $(C_3-C_8)$cycloalkyl, $(C_1-C_8)$haloalkyl, aryl, $NR^{12}R^{13}$, $(C_3-C_8)$heterocycloalkyl, $X^2$—C(O)O$R^{15}$, $X^2$—C(O)N$(R^{15})_2$, and —$X^2$—$NR^{12}R^{13}$; wherein each symbol $X^2$ represents $(C_1-C_8)$alkylene.

The symbol $R^{11}$ represents a member independently selected from the group consisting of hydrogen, $(C_1-C_8)$alkyl, $(C_2-C_8)$alkenyl, $(C_3-C_8)$cycloalkyl, $(C_2-C_8)$heteroalkyl, aryl, heteroaryl, heteroaryl$(C_1-C_8)$alkyl, $(C_3-C_8)$heterocycloalkyl and aryl$(C_1-C_8)$alkyl; and the symbols $R^{12}$ and $R^{13}$ each represent a member independently selected from the group consisting of hydrogen, $(C_1-C_8)$alkyl, $(C_2-C_8)$alkenyl, $(C_3-C_8)$cycloalkyl, $(C_2-C_8)$heteroalkyl, $(C_1-C_8)$alkoxy, aryl and aryl$(C_1-C_8)$alkyl; optionally, $R^{12}$ and $R^{13}$ are combined with the nitrogen to which each is attached to form a 3-, 4-, 5-, 6- or 7-membered ring which can be saturated or unsaturated and contain 0 to 2 additional heteroatoms selected from N, O and S; wherein said ring is optionally substituted with from one to four substituents selected from the group consisting of hydroxy, oxo, and $(C_1-C_8)$alkyl.

Each symbol $R^{15}$ represents a member selected from the group consisting of H, $(C_1-C_8)$alkyl, $(C_2-C_8)$alkenyl and $(C_3-C_8)$cycloalkyl; and the subscript m represents an integer of 0 to 2.

A number of preferred embodiments are provided herein. For example, in one preferred embodiment, Ar is phenyl, optionally substituted with from one to three $R^8$ substitutents, wherein each $R^8$ is independently selected from the group consisting of halogen, $(C_1-C_8)$alkyl, $(C_1-C_8)$alkoxy, and $(C_1-C_8)$haloalkyl.

In a further preferred embodiment $R^1$ is H.

One of skill in the art will understand that a number of structural isomers are represented by formula I. In one group of embodiments, the isomers are those in which W is N; X is $C(R^4)$; Y is $C(R^5)$; and Z is $C(R^6)$. In another group of embodiments, the isomers are those in which W is $C(R^3)$; Y is $C(R^5)$; Z is $C(R^6)$; and X is N. In another group of embodiments, the isomers are those in which W and X are N; Y is $C(R^5)$ and Z is $C(R^6)$. In another group of embodiments, the isomers are those in which W and Z are N and X is $C(R^4)$ and Y is $C(R^5)$. In another group of embodiments, the isomers are those in which W is $C(R^4)$ and Z is $C(R^6)$ and X and Y are N. In another group of embodiments, the isomers are those in which W and Y are N and X is $C(R^4)$ and Z is $C(R^6)$.

In a further preferred embodiment each $R^3$, $R^4$, $R^5$, or $R^6$ is independently selected from the group consisting of hydrogen, hydroxy, halogen, $NR^{12}R^{13}$, $(C_1-C_8)$alkyl, $(C_3-C_8)$cycloalkyl, $(C_1-C_8)$alkoxy, $(C_1-C_8)$thioalkoxy, $(C_2-C_8)$heteroalkyl, $(C_1-C_8)$haloalkyl, CN, —C(O)$R^{11}$, —CO$_2R^{11}$ and —C(O)N$R^{12}R^{13}$.

In still other preferred embodiments, L is O. In yet other preferred embodiments, L is S.

In still other preferred embodiments, B is aryl, which is optionally substituted with from one to two $R^9$ substituents. In yet other preferred embodiments, B is phenyl or naphthyl, each of which is optionally substituted with from one to two $R^9$ substituents. In still other preferred embodiments, B is phenyl, which is optionally substituted with from one to two $R^9$ substituents.

In still other preferred embodiments, B is heteroaryl, which is optionally substituted with from one to two $R^9$ substituents. In yet other preferred embodiments, B is benzothiazolyl, which is optionally substituted with from one to two $R^9$ substituents.

In another group of preferred embodiments, $R^2$ is $SO_2R^7$.

In still other preferred embodiments, $R^7$ is selected from the group consisting of $(C_1-C_8)$alkyl, $NR^{12}R^{13}$ and $(C_3-C_8)$heterocycloalkyl. In yet other preferred embodiments, $R^7$ is selected from the group consisting of cyclopentyl, cyclohexyl, tetrahydropyranyl, pyrrolidinyl, piperidinyl, morpholinyl, piperazinyl, thiomorpholinyl, and azepinyl. In still other preferred embodiments, $R^7$ is selected from the group consisting of

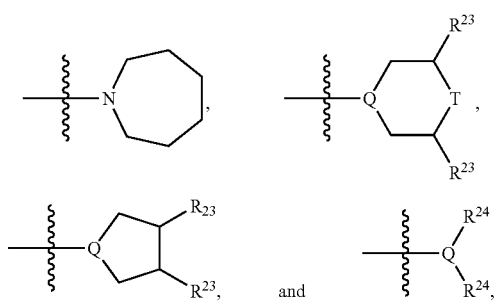

wherein Q is N or CH; T is CHR$^{16}$, NR$^{16}$, O, or S(O)$_l$; R$^{16}$ is H or (C$_1$-C$_8$)alkyl; each R$^{23}$ is a member independently selected from the group consisting of H and (C$_1$-C$_8$)alkyl; each R$^{24}$ is selected from the group consisting of H, (C$_1$-C$_8$) alkyl and heteroalkyl; and the subscript l is an integer of from 0 to 2 In other preferred embodiments, R$^7$ is X$^2$—C(O)OR$^{15}$ or X$^2$—C(O)N(R$^{15}$)$_2$; and each R$^{15}$ is H or (C$_1$-C$_8$)alkyl.

One of skill in the art will understand that a number of structural isomers are represented by formula I. In other embodiments, the compounds are those having the structural orientations represented by the formulae (II-VII):

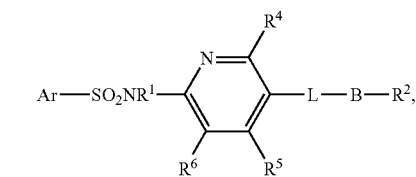

II

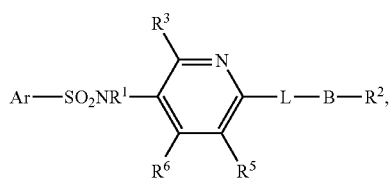

III

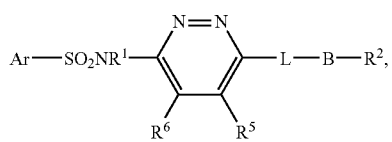

IV

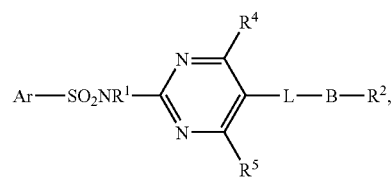

V

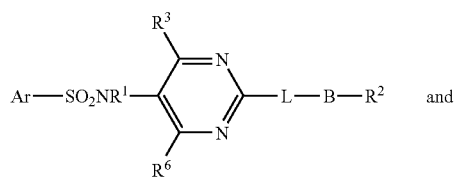

VI and

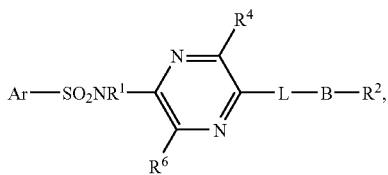

VII wherein Ar, R$^8$, B, R$^9$, L, R$^1$, R$^2$, R$^3$, R$^4$, R$^5$, R$^6$, R$^7$, R$^8$, R$^9$, R$^{11}$, R$^{12}$, R$^{13}$, R$^{15}$, X$^1$, Q$^1$, X$^2$, k and m are as defined above as well as preferred embodiments.

In another embodiment, the present invention provides compounds which are represented by the formula (VIII):

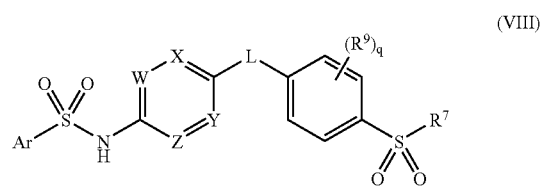

(VIII)

or a pharmaceutically acceptable salt thereof, wherein Ar, R$^8$, B, R$^9$, L, R$^1$, R$^2$, R$^3$, R$^4$, R$^5$, R$^6$, R$^7$, R$^8$, R$^9$, R$^{11}$, R$^{12}$, R$^{13}$, R$^{15}$, X$^1$, Q$^1$, X$^2$, k and m are as defined above as well as in preferred embodiments and q is independently 0 to 2.

In another embodiment, the present invention provides compounds which are represented by the formula (IX):

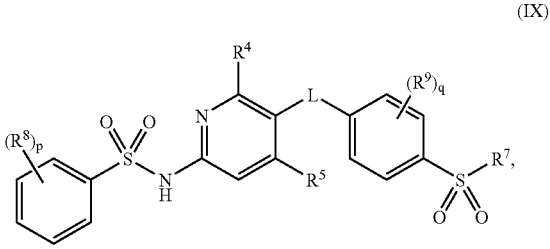

(IX)

wherein R$^4$ is selected from the group consisting of H, (C$_1$-C$_8$) alkyl, halo(C$_1$-C$_8$)alkyl; (C$_1$-C$_8$)alkoxy, —CO$_2$R$^{11}$, —C(O)NR$^{12}$R$^{13}$, hydroxy(C$_1$-C$_8$)alkyl and C(O)R$^{11}$; R$^5$ is selected from the group consisting of H, (C$_1$-C$_8$) alkyl, C(O)R$^{11}$ and —CO$_2$R$^{11}$; L is selected from the group consisting of O, S(O)$_k$, CR$^a$R$^b$ and C(O); each R$^a$ or R$^b$ is independently selected from the group consisting of hydrogen, cyano, nitro, and (C$_1$-C$_8$) alkyl; R$^7$ is selected from the group consisting of (C$_1$-C$_8$)alkyl, (C$_3$-C$_8$)cycloalkyl, (C$_1$-C$_8$)haloalkyl, aryl, NR$^{12}$R$^{13}$, (C$_3$-C$_8$)heterocycloalkyl, X$^2$—C(O)OR$^{15}$, X$^2$—C(O)N(R$^{15}$)$_2$, and —X$^2$—NR$^{12}$R$^{13}$; each X$^2$ is (C$_1$-C$_8$)alkylene; each R$^8$ is independently selected from the group consisting of halo, (C$_1$-C$_8$) alkyl, halo(C$_1$-C$_8$)alkyl; each R$^9$ is a member independently selected from the group consisting of halogen, nitro, (C$_1$-C$_8$)alkyl, (C$_1$-C$_8$)alkoxy and NR$^{12}$R$^{13}$; each R$^{11}$ is independently selected from the group consisting of hydrogen, (C$_1$-C$_8$)alkyl, (C$_2$-C$_8$)alkenyl, (C$_3$-C$_8$)cycloalkyl, (C$_2$-C$_8$)heteroalkyl, aryl, heteroaryl, heteroaryl(C$_1$-C$_8$)alkyl, (C$_3$-C$_8$) heterocycloalkyl and aryl(C$_1$-C$_8$)alkyl; each R$^{12}$ and R$^{13}$ are independently selected from the group consisting of hydrogen, (C$_1$-C$_8$)alkyl, (C$_2$-C$_8$) alkenyl, (C$_3$-

$C_8$)cycloalkyl, ($C_2$-$C_8$)heteroalkyl, ($C_1$-$C_8$)alkoxy, aryl and aryl($C_1$-$C_8$)alkyl; optionally, $R^{12}$ and $R^{13}$ are combined with the nitrogen atom to which each is attached to form a 3-, 4-, 5-, 6- or 7-membered ring which can be saturated or unsaturated and contain 0 to 2 additional heteroatoms selected from N, O and S; wherein said ring is optionally substituted with from one to four substituents selected from the group consisting of hydroxy, oxo, and ($C_1$-$C_8$)alkyl; each $R^{15}$ is selected from the group consisting of H, ($C_1$-$C_8$)alkyl, ($C_2$-$C_8$)alkenyl and ($C_3$-$C_8$)cycloalkyl; and the subscript q is an integer of from 0 to 2; and the subscript p is an integer of from 0 to 3.

In a particularly preferred embodiment of the invention, L is S.

Other preferred embodiments are those embodiments in which $R^9$ is hydrogen.

In the other preferred embodiments, $R^7$ is selected from the group consisting of ($C_1$-$C_8$)alkyl, $NR^{12}R^{13}$, and ($C_3$-$C_8$)heterocycloalkyl.

Still further preferred are those embodiments in which $R^7$ is selected from the group consisting of cyclopentyl, cyclohexyl, tetrahydropyranyl, pyrrolidinyl, piperidinyl, morpholinyl, piperazinyl, thiomorpholinyl, and azepinyl.

In the most preferred embodiments, $R^7$ is selected from the group consisting of

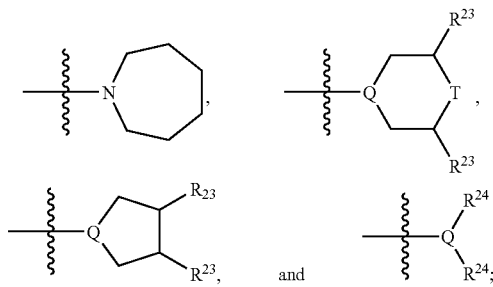

wherein Q is N or CH; T is $CHR^{16}$, $NR^{16}$, O, or $S(O)_l$; $R^{16}$ is H or ($C_1$-$C_8$)alkyl; each $R^{23}$ is a member independently selected from the group consisting of H and ($C_1$-$C_8$)alkyl; each $R^{24}$ is selected from the group consisting of H, ($C_1$-$C_8$) alkyl and heteroalkyl; and the subscript l is an integer of from 0 to 2.

In other most preferred embodiments $R^7$ is $X^2$—C(O)O$R^{15}$ or $X^2$—C(O)N($R^{15}$)$_2$; and each $R^{15}$ is H or ($C_1$-$C_8$)alkyl.

In another embodiment, the present invention provides compounds which are represented by the formula (X):

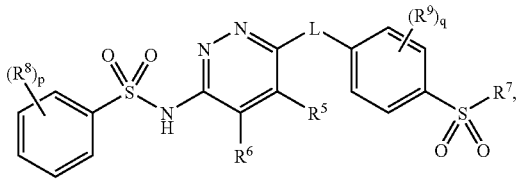

wherein $R^5$ is H or ($C_1$-$C_8$)alkyl; $R^6$ is H or ($C_1$-$C_8$)alkyl; L is selected from the group consisting of O, $S(O)_k$, $CR^aR^b$ and C(O); each $R^a$ or $R^b$ is independently selected from the group consisting of hydrogen, cyano, nitro, and ($C_1$-$C_8$) alkyl; $R^7$ is selected from the group consisting of ($C_1$-$C_8$)alkyl, $NR^{12}R^{13}$, and ($C_3$-$C_8$)heterocycloalkyl; each $R^8$ is a member independently selected from the group consisting of halo, ($C_1$-$C_8$) alkyl, and halo($C_1$-$C_8$)alkyl; each $R^9$ is a member independently selected from the group consisting of halogen, nitro, ($C_1$-$C_8$)alkyl, ($C_1$-$C_8$)alkoxy and $NR^{12}R^{13}$; each $R^{12}$ and $R^{13}$ are independently selected from the group consisting of hydrogen, ($C_1$-$C_8$)alkyl, ($C_2$-$C_8$) alkenyl, ($C_3$-$C_8$)cycloalkyl, ($C_2$-$C_8$)heteroalkyl, ($C_1$-$C_8$)alkoxy, aryl and aryl($C_1$-$C_8$) alkyl; optionally, $R^{12}$ and $R^{13}$ are combined with the nitrogen atom to which each is attached to form a 3-, 4-, 5-, 6- or 7-membered ring which can be saturated or unsaturated and contain 0 to 2 additional heteroatoms selected from N, O and S; wherein said ring is optionally substituted with from one to four substituents selected from the group consisting of hydroxy, oxo, and ($C_1$-$C_8$)alkyl; the subscript q is an integer of from 0 to 2; and the subscript p is an integer of from 0to 3.

In a particularly preferred embodiment of the invention, L is S.

In another particularly preferred embodiment of the invention, L is O.

Other preferred embodiments are those embodiments in which $R^9$ is hydrogen.

In the most preferred embodiments, $R^7$ is selected from the group consisting of

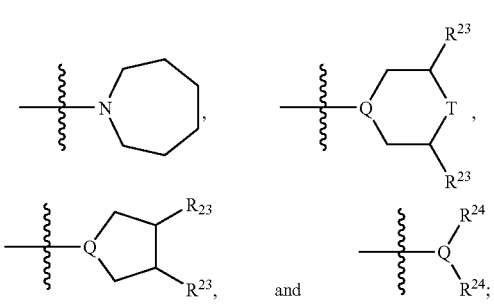

wherein Q is N or CH; T is $CHR^{16}$, $NR^{16}$, O, or $S(O)_l$; $R^{16}$ is H or ($C_1$-$C_8$)alkyl; each $R^{23}$ is a member independently selected from the group consisting of H and ($C_1$-$C_8$)alkyl; each $R^{24}$ is selected from the group consisting of H, ($C_1$-$C_8$) alkyl and heteroalkyl; and the subscript l is an integer of from 0 to 2.

Still further preferred are those embodiments in which $R^7$ is selected from the group consisting of cyclopentyl, cyclohexyl, tetrahydropyranyl, pyrrolidinyl, piperidinyl, morpholinyl, piperazinyl, thiomorpholinyl, and azepinyl.

Still further preferred are those embodiments in which $R^7$ is selected from the group consisting of

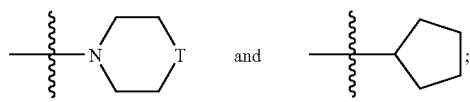

wherein T is O or $CH_2$.

In other most preferred embodiments $R^7$ is $X^2$—C(O)O$R^{15}$ or $X^2$—C(O)N($R^{15}$)$_2$; and each $R^{15}$ is H or ($C_1$-$C_8$)alkyl.

In another embodiment, the present invention provides compounds which are represented by the formula (XII):

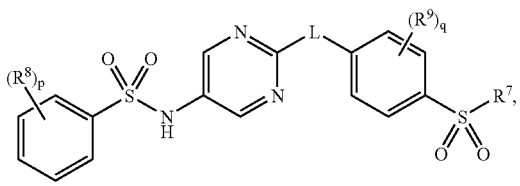

(XII)

wherein L is selected from the group consisting of O, S(O)$_k$, CR$^a$R$^b$ and C(O); each R$^a$ or R$^b$ is independently selected from the group consisting of hydrogen, cyano, nitro, and (C$_1$-C$_8$) alkyl; R$^7$ is selected from the group consisting of (C$_1$-C$_8$)alkyl, NR$^{12}$R$^{13}$, and (C$_3$-C$_8$)heterocycloalkyl; each R$^8$ is is a member independently selected from the group consisting of halo, (C$_1$-C$_8$)alkyl, and halo(C$_1$-C$_8$)alkyl; each R$^9$ is a member independently selected from the group consisting of halogen, nitro, (C$_1$-C$_8$)alkyl, (C$_1$-C$_8$)alkoxy and NR$^{12}$R$^{13}$; each R$^{12}$ and R$^{13}$ are independently selected from the group consisting of hydrogen, (C$_1$-C$_8$)alkyl, (C$_2$-C$_8$) alkenyl, (C$_3$-C$_8$)cycloalkyl, (C$_2$-C$_8$)heteroalkyl, (C$_1$-C$_8$)alkoxy, aryl and aryl(C$_1$-C$_8$)alkyl; optionally, R$^{12}$ and R$^{13}$ are combined with the nitrogen atom to which each is attached to form a 3-, 4-, 5-, 6- or 7-membered ring which can be saturated or unsaturated and contain 0 to 2 additional heteroatoms selected from N, O and S; wherein said ring is optionally substituted with from one to four substituents selected from the group consisting of hydroxy, oxo, and (C$_1$-C$_8$)alkyl; the subscript q is an integer of from 0 to 2; and the subscript p is an integer of from 0 to 3.

In a particularly preferred embodiment of the invention, L is S.

In another particularly preferred embodiment of the invention, L is O.

Other preferred embodiments are those embodiments in which R$^8$ is halogen; and R$^9$ is hydrogen.

In the most preferred embodiments, R$^7$ is selected from the group consisting of

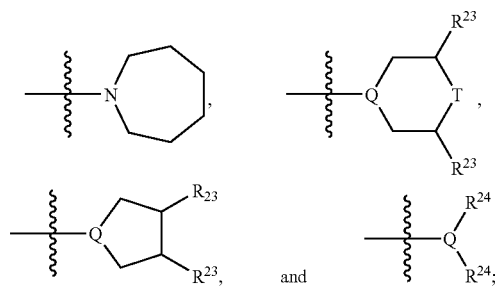

wherein Q is N or CH; T is CHR$^{16}$, NR$^{16}$, O, or S(O)$_l$; R$^{16}$ is H or (C$_1$-C$_8$)alkyl; each R$^{23}$ is a member independently selected from the group consisting of H and (C$_1$-C$_8$)alkyl; each R$^{24}$ is selected from the group consisting of H, (C$_1$-C$_8$) alkyl and heteroalkyl; and the subscript l is an integer of from 0 to 2.

Still further preferred are those embodiments in which R$^7$ is selected from the group consisting of cyclopentyl, cyclohexyl, tetrahydropyranyl, pyrrolidinyl, piperidinyl, morpholinyl, piperazinyl, thiomorpholinyl, and azepinyl.

Still further preferred are those embodiments in which R$^7$ is selected from the group consisting of

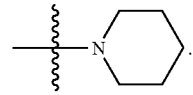

In other most preferred embodiments R$^7$ is X$^2$—C(O)OR$^{15}$ or X$^2$—C(O)N(R$^{15}$)$_2$; and each R$^{15}$ is H or (C$_1$-C$_8$)alkyl.

In another embodiment, the present invention provides compounds which are represented by the formula (XIII):

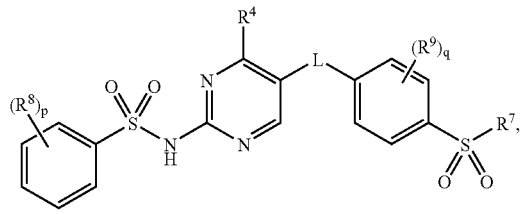

(XIII)

wherein R$^5$, R$^6$, R$^7$, R$^8$, R$^9$, R$^{12}$, R$^{13}$, L, q and p are as defined above as well as in preferred embodiments for formula (XII).

In another embodiment, the present invention provides compounds which are represented by the formula (XIV):

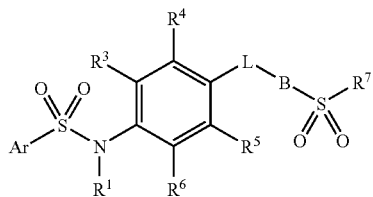

(XIV)

In formula I, the symbol Ar is a member selected from the group consisting of phenyl, naphthyl and pyridyl; each of which is optionally substituted with from one to three R$^3$ substituents, wherein each R$^8$ is a member independently selected from the group consisting of halogen, cyano, nitro, (C$_1$-C$_8$)alkyl, (C$_1$-C$_8$)alkoxy, (C$_1$-C$_8$)haloalkyl, (C$_1$-C$_8$)haloalkoxy, (C$_2$-C$_8$) alkenyl, (C$_2$-C$_8$) alkynyl, hydroxyl and NR$^{12}$R$^{13}$.

The letter B represents an aryl or heteroaryl group; each of which is optionally substituted with from one to two R$^9$ substituents, wherein each R$^9$ is a member independently selected from the group consisting of halogen, nitro, (C$_1$-C$_8$) alkyl, (C$_1$-C$_8$)alkoxy and NR$^{12}$R$^{13}$.

The letter L represents a member selected from the group consisting of O, S(O)$_k$, CR$^a$R$^b$ and C(O); wherein each R$^a$ or R$^b$ is independently selected from the group consisting of hydrogen, cyano, nitro, and (C$_1$-C$_8$) alkyl; and the subscript k represents an integer of from 0 to 2.

Each symbol R$^3$, R$^4$, R$^5$, or R$^6$ is a member independently selected from the group consisting of hydrogen, hydroxy, halogen, cyano, nitro, NR$^{12}$R$^{13}$, (C$_1$-C$_8$)alkyl, halo(C$_1$-C$_8$) alkyl, hydroxy(C$_1$-C$_8$)alkyl, (C$_3$-C$_8$)cycloalkyl, (C$_1$-C$_8$) alkoxy, (C$_1$-C$_8$)thioalkoxy, (C$_2$-C$_8$)heteroalkyl, aryl, heteroaryl, —C(O)R$^{11}$, —CO$_2$R$^{11}$, —C(O)NR$^{12}$R$^{13}$, —C(O)CH$_2$CN, —X$^1$Q$^1$, X$^2$ OR$^{11}$ and X$^2$NR$^{12}$R$^{13}$; or optionally, adjacent R$^3$, R$^4$, R$^5$, or R$^6$ groups can be combined to form an additional 5- or 6-membered fused ring which can be saturated or unsaturated.

The symbol R$^1$ represents a member selected from the group consisting of hydrogen, (C$_1$-C$_8$)alkyl, (C$_2$-C$_8$)heteroalkyl and aryl(C$_1$-C$_8$)alkyl; and the symbol R$^2$ represents a member selected from the group consisting of hydrogen, halogen, cyano, nitro, NR$^{12}$R$^{13}$ and S(O)$_m$R$^7$.

The symbol X$^1$ represents a member selected from the group consisting of(C$_1$-C$_2$)alkylene and C(O); and the symbol Q$^1$ represents a member independently selected from the group consisting of pyrrolidinyl, piperidinyl, and morpholinyl.

The symbol R$^7$ is selected from the group consisting of (C$_1$-C$_8$)alkyl, (C$_3$-C$_8$)cycloalkyl, (C$_1$-C$_8$)haloalkyl, aryl, NR$^{12}$R$^{13}$, (C$_3$-C$_8$)heterocycloalkyl, X$^2$—C(O)OR$^{15}$, X$^2$—C(O)N(R$^{15}$)$_2$, and —X$^2$—NR$^{12}$R$^{13}$; wherein each symbol X$^2$ represents (C$_1$-C$_8$)alkylene.

The symbol R$^{11}$ represents a member independently selected from the group consisting of hydrogen, (C$_1$-C$_8$)alkyl, (C$_2$-C$_8$)alkenyl, (C$_3$-C$_8$)cycloalkyl, (C$_2$-C$_8$)heteroalkyl, aryl, heteroaryl, heteroaryl(C$_1$-C$_8$)alkyl, (C$_3$-C$_8$)heterocycloalkyl and aryl(C$_1$-C$_8$)alkyl; and the symbols R$^{12}$ and R$^{13}$ each represent a member independently selected from the group consisting of hydrogen, (C$_1$-C$_8$)alkyl, (C$_2$-C$_8$)alkenyl, (C$_3$-C$_8$)cycloalkyl, (C$_2$-C$_8$)heteroalkyl, (C$_1$-C$_8$)alkoxy, aryl and aryl(C$_1$-C$_8$)alkyl; optionally, R$^{12}$ and R$^{13}$ are combined with the nitrogen to which each is attached to form a 3-, 4-, 5-, 6- or 7-membered ring which can be saturated or unsaturated and contain 0 to 2 additional heteroatoms selected from N, O and S; wherein said ring is optionally substituted with from one to four substituents selected from the group consisting of hydroxy, oxo, and (C$_1$-C$_8$)alkyl.

Each symbol R$^{15}$ represents a member selected from the group consisting of H, (C$_1$-C$_8$)alkyl, (C$_2$-C$_8$)alkenyl and (C$_3$-C$_8$)cycloalkyl; and the subscript m represents an integer of 0 to 2.

A number of preferred embodiments are provided herein. For example, in one preferred embodiment, Ar is phenyl, optionally substituted with from one to three R$^8$ substitutents, wherein each R$^8$ is independently selected from the group consisting of halogen, (C$_1$-C$_8$)alkyl, (C$_1$-C$_8$)alkoxy, and (C$_1$-C$_8$)haloalkyl. In another preferred embodiments, Ar is 1-naphthyl, optionally substituted with from one to three R$^8$ substitutents, wherein each R$^8$ is independently selected from the group consisting of halogen, (C$_1$-C$_8$)alkyl, (C$_1$-C$_8$)alkoxy, and (C$_1$-C$_8$)haloalkyl. In another preferred embodiments, Ar is 2-pyridyl or 3-pyridyl, optionally substituted with from one to three R$^8$ substitutents, wherein each R$^8$ is independently selected from the group consisting of halogen, (C$_1$-C$_8$)alkyl, (C$_1$-C$_8$)alkoxy, and (C$_1$-C$_8$)haloalkyl.

Within these embodiments, R$^8$ is preferably haloalkyl or haloalkoxy; and more preferably at least one R$^8$ is selected from the group consisting of 2-CF$_3$, 3-CF$_3$, 4-CF$_3$, 2-OCF$_3$, 3-OCF$_3$ and 4-OCF$_3$.

In a further preferred embodiment R$^1$ is H.

In a further preferred embodiment each R$^3$, R$^4$, R$^5$, or R$^6$ is independently selected from the group consisting of hydrogen, hydroxy, halogen, NR$^{12}$R$^{13}$, (C$_1$-C$_8$)alkyl, hydroxy(C$_1$-C$_8$)alkyl, (C$_1$-C$_8$)haloalkyl, (C$_3$-C$_8$)cycloalkyl, (C$_1$-C$_8$)alkoxy, (C$_1$-C$_8$)thioalkoxy, (C$_2$-C$_8$)heteroalkyl, heteroaryl, CN, —C(O)R$^{11}$, —CO$_2$R$^{11}$ and —C(O)NR$^{12}$R$^{13}$. Still further preferred are embodiments wherein each R$^4$ or R$^5$ is a member independently selected from the group consisting of hydrogen, halogen, haloalkyl, CN, heterocyclyl, and CONR$^{17}$OR$^{17}$; and R$^{17}$ is alkyl or hydroxyalkyl. Still further preferred are embodiments wherein each R$^4$ or R$^5$ is a member independently selected from the group consisting of CF$_2$CH$_3$, CN, 2-cyanomethylthiazol-4-yl, 2-methylthiazol-4-yl, 2-ethoxycarbonylthiazol-4-yl, and CONR$^{17}$OR$^{17}$; and R$^{17}$ is CH$_3$ or hydroxymethyl In still other preferred embodiments, L is O. In yet other preferred embodiments, L is S(O)$_k$. Within this embodiment more preferred embodiments are when L is S.

In still other preferred embodiments, B is aryl, which is optionally substituted with from one to two R$^9$ substituents. In yet other preferred embodiments, B is phenyl or naphthyl, each of which is optionally substituted with from one to two R$^9$ substituents. In still other preferred embodiments, B is phenyl, which is optionally substituted with from one to two R$^9$ substituents.

In still other preferred embodiments, B is heteroaryl, which is optionally substituted with from one to two R$^9$ substituents. In yet other preferred embodiments, B is pyridyl or benzothiazolyl, which is optionally substituted with from one to two R$^9$ substituents.

In another group of preferred embodiments, R$^2$ is SO$_2$R$^7$.

In still other preferred embodiments, R$^7$ is selected from the group consisting of (C$_1$-C$_8$)alkyl, NR$^{12}$R$^{13}$ and (C$_3$-C$_8$)heterocycloalkyl. In yet other preferred embodiments, R$^7$ is selected from the group consisting of cyclopentyl, cyclohexyl, tetrahydropyranyl, pyrrolidinyl, piperidinyl, morpholinyl, piperazinyl, thiomorpholinyl, and azepinyl. In still other preferred embodiments, R$^7$ is selected from the group consisting of

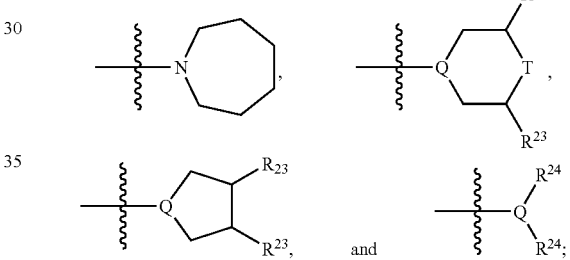

wherein Q is N or CH; T is CHR$^{16}$, NR$^{16}$, O, or S(O)$_l$; R$^{16}$ is H or (C$_1$-C$_8$)alkyl; each R$^{23}$ is a member independently selected from the group consisting of H and (C$_1$-C$_8$)alkyl; each R$^{24}$ is selected from the group consisting of H, (C$_1$-C$_8$) alkyl and heteroalkyl; and the subscript l is an integer of from 0 to 2. Still further preferred is when R$^7$ is a member selected from the group consisting of

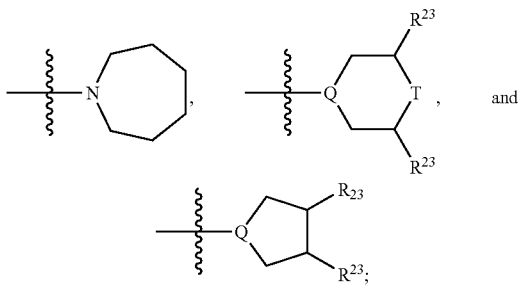

wherein Q is N or CH; T is CHR$^{16}$, NR$^{16}$, O, or S(O)$_l$; R$^{16}$ is H or (C$_1$-C$_8$)alkyl; each R$^{23}$ is a member independently selected from the group consisting of H and (C$_1$-C$_8$)alkyl; and the subscript l is an integer of from 0 to 2. In other preferred embodiments, R$^7$ is X$^2$—C(O)OR$^{15}$ or X$^2$—C(O)N(R$^{15}$)$_2$; and each R$^{15}$ is H or (C$_1$-C$_8$)alkyl.

In another embodiment, the present invention provides compounds which are represented by the formula (XV):

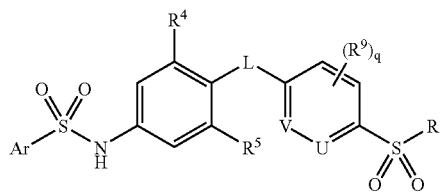

(XV)

or a pharmaceutically acceptable salt thereof, wherein Ar is a member selected from the group consisting of phenyl, naphthyl and pyridyl; each of which is optionally substituted with from one to three $R^8$ substituents, wherein each $R^8$ is a member independently selected from the group consisting of halogen, cyano, nitro, $(C_1-C_8)$alkyl, $(C_1-C_8)$alkoxy, $(C_1-C_8)$haloalkyl, $(C_1-C_8)$haloalkoxy, $(C_2-C_8)$ alkenyl, $(C_2-C_8)$ alkynyl, hydroxyl and $NR^{12}R^{13}$; L is selected from the group consisting of O, $S(O)_k$, $CR^aR^b$ and $C(O)$; each $R^a$ or $R^b$ is independently selected from the group consisting of hydrogen, cyano, nitro, and $(C_1-C_8)$ alkyl; U is selected from the group consisting of N and CH; V is selected from the group consisting of N and CH; each $R^4$ or $R^5$ is a member independently selected from the group consisting of hydrogen, hydroxy, halogen, cyano, nitro, $NR^{12}R^{13}$, $(C_1-C_8)$alkyl, halo$(C_1-C_8)$alkyl, hydroxy$(C_1-C_8)$alkyl, $(C_3-C_8)$cycloalkyl, $(C_1-C_8)$alkoxy, $(C_1-C_8)$thioalkoxy, $(C_2-C_8)$heteroalkyl, heteroaryl, $-C(O)R^{11}$, $-CO_2R^{11}$, $-C(O)NR^{12}R^{13}$, $-C(O)CH_2CN$, $-X^1Q^1$, $X^2OR^{11}$ and $X^2NR^{12}R^{13}$; optionally, adjacent R groups selected from $R^3$, $R^4$, $R^5$ and $R^6$ can be combined to form an additional 5- or 6-membered fused ring which can be saturated or unsaturated; each $X^1$ is independently selected from the group consisting of $(C_1-C_2)$alkylene and $C(O)$; each $Q^1$ is independently selected from the group consisting of pyrrolidinyl, piperidinyl, and morpholinyl; $R^7$ is a member selected from the group consisting of

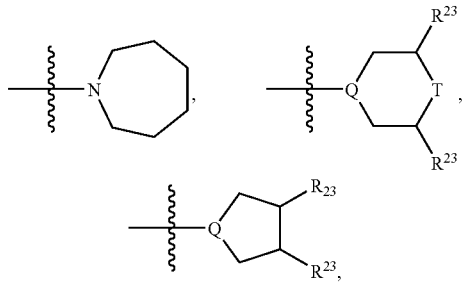

$X^2-C(O)OR^{15}$ and $X^2-C(O)N(R^{15})_2$; each $X^2$ is $(C_1-C_8)$ alkylene; $X^2$ is $(C_1-C_8)$alkylene; each $R^9$ is a member independently selected from the group consisting of halogen, nitro, $(C_1-C_8)$alkyl, $(C_1-C_8)$alkoxy and $NR^{12}R^{13}$; each $R^{11}$ is independently selected from the group consisting of hydrogen, $(C_1-C_8)$alkyl, $(C_2-C_8)$alkenyl, $(C_3-C_8)$cycloalkyl, $(C_2-C_8)$heteroalkyl, aryl, heteroaryl, heteroaryl$(C_1-C_8)$alkyl, $(C_3-C_8)$ heterocycloalkyl and aryl$(C_1-C_8)$alkyl; each $R^{12}$ and $R^{13}$ are independently selected from the group consisting of hydrogen, $(C_1-C^8)$alkyl, $(C_2-C_8)$ alkenyl, $(C_3-C_8)$cycloalkyl, $(C_2-C_8)$heteroalkyl, $(C_1-C_8)$alkoxy, aryl and aryl$(C_1-C_8)$alkyl; optionally, $R^{12}$ and $R^{13}$ are combined with the nitrogen atom to which each is attached to form a 3-, 4-, 5-, 6- or 7-membered ring which can be saturated or unsaturated and contain 0 to 2 additional heteroatoms selected from N, O and S; wherein said ring is optionally substituted with from one to four substituents selected from the group consisting of hydroxy, oxo, and $(C_1-C_8)$alkyl; each $R^{15}$ is selected from the group consisting of H, $(C_1-C_8)$alkyl, $(C_2-C_8)$alkenyl and $(C_3-C_8)$cycloalkyl; and the subscripts k, l, m, and q are independently 0 to 2.

In one preferred embodiment, Ar is phenyl, optionally substituted with from one to three $R^8$ substitutents, wherein each $R^8$ is independently selected from the group consisting of halogen, $(C_1-C_8)$alkyl, $(C_1-C_8)$alkoxy, and $(C_1-C_8)$haloalkyl.

Within these embodiments, $R^8$ is preferably haloalkyl or haloalkoxy; and more preferably at least one $R^8$ is selected from the group consisting of 2-$CF_3$, 3-$CF_3$, 4-$CF_3$, 2-$OCF_3$, 3-$OCF_3$ and 4-$OCF_3$.

In a further preferred embodiment $R^1$ is H.

In a further preferred embodiment each $R^3$, $R^4$, $R^5$, or $R^6$ is independently selected from the group consisting of hydrogen, hydroxy, halogen, $NR^{12}R^{13}$, $(C_1-C_8)$alkyl, hydroxy$(C_1-C_8)$alkyl, $(C_1-C_8)$haloalkyl, $(C_3-C_8)$cycloalkyl, $(C_1-C_8)$alkoxy, $(C_1-C_8)$thioalkoxy, $(C_2-C_8)$heteroalkyl, heteroaryl, CN, $-C(O)R^{11}$, $-CO_2R^{11}$ and $-C(O)NR^{12}R^{13}$. Still further preferred are embodiments wherein each $R^4$ or $R^5$ is a member independently selected from the group consisting of hydrogen, halogen, haloalkyl, CN, heterocyclyl, and $CONR^{17}OR^{17}$; and $R^{17}$ is alkyl or hydroxyalkyl. Still further preferred are embodiments wherein each $R^4$ or $R^5$ is a member independently selected from the group consisting of $CF_2CH_3$, CN, 2-cyanomethylthiazol-4-yl, 2-methylthiazol-4-yl, 2-ethoxycarbonyllthiazol-4-yl, and $CONR^{17}OR^{17}$; and $R^{17}$ is $CH_3$ or hydroxymethyl.

In still other preferred embodiments, U is CH and V is N. In yet other preferred embodiments, U is N and V is CH. In yet other preferred embodiments, both U and V are CH.

Within these preferred embodiments, L is O. In yet other preferred embodiments, L is S.

In still other preferred embodiments, $R^7$ is a member selected from the group consisting of

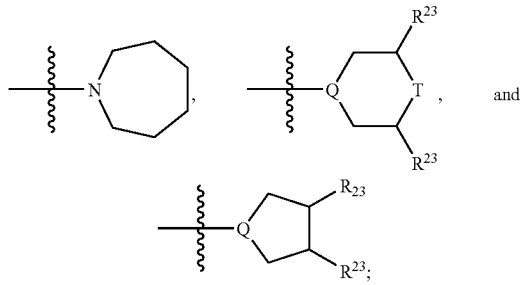

wherein Q is N or CH; T is $CHR^{16}$, $NR^{16}$, O, or $S(O)_l$; $R^{16}$ is H or $(C_1-C_8)$alkyl; each $R^{23}$ is a member independently selected from the group consisting of H and $(C_1-C_8)$alkyl; and the subscript l is an integer of from 0 to 2. In other preferred embodiments, $R^7$ is $X^2-C(O)OR^{15}$ or $X^2-C(O)N(R^{15})_2$; and each $R^{15}$ is H or $(C_1-C_8)$alkyl.

In another embodiment, the present invention provides compounds which are represented by the formula (XVI):

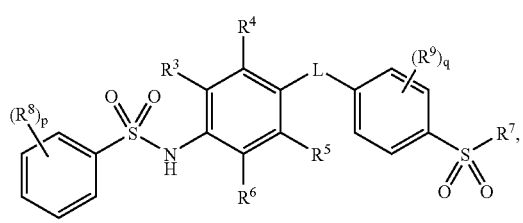

(XVI)

wherein $R^3$ $R^4$, $R^5$, $R^6$, $R^7$, L, p and q are as defined above as well as in the preferred embodiments of formula (XV).

.2.2 Preparation of Compounds

The compounds of the present invention can be prepared using standard synthetic methods. Schemes 1-14 illustrate exemplary methods for the preparation of compounds of structural formula (I). One of skill in the art will understand that similar methods can be used for the synthesis of compounds in the other structural classes.

As shown in Scheme 1, compounds of the present invention can be prepared beginning with commercially available alkylhaloacetate (a). (i) Treatment of a with appropriately substituted phenol or thiophenol (e.g. ArOH or ArSH) and a base, for example, potassium carbonate, in a solvent, for example, acetone provides the adduct (b). (ii) Treatment of (b) with t-butoxybis(dimethylamino)methane and a base, for example sodium methoxide (NaOMe), in an polar, aprotic solvent, for example, dimethylformamide (DMF) and subsequent coupling with an appropriately substituted benzene sulfonylguanidine (d) provides tri-aryl derivative (e). (ii) Compound (d) is formed by treating guanidine (c) with an appropriate arylsulfonyl halide (e.g. ArSO$_2$Cl) in the presence of base (typically sodium hydroxide). (iv) Hydroxy compound (e) can be converted into corresponding halide by treatment with a halogenating reagent. For example for a chlorine substitutent, treatment of hydroxyl compound (e) with POCl$_3$ provides target chloro-compound (f). (v) The halogen substituent of compound (f) can be further functionalized with an alkoxy, amino, or thiol group by as follows. Thus treating compound (f) with an appropriately substituted amine, in a solvent such as tetrahydrofuran (THF) provides compound (g), wherein R$^4$ is an amino group. (vi) Treating compound (f) with an appropriately substituted alkoxide (R$^4$ONa), in an alcoholic solvent (R$^4$OH) provides compound (g), wherein R$^4$ is an alkoxy group. (vii) Treating compound (f) with an appropriately substituted mercaptan (R$^4$SH), in the presence of base (typically Cs$_2$CO$_3$) in a polar, aprotic solvent, for example DMF, provides compound (g), wherein R$^4$ is thiol group.

Scheme 1: General Route 1

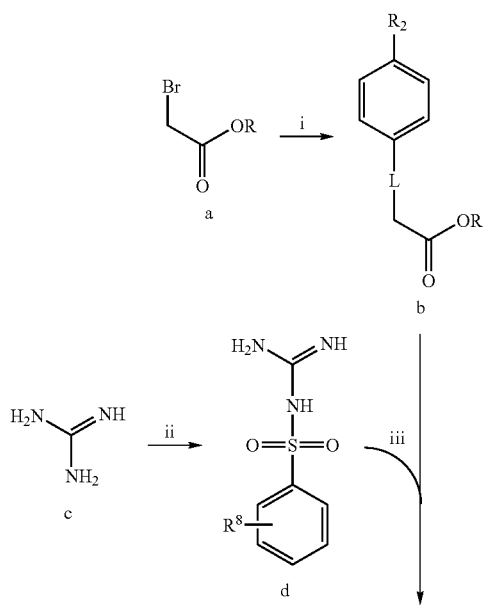

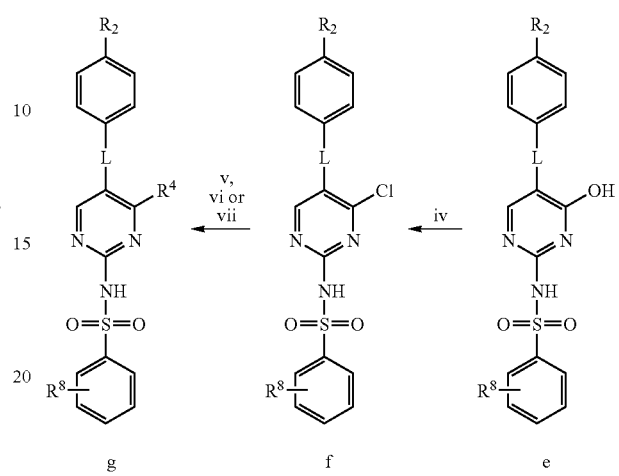

Alternatively as shown in Scheme 2, compounds of the present invention can be prepared beginning with commercially available epihalohydrin (h). (i) Treatment of a with appropriately substituted organometallic (e.g. RMgBr) in an aprotic solvent, for example, tetrahydrofuran provides the adduct (j). (ii) Oxidation of the alcohol with for example, Dess-Martin Periodinane, (DCM), provides halocarbonyl derivative (k). (iii) The halogen substituent of compound (k) can be further derivitized by treatment with an appropriately substituted phenol or thiophenol (iii, ArOH or ArSH) and a base, for example, potassium carbonate, in a solvent, for example, acetone provides the adduct (l). (iv) Treatment of (l) with DMFdimethylacetal in the presence of isopropanol and a base, for example sodium methoxide (NaOMe), and subsequent coupling with an appropriately substituted benzene sulfonylguanidine (m) provides tri-aryl derivative (n).

Scheme 2: General Route 2

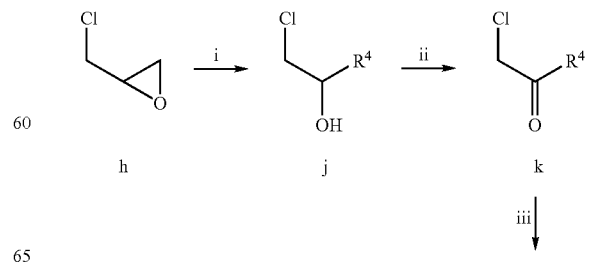

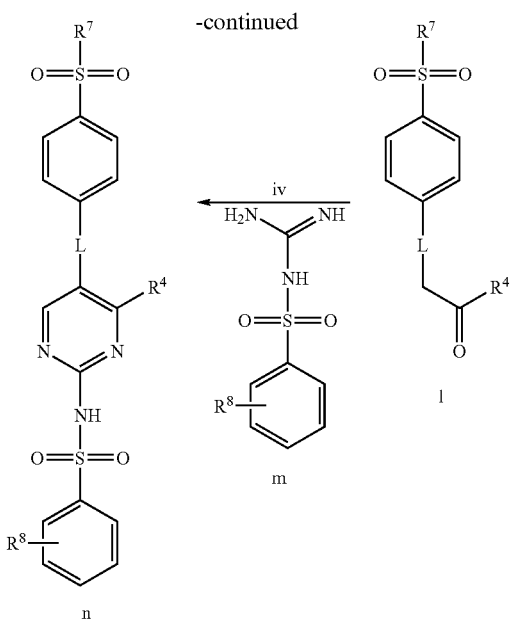

Scheme 3 depicts an alternative preparation of compounds of formula I, wherein Ar is a substituted or unsubstituted pyridine. (i) Thus, treatment of n with appropriately substituted thiophenol (e.g. ArSH) and a palladium catalyst, in a solvent, for example, NMP provides the adduct (o). (ii) Coupling with an appropriately substituted arylsulfonylhalide in the presence of a base, for example pyridine, in a solvent, for example, dichloromethane (DCM) provides tri-aryl derivative (p). (iii) When $R^5$ is an ester, the corresponding acid (q) is formed by hydrolysing (p) for example, with lithium hydroxide in aqueous tetrahydrofuran. (iv) Acid compound (q) can be converted into corresponding hydroxamic ester (r) by treatment with an appropriately substituted amine (e.g. N-methyl O-methylhydroxylamine) in a solvent such as TBTU in the presence of a base, such as diisopropylethylamine (DIPEA)). (v) The amide/hydroxamide substituent of compound (r) can be further functionalized into a ketone by treating compound (r) with an organometallic, such as an alkyl Grignard, in an etheral solvent such as tetrahydrofuran (THF).

Scheme 3: Pyridines 1

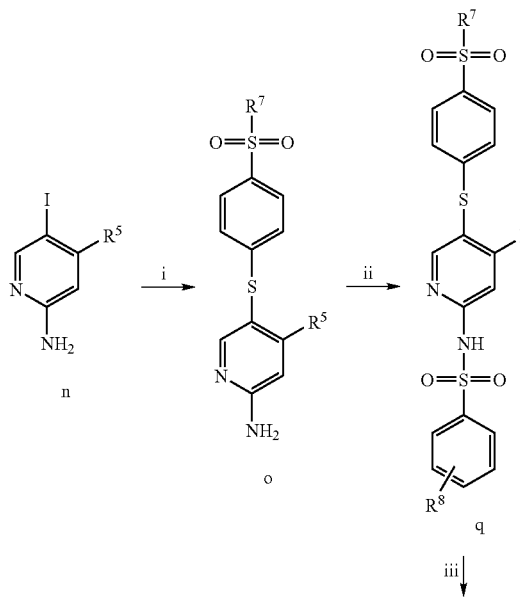

Scheme 4 depicts an alternative preparation of compounds of formula I, wherein Ar is a substituted or unsubstituted pyridine. (i) Initial treatment of t with an appropriate arylsulfonyl halide (e.g. ArSO$_2$Cl) in the presence of base (typically sodium hydroxide) provides target chloro-compound (u). (ii) Subsequent treatment with appropriately substituted phenol or thiophenol (e.g. ArOH or ArSH) and a base, for example, potassium carbonate, in a solvent, for example, acetone provides the adduct (v).

Scheme 4: Pyridines 2

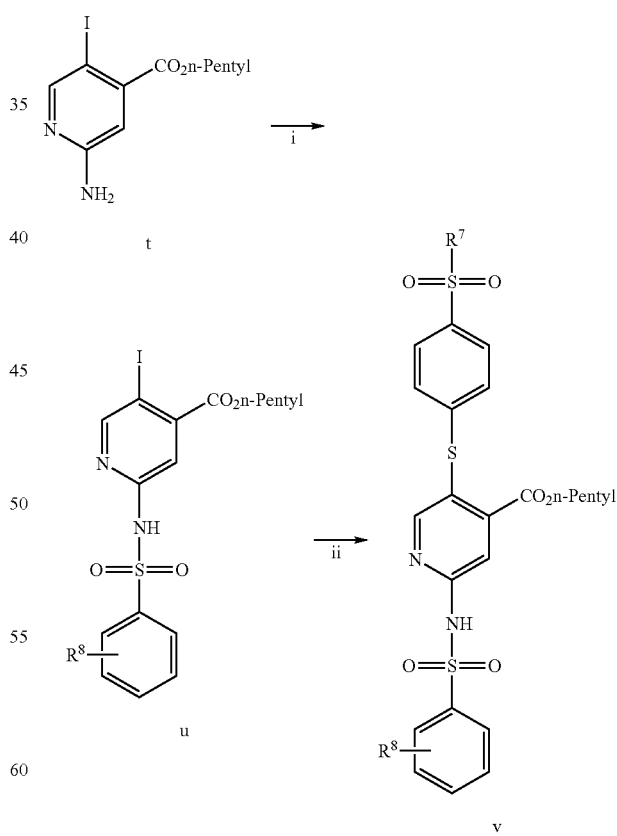

Scheme 5 depicts an alternative preparation of compounds of formula I, wherein Ar is a substituted or unsubstituted pyridine. (i) Thus, treatment of w with appropriately substituted thiophenol (e.g. ArSH) and a palladium catalyst, in a solvent, for example, NMP provides the adduct (x). (ii) The corresponding acid (y) is formed by hydrolysing (x) for example, with lithium hydroxide in aqueous tetrahydrofuran. (iii) Acid compound (y) can be converted into corresponding hydroxamic ester (z) by treatment with an appropriately substituted amine (e.g. N-methyl O-methylhydroxylamine) in a solvent such as TBTU in the presence of a base, such as diisopropylethylamine (DIPEA)). (iv) Coupling with an appropriately substituted arylsulfonylhalide in the presence of a base, for example pyridine, in a solvent, for example, dichloromethane (DCM) provides tri-aryl derivative (aa). (v-vii) The amide/hydroxamide substituent of compound (aa) can be further functionalized into a ketone (dd) by converting to aldehyde intermediate (bb) and subsequent treatment with an organometallic, such as an alkyl Grignard, in an etheral solvent such as tetrahydrofuran (THF) to provide (cc) and oxidation as already described herein.

Scheme 6 depicts an alternative preparation of compounds of formula I, wherein Ar F is a substituted or unsubstituted pyridazine. (i) Thus, treatment of dichloropyrazine ee with silver nitrate, alkanoate, and sulfuric acid, in a solvent, for example, water and subsequent treatment with ammonium persulfate provides the adduct (ff). (ii) Treatment of ff with aqueous ammonium hydroxide provides aminopyridazine (gg). (iii) Treatment of gg with an appropriately substituted thiophenol (e.g. ArSH), in a solvent, for example, pyridine provides the adduct (hh). (iv) Coupling with an appropriately substituted arylsulfonylhalide in the presence of a base, for example pyridine, in a solvent, for example, dichloromethane (DCM) provides tri-aryl derivative (jj).

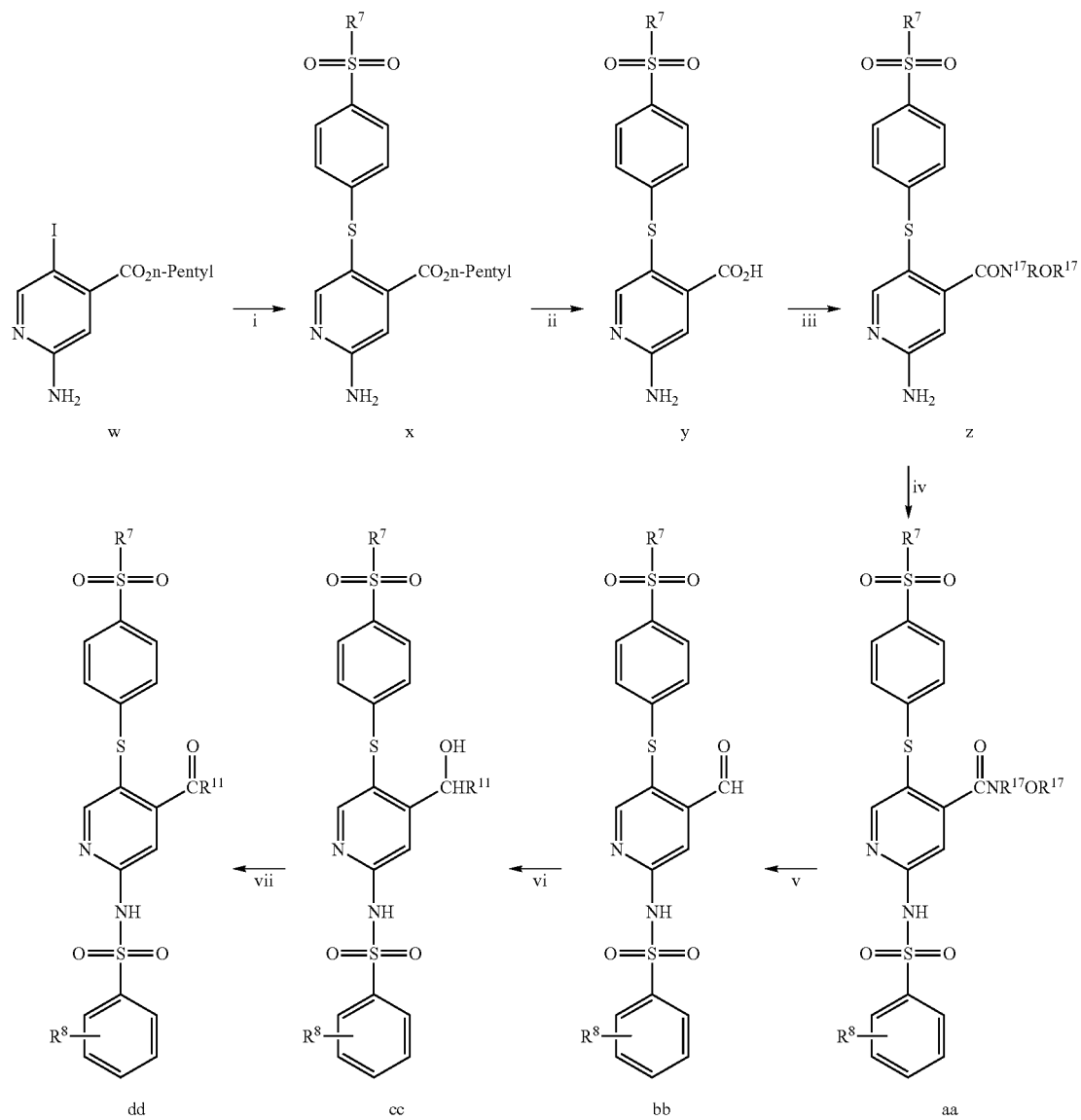

Scheme 5: Pyridines 3

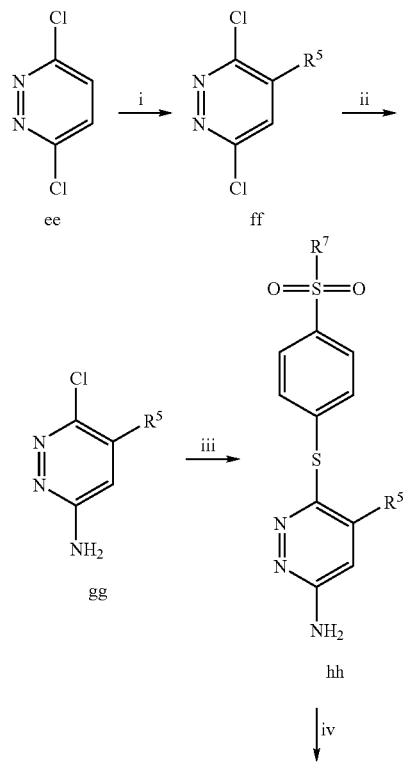

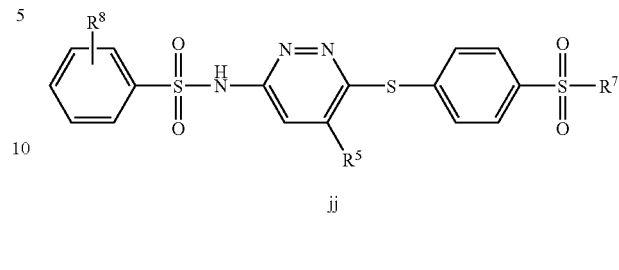

As shown in Scheme 7, compounds of the present invention can be prepared beginning with commercially available 4-hydroxy-5-nitrobenzenesulfonic acid sodium salt (kk). (i and ii) Treatment of kk with thionyl chloride and an appropriately substituted amine in dichloromethane provides the adduct (ll). (iii) Deprotonation of the hydroxyl group with sodium hydride in dimethylformamide (DMF) and then coupling with, for example, an appropriately substituted 4-fluoro or 4-chloronitrobenzene provides bi-aryl derivative (mm). (iv) Reduction of the nitro group of mm with, for example, iron powder and ammonium chloride in the presence of an aqueous alcohol solution provides amine (nn). (v) Treatment of nn with appropriately substituted arylsulfonylhalide (e.g. ArSO$_2$Cl) in the presence of base (typically pyridine or a tertiary amine) in dichloromethane provides the target sulfonamide adduct (oo).

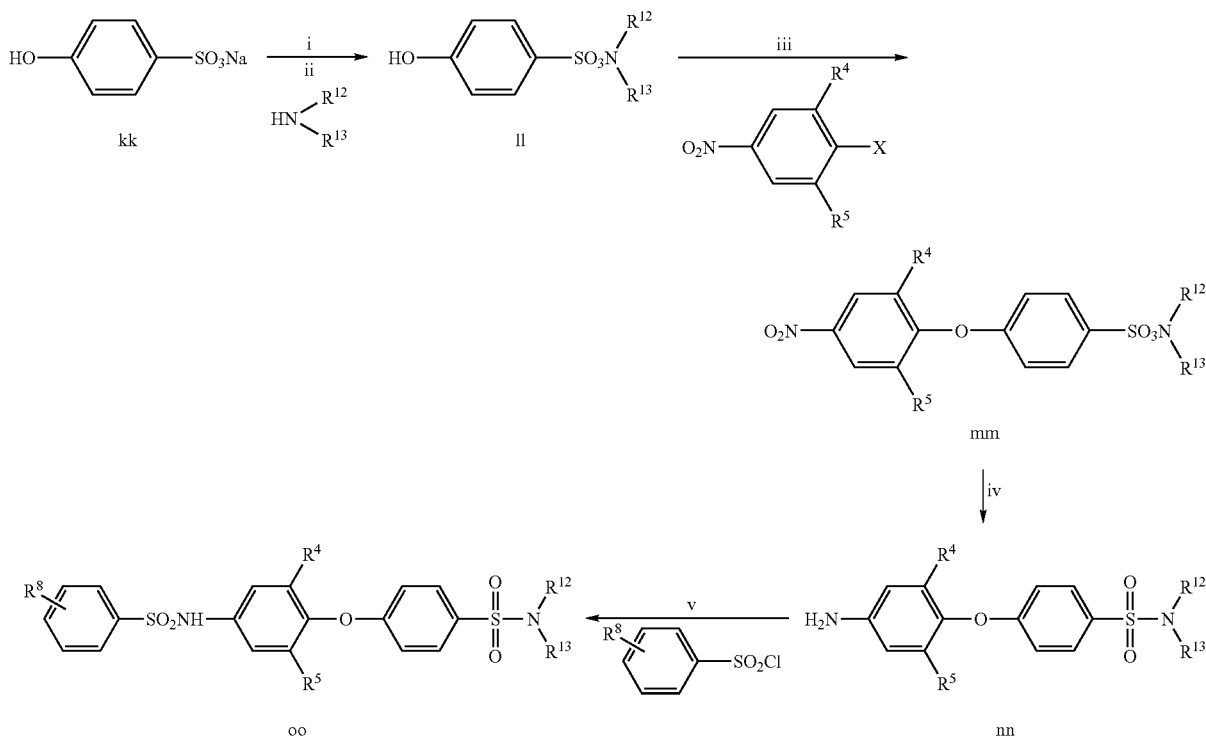

Scheme 8 depicts an alternative preparation of compounds of formula XIV, wherein Ar and B is substituted or unsubstituted benzene and $R^3$, $R^4$, $R^5$, or $R^6$ is an alkyl ether —$OR^{11}$. (i) Treatment of pp with sodium hydride and the appropriately substituted haloaryl compound in an aprotic solvent, for example, DMF provides the adduct (qq). (ii) Hydrolysis of the ester with for example, lithium hydroxide in aqueous THF, provides acid derivative (rr). (iii and iv) The acid substituent of compound (rr) can be reduced by initial treatment with, for example, isobutylchloroformate in tetrahydrofuran and a base, for example, triethylamine, in a solvent, for example, tetrahydrofuran and subsequent treatment with a reducing agent, for example, sodium borohydride in methanol provides the adduct (ss). (v) Treatment with thionyl chloride in a solvent, for example, dichloromethane provides the haloalkyl derivative (tt). (vi) Solvolysis of the halide with for example, an alkylalcohol or alkoxide provides ether derivative (uu). (viii) Reduction of the nitro group of uu with, for example, iron powder and ammonium chloride in the presence of an aqueous alcohol solution provides amine (vv). (ix) Treatment of vv with appropriately substituted arylsulfonylhalide (e.g., $ArSO_2Cl$) in the presence of base (typically pyridine or a tertiary amine) in dichloromethane provides the target sulfonamide adduct (ww).

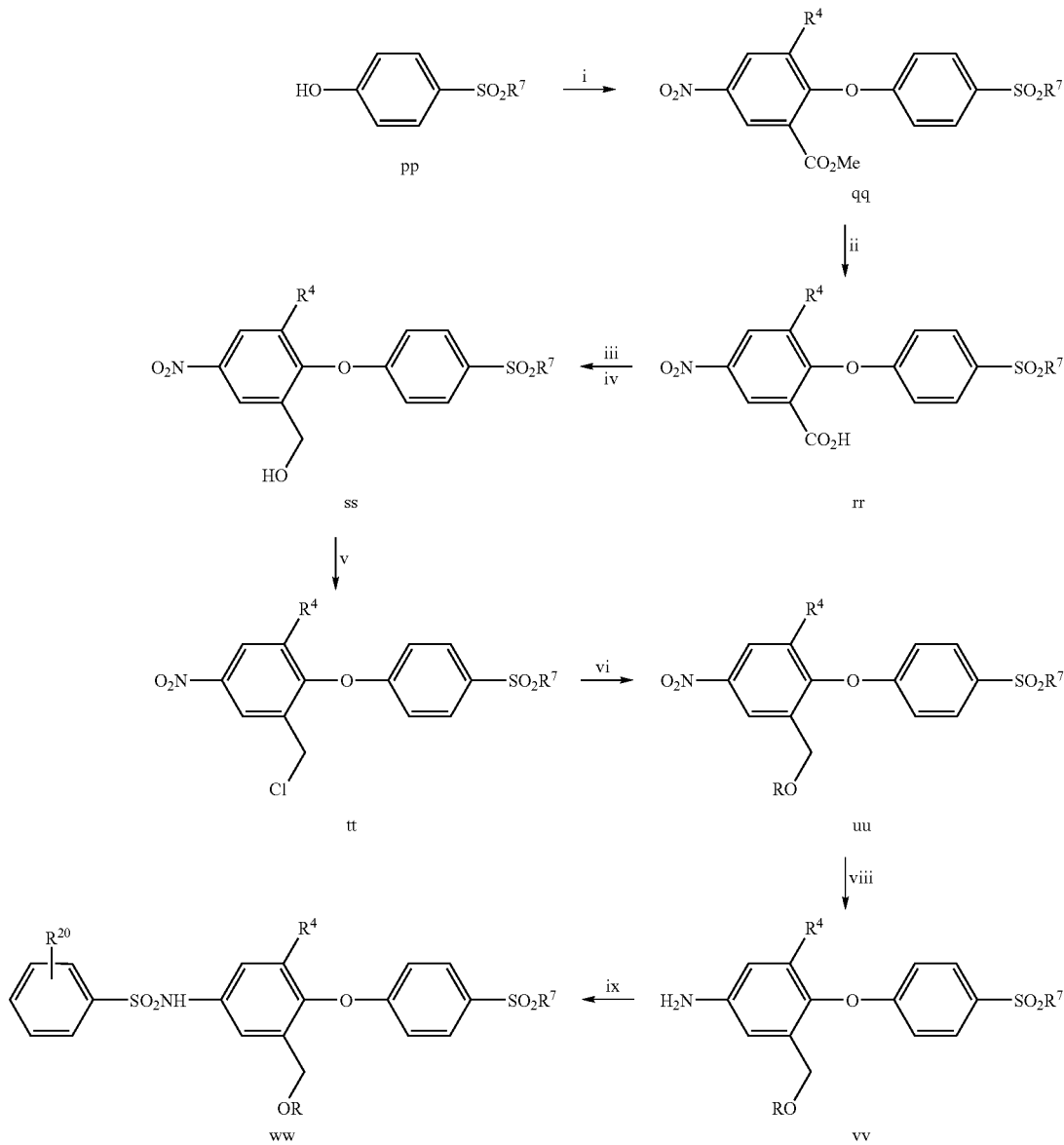

Scheme 9 depicts an alternative preparation of compounds of formula XIV, wherein Ar and B is substituted or unsubstituted benzene and $R^3$, $R^4$, $R^5$, or $R^6$ is an alkylamine-N ($R^{12}R^{13}$)—. (viii) Treatment of halomethyl intermediate xx with an appropriately substituted amine, for example, pyrrolidine, provides amine derivative (yy). (ix) Reduction of the nitro group of yy with, for example, iron powder and ammonium chloride iv in the presence of an aqueous alcohol solution provides amine (zz). (x) Treatment of zz with appropriately substituted arylsulfonylhalide (e.g. $ArSO_2Cl$) in the presence of base (typically pyridine or a tertiary amine) in dichloromethane provides the target sulfonamide adduct (aaa).

Scheme 9

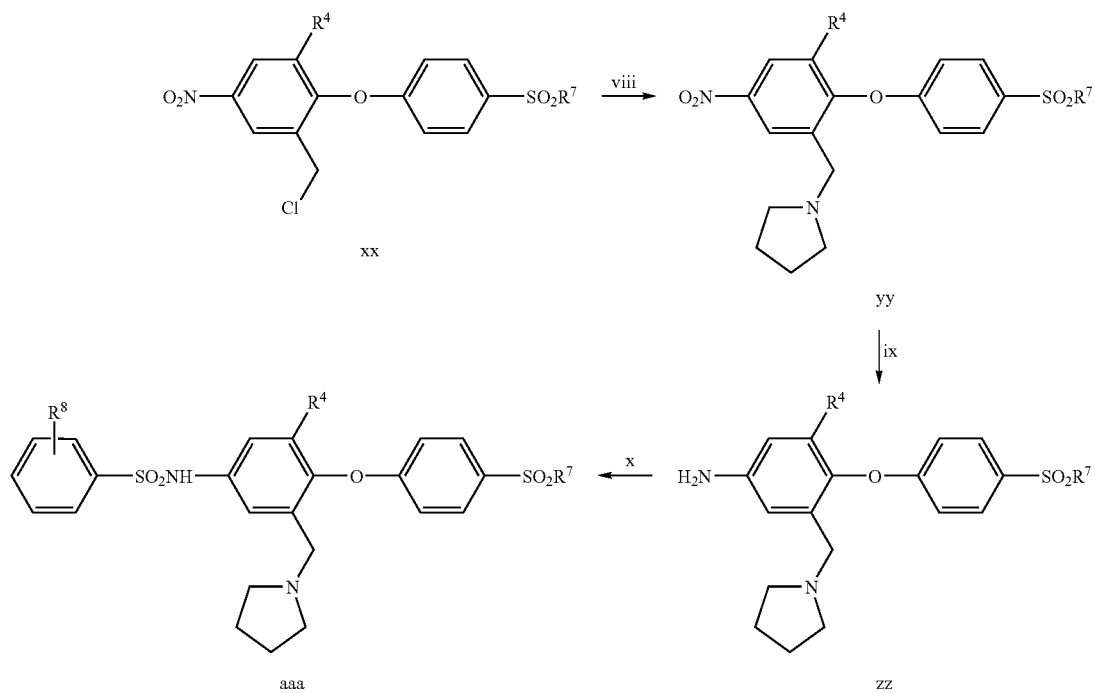

Scheme 10 depicts an alternative preparation of compounds of formula XIV, wherein Ar and B is a substituted or unsubstituted benzene and $R^3$, $R^4$, $R^5$, or $R^6$ is an amide-CON($R^{11}$)—. (v) Treatment of acid bbb with thionyl chloride provides acid chloride ccc. (vi) Treatment of ccc with an appropriately substituted amine (e.g. HN(alkyl)alkyl) in an aprotic solvent, for example, dichloromethane (DCM) provides the amide adduct (ddd). (vii) Reduction of the nitro group of ddd with, for example, iron powder and ammonium chloride in the presence of an aqueous alcohol solution provides amine (eee). Alternatively, the nitro group can be reduced by hydrogenation with palladium on carbon in an alcohol solution. (viii) Treatment of eee with appropriately substituted arylsulfonylhalide (e.g. ArSO$_2$Cl) in the presence of base (typically pyridine or a tertiary amine) in dichloromethane provides the target sulfonamide adduct (fff).

Scheme 10:

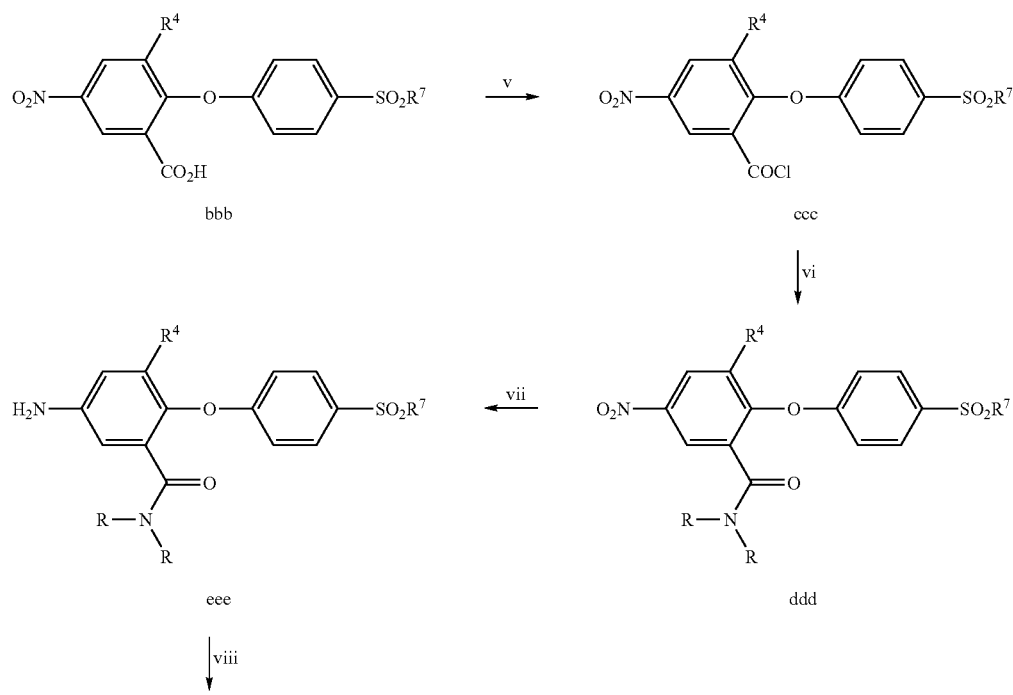

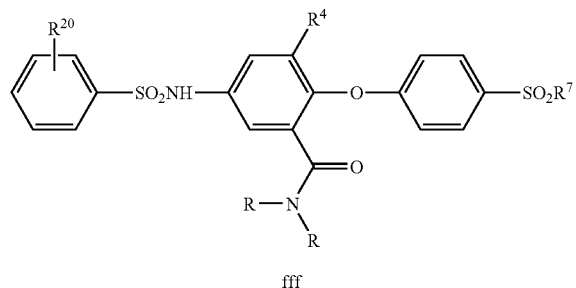

fff

Scheme 11 depicts an alternative preparation of compounds of formula XIV, wherein Ar and B is a substituted or unsubstituted benzene and $R^3$, $R^4$, $R^5$, or $R^6$ are halogens which can be carried through the reaction conditions outlined above.

(DMF) provides the thioether adduct (jjj). (ii) Reduction of the nitro group of jjj with, for example, iron powder and ammonium chloride in the presence of an aqueous alcohol solution provides amine (kkk). (iii) Treatment of kkk with appropriately substituted arylsulfonylhalide (e.g. $ArSO_2Cl$)

Scheme 11:

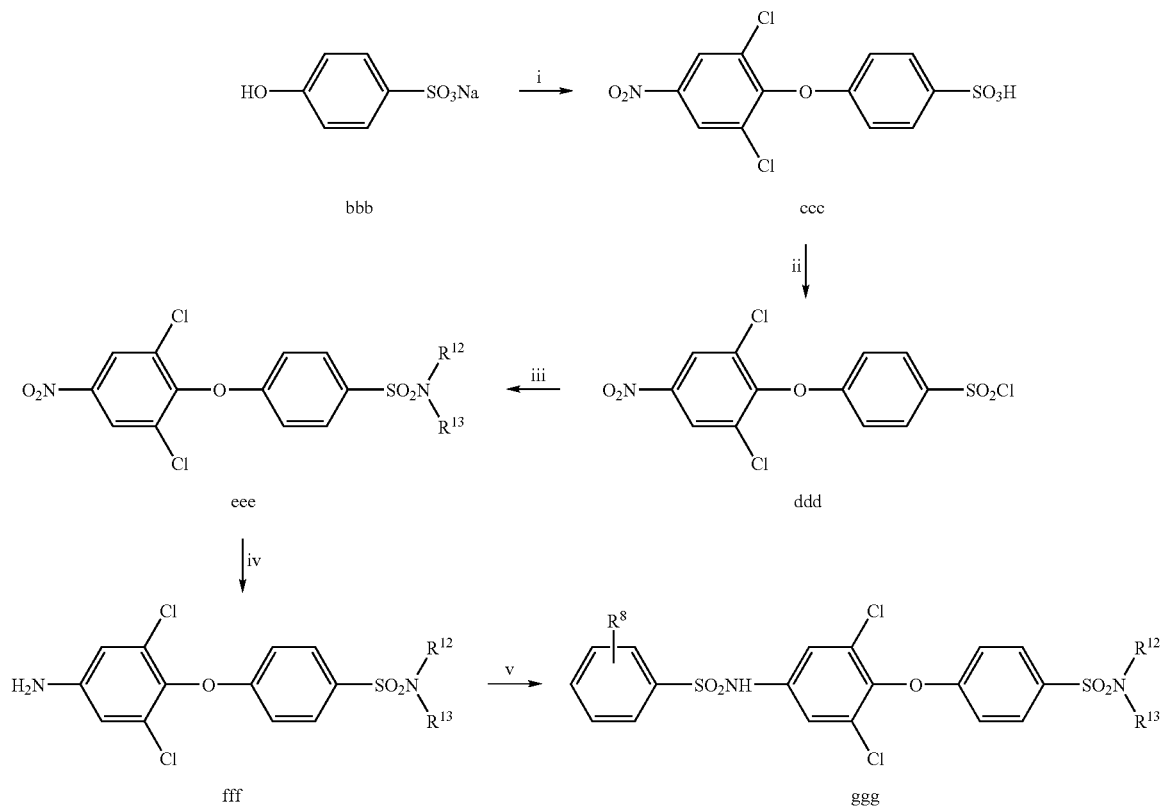

Scheme 12 depicts an alternative preparation of compounds of formula XIV, wherein B is a substituted or unsubstituted benzene and $R^3$, $R^4$, $R^5$, or $R^6$ can be a variety of substituents. (i) Displacement of the halogen of hhh with an protected thiol equivalent (e.g. 4-methoxybenzyl mercaptan) in the presence of a base, for example, sodium hydride (NaH) in an aprotic solvent, for example, dimethylformamide in the presence of base (typically pyridine or a tertiary amine) in dichloromethane provides the sulfonamide adduct (lll). (iv) Deprotection of the thiol group with trifluoroacetic acid and (vi) coupling with an appropriately substituted haloaryl compound in the presence of a base, for example an alkylamine in a solvent, for example, DMF provides tri-aryl derivative (nnn).

Scheme 12:

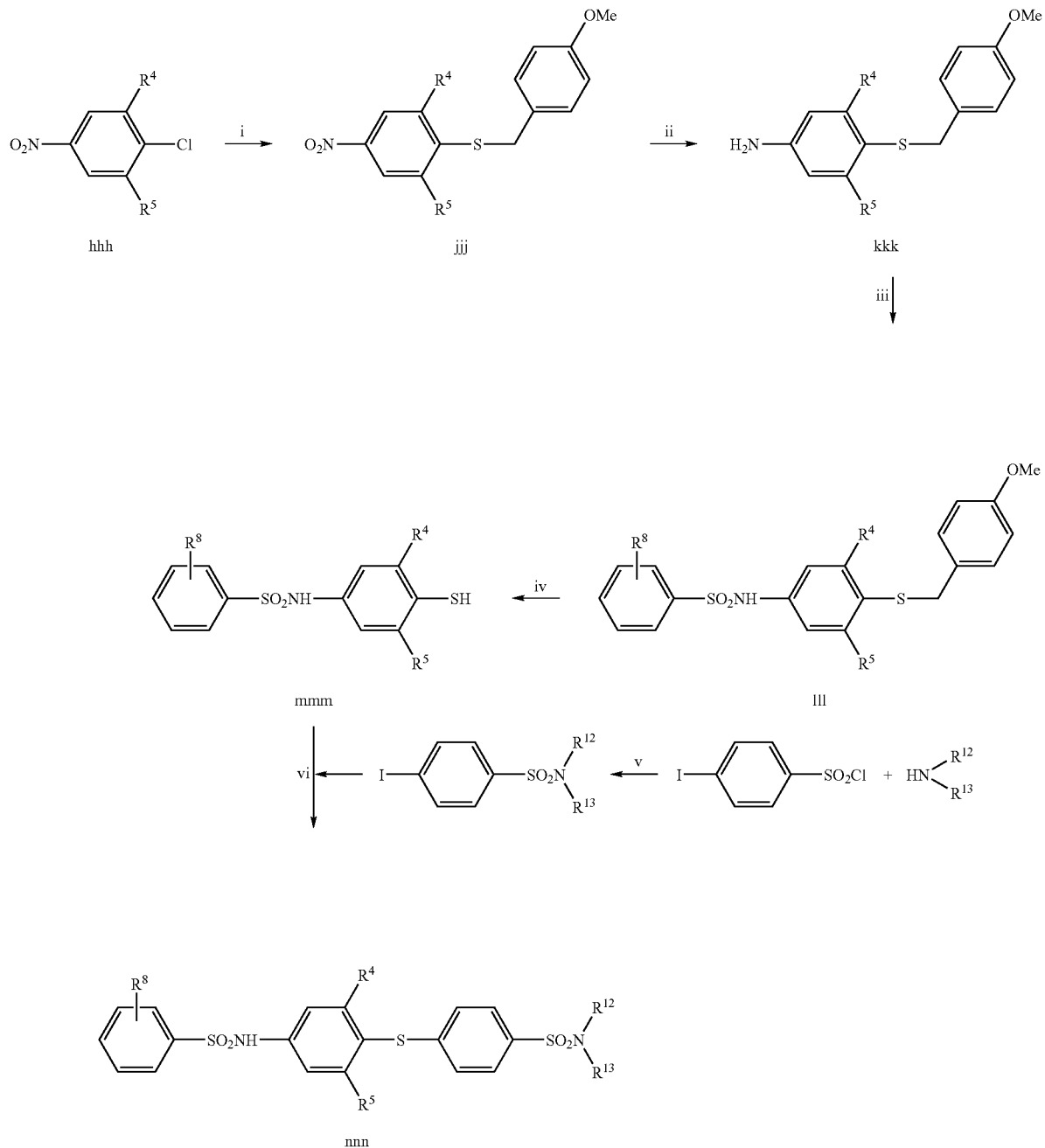

Scheme 13a depicts an alternative preparation of compounds of formula XIV, wherein B is a substituted or unsubstituted pyridine and $R^3$, $R^4$, $R^5$, or $R^6$ can be a variety of substituents. (i) Displacement of the halogen of ooo with an protected thiol equivalent (e.g. 4-methoxybenzyl mercaptan) in the presence of a base, for example, sodium hydride (NaH) in an aprotic solvent, for example, dimethylformamide (DMF) provides the thioether adduct (ppp). (ii) Reduction of the nitro group of ppp with, for example, iron powder and ammonium chloride in the presence of an aqueous alcohol solution provides amine (qqq). (iii) Treatment of qqq with appropriately substituted arylsulfonylhalide (e.g. ArSO$_2$Cl) in the presence of base (typically pyridine or a tertiary amine) in dichloromethane provides the sulfonamide adduct (rrr). (iv) Coupling with an appropriately substituted halopyridine (vvv) in the presence of a base, for example an alkylamine in a solvent, for example, DMF provides tri-aryl derivative (www).

Scheme 13a:

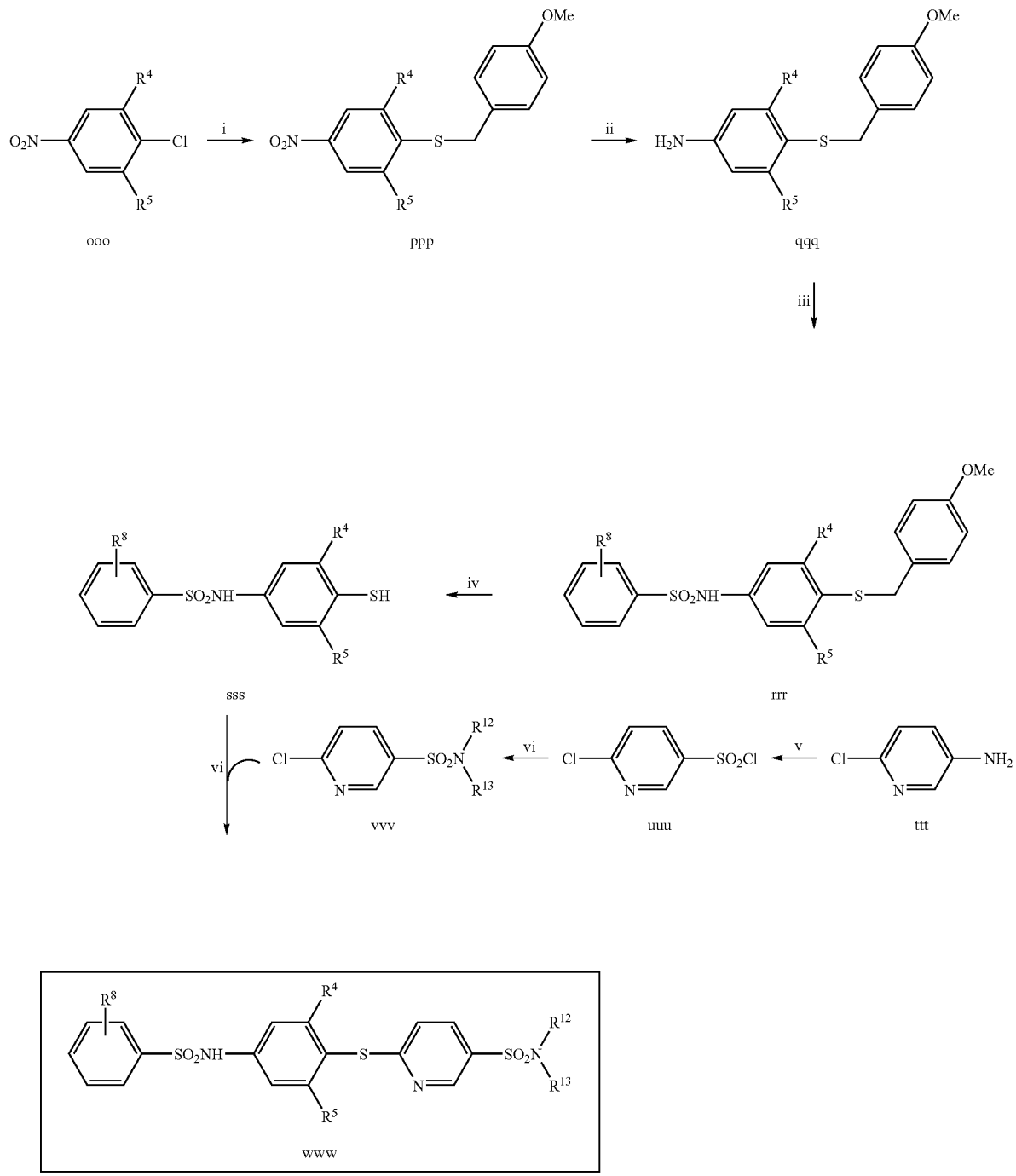

For compounds where $R^5$ is a ketone $COR^{11}$ wherein $R^{11}$ is an alkyl group larger than Me, compound rrr can be further converted to compounds zzz as shown in Scheme 13b. (i) Hydrolysis of rrr with aqueous base, for example lithium hydroxide in aqueous tetrahydrofuran provides the acid sss. (ii) The carboxylic acid is converted to the hydroxamic ester ttt for example by reaction with N,O-dimethyl hydroxylamine in the presence of TBTU in a polar solvent such as DMF. (iii) Reaction of the hydroxamic ester with an organometallic reagent (eg. RMgX where R is alkyl and X is halogen) in an aprotic solvent such as tetrahydrofuran gives the ketone uuu. (iv) Treatment of the ketone with trifluoroacetic acid in dichloromethane in the presence of a radical scavenger such as thioanisole gives the free thiol vvv. (v) Coupling with an appropriately substituted halopyridine vvv in the presence of a base, for example an alkylamine in a solvent, for example, DMF provides the triaryl derivative www.

Scheme 13b:

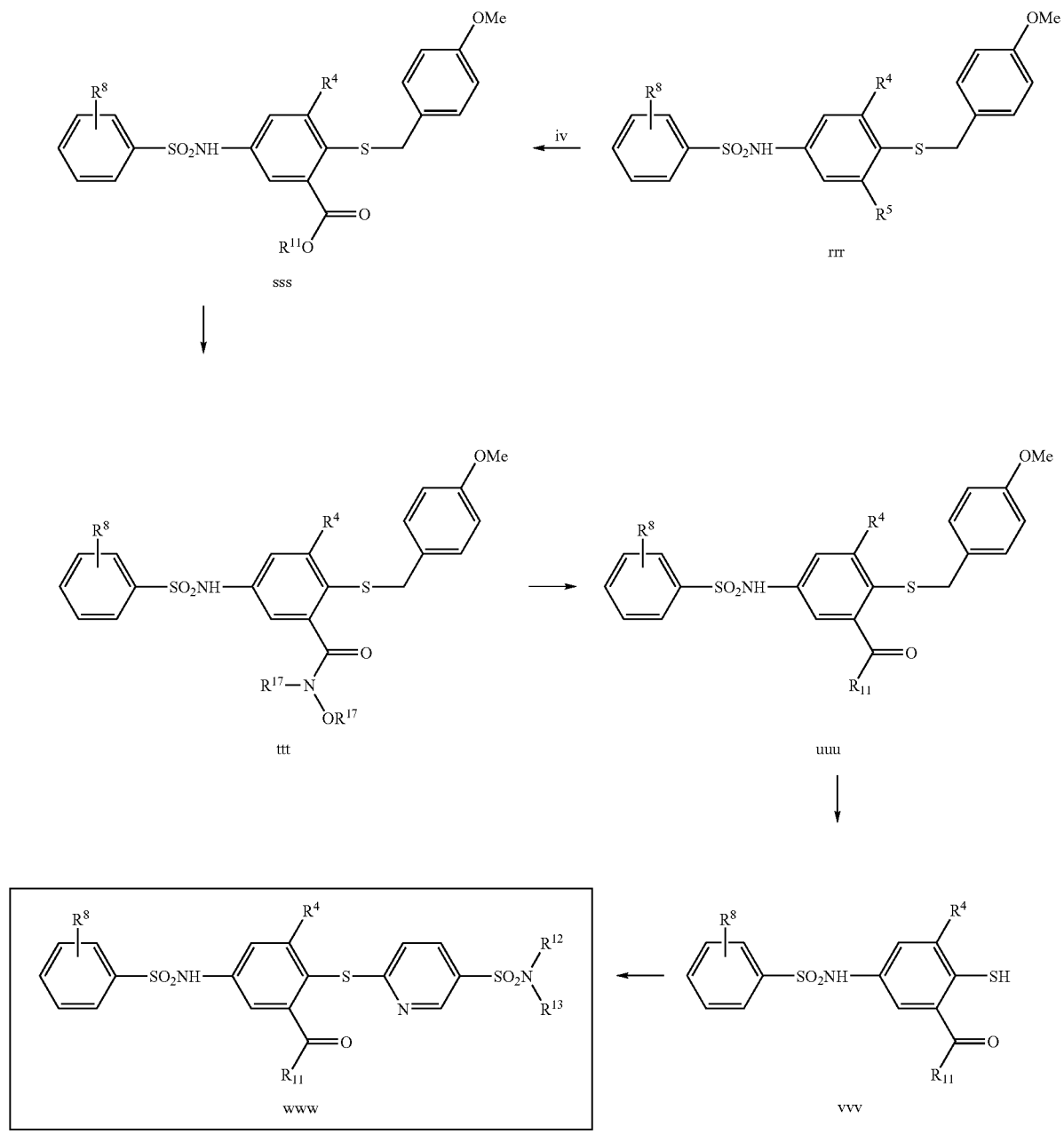

Scheme 14 depicts an alternative preparation of compounds of formula XIV, wherein B is a substituted or unsubstituted benzene and $R^3$, $R^4$, $R^5$, or $R^6$ can be a variety of substitutents. (i) Treatment of aaaa with an appropriately substituted alkoxyamine (e.g. HN(OMe)Me) in an aprotic solvent, for example, dichloromethane (DCM) provides the hydroxamic ester adduct (bbbb). (ii) The halogen substituent of compound (bbbb) can be further derivitized by treatment with an appropriately substituted phenol or thiophenol (e.g. ArOH (cccc) or ArSH) and a base, for example, potassium carbonate, in a solvent, for example, dimethylformamide (DMF) provides the adduct (dddd). (iii) Reduction of the nitro group of dddd with, for example, iron powder and ammonium chloride in the presence of an aqueous alcohol solution provides amine (eeee). Alternatively, the nitro group can be reduced by hydrogenation with palladium on carbon in an alcohol solution. (iv) Treatment of eeee with appropriately substituted arylsulfonylhalide (e.g. $ArSO_2Cl$) in the presence of base (typically pyridine or a tertiary amine) in dichloromethane provides the target sulfonamide adduct (ffff). (v) The hydroxamic ester substituent of compound (ffff) can be further derivitized by treatment with appropriately substituted organometalic (e.g. RMgBX, wherein R is alkyl and X is a halogen) in an aprotic solvent, for example, tetrahydrofuran provides the adduct (gggg).

Scheme 14:

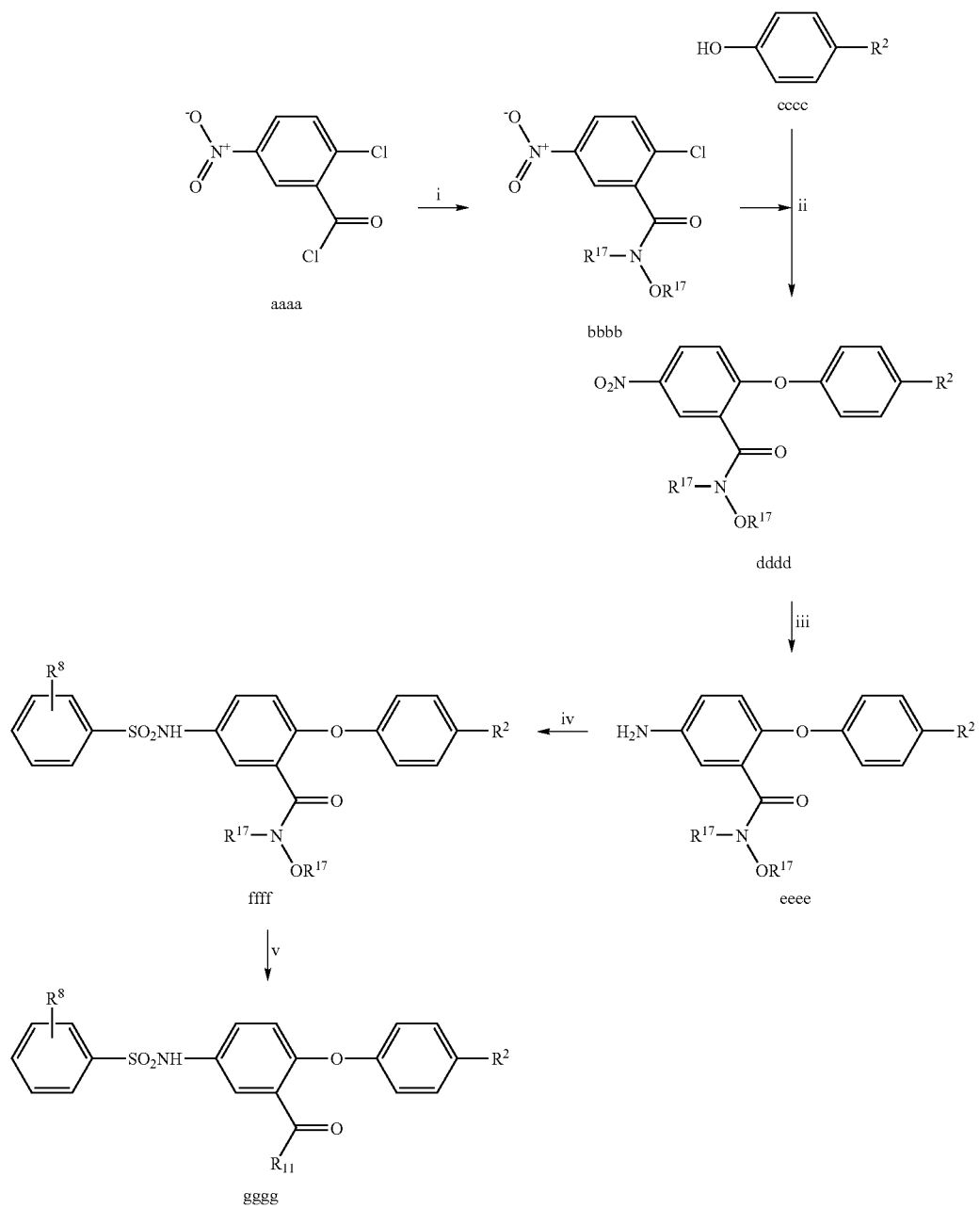

Other compounds of the present invention can be prepared as shown in the Examples below.

.2.3 Analysis of the Compounds

The compounds of the present invention can be evaluated for modulation of the PPARγ receptor using assays such as those described in Jiang, et al., *Nature* 391:82-86 (1998), Ricote, et al., *Nature* 391:79-82 (1998) and Lehmann, et al., *J. Biol. Chem.* 270(12): 12953-12956 (1995). Alternatively, the compounds can be evaluated for their ability to displace radiolabeled BRL 49653 from a PPARγ-GST fusion protein as follows:

Materials:

PPARγ-GST fusion protein (prepared according to standard procedures), [$^3$H]-BRL 49653 having 50 Ci/mmol specific activity, Polyfiltronics Unifilter 350 filtration plate and glutathione-Sepharose® beads (from Pharmacia: washed twice with 10× binding buffer in which BSA and DTI can be left out).

Method:

Binding buffer (10 mM Tris-HCl, pH 8.0, 50 mM KCl, 10 mM DTT, 0.02% BSA and 0.01% NP-40) is added in 80-μL amounts to the wells of the filtration plate. The test compound is then added in 10 μL of DMSO. The PPARγ-GST fusion protein and radiolabeled BRL compound are premixed in binding buffer containing 10 mM DTT and added in 10-μL amounts to the wells of the plate to provide final concentrations of 1 g/well of PPARγ-GST fusion protein and 10 nM [$^3$H]-BRL 49653 compound. The plate is incubated for 15 min. Glutathione-agarose bead is added in 50 µL of binding buffer, and the plate is vigorously shaken for one hour. The plate is washed four times with 200 µL/well of binding buffer (without BSA and DTT). The bottom of the plate is sealed and 200 µL/well of scintillation cocktail is added. The top of the plate is then sealed and the radioactivity is determined.

The compounds of the present invention can also be evaluated for modulation of the PPARγ or PPARδ receptor using PPAR transient tranactivation assays, as described in U.S. Pat. No. 6,602,901 and U.S. Pat No. 6,869,967, the contents of which are incorporated by reference in their entirety. The PPAR transient transactivation assays are based on transient transfection into human HEK293 cells of two plasmids encoding a chimeric test protein and a reporter protein respectively. The chimeric test protein is a fusion of the DNA binding domain (DBD) from the yeast GAL4 transcription factor to the ligand binding domain (LBD) of a human PPAR. The PPAR-LBD moiety harbors in addition to a ligand binding pocket also a native activation domain (activating function 2, "AF2") allowing the fusion protein to function as a PPAR ligand dependent transcription factor. The GAL4 DBD will direct the chimeric protein to bind to Gal4 enhancers (of which none existed in HEK293 cells). The reporter plasmid contains a Gal4 enhancer driving the expression of the firefly luciferase protein. After transfection, HEK293 cells express the GAL4-DBD-PPAR-LBD fusion protein. The fusion protein will in turn bind to the Gal4 enhancer controlling the luciferase expression, and do nothing in the absence of ligand. Upon addition to the cells a PPAR ligand luciferase protein will be produced in amounts corresponding to the activation of the PPAR protein. The amount of luciferase protein is measured by light emission after addition of the appropriate substrate.

Cell Culture and Transfection

HEK293 cells are grown in DMEM+10% FCS. Cells are seeded in 96-well plates the day before transfection to give a confluency of 50-80% at transfection. A total of 0.8 µg DNA containing 0.64 µg pM1α/γLBD, 0.1 µg pCMVβGal, 0.08 µg pGL2(Gal4)$_5$ and 0.02 µg pADVANTAGE is transfected per well using FuGene transfection reagent according to the manufacturers instructions (Roche). Cells are allowed to express protein for 48 h followed by addition of compound.

Plasmids: Human PPAR α, γ or δ is obtained by PCR amplification using cDNA synthesized by reverse transcription of mRNA from human liver, adipose tissue and placenta respectively. Amplified cDNAs are cloned into pCR2.1 and sequenced. The ligand binding domain (LBD) of each PPAR isoform is generated by PCR (PPARα: aa 167-C-terminus; PPARγ. aa 165-C-terminus; PPARδ: aa 128-C-terminus) and fused to the DNA binding domain (DBD) of the yeast transcription factor GAL4 by subcloning fragments in frame into the vector pM1 (Sadowski et al. (1992), Gene 118, 137) generating the plasmids pM1αLBD, pM1γLBD and pM1δ. Ensuing fusions are verified by sequencing. The reporter is constructed by inserting an oligonucleotide encoding five repeats of the GAL4 recognition sequence (5× CGGAG-TACTGTCCTCCG(AG)) (Webster et al. (1988), Nucleic Acids Res. 16, 8192) into the vector pGL2 promotor (Promega) generating the plasmid pGL2(GAL4)$_5$. pCMVβ-Gal can be purchased from Clontech and pADVANTAGE can be purchased from Promega.

In vitro Transactivation Assay

Compounds: All compounds are dissolved in DMSO and diluted 1:1000 upon addition to the cells. Compounds are tested in quadruple in concentrations ranging from 0.001 to 300 µM. Cells are treated with compound for 24 h followed by luciferase assay. Each compound is tested in at least two separate experiments.

Luciferase assay: Medium including test compound is aspirated and 100 µl PBS incl. 1 mM Mg++ and Ca++ is added to each well. The luciferase assay is performed using the LucLite kit according to the manufacturers instructions (Packard Instruments). Light emission is quantified by counting on a Packard LumiCounter. To measure β-galactosidase activity 25 µl supernatant from each transfection lysate is transferred to a new microplate. β-galactosidase assays are performed in the microwell plates using a kit from Promega and read in a Labsystems Ascent Multiscan reader. The β-galactosidase data are used to normalize (transfection efficiency, cell growth etc.) the luciferase data.

Statistical Methods

The activity of a compound is calculated as fold induction compared to an untreated sample. For each compound the efficacy (maximal activity) can be given as a relative activity compared to to Wy14,643 for PPARα, Rosiglitazone for PPARγ, and Carbacyclin for PPARδ. The EC50 is the concentration giving 50% of maximal observed activity. EC50 values are calculated via non-linear regression using Graph-Pad PRISM 3.02 (GraphPad Software, San Diego, Calif.). The results are expressed as means±SD.

.2.4 Compositions and Methods of Treatment

The compounds of the present invention can administered via any suitable route, most preferably orally or parenterally, in a preparation appropriately tailored to that route. Thus, the compounds of the present invention can be administered by injection, for example, intravenously, intramuscularly, intracutaneously, subcutaneously, intraduodenally, or intraperitoneally. The present invention also contemplates the use of depot formulations in which the active ingredient(s) is released over a defined time period. Also, the compounds described herein can be administered by inhalation, for example, intranasally. Additionally, the compounds of the present invention can be administered transdermally. Accordingly, the present invention also provides pharmaceutical compositions comprising a pharmaceutically acceptable carrier or excipient and either a compound of formula I and XIV or a pharmaceutically acceptable salt of a compound of formula I and XIV For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which can also act as diluents, flavoring agents, binders, preservatives, tablet disintegrating agents, or an encapsulating material.

In powders, the carrier is a finely divided solid which is in a mixture with the finely divided active component. In tablets, the active component is mixed with the carrier having the necessary binding properties in suitable proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it.

Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations can contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation can be varied or adjusted from 0.1 mg to 1000 mg, preferably 1.0 mg to 100 mg according to the particular application and the potency of the active component. The composition can, if desired, also contain other compatible therapeutic agents.

In therapeutic use for the treatment of obesity, diabetes, inflammatory conditions or other conditions or disorders mediated by PPARγ or PPARδ, the compounds utilized in the pharmaceutical method of the invention are administered at the initial dosage of about 0.001 mg/kg to about 100 mg/kg daily. A daily dose range of about 0.1 mg/kg to about 10 mg/kg is preferred. The dosages, however, can be varied depending upon the requirements of the patient, the severity of the condition being treated, and the compound being employed. Determination of the proper dosage for a particular situation is within the skill of the practitioner. Generally, treatment is initiated with smaller dosages which are less than the optimum dose of the compound. Thereafter, the dosage is increased by small increments until the optimum effect under the circumstances is reached. For convenience, the total daily dosage can be divided and administered in portions during the day, if desired.

The compositions can be advantageously combined and/or used in combination with agents useful in the treatment and/or prevention of metabolic disorders, inflammatory conditions, neoplastic diseases and complications thereof and pathologies associated therewith (e.g., cardiovascular disease and hypertension). In many instances, administration of the subject compounds or compositions in conjunction with these alternative agents enhances the efficacy of such agents. Accordingly, in some instances, the present compounds, when combined or administered in combination with, e.g., anti-diabetic agents, can be used in dosages which are less than the expected amounts when used alone, or less than the calculated amounts for combination therapy.

Suitable agents for combination therapy include those that are currently commercially available and those that are in development or will be developed. Exemplary agents useful in the treatment of metabolic disorders include, but are not limited to: (a) anti-diabetic agents such as insulin, sulfonylureas (e.g., meglinatide, tolbutamide, chlorpropamide, acetohexamide, tolazamide, glyburide, glipizide and glimepiride), biguanides, e.g., metformin (Glucophage®), β-glucosidase inhibitors (acarbose), thiazolidinone compounds, e.g., rosiglitazone (Avandia®), troglitazone (Rezulin®) and pioglitazone (Actos®); (b) $\beta_3$ adrenergic receptor agonists, leptin or derivatives thereof and neuropeptide Y antagonists; (c) bile acid sequestrants (e.g., cholestyramine and colestipol), HMG-CoA reductase inhibitors, e.g., statins (e.g., lovastatin, atorvastatin, fluvastatin, pravastatin and simvastatin), nicotinic, acid (niacin), fibric acid derivatives (e.g., gemfibrozil and clofibrate) and nitroglycerin.

Exemplary agents useful in the treatment of inflammatory conditions include, but are not limited to: (a) non-steroidal antiinflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (e.g., indomethacin, acemetacin, aldlofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone); (b) cyclooxygenase-2 (COX-2) inhibitors such as celecoxib (Celebrex®) and rofecoxib (Vioxx®) and (c) inhibitors of phosphodiesterase type IV (PDE-IV).

.2.5 Methods of Use

In another aspect, the present invention provides methods for treating a metabolic disorder, a cardiovascular disease, an inflammatory condition or a neoplastic disease, comprising administering to a subject in need thereof a therapeutically effective amount of at least one compound of the present invention. The "subject" is defined herein to include animals such as mammals, including, but not limited to, primates (e.g., humans), cows, sheep, goats, horses, dogs, cats, rabbits, rats, mice and the like.

In one aspect, the present invention provides methods of treating a condition or disorder mediated by PPARγ. These methods comprise administering to a subject in need thereof, a therapeutically effective amount of a compound of the present invention.

In one aspect, the present invention provides methods of treating a condition or disorder mediated by PPARδ. These methods comprise administering to a subject in need thereof, a therapeutically effective amount of a compound of the present invention.

In still another aspect, the present invention provides methods of using the foregoing compounds and compositions to modulate PPARγ. The methods comprise contacting a cell with the compound of formula I and XIV.

In still another aspect, the present invention provides methods of using the foregoing compounds and compositions to modulate PPARδ. The methods comprise contacting a cell with the compound of formula I and XIV.

Diseases and conditions associated with lipid metabolism, inflammation and cell proliferation can be treated with the present compounds and compositions. In one group of embodiments, diseases or conditions, including chronic diseases, of humans or other species can be treated with activators of PPARδ or PPARγ function. These diseases or conditions include: (1) metabolic disorders, such as hypercholesterolemia, hyperlipidemia, dyslipidemia (e.g., elevated LDL cholesterol, elevated total cholesterol, low HDL cholesterol), mixed dyslipidemia, hypertriglyceridemia, hyperglycemia, diabetes, obesity, syndrome X, eating disorders, insulin resistance and hyperinsulinemia, (2) cardiovascular diseases, including, but not limited to, aneurysm, atherosclerosis, arteriosclerosis, cardiomyopathy, congestive heart failure, coronary artery disease, hypertension, ischemia/reperfusion, restenosis and vascular stenosis, (3) inflammatory conditions or diseases such as atherosclerosis, rheumatoid arthritis, osteoarthritis, prosthetic joint failure, allergic diseases (e.g., systemic anaphylaxis or hypersensitivity responses, drug allergies, insect sting allergies and food allergies), inflammatory bowel diseases (e.g., Crohn's disease, ulcerative colitis, ileitis, enteritis, gastritis and mucosal inflammation resulting from infection, the enteropathy provoked by non-steroidal anti-inflammatory drugs), vaginitis, psoriasis and inflammatory dermatoses (e.g., dermatitis, eczema, atopic dermatitis, allergic contact dermatitis, urticaria and burn injury), vasculitis, spondyloarthropathies, scleroderma, asthma and respiratory allergic diseases (e.g., allergic rhinitis, hypersensitivity lung diseases, adult respiratory distress syndrome, cystic fibrosis, and the like), (4) autoimmune diseases, (e.g., rheumatoid arthritis, psoriatic arthritis, multiple sclerosis, systemic lupus erythematosus, type I diabetes, glomerulonephritis, and the like), (5) graft rejection (including allograft rejection and graft-v-host disease) and conditions associated therewith, (6) inflammatory sequelae of viral or bacterial infections, including septic shock, (7) other diseases in which undesired inflammatory responses are to be inhibited, e.g., atherosclerosis, myositis, neurodegenerative diseases (e.g., Alzheimer's disease), encephalitis, meningitis, hepatitis, nephritis, sepsis, sarcoidosis, conjunctivitis, otitis, chronic obstructive pulmonary disease, sinusitis, myocarditis, glaucoma and Behcet's syndrome, (8) neoplastic diseases such as solid tumors, skin cancer, melanoma, lymphoma and endothelial cancers, e.g., breast cancer, lung dancer, colorectal cancer, prostate cancer, kidney cancer, liver cancer, stomach cancer, bladder cancer, ovarian cancer and cancer of the gastrointestinal tract, and (9) other conditions and diseases that are sensitive or responsive to modulation of PPARδ or PPARγ function.

The compounds and compositions of the present invention can also be used to treat diseases or conditions including (1) inflammatory conditions and immune disorders, e.g., rheumatoid arthritis, osteoarthritis, prosthetic joint failure, ulcerative colitis, Crohn's disease and other inflammatory bowel diseases, gastritis and mucosal inflammation resulting from infection, enteropathy provoked by non-steroidal antiinflammatory drugs, adult respiratory distress syndrome, asthma, cystic fibrosis, or chronic obstructive pulmonary disease, myocarditis, multiple sclerosis, diabetes melitus and complications thereof, glomerulonephritis, dermatitis, psoriasis, eczema, urticaria, glaucoma, organ transplant rejection, systemic lupus erythematosis, inflammatory sequelae of viral or bacterial infections, atherosclerosis, injury following hypoxic or ischemic insults (with or without reperfusion), for example, cerebral or cardiac, (2) shock states, e.g., septic shock, hemorrhagic shock, traumatic shock, or shock caused by fulminant hepatic failure or by therapy with cytokines such as TNF, IL-1 and IL-2 or therapy with cytokine-inducing agents, for example 5,6-dimethylxanthenone acetic acid, (3) disorders of gastrointestinal motility, e.g., ileus, and (4) diseases of the central nervous system (CNS), e.g., migraine, psychosis, anxiety, schizophrenia, sleep disorders, cerebral ischemia, CNS trauma, epilepsy, multiple sclerosis, AIDS dementia, chronic neurodegenerative disease such as Lewy Body Dementia, Huntington's disease, Parkinson's disease or Alzheimer's disease, acute and chronic pain and conditions in which non-adrenergic non-cholinergic nerves may be implicated, such as priapism, obesity and hyperphagia.

The following examples are offered by way of illustration and are not intended to limit the scope of the invention.

EXAMPLES

Reagents and solvents used below can be obtained from commercial sources such as Aldrich Chemical Co. (Milwaukee, Wis., USA). 1H-NMR spectra were recorded on a Varian Gemini 400 MHz NMR spectrometer. Significant peaks are tabulated in the order: number of protons, multiplicity (s, singlet; d, doublet; t, triplet; q, quartet; m, multiplet; br s, broad singlet) and coupling constant(s) in Hertz (Hz). Electron Ionization (EI) mass spectra were recorded on a Hewlett Packard 5989A mass spectrometer. Mass spectrometry results are reported as the ratio of mass over charge, followed by the relative abundance of each ion (in parentheses). In tables, a single m/e value is reported for the M+H (or as noted M−H) ion containing the most common atomic isotopes. Isotope patterns correspond to the expected formula in all cases. Electrospray ionization (ESI) mass spectrometry analysis was conducted on a Hewlett-Packard 1100 MSD electrospray mass spectrometer using the HP1 100 HPLC for sample delivery. Normally the analyte was dissolved in methanol at 0.1 mg/mL and 1 ÿL was infused with the delivery solvent into the mass spectrometer which scanned from 100 to 1500 daltons (D). All compounds could be analyzed in the positive ESI mode, using 1:1 acetonitrile/water with 1% acetic acid as the delivery solvent. The compounds provided below could also be analyzed in the negative ESI mode, using 2 mM $NH_4OAc$ in acetonitrile/water as delivery solvent.

Abbreviations

Triethylamine ($Et_3N$), methanol (MeOH), dimethylsulfoxide (DMSO), N-methylmorpholine (NMM), dimethylformamide (DMF), 4-(dimethylamino)pyridine (DMAP), 3-chloroperoxybenzoic acid (mCPBA), ethyl acetate (AcOEt), ethanol (EtOH), hexamethylphosphoramide (HMPA), acetic acid (AcOH), silver benzoate (AgOBz), tetrahydrofuran (THF), N-hydroxybenzotriazole (HOBT), 2-(1H-benzotriazole-1-yl)-1,1,3,3-tetramethyluronium hexafluorophosphate (HBTU), 1-hydroxy-7-azabenzotriazole (HOAT), O-(7-azabenzotriazole-1-yl)-N,N,N',N'-tetramethyluronium hexafluorophosphate (HATU), 1-(3-dimethylaminopropyl)-3-ethylcarbodiimide hydrochloride (EDCI).

Certain intermediates used in preparing the compounds below are described in co-pending U.S. patent application Ser. No. 09/606,433, filed Jun. 28, 2000.

General Experimental Information.

Reagents purchased from suppliers (unless stated otherwise) were used as supplied. $^1H$ NMR spectra were measured using a Bruker Spectrospin Avance DPX-300 using CDCl$_3$ as solvent (unless stated otherwise) and are referenced to residual solvent signals.

HPLC of samples were taken using a Phenomenex Luna (2) C18 column 30 mm×4.6 mm (3 micron) and one of the following gradients: (Solvent A was water containing 0.1% trifluoroacetic acid). (Solvent B was 90% acetonitrile in water 10% containings 0.1% trifluoroacetic acid). Gradient MS8 Flow rate 1 ml/min t=0 min 80% solvent A. 20% solvent B. t=5 min 100% solvent B(linear gradient) run time can be extended up to 11 min at 100% solvent B. Gradient File5 Flow rate 1.6 ml/min t=0 min 100% solvent A t=7 min 100% solvent B (linear gradient). Reverse phase preparative HPLC was carried out using Waters Deltaprep 4000 equipment and either a Phenomenex Luna C18 column (10 micron) 250 mm×21.2 mm or a Phenomenex Luna (2) C18 column (15 micron) 250 mm×50 mm and the appropriate gradient using solvents A and B as described above.

Automated reverse phase preparative HPLC was carried out on a Gilson HPLC with a Phenomenex Luna C18 column (10 micron) 250 mm×21.2 mm and a Finnegan AQA. Thermoquest mass spec. detector. Appropriate gradient with solvents A and B as described above were used. LCMS data was collected using a PE Sciex API 150EX in both positive and negative mode as appropriate. The HPLC of samples for mass spectroscopy was carried out using a Phenominex Luna (2) C18 column 30 mm×4.6 mm (3 micron) and the following gradient: Solvent C: water containing 0.1% formic acid. Solvent D acetonitrile containing 0.1% formic acid. Flow rate 1 ml/min t=0 min 95% solvent C 5% solvent D. 0.1 min 80% solvent C. 20% solvent D. t=5 min 100% solvent D(linear gradient) run time can be extended up to 11 min at 100% solvent D. Microwave chemistry was carried out using a CEM Discover microwave apparatus.

Preparation of Intermediates.

Compounds 2 and 3

2-Amino-5-bromo-isonicotinic acid methyl (2) and ethyl esters (3)

These compounds can be prepared from 2-amino-6-methylpyridine using the procedures described by T. Ross Kelly et al. *J. Org. Chem.* 1996, 4623-4633.

2-Amino-5-bromo-isonicotinic acid methyl ester

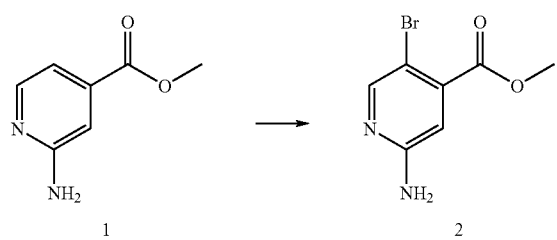

Bromine (1.78 ml, 34.8 mmol) was added dropwise over an hour to a stirred solution of 2-amino-isonicotinic acid methyl ester (5.13 g, 33.75 mmol) in chloroform (350 ml) at room temperature and the orange solution stirred at room temperature overnight. A 2N solution of sodium thiosulfate (300 ml) was added to the reaction and stirred for ten minutes. The two layers were separated and the aqueous extracted with chloroform (100 ml). The combined organics were dried (MgSO$_4$) and concentrated under reduced pressure. The desired isomer was purified by flash column chromatography using ethyl acetate 2/3 hexane as eluent to afford 2-amino-5-bromo-isonicotinic acid methyl ester as a yellow solid (1.79 g, 23%). $^1$H NMR (CDCl$_3$): 8.21 (1H, s, py); 6.79 (1H, s, py); 4.53 (2H, br s, NH$_2$); 3.88 (3H, S, CO$_2$CH$_3$).

Compound 4

2-amino-5-iodo-isonicotinic acid pentyl ester (4)

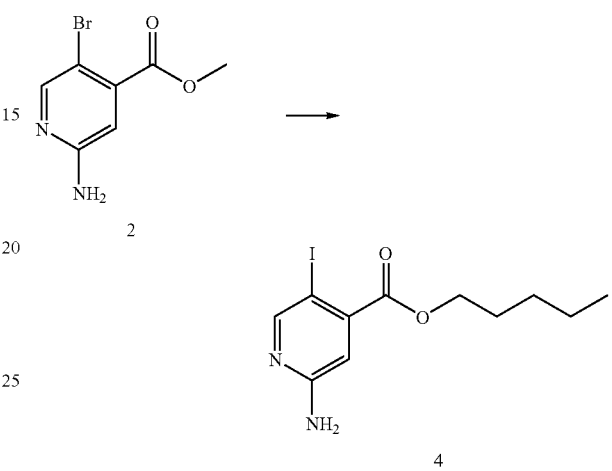

Conversion of 2-Amino-5-bromo-isonicotinic acid methyl and ethyl esters to 2-amino-5-iodo-isonicotinic acid pentyl ester was carried out using the procedure described by S. Buchwald et al. *J. Am. Chem. Soc.* 2002, 14844-14845.

2-amino-5-bromo-isonicotinic acid methyl ester (1.79 g, 7.75 mmol) was added to a stirred mixture of copper iodide (145 mg, 0.76 mmol), sodium iodide (2.36 g, 15.73 mmol) and 1,3-diaminopropane (0.13 ml, 1.55 mmol) in n-pentanol (20 ml) and heated to reflux overnight. The reaction was cooled to room temperature, ethyl acetate (100 ml) added and washed with NaHCO$_3$ solution (50 ml) and brine (50 ml) before being dried (MgSO$_4$) and concentrated under reduced pressure. The residue was purified by flash column chromatography using ethyl acetate 1/4 hexane as eluent to afford 2-amino-5-iodo-isonicotinic acid pentyl ester as a yellow solid (1.51 g, 58%). $^1$H NMR (CDCl$_3$): 8.36 (1H, s, py); 6.77 (1H, s, py); 4.50 (2H, br s, NH$_2$); 4.24 (2H, t, OCH$_2$); 1.72 (2H, m, OCH$_2$CH$_2$); 1.32 (4H, m, OCH$_2$CH$_2$CH$_2$CH$_2$CH$_3$); 0.81 (3H, t, CH$_2$CH$_3$).

Compound 5

6-Amino-3-iodo-pyridine-2-carboxylic acid pentyl ester (5)

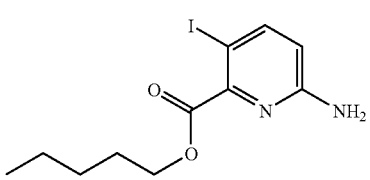

6-Amino-3-iodo-pyridine-2-carboxylic acid pentyl ester was prepared from 2-amino-6-methylpyridine using a similar sequence of reactions to that described for the preparation 2-amino-5-iodo-isonicotinic acid pentyl ester.

Compound 6

6-Acetylamino-3-bromo-pyridine-2-carboxylic acid ethyl ester (6)

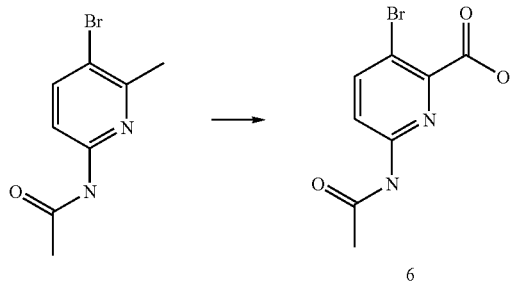

The intermediate 6-acetylamino-3-bromo-pyridine-2-carboxylic acid can be prepared by oxidation of N-(5-bromo-6-methyl-pyridin-2-yl)-acetamide as described below.

To a solution of N-(5-bromo-6-methyl-pyridin-2-yl)-acetamide 48.46 g in pyridine 250 ml was added water 250 ml and the mixture warmed to 90° C. and potassium carbonate 2.2 g was added. Potassium permanganate was added portionwise over 10 h and the mixture allowed to cool slowly overnight. The reaction mixture was re-heated to 90° C. for 2 h, cooled slightly and filtered to remove manganese dioxide. The filtrate was evaporated in vacuo and the residue partitioned between water 1 L and ethyl acetate 500 ml. The aqueous solution was washed with ethyl acetate. The organic solutions were combined, washed with brine, dried $MgSO_4$ and evaporated in vacuo to recover unchanged starting materials 12.6 g. The aqueous solution was acidified with concentrated hydrochloric acid (circa 80 ml) and the solid product filtered off, washed with a minimum of water, sucked dry and then dried at 80° C. (vac) to give 6-acetylamino-3-bromo-pyridine-2-carboxylic acid 24.9 g This material was converted to 6-amino-3-bromo-pyridine-2-carboxylic acid ethyl ester using the methods described by T. Ross Kelly et al. *J. Org. Chem.* 1996, 4623-4633.

Compound 7

6-amino-2-butyl-3-iodo-pyridine (7)

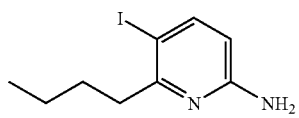

2-Amino-6-butyl pyridine was prepared from 2-amino-6-methylpyridine using the procedure described by S. P. Bruekelman et al. *J. Chem. Soc. Perkin Trans.* 1 1984 2801-2807. 2-Amino-6-butyl pyridine was converted to 6-amino-2-butyl-3-iodo-pyridine using the procedure described by A. Boullon et al. *Tetrahedron* (2002) 2885-2890.

General Thiol linkage Method 1

Step 1: Reaction of nitrobenzenesulfonyl Chloride with piperidine

Compound 8

1-(4-nitro-benzenesulfonyl)-piperidine (8)

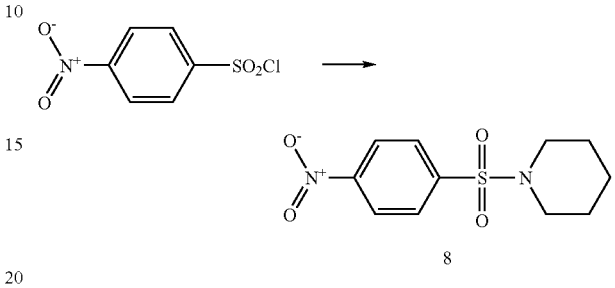

To a solution of 4-nitrobenzenesulfonyl chloride 40 g 0.181 mole in dichloromethane 400 ml was added over 30 mins a solution of pyridine 15 g 15.3 ml and piperidine 16.15 g 18.8 ml in dichloromethane 100 ml. The mixture was stirred at room temperature for 2 h and then washed with water, 2M hydrochloric acid and brine, dried $MgSO_4$ and evaporated in vacuo to give 1-(4-nitro-benzenesulfonyl)-piperidine 44.5 g. $^1$H NMR $CDCl_3$ 7.76 (2H, d), 7.40 (2H, d), 3.21 (6H, q), 1.07 (6H, t).

Step 2: Reduction of Nitro Group

Compound 9

4-(piperidine-1-sulfonyl)-phenylamine (9)

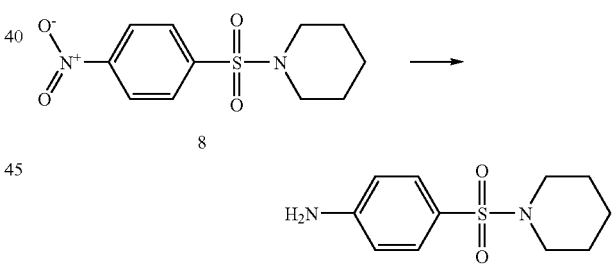

1-(4-Nitro-benzenesulfonyl)-piperidine (30 g) was mixed with iron powder (50 g), ammonium chloride (50 g), ethanol (200 ml) and water (50 ml). The mixture was heated under reflux conditions for 2 h. LCMS showed that the reduction goes through a hydroxylamine intermediate. The mixture was filtered through Celite while hot and the iron residues washed with warm ethanol, ethyl acetate, water and dichloromethane. All volatiles were removed under reduced pressure and the residue partitioned between water and ethyl acetate. The organic solution was separated and washed with brine, dried over $MgSO_4$ concentrated to give 4-(piperidine-1-sulfonyl)-phenylamine, 23 g. $^1$H NMR $CDCl_3$ 7.43 (2H, d), 6.67 (2H, d), 3.33 (2H, bs), 2.84 (4H, t), 1.53 (4H, m), 1.31 (2H, m)

Step 3: Diazotisation and 'thiolation'

Compound 10

4-(Piperidine-1-sulfonyl)-benzenethiol

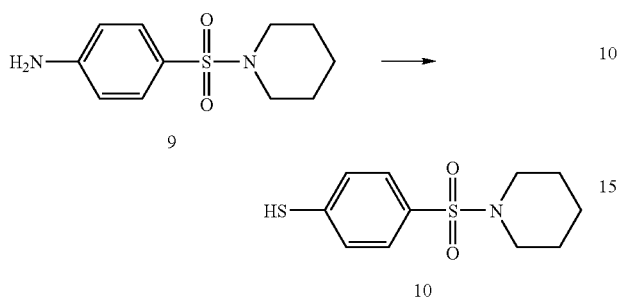

A procedure based on the method in Organic Syntheses—Collective Volume 3 p809-811 was used. Note there is a danger of a potential explosion if the addition of the diazonium salt to the xanthate solution is not done at ~45° C. During the reaction some white smoke can be seen during the addition of the diazonium solution to the xanthate as the mixture exotherms to ca. 50° C. Efficient stirring is important for both the diazonium formation and reaction with the xanthate which must be carried out as described. Under no circumstances should the diazonium salt and the potassium xanthate solution be mixed cold and then heated.

A mixture of ice 16.7 g and conc. hydrochloric acid 16.7 ml was stirred with an overhead stirrer. 4-(Piperidine-1-sulfonyl)-phenylamine was added portionwise to form a thick suspension. This mixture was cooled to 0-5° C. in an ice bath and a cold solution of sodium nitrite 6.11 g in water 13.9 ml. added over 1 h, maintaining temperature at 0-5° C. Much of the solid was dissolved at this point. Occasionally there can be significant quantities of solid present which can cause frothing at this stage and the diazonium formation is difficult to handle. It is best to keep the diazonium salt mixture cold to prevent decomposition.

Potassium xanthate 15.54 g was then dissolved in water 20 ml and warmed to 45° C. internal temperature. The cold diazonium salt was added portionwise over 1.5 h, keeping the temperature at ~48° C.

The mixture can become very thick and an overhead stirrer is recommended. The mixture was maintained at ~48° C. for a further 45 min. A red oily suspension was separated and the aqueous solution was extracted with ether (3 times). The oil and the ether extracts were combined and washed with 300 ml 10% sodium hydroxide and then water and brine. Drying (MgSO$_4$) and concentration in vacuo gives a red oil. The red oily xanthate product has been found to give 2 peaks on hlpc. This can be due to decomposition. Once this oil has been hydrolysed the product is clean apart from disulfide.

The oil was dissolved in ethanol 53 ml and warm water (3 ml). The solution was removed from the heat source and solid potassium hydroxide 19.4 g added portionwise, after exotherm, solution was heated up to reflux. Once all the potassium hydroxide is added the solution was refluxed for 1 h and the hlpc showed 1 peak. The mixture was cooled and some ethanol evaporated off. The solids from the interface were discarded as possible impurities from the aniline.

The mixture was diluted with water and extracted with ether (×4). Any solids on the interface were filtered off. The aqueous solution was acidified to pH1 with conc.HCl and a sticky solid formed which was filtered off and dried to give 4-(piperidine-1-sulfonyl)-benzenethiol as a pale brown solid 9.75 g. This product was always contaminated by disulfide. Protect the product from air, ie. store under nitrogen or argon. Carrying out the hydrolysis under nitrogen (to exclude air not moisture) and by covering the final filtration with an upturned funnel through which we blow nitrogen gently, the quality of the final product can be improved.

Alternative Thiol Linkage Method 2

Step 1

Compound 11

N-Ethyl-4-iodo-benzenesulfonamide (11)

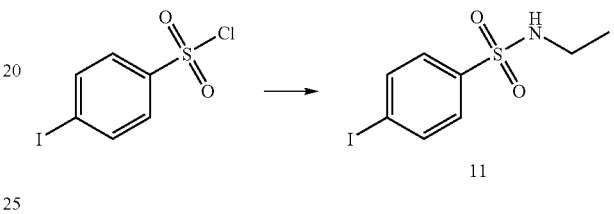

Pipsyl chloride 25 g was dissolved in dichloromethane 250 ml to which was added a solution of ethyl amine 2M, in THF 42 ml and triethylamine 9 g in dichloromethane 100 ml over 30 min. The mixture was stirred a further 1 h at room temperature and then washed with water and 1N hydrochloric acid, dried (MgSO$_4$) and evaporated in vacuo to give N-ethyl-4-iodo-benzenesulfonamide as a white solid, 26.2 g. $^1$H NMR 7.88 (2H, d), 7.59 (2H, d), 4.65 (1H, m), 3.01 (2H, m), 1.11 (3H, t).

Step 2

Compound 12

N-Ethyl-4-(4-methoxy-benzylsulfanyl)-benzenesulfonamide (12)

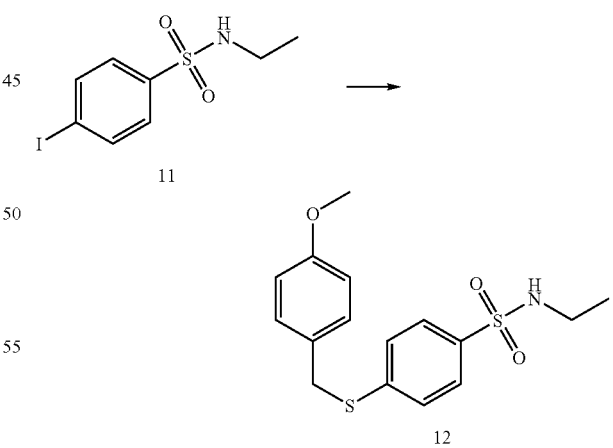

To a suspension of N-ethyl-4-iodo-benzenesulfonamide 6 g in isopropanol 26 ml was added ethylene glycol 1.9 ml, potassium carbonate 4.68 g, cuprous iodide 320 mg and then 4-methoxybenzyl mercaptan 3.55 g. The mixture was heated at ~80° C. for 16 h and then cooled, diluted with chloroform 250 ml and washed with water ×3, (any solid at the interface was filtered off). The organic solution was dried, MgSO$_4$ and evaporated. The solid was triturated with cyclohexane ×2 and dried to give N-ethyl-4-(4-methoxy-benzylsulfanyl)-benzenesulfonamide, 5.98 g 92%. $^1$H NMR 7.63 (2H, d), 7.28 (2H, d), 7.18 (2H, d), 6.79 (2H, d), 4.40 (1H, m), 4.08 (1H, s), 3.72 (3H, s), 2.90 (2H, m), 1.03 (3H, t).

Step 3:

Compound 13

N-ethyl-4-mercapto-benzenesulfonamide (13)

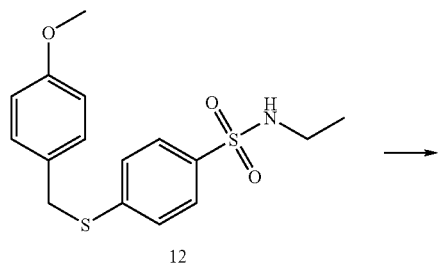

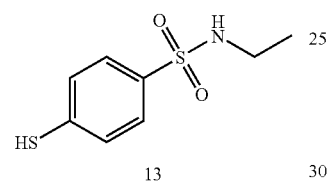

To N-ethyl-4-(4-methoxy-benzylsulfanyl)-benzenesulfonamide 5.95 g was added trifluoroacetic acid 60 ml containing triethyl silane 3 ml and the mixture heated at 80° C. for 2 h. The reaction mixture was cooled and evaporated in vacuo. The residue was taken up in ethyl acetate and evaporated in vacuo ×2. The residue was then taken up in ethyl acetate and extracted with 2M sodium hydroxide 3×30 ml and the combined aqueous solution washed with ethyl acetate (×1). The aqueous solution was then acidified with conc. hydrochloric acid and extracted with dichloromethane ×3 and the organic solution washed with water, dried MgSO$_4$ and evaporated in vacuo to give N-ethyl-4-mercapto-benzenesulfonamide, as a pale yellow oil, 3.05 g 79%. $^1$H NMR 7.72 (2H, d), 7.34 (2H, d), 4.65 (1H, bs), 3.70 (1H, s), 2.99 (2H, q), 1.11 (3H, t).

Using either Thiol Linkage Method 1 or the alternative Thiol Linkage Method 2 and the appropriate starting materials the following intermediates were also prepared:

Compound 14

4-(Pyrrolidine-1-sulfonyl)-benzenethiol (14)

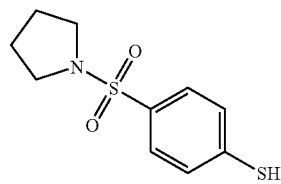

Compound 15

N,N-Diethyl-4-mercapto-benzenesulfonamide

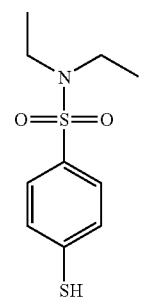

Compound 16

4-(Morpholine-4-sulfonyl)-benzenethiol

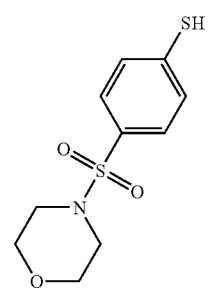

Compound 17

2-amino-5-iodo-6-n-pentyloxycarbonylpyridine (17)

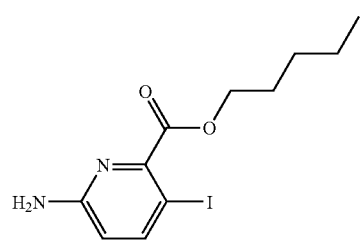

To a stirred solution of 2-amino-5-bromo-6-methoxycarbonylpyridine (13.8 g, 59.3 mmol) in n-pentanol (75 mL) was added 1,3-diaminopropane (900 mg, 12.1 mmol), copper (I) iodide (1.15 g, 6.0 mmol) and sodium iodide (18.0 g, 120 mmol). The reaction mixture heated to 135° C. After 16 hours (HPLC analysis shows ~70% conversion), further portions of copper (I) iodide (600 mg, 3.0 mmol), sodium iodide (9.0 g, 60 mmol) and 1,3-diaminopropane (450 mg, 6.0 mmol) were added. After a further 4 hours, the reaction mixture was cooled to room temperature, diluted with water (200 mL), and extracted with ethyl acetate (2×200 mL). The combined organic extracts were dried over magnesium sulphate and concentrated under reduced pressure. Filtration through a short plug of silica, washing with ethyl acetate:cyclohexane 1:2 affords 2-amino-5-iodo-6-"pentyloxycarbonylpyridine (8.94 g, 26.7 mmol, 45%) as a pale yellow solid. $^1$H NMR (CDCl$_3$) 7.82 (1H, d, J 12 Hz, C4-H), 6.36 (1H, d, J 12 Hz, C3-H), 4.65 (2H, m, NH$_2$), 4.36 (2H, d, J 8 Hz, COCH$_2$), 1.87-0.89 (9H, m, CH$_2$CH$_2$CH$_2$CH$_3$)

Method 3

Compound 18

N-(2,4-Dichlorobenzenesulfonyl)-guanidine (18)

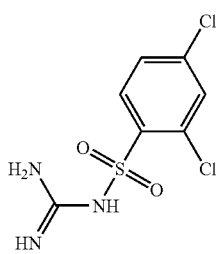

NaOH (aq) (70 mL of a 3N solution) and water (230 mL) were added to guanidine carbonate (22 g, 0.12 mmol) and the mixture stirred until all of the guanidine carbonate had dissolved. The mixture was cooled to 0° C. and a solution of 2,4-dichlorobenzenesulfonyl chloride (5.3 g, 0.02 mmol) in THF (60 mL) added dropwise over an hour. A white precipitate formed during this addition. The reaction was allowed to warm to room temperature and the precipitate was filtered, washed with water and dried under vacuum to afford the title compound 1 as a white solid, 3.9 g. N.B. On occasion some of the bissulfonylated product was observed and was difficult to separate from the title compound 1. In these instances, the mixture was used in subsequent reactions. $^1$H NMR (DMSO): δ 6.90 (br s, 4H), 7.56 (d, 1H), 7.76 (s, 1H) 7.97 (d, 1H) ppm. Mass Spectrum m/e=267.9 (M+1).

By a similar method the following were prepared:

Compound 19

N-(2-Chloro-4-trifluoromethylbenzenesulfonyl)-guanidine (19)

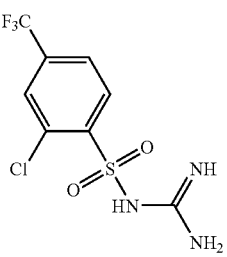

$^1$H NMR (DMSO): δ 7.87 (d,1H), 8.01 (s, 1H), 8.18 (d, 1H) ppm. Mass Spectrum m/e=302.0 (M+1).

Compound 20

N-(2-Chlorobenzenesulfonyl)-guanidine (20)

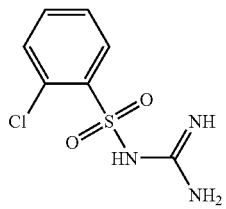

$^1$H NMR (DMSO): δ 6.73 (br s, 4H), 7.58 (d, 2H), 7.74 (d, 2H) ppm. Mass Spectrum m/e=233.9 (M+1).

Compound 21

N-(2-Methoxybenzenesulfonyl)-guanidine (21)

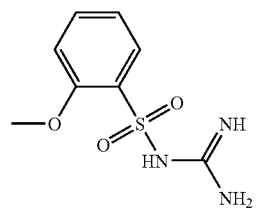

$^1$H NMR (DMSO): δ 3.81 (s, 3H), 6.65 (br, s, 4H), 7.02 (m, 2H), 7.69 (m, 2H) ppm. Mass Spectrum m/e=230.0 (M+1).

Method 4

Compound 22

[4-(Piperidine-1-sulfonyl)-phenylsulfanyl]-acetic acid ethyl ester (22)

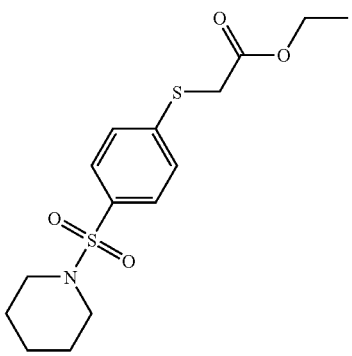

Potassium carbonate (1.25 g, 9.4 mmol) was added to a solution of 10 (2.0 g, 7.8 mmol) in acetone (15 mL). The mixture was brought to a gentle reflux for 45 minutes then cooled to 50° C. Ethylbromoacetate (1.42 g, 8.5 mmol) was added slowly and the mixture was stirred at 60° C. for 16 hours. The reaction was cooled to room temperature and the potassium salts were removed by filtration and washed with acetone. The filtrate was concentrated under reduced pressure to give an orange oil. Purification by flash column chromatography (30% EtOAc in hexanes) afforded 22 as a pale yellow oil (2.36 g). $^1$H NMR (CDCl$_3$): δ 1.31 (br, 2H), 1.33 (t, 3H), 1.45 (quin, 4H), 2.99 (q, 4H), 3.40 (s, 2H), 4.20 (q, 2H), 7.47 (d, 2H), 7.68 (d, 2H) ppm. Mass Spectrum m/e=344.0 (M+1)

By a similar method the following were prepared:

Compound 23

(Naphthalen-2-ylsulfanyl)-acetic acid ethyl ester (23)

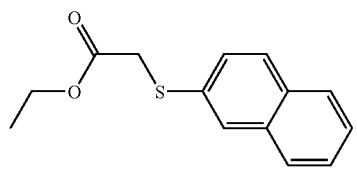

23

$^1$H NMR (CDCl$_3$): δ 1.26 (t, 3H), 3.74 (s, 2H), 4.21 (q, 2H), 7.45-7.52 (m, 3H), 7.75-7.84 (m, 3H), 7.89 (s, 1H) ppm. Mass Spectrum m/e=247.1 (M+1)

Compound 24

[4-(Morpholine-4-sulfonyl)-phenoxy]-acetic acid ethyl ester (24)

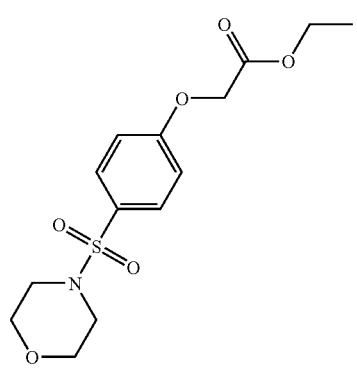

24

Mass Spectrum m/e=346.0 (M+1)

Compound 25

(3,4-Dichloro-phenoxy)-acetic acid ethyl ester (25)

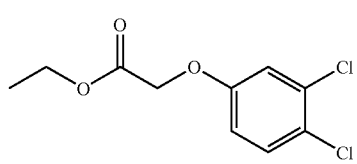

25

$^1$H NMR (CDCl$_3$): δ 1.30 (t, 3H), 4.27 (q, 2H), 4.59 (s, 2H), 6.77 (dd, 1H), 7.01 (s, 1H), 7.32 (d, 1H) ppm. Mass Spectrum m/e=250.1 (M+1)

Method 5

Compound 33

1-Chloro-hexan-2-one (33)

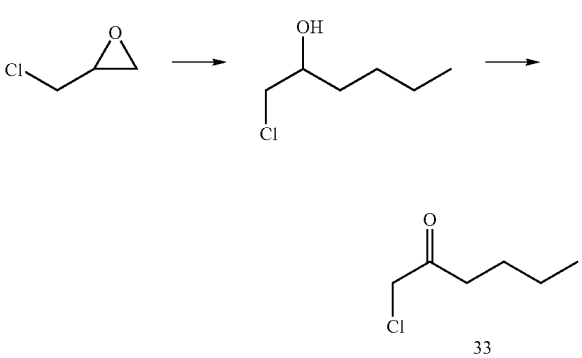

33

Propylmagnesium chloride (8 mL, 16 mmol of a 2M solution in Et$_2$O) was slowly added to a solution of epichlorohydrin (1 mL, 12.75 mmol) and CuCN (63 mg, 0.7 mmol) in THF (10 mL) at −50° C. and the resultant mixture stirred at −50° C. for 3 hours. The reaction mixture was then poured into a saturated aqueous solution of ammonium chloride (30 mL) and extracted with EtOAc. The organic phase was dried (MgSO$_4$) and the solvent evaporated in vacuo to afford crude 1-chloro-hexan-2-ol (1.7 g), which was used without purification.

1-Chloro-hexan-2-ol (1.54 g, 11.3 mmol crude material) was dissolved in DCM (15 mL) and Dess-Martin Periodinane (4.8 g, 11.3 mmol) added. The resultant mixture was heated to 40° C. for 13 hours. The reaction was cooled to r.t., filtered through celite and concentrated in vacuo. The resultant crude product was purified by flash column chromatography (50% EtOAc in hexanes) to afford 1-chloro-hexan-2-one 33 (1.32g). $^1$H NMR (CDCl$_3$): δ 0.93 (t, 3H), 1.35 (m, 2H), 1.63 (m, 2H), 2.60 (t, 2H), 4.09 (s, 2H) ppm.

Compound 34

1-Chloro-heptan-2-one (34)

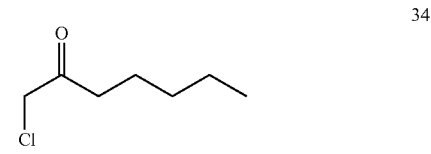

34

By a similar method using the appropriate starting materials the above compound was prepared. $^1$H NMR (CDCl$_3$): δ 0.91(t, 3H), 1.32 (m, 4H), 1.63 (m, 2H), 2.58 (t, 2H), 4.09 (s, 1H) ppm.

Method 6

Compound 35

1-[4-(Piperidine-1-sulfonyl)-phenylsulfanyl]-hexan-2-one (35)

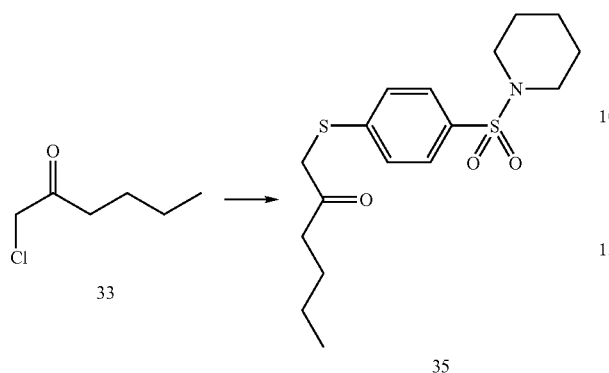

Dithiocarbonic acid O-ethyl ester S-[4-(piperidine-1-sulfonyl)-phenyl]ester (1.24 g, 3.6 mmol) in ethanol (5 mL) and water (0.5 mL) was heated to 60° C. to form a solution. The flask was removed from the oil bath and KOH (561 mg, 10 mmol) added portionwise (exothermic reaction). The mixture was heated to 111° C. for one hour and 33 was added (553 mg, 4.13 mmol)The reaction mixture was then heated to 110° C. for 3 hours. The mixture was allowed to cool to r.t. and a saturated aqueous solution of ammonium chloride added (20 mL). The aqueous phase was extracted with EtOAc, the combined organics dried, and the solvent evaporated in vacuo. The resultant crude product 35 was taken on without purification. Mass Spectrum m/e=356.0 (M+1)

Compound 36

1-[4-(Piperidine-1-sulfonyl)-phenylsulfanyl]-heptan-2-one (36)

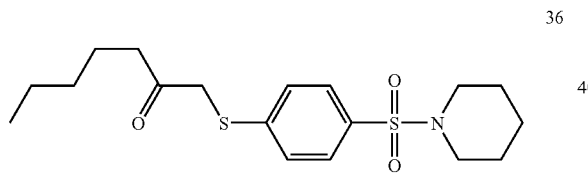

By a similar method using the appropriate starting materials the above compound was prepared. Mass Spectrum m/e=370.0 (M+1)

Compound 37

1-[4-(Piperidine-1-sulfonyl)-phenylsulfanyl]-propan-2-one (37)

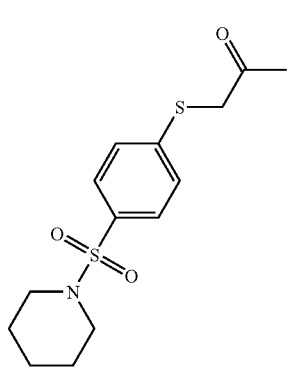

By a similar method using the appropriate starting materials the above compound was prepared. $^1$H NMR (CDCl$_3$): δ 1.45 (m, 2H), 1.66 (m, 2H), 2.35 (s, 3H), 2.99 (m, 4H), 3.80 (s, 2H), 7.4 (d, 2H), 7.67 (d, 2H) ppm. Mass Spectrum m/e=313.9 (M+1)

Compound 38

1-[4-(Morpholine-4-sulfonyl)-phenylsulfanyl]-propan-2-one (38)

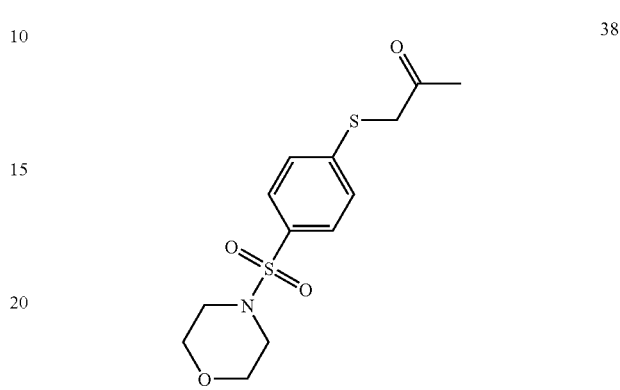

By a similar method using the appropriate starting materials the above compound was prepared. $^1$H NMR (CDCl$_3$): δ 2.35 (s, 3H), 3.02 (t, 4H), 3.75 (t, 4H), 3.81 (s, 2), 7.42 (d, 2H), 7.67 (d, 2H) ppm. Mass Spectrum m/e=316 (M+1)

Compound 39

1-[4-(Morpholine-4-sulfonyl)-phenoxy]-propan-2-one (39)

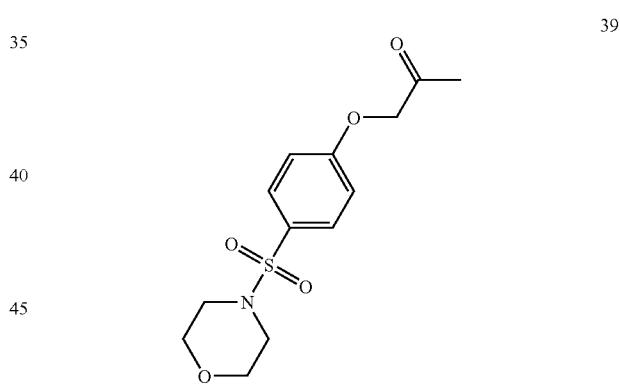

By a similar method using the appropriate starting materials the above compound was prepared. $^1$H NMR (CDCl$_3$): 2.32 (s, 3H), 3.00 (t, 4H), 3.76 (t, 4H), 4.66 (s, 2H), 7.02 (m, 2H), 7.72 (m, 2H) ppm. Mass Spectrum m/e=300.0 (M+1).

Compound 40

1-(Naphthalen-2-ylsulfanyl)-propan-2-one (40)

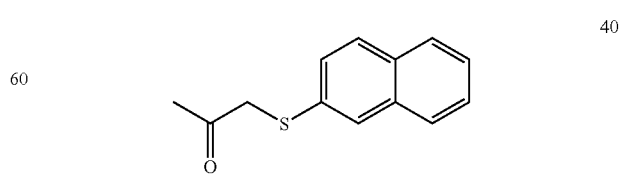

By a similar method using the appropriate starting materials the above compound was prepared. $^1$H NMR (CDCl$_3$): 2.88 (s, 3H), 3.75 (s, 2H), 7.46 (m, 3H), 7.76 (m, 4H) ppm.

Compound 41

1-(5-Chloro-benzothiazol-2-ylsulfanyl)-propan-2-one (41)

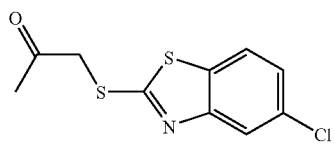

By a similar method using the appropriate starting materials the above compound was prepared. Mass Spectrum m/e=258.0 (M−1)

Compound 42

1-(3,4-Dichloro-phenoxy)-propan-2-one (42)

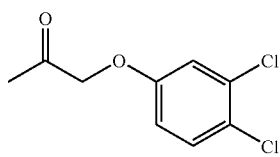

By a similar method using the appropriate starting materials the above compound was prepared. Mass Spectrum m/e=220.0 (M+1)

2-amino-5-iodo-6-"propoxypyridine (43)

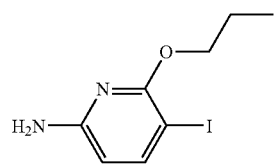

Sodium metal (970 mg, 42.2 mmol) was added to "Propanol (21 mL) and the mixture was allowed to stir until all of the sodium had dissolved. The resulting sodium propoxide solution (1.5 mL) was then added to each of 9 portions of 2-amino-6-bromopyridine (220 mg, 1.26 mmol). The reactions were then each microwaved for 5 mins at 160° C., and were pooled and poured onto brine (50 mL). The solution was then extracted with ethyl acetate (2×50 mL), and the organic portions combined, dried over magnesium sulphate, evaporated, and dissolved in chloroform (40 mL). A solution of bromine (0.60 mL, 1.87 g, 11.7 mmol) in chloroform (10 mL) was then added dropwise over 2 hours. After stirring for a further 16 hours, the reaction was quenched by the addition of sodium thiosulfate (2N, aq., 50 mL) and extracted with chloroform (2×50 mL). The combined organic layers were evaporated and loaded onto a flash column (SiO$_2$, ethyl; acetate:cyclohexane 1:10). The spot at rf0.30 in ethyl acetate:cyclohexane 1:6 was collected, and found to be a mixture of 2-amino-4-bromo-5-"Propoxypyridine and a dibromo product (2.13 g). This mixture was then dissolved in "pentanol (10 mL) and copper (I) iodide (200 mg, 1.05 mmol), sodium iodide (3.00 g, 20.0 mmol) and 1,3-diaminopropane (150 mg, 2.02 mmol) added. The reaction mixture was heated to 130° C. for 20 hours, cooled, and diluted with ethyl acetate (100 mL). The mixture was then extracted with water (3×50 mL), and evaporated. Careful flash chromatography (SiO$_2$, ethyl acetate:cyclohexane 1:49) affords 2-amino-5-iodo-6-"propoxypyridine as a yellow solid (522 mg, 13%). $^1$H NMR (CDCl$_3$) 7.57 (1H, d, J 11 Hz, C4-H), 5.82 (1H, d, J 11 Hz, C3-H), 4.63 (2H, m, NH$_2$), 4.02 (2H, t, J 8 Hz, OCH$_2$), 1.68 (2H, sextet, J 8 Hz, CH$_2$CH$_3$) 0.92 (3H, t, J 8 Hz, CH$_3$).

Example 1

Method 7

2,4-Dichloro-N-{5-[4-(piperidine-1-sulfonyl)-phenylsulfanyl]-4-propylamino-pyrimidin-2-yl}-benzenesulfonamide (12)

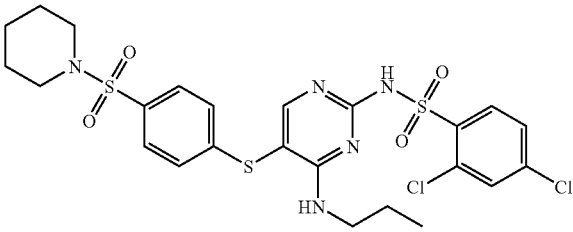

Step 1

2,4-Dichloro-N-{4-hydroxy-5-[4-(piperidine-1-sulfonyl)-phenylsulfanyl]-pyrimidin-2-yl}-benzenesulfonamide (10)

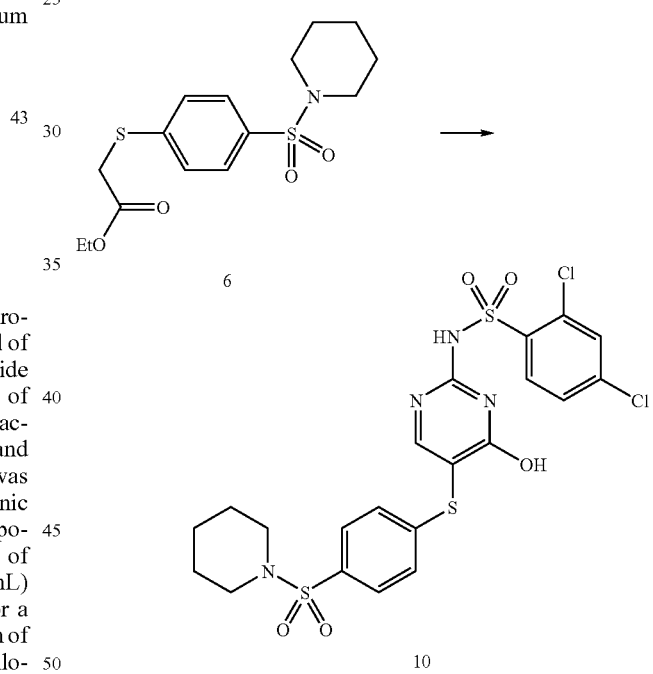

A solution of 6 (2.30 g, 6.7 mmol) in t-butoxybis(dimethylamino)methane (1.76 g, 10.1 mmol) was heated to 90° C. for 2 hours. 1 (2.10 g, 8.0 mmol) was added, followed by DMF (10 mL) and sodium methoxide (1.9 mL, 8.7 mmol of a 25% wt solution in methanol). Heating was continued at 100° C. for 16 hours. The condenser was removed from the flask and the mixture was heated at 130° C. for 2 hours. The mixture was cooled to room temperature and quenched with 30 mL of 3N HCl. The gummy mixture was treated in an ultrasonic bath for 5 minutes to afford a nice solid which was collected by filtration, washed with water and dried. The solid obtained was recrystallized in hot ethanol to afford 10 as a pale yellow powder. (2.95 g). $^1$H NMR (DMSO): δ 1.37 (m, 2H), 1.52 (quin, 4H), 2.68 (t, 4H), 7.45 (d, 2H), 7.60 (d, 2H), 7.66 (dd, 1H), 7.90 (d, 1H), 8.02 (s, 1H), 8.11 (d, 1H) ppm. Mass Spectrum m/e=575.0 (M+1).

Step 2

2,4-Dichloro-N-{4-chloro-5-[4-(piperidine-1-sulfonyl)-phenylsulfanyl]-pyrimidin-2-yl}-benzenesulfonamide (11)

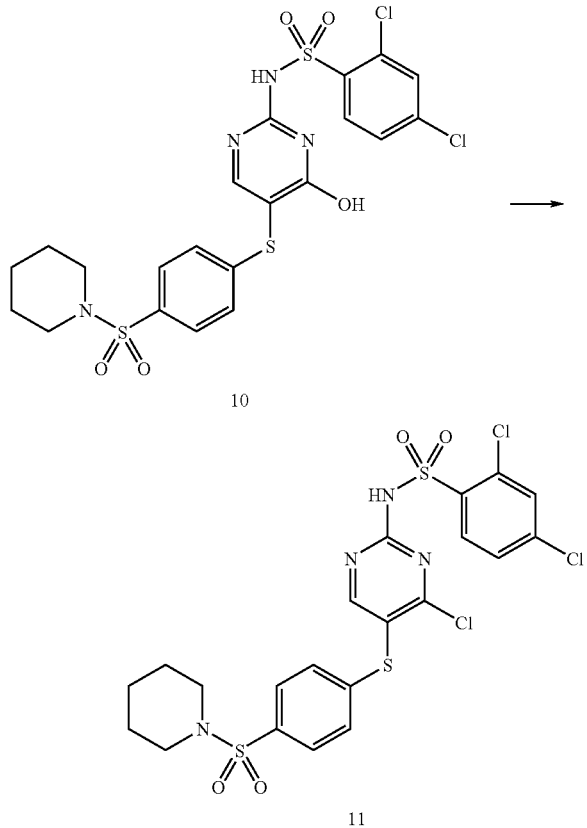

A solution of 10 (150 mg, 0.26 mmol) in POCl$_3$ (0.24 mL, 2.6 mmol) was heated to 90° C. for 3.5 hours. The mixture was cooled to room temperature and poured onto ice. The precipitate was collected by filtration, washed with water and dried under vacuum to afford 11 as a pale yellow solid (143 mg), which was used without further purification. Mass Spectrum m/e=594.8 (M+1)

Step 3

2,4-Dichloro-N-{5-[4-(piperidine-1-sulfonyl)-phenylsulfanyl]-4-propylamino-pyrimidin-2-yl}-benzenesulfonamide (12)

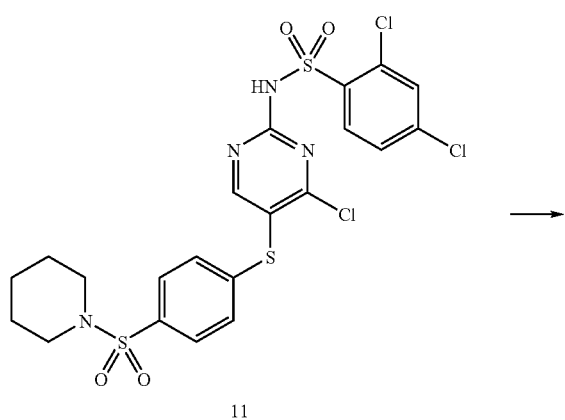

-continued

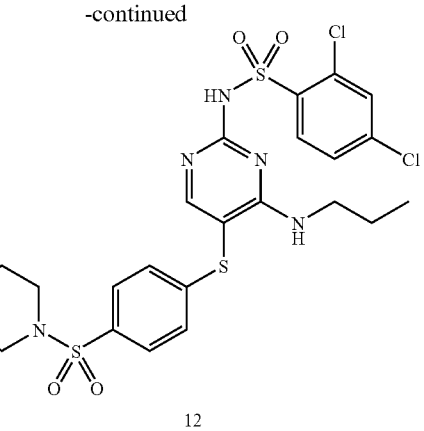

n-Propylamine (25 mg, 0.42 mmol) was added to a solution of 11 (50 mg, 0.08 mmol) in THF (5 mL) and the mixture was stirred at 50° C. for 2 hours. The solution was cooled to room temperature, filtered and the precipitate was washed with THF. The filtrate was concentrated under reduced pressure to afford a yellow oil. Trituration with ether gave a solid which was purified by flash column chromatography (2% MeOH in DCM) to afford 12 as a white solid (28 mg). $^1$H NMR (DMSO): δ 0.54 (t, 3H), 1.22 (q, 2H), 1.33-1.34 (m, 2H), 1.51 (quin, 4H), 2.80-2.84 (m, 6H), 7.32 (d, 2H), 7.56 (d, 1H), 7.58 (d, 2H), 7.70 (s, 1H), 7.97 (br s, 1H), 8.07 (d, 1H), 8.15, (s, 1H) ppm. Mass Spectrum m/e=618.0 (M+1)

Example 2

2,4-Dichloro-N-{4-ethylamino-5-[4-(piperidine-1-sulfonyl)-phenylsulfanyl]-pyrimidin-2-yl}-benzenesulfonamide (13)

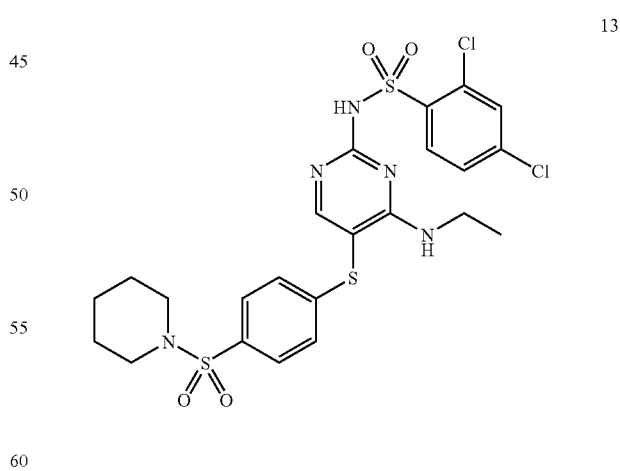

By a similar method using the appropriate starting materials the above compound was prepared. $^1$H NMR (DMSO): δ 0.72 (t, 3H), 1.35 (m, 2H), 1.52 (m, 4H), 2.88 (m, 6H), 7.29 (d, 2H), 7.60 (m, 3H), 7.69 (s, 1H), 8.10 (d, 2H), 8.14 (s, 1H) ppm. Mass Spectrum m/e=602.0 (M+1).

Example 3

N-{4-Butylamino-5-[4-(piperidine-1-sulfonyl)-phenylsulfanyl]-pyrimidin-2-yl}-2,4-dichloro-benzenesulfonamide (14)

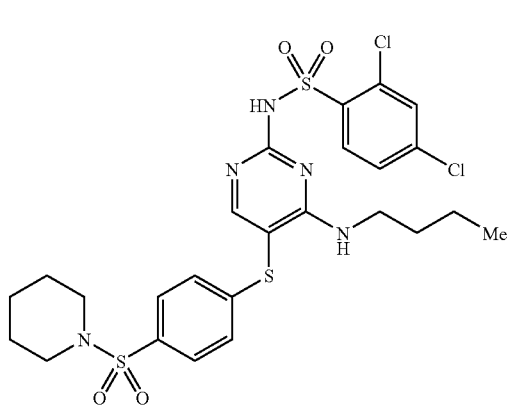

By a similar method using the appropriate starting materials the above compound was prepared. ¹H NMR (DMSO): δ 0.72 (t, 3H), 0.91 (m, 2H), 1.13 (m, 2H), 1.34 (m, 2H), 1.52 (m, 4H), 2.87 (m, 6H), 7.32 (d, 2H), 7.55 (d, 1H), 7.63 (d, 2H), 7.70 (s, 1H), 7.93 (br s, 1H), 8.07 (d, 1H), 8.15 (s, 1H) ppm. Mass Spectrum m/e=630.0 (M+1).

Example 4

2,4-Dichloro-N-{4-(methyl-propyl-amino)-5-[4-(piperidine-1-sulfonyl)-phenylsulfanyl]-pyrimidin-2-yl}-benzenesulfonamide (15)

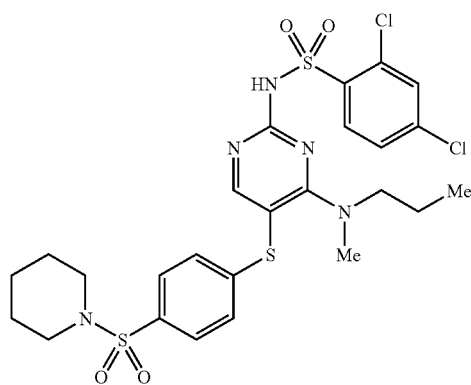

By a similar method using the appropriate starting materials the above compound was prepared. ¹H NMR (DMSO): δ 0.56 (t, 3H), 1.09 (t, 2H), 1.34-1.35 (m, 4H), 1.52 (m, 4H), 2.84-2.86 (m, 3H), 2.95 (br, 2H), 3.37-3.41 (m, 2H), 7.31 (d, 2H), 7.58 (d, 1H), 7.65 (d, 2H), 7.27 (s, 1H), 8.07 (d, 1H), 8.12 (s, 1H) ppm. Mass Spectrum m/e=631.0 (M+1)

Example 5

2,4-Dichloro-N-{4-(2-methoxy-ethylamino)-5-[4-(piperidine-1-sulfonyl)-phenylsulfanyl]-pyrimidin-2-yl}-benzenesulfonamide (16)

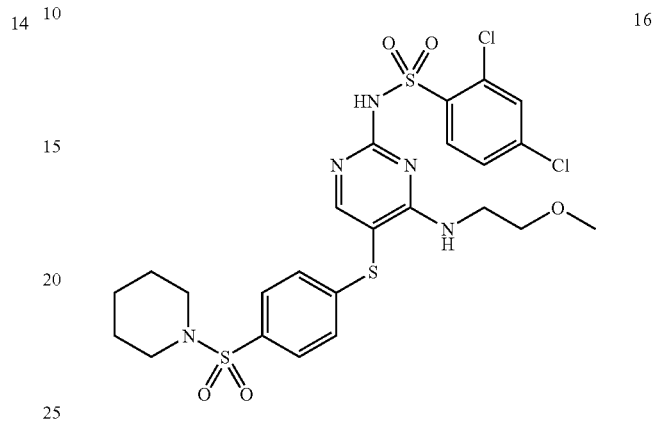

By a similar method using the appropriate starting materials the above compound was prepared. ¹H NMR (DMSO): δ 1.34 (m, 2H), 1.52 (m, 4H), 2.84 (m, 4H), 3.05 (m, 2H), 3.10 (s, 3H), 3.12 (m, 2H), 7.31 (d, 2H), 7.55 (d, 2H), 7.63 (d, 2H), 7.70 (s, 1H), 7.90 (br s, 1H), 8.06 (d, 2H), 8.16 (s, 1H) ppm. Mass Spectrum m/e=632.0 (M+1).

Example 6

2,4-Dichloro-N-{4-isopropylamino-5-[4-(piperidine-1-sulfonyl)-phenylsulfanyl]-pyrimidin-2-yl}-benzenesulfonamide (17)

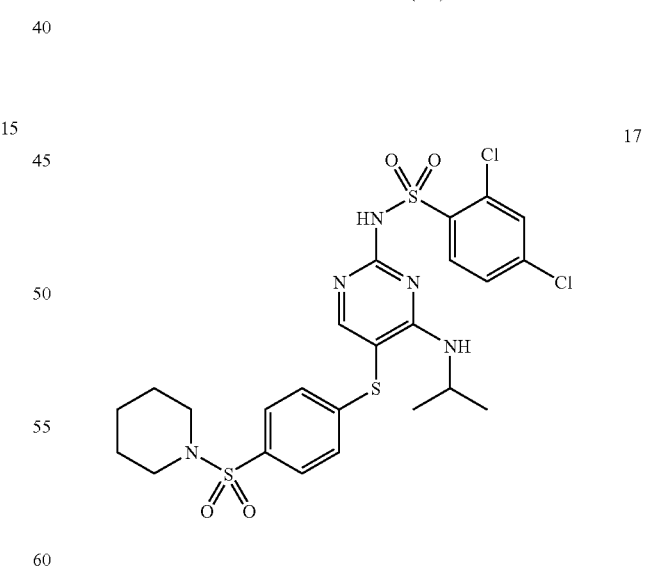

By a similar method using the appropriate starting materials the above compound was prepared. ¹H NMR (DMSO): δ 0.98 (d, 6H), 1.43 (m, 2H), 1.64 (m, 4H), 2.98 (m, 4H), 3.87 (m, 1H), 6.02 (d, 1H), 7.19 (d, 2H), 7.35 (d, 1H), 7.46 (s, 1H), 7.66 (d, 2H), 8.26 (d, 2H), 8.36 (s, 1H) ppm. Mass Spectrum m/e=616.0 (M+1).

Example 7

2,4-Dichloro-N-{4-(1-ethyl-propylamino)-5-[4-(piperidine-1-sulfonyl)-phenylsulfanyl]-pyrimidin-2-yl}-benzenesulfonamide (18)

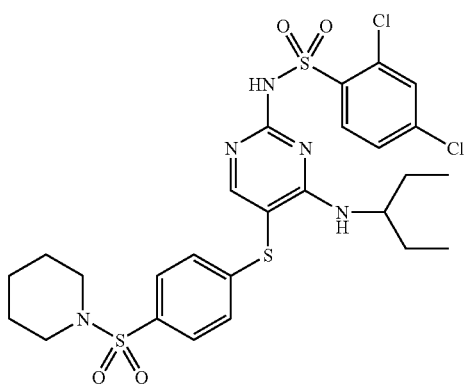

By a similar method using the appropriate starting materials the above compound was prepared. $^1$H NMR (CDCl$_3$): δ 0.63 (t, 6H), 1.25 (m, 2H), 1.42 (m, 4H), 1.63 (m, 4H), 3.60 (m, 1H), 5.93 (d, 1H), 7.20 (d, 2H), 7.35 (d, 1H), 7.47 (s, 1H), 7.65 (d, 2H), 8.25 (d, 1H), 8.37 (s, 1H) ppm. Mass Spectrum m/e=644.0 (M+1).

Example 8

2,4-Dichloro-N-{4-(cyclopropylmethyl-amino)-5-[4-(piperidine-1-sulfonyl)-phenylsulfanyl]-pyrimidin-2-yl}-benzenesulfonamide (19)

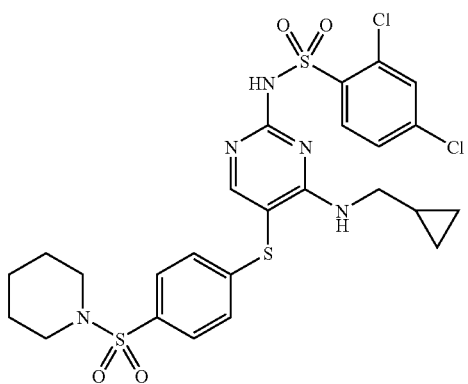

By a similar method using the appropriate starting materials the above compound was prepared. $^1$H NMR (DMSO): δ 0.01 (m, 2H), 0.22 (m, 2H), 0.67-0.69 (m, 1H), 1.34-1.36 (m, 2H), 1.53 (m, 4H), 2.73 (t, 2H), 2.84 (t, 4H), 7.32 (d, 2H), 7.56 (d, 1H), 7.65 (d, 2H), 7.69 (d, 1H), 8.10 (d, 1H), 8.16 (s, 1H). ppm. Mass Spectrum m/e=628.9 (M+1)

Example 9

2,4-Dichloro-N-{4-isobutylamino-5-[4-(piperidine-1-sulfonyl)-phenylsulfanyl]-pyrimidin-2-yl}-benzenesulfonamide (20)

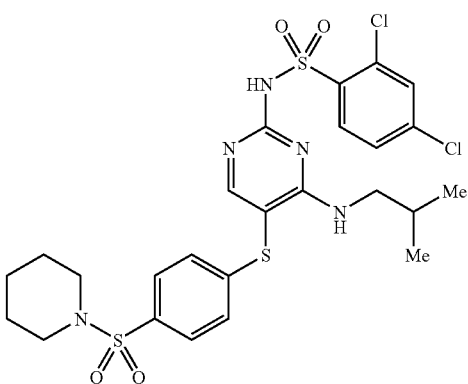

By a similar method using the appropriate starting materials the above compound was prepared. $^1$H NMR (DMSO): δ 0.54 (d, 6H), 1.33-1.35 (m, 2H), 1.53 (m, 4H), 2.70 (t, 2H), 2.82 (t, 4H), 3.39-3.41 (m, 1H), 7.36 (d, 2H), 7.58 (d, 1H), 7.64 (d, 2H), 7.70 (d, 1H), 8.07 (d, 1H), 8.17 (s, 1H) ppm. Mass Spectrum m/e=632.0 (M+1)

Example 10

2,4-Dichloro-N-{4-(3-methyl-butylamino)-5-[4-(piperidine-1-sulfonyl)-phenylsulfanyl]-pyrimidin-2-yl}-benzenesulfonamide (21)

By a similar method using the appropriate starting materials the above compound was prepared. $^1$H NMR (DMSO): δ 0.70 (d, 6H), 1.06-1.07 (m, 1H), 1.42, (s, 2H), 1.44 (q, 4H), 1.45-1.46 (m, 4H), 1.63 (quin, 2H), 2.76-2.79 (m, 2H), 7.30 (d, 2H), 7.53 (d, 1H), 7.61 (d, 2H), 7.68 (s, 1H), 8.06, (d, 1H), 8.12 (s, 1H) ppm. Mass Spectrum m/e=645.0 (M+1)

Example 11

4-Chloro-N-{5-[4-(piperidine-1-sulfonyl)-phenylsulfanyl]-4-propylamino-pyrimidin-2-yl}-benzenesulfonamide (22)

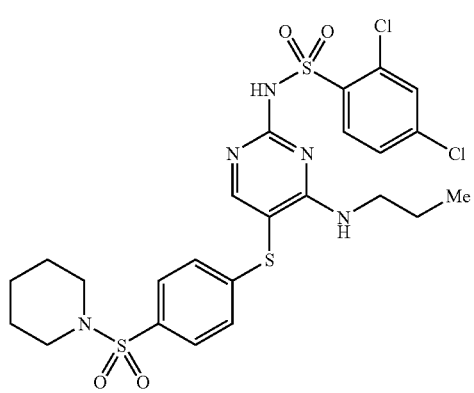

By a similar method using the appropriate starting materials the above compound was prepared. $^1$H NMR (DMSO): δ 0.91 (t, 3H), 1.24 (m, 2H), 1.33 (m, 2H), 1.51-1.56 (m, 4H), 2.72 (t, 2H), 2.73 (t, 4H), 7.21 (d, 2H), 7.45 (d, 2H), 7.59 (d, 2H), 7.73 (d, 2H), 7.92 (s, 1H) ppm. Mass Spectrum m/e=583.0 (M+1)

Example 12

4-Methoxy-N-{5-[4-(piperidine-1-sulfonyl)-phenylsulfanyl]-4-propylamino-pyrimidin-2-yl}-benzenesulfonamide (23)

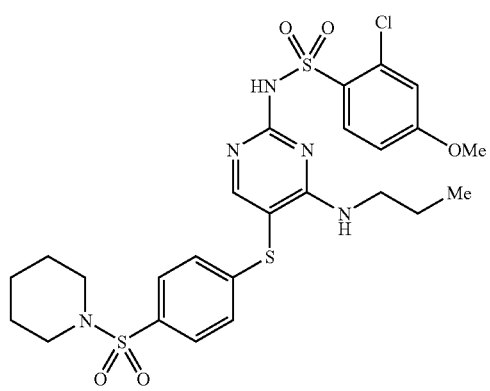

By a similar method using the appropriate starting materials the above compound was prepared. $^1$H NMR (DMSO): δ 0.64 (t, 3H), 1.34 (m, 4H), 1.52 (m, 4H), 2.82 (m, 4H), 3.10 (m, 2H), 3.80 (s, 3H), 7.02 (d, 2H), 7.30 (d, 2H), 7.62 (d, 2H), 7.76 (d, 2H), 8.09 (s, 1H) ppm. Mass Spectrum m/e=578.2 (M+1).

Example 13

4-Chloro-N-{5-[4-(morpholine-4-sulfonyl)-phenoxy]-4-propylamino-pyrimidin-2-yl}-benzenesulfonamide (24)

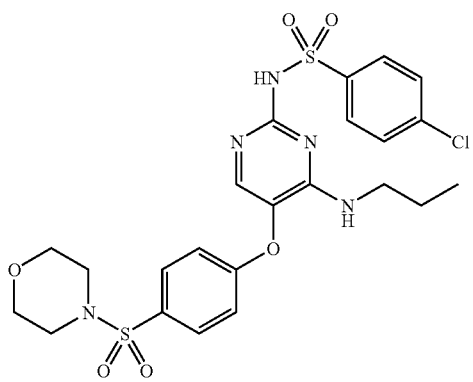

By a similar method using the appropriate starting materials the above compound was prepared. $^1$H NMR (CDCl$_3$): 0.88 (t, 3H), 1.49 (m, 2H), 3.02 (m, 4H), 3.27 (m, 2H), 3.75 (m, 4H), 5.74 (m, 1H), 7.10 (d, 2H), 7.46 (d, 2H), 7.75 (d, 2H), 7.91 (m, 3H) ppm. Mass Spectrum m/e=568.2 (M+1).

Example 14

2,4-Dichloro-N-[4-methylamino-5-(naphthalen-2-ylsulfanyl)-pyrimidin-2-yl]-benzenesulfonamide (25)

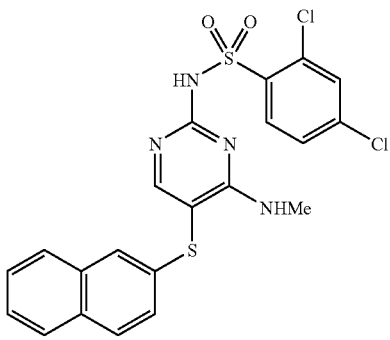

By a similar method using the appropriate starting materials the above compound was prepared. $^1$H NMR (DMSO): δ 2.37 (s, 3H), 7.31 (d, 1H), 7.46-7.55 (m, 3H), 7.66 (s, 2H), 7.82-7.87 (m, 3H), 8.11-8.12 (m, 2H) ppm. Mass Spectrum m/e=491.0 (M+1).

Example 15

2,4-Dichloro-N-[4-dimethylamino-5-(naphthalen-2-ylsulfanyl)-pyrimidin-2-yl]-benzenesulfonamide (26)

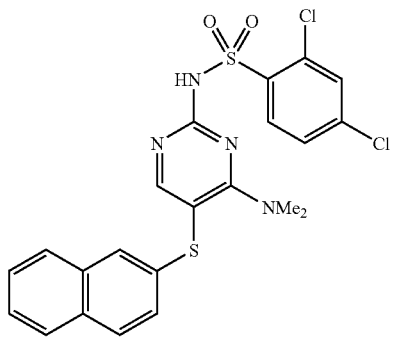

By a similar method using the appropriate starting materials the above compound was prepared. Mass Spectrum m/e=505.9 (M+1).

Example 16

2,4-Dichloro-N-[5-(3,4-dichloro-phenoxy)-4-propylamino-pyrimidin-2-yl]-benzenesulfonamide (27)

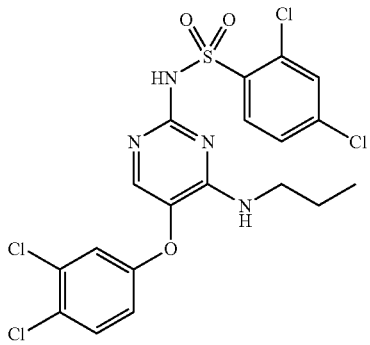

By a similar method using the appropriate starting materials the above compound was prepared. $^1$H NMR (DMSO): δ 0.67 (t, 3H), 1.24-1.31 (m, 2H), 2.87 (t, 2H), 6.99-7.01 (m, 1H), 7.36 (d, 1H), 7.55-7.58 (m, 2H), 7.68 (s, 1H), 7.72-7.74 (m, 1H), 8.09 (d, 1H) ppm. Mass Spectrum m/e=522.8 (M+1).

Example 17

Method 8

2,4-Dichloro-N-{5-[4-(piperidine-1-sulfonyl)-phenylsulfanyl]-4-propoxy-pyrimidin-2-yl}-benzenesulfonamide (28)

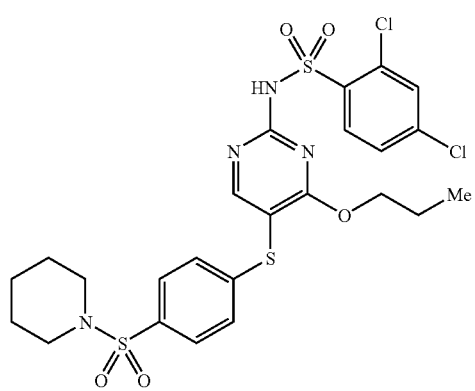

Steps 1 and 2 of method 7 were followed. Subsequently, a solution of 2.0 M n-PrONa in n-PrOH was prepared by dissolving sodium (460 mg, 20.0 mmol) in n-PrOH (10 mL). The prepared solution was added to a solution of 11 (50 mg, 0.10 mmol) in n-PrOH (3 mL). The solution was stirred at 50° C. for 30 minutes. The mixture was cooled to room temperature, filtered and the precipitate washed with propanol. The filtrate was concentrated to a solid which was reprecipitated in water to afford 28 as a white solid (51 mg). $^1$H NMR (DMSO): δ 0.58 (t, 3H), 1.32-1.37 (m, 2H), 1.42 (q, 2H), 1.47-1.52 (m, 4H), 2.81 (t, 4H), 3.68 (t, 2H), 7.16 (d, 2H), 7.46 (d, 1H), 7.46 (d, 1H), 7.55 (s, 1H), 7.56 (d, 2H), 8.04 (d, 1H), 8.08 (s, 1H) ppm. Mass Spectrum m/e=618.8 (M+1)

Example 18

4-Chloro-N-{5-[4-(morpholine-4-sulfonyl)-phenoxy]-4-propoxy-pyrimidin-2-yl}-benzenesulfonamide (29)

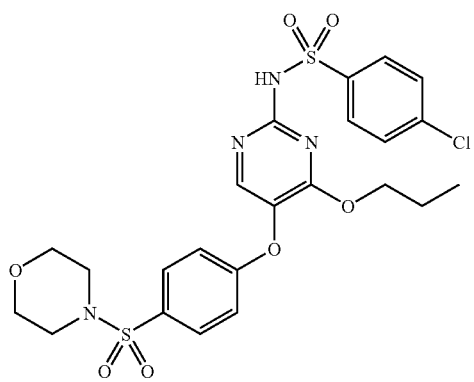

By a similar method using the appropriate starting materials the above compound was prepared. $^1$H NMR (CDCl$_3$): 0.75 (t, 3H), 1.58 (m, 2H), 2.98 (m, 4H), 3.73 (m, 4H), 4.12 (t, 2H), 6.97 (d, 2H), 7.49 (d, 2H), 7.68 (d, 2H), 7.98 (d, 2H), 8.29 (s, 1H) ppm. Mass Spectrum m/e=569.0 (M+1).

Example 19

2,4-Dichloro-N-[4-methoxy-5-(naphthalen-2-ylsulfanyl)-pyrimidin-2-yl]-benzenesulfonamide (30)

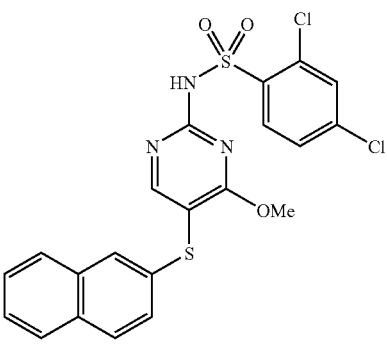

By a similar method using the appropriate starting materials the above compound was prepared. $^1$H NMR (DMSO): δ 3.50 (s, 3H), 7.27 (dd, 1H), 7.50 (m, 2H), 7.56 (dd, 1H), 7.63 (s, 1H), 7.69 (s, 1H), 7.80-7.87 (m, 3H), 8.15 (d, 1H), 8.27 (s, 1H) ppm. Mass Spectrum m/e=492.0 (M). 494.0 (M+2)

Example 20

2,4-Dichloro-N-[5-(3,4-dichloro-phenoxy)-4-propoxy-pyrimidin-2-yl]-benzenesulfonamide (31)

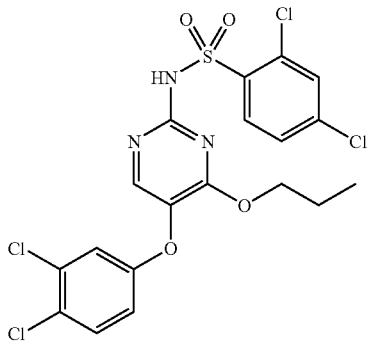

31

By a similar method using the appropriate starting materials the above compound was prepared. ¹H NMR (DMSO): δ 0.63 (t, 3H), 1.42 (sex, 2H), 3.87 (t, 2H), 7.00 (d, 1H), 7.35 (d, 1H), 7.54 (d, 1H), 7.63 (d, 1H), 7.79 (s, 1H), 8.17 (d, 1H), 8.27 (s, 1H) ppm. Mass Spectrum m/e=523.9 (M+1).

Example 21

Method 9

2,4-Dichloro-N-{5-[4-(piperidine-1-sulfonyl)-phenylsulfanyl]-4-propylsulfanyl-pyrimidin-2-yl}-benzenesulfonamide (32)

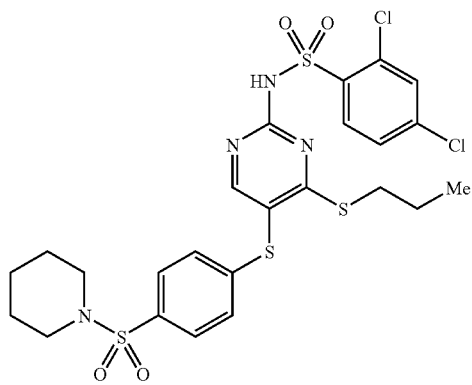

32

Steps 1 and 2 of method 7 were followed.

Cesium carbonate (65 mg, 0.2 mmol) was added to a solution of propanethiol (8 μl, 0.09 mmol) in acetone (0.5 mL). The reaction mixture was heated to 50° C. for 45 minutes then cooled to r.t. DMF (2 mL) and 2,4-Dichloro-N-{4-chloro-5-[4-(piperidine-1-sulfonyl)-phenylsulfanyl]-pyrimidin-2-yl}-benzenesulfonamide 11 (50 mg, 0.08 mmol) were added and the resultant mixture heated to 50° C. for 2 hours. The reaction was allowed to cool, filtered through celite and the solvent evaporated in vacuo. The crude product was purified by flash column chromatography (2% MeOH in DCM) to afford 2,4-Dichloro-N-{5-[4-(piperidine-1-sulfonyl)-phenylsulfanyl]-4-propylsulfanyl-pyrimidin-2-yl}-benzenesulfonamide 32 (20 mg). ¹H NMR (CDCl₃): δ 1.00 (m, 3H), 1.27 (m, 2H), 1.66 (m, 6H), 2.88 (m, 2H), 2.99 (m, 4H), 7.26 (m, 2H), 7.45 (d, 1H), 7.55 (s, 1H), 7.66 (d, 2H), 8.27 (d, 1H), 8.5149 (s, 1H), 12.61 (br s, 1H) ppm. Mass Spectrum m/e=632.8 (M+1).

Example 43

Method 10

N-{4-Butyl-5-[4-(piperidine-1-sulfonyl)-phenylsulfanyl]-pyrimidin-2-yl}-2,4-dichloro-benzenesulfonamide (43)

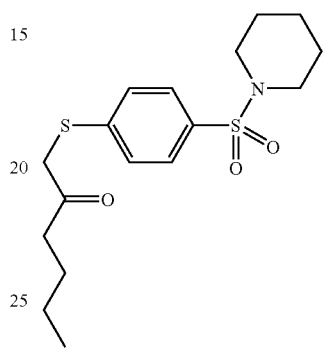

35

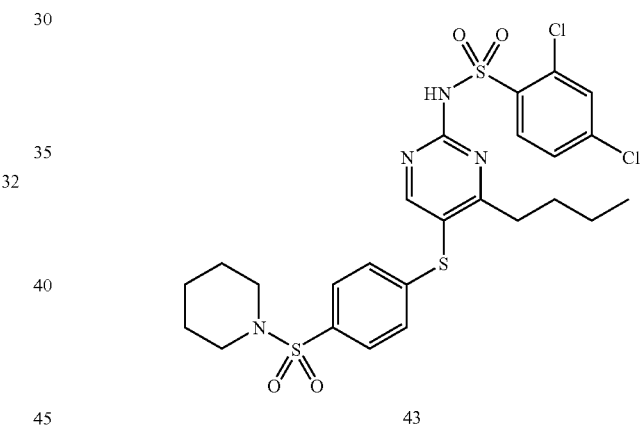

43

A mixture of 1-[4-(Piperidine-1-sulfonyl)-phenylsulfanyl]-hexan-2-one 35 (303 mg, 0.85 mmol), methanol (0.3 mL) and dimethylformamide dimethylacetal (0.12 mL, 0.9 mmol) were heated together to 90° C. for 30 minutes The reaction was cooled to r.t. and 1 (312 mg, 1.16 mmol), iPrOH (2 mL) and sodium methoxide (0.25 mL, 1.15 mmol of a 25wt % solution in methanol) added and the resultant mixture heated to 90° C. for 3 hours. The reaction was allowed to cool to r.t. and poured into 3N HCl (20 mL). The resultant precipitate was filtered and dried. This crude product was then purified by flash column chromatography (5% MeOH in DCM) to afford an oil which was then triturated with ether. The solid material was filtered and dried to afford N-{4-Butyl-5-[4-(piperidine-1-sulfonyl)-phenylsulfanyl]-pyrimidin-2-yl}-2,4-dichloro-benzenesulfonamide 43 (115 mg). ¹H NMR (CDCl₃): δ 0.85 (t, 3H), 1.18 (m, 2H), 1.22 (m, 4H), 1.60 (m, 4H), 2.71 (t, 2H), 2.96 (m, 4H), 7.15 (d, 2H), 7.44 (d, 1H), 7.50 (s, 1H), 7.62 (d, 2H), 8.32 (d, 1H), 8.58 (s, 1H) ppm. Mass Spectrum m/e=615.0 (M+1).

Example 44

N-{4-Butyl-5-[4-(piperidine-1-sulfonyl)-phenylsulfanyl]-pyrimidin-2-yl}-4-chloro-benzenesulfonamide (44)

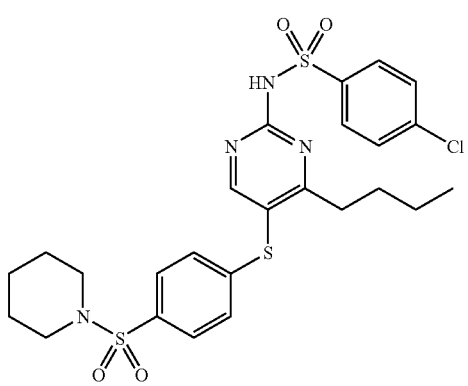

By a similar method using the appropriate starting materials the above compound was prepared. $^1$H NMR (CDCl$_3$): δ 0.87 (t, 3H), 1.28 (m, 2H), 1.42 (m, 2H), 1.49 (m, 2H), 1.61 (m, 4H), 2.77 (t, 2H), 2.96 (m, 4H), 7.13 (d, 2H), 7.51 (d, 2H), 7.62 (d, 2H), 8.08 (d, 2H), 8.58 (s, 1H) ppm. Mass Spectrum m/e=581.1 (M+1).

Example 45

N-{4-Butyl-5-[4-(piperidine-1-sulfonyl)-phenylsulfanyl]-pyrimidin-2-yl}-4-methoxy-benzenesulfonamide (45)

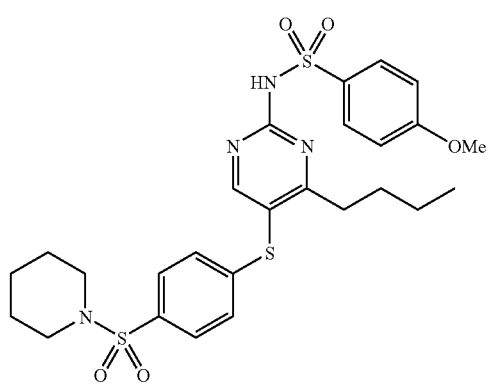

By a similar method using the appropriate starting materials the above compound was prepared. $^1$H NMR (CDCl$_3$): δ 0.73 (t, 3H), 1.12 (m, 2H), 1.34 (m, 4H), 1.50 (m, 4H), 2.59 (t, 2H), 2.82 (m, 4H), 3.79 (s, 3H), 7.03 (d, 2H), 7.21 (d, 2H), 7.58 (d, 2H), 7.87 (d, 2H), 8.45 (s, 1H) ppm. Mass Spectrum m/e=577.2 (M+1).

Example 46

N-{4-Butyl-5-[4-(piperidine-1-sulfonyl)-phenylsulfanyl]-pyrimidin-2-yl}-2-chloro-4-trifluoromethyl-benzenesulfonamide (46)

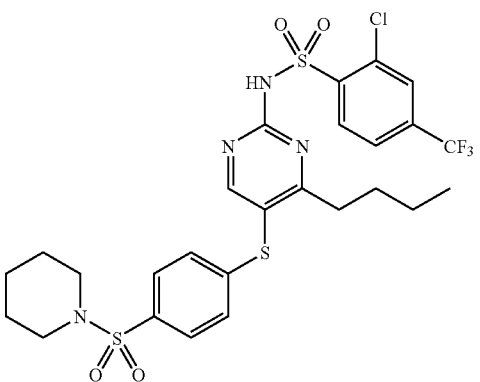

By a similar method using the appropriate starting materials the above compound was prepared. 1H NMR (CDCl$_3$): δ 0.66 (t, 3H), 1.02 (m, 2H), 1.11 (m, 2H), 1.34 (m, 2H), 1.52 (m, 4H), 2.56 (t, 2H), 2.83 (m, 4H), 7.29 (d, 2H), 7.61 (d, 2H), 7.98 (d, 1H), 8.09 (s, 1H), 8.42 (d, 1H), 8.62 (s, 1H) ppm. Mass Spectrum m/e=549.2 (M+1).

Example 47

2,4-Dichloro-N-{4-pentyl-5-[4-(piperidine-1-sulfonyl)-phenylsulfanyl]-pyrimidin-2-yl}-benzenesulfonamide (47)

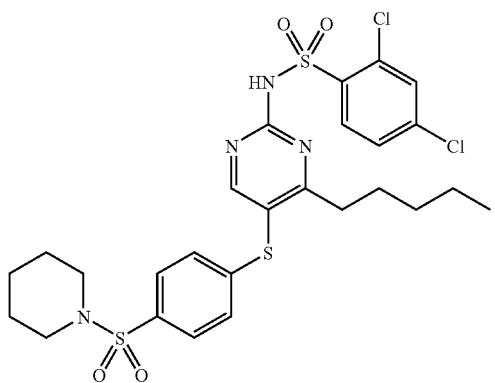

By a similar method using the appropriate starting materials the above compound was prepared. $^1$H NMR (CDCl$_3$): δ 0.88 (t, 3H), 1.25 (m, 4H), 1.45 (m, 2H), 1.62 (m, 6H), 2.72 (t, 2H), 2.99 (m, 4H), 7.17 (d, 2H), 7.46 (d, 1H), 7.53 (s, 1H), 7.65 (d, 2H), 8.34 (d, 1H), 8.58 (s, 1H) ppm. Mass Spectrum m/e=629.0 (M+1).

Example 48

4-Chloro-N-{4-pentyl-5-[4-(piperidine-1-sulfonyl)-phenylsulfanyl]-pyrimidin-2-yl}-benzenesulfonamide (48)

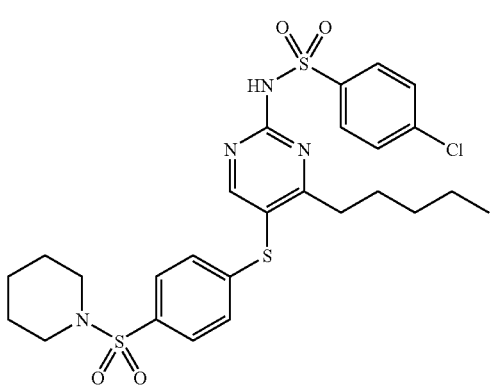

By a similar method using the appropriate starting materials the above compound was prepared. $^1$H NMR (CDCl$_3$): δ 0.89 (t, 3H), 1.28 (m, 4H), 1.55 (m, 2H), 1.64 (m, 6H), 2.80 (m, 2H), 2.99 (m, 4H), 7.16 (d, 2H), 7.52 (d, 2H), 7.64 (d, 2H), 8.11 (d, 1H), 8.59 (s, 1H), 9.58 (br s, 1H) ppm. Mass Spectrum m/e=593.2 (M−1).

Example 49

2,4-Dichloro-N-{4-methyl-5-[4-(piperidine-1-sulfonyl)-phenylsulfanyl]-pyrimidin-2-yl}-benzenesulfonamide (49)

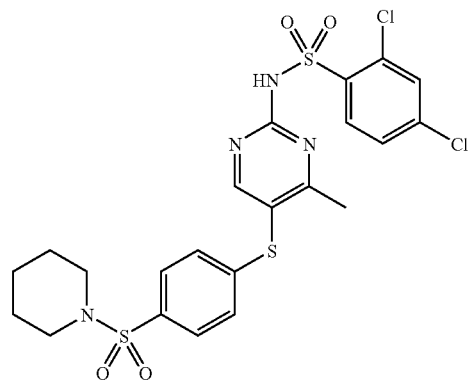

By a similar method using the appropriate starting materials the above compound was prepared. $^1$H NMR (CDCl$_3$): 1.44 (m, 2H), 1.65 (m, 4H), 2.42 (m, 3H), 2.99 (m, 4H), 7.17 (d, 2H), 7.49 (d, 1H), 7.52 (s, 1H), 7.65 (d, 2H), 8.35 (d, 1H), 8.57 (s, 1H), 10.08 (br s, 1H) ppm. Mass Spectrum m/e=572.8 (M+1).

Example 50

2-Chloro-N-{4-methyl-5-[4-(piperidine-1-sulfonyl)-phenylsulfanyl]-pyrimidin-2-yl}-4-trifluoromethyl-benzenesulfonamide (50)

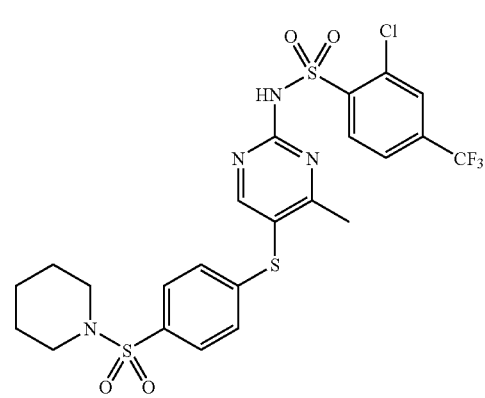

By a similar method using the appropriate starting materials the above compound was prepared. $^1$H NMR (CDCl$_3$): 1.44 (m, 2H), 1.66 (m, 4H), 2.41 (m, 3H), 2.99 (m, 4H), 7.18 (d, 2H), 7.66 (d, 2H), 7.78 (m, 2H), 8.55 (d, 1H), 8.58 (s, 1H), 10.32 (br s, 1H) ppm. Mass Spectrum m/e=606.8 (M+1).

Example 51

4-Chloro-N-{4-methyl-5-[4-(piperidine-1-sulfonyl)-phenylsulfanyl]-pyrimidin-2-yl}-benzenesulfonamide (51)

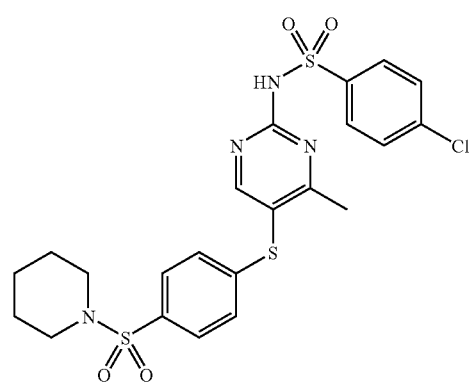

By a similar method using the appropriate starting materials the above compound was prepared. $^1$H NMR (CDCl$_3$): 1.44 (m, 2H), 1.64 (m, 4H), 2.50 (m, 3H), 3.00 (m, 4H), 7.18 (d, 2H), 7.52 (d, 2H), 7.65 (d, 2H), 8.11 (d, 2H), 8.66 (s, 1H), 10.43 (br s, 1H) ppm. Mass Spectrum m/e=539.0 (M+1).

Example 52

2,4-Dichloro-N-{4-methyl-5-[4-(morpholine-4-sulfonyl)-phenylsulfanyl]-pyrimidin-2-yl}-benzenesulfonamide (52)

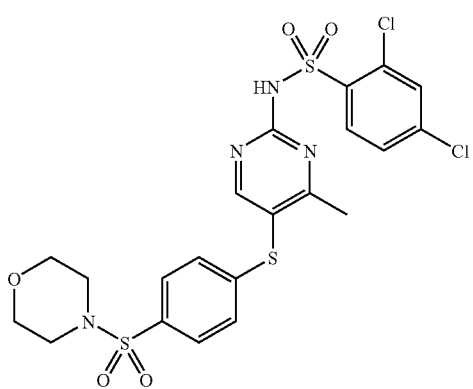

By a similar method using the appropriate starting materials the above compound was prepared. $^1$H NMR (MeOD): δ 2.25 (s, 3H), 2.95 (t, 4H), 3.71 (t, 4H), 7.19 (d, 2H), 7.92 (d, 1H), 7.51 (d, 1H), 7.63 (d, 2H), 8.19 (d, 1H), 8.22 (s, 1H) ppm. Mass Spectrum m/e=576 (M+1)

Example 53

2-Chloro-N-{4-methyl-5-[4-(morpholine-4-sulfonyl)-phenylsulfanyl]-pyrimidin-2-yl}-4-trifluoromethyl-benzenesulfonamide (53)

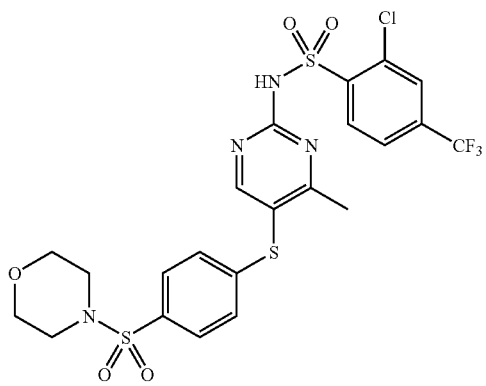

By a similar method using the appropriate starting materials the above compound was prepared. $^1$H NMR (DMSO): δ 2.30 (s, 3H), 2.83 (t, 4H), 3.61 (t, 4H), 7.31 (d, 2H), 7.61 (d, 2H), 7.98 (d, 1H), 8.08 (s, 1H), 8.41 (d, 1H), 8.56 (s, 1H) ppm. Mass Spectrum m/e=610 (M+1)

Example 54

2,4-Dichloro-N-{4-methyl-5-[4-(morpholine-4-sulfonyl)-phenoxy]-pyrimidin-2-yl}-benzenesulfonamide (54)

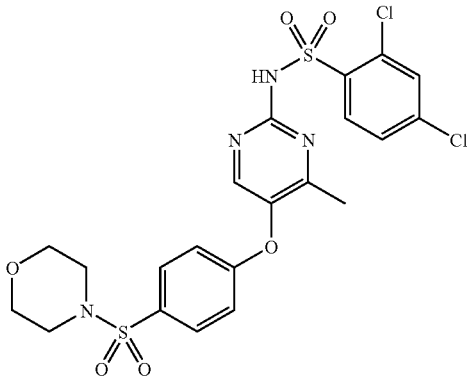

By a similar method using the appropriate starting materials the above compound was prepared. $^1$H NMR (CDCl$_3$): 2.29 (s, 3H), 3.02 (t, 4H), 3.77 (t, 4H), 7.00 (d, 2H), 7.48 (d, 1H), 7.53 (s, 1H), 7.75 (d, 2H), 8.28 (s, 1H), 8.35 (d, 1H), 9.99 (br s, 1H) ppm. Mass Spectrum m/e=559.0 (M+1).

Example 55

2-Chloro-N-{4-methyl-5-[4-(morpholine-4-sulfonyl)-phenoxy]-pyrimidin-2-yl}-4-trifluoromethyl-benzenesulfonamide (55)

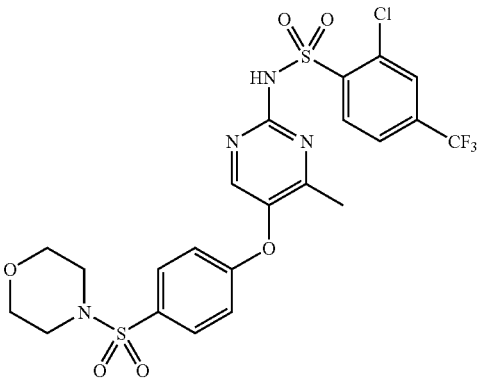

By a similar method using the appropriate starting materials the above compound was prepared. $^1$H NMR (CDCl$_3$): 2.29 (s, 3H), 3.02 (t, 4H), 3.75 (t, 4H), 7.01 (d, 2H), 7.76 (m, 4H), 8.31 (s, 1H), 8.55 (d, 1H), 10.45 (br s, 1H) ppm. Mass Spectrum m/e=593.0 (M+1).

Example 56

4-Chloro-N-{4-methyl-5-[4-(morpholine-4-sulfonyl)-phenoxy]-pyrimidin-2-yl}-benzenesulfonamide (56)

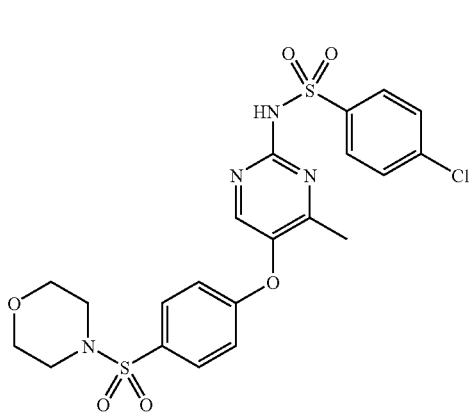

By a similar method using the appropriate starting materials the above compound was prepared. $^1$H NMR (CDCl$_3$): 2.36 (s, 3H), 3.02 (t, 4H), 3.77 (t, 4H), 7.00 (d, 2H), 7.52 (d, 2H), 7.75 (d, 2H), 8.11 (d, 2H), 8.35 (s, 1H), 10.11 (br s, 1H) ppm. Mass Spectrum m/e=525.0 (M+1).

Example 57

2,4-Dichloro-N-[4-methyl-5-(naphthalen-2-ylsulfanyl)-pyrimidin-2-yl]-benzenesulfonamide (57)

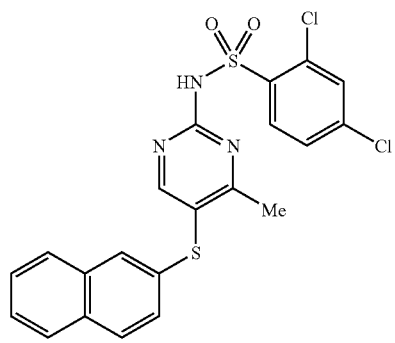

By a similar method using the appropriate starting materials the above compound was prepared. $^1$H NMR (CDCl$_3$): δ 2.41 (s, 3H), 5.32 (s, 1H), 7.25 (d, 1H), 7.43-7.52 (m, 4H), 7.63 (s, 1H), 7.72-7.82 (m, 3H), 8.33 (d, 1H), 8.58 (s, 1H) ppm. Mass Spectrum m/e=477.0 (M+1)

Example 58

2,4-Dichloro-N-[4-methyl-5-(5-methyl-benzothiazol-2-ylsulfanyl)-pyrimidin-2-yl]-benzenesulfonamide (58)

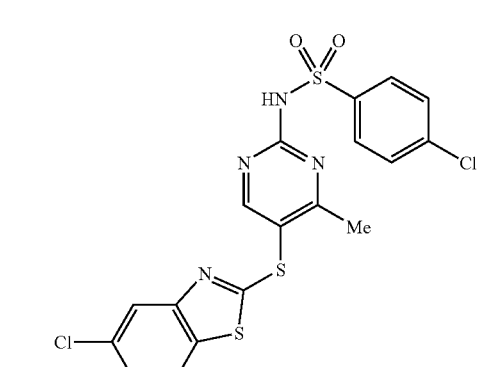

By a similar method using the appropriate starting materials the above compound was prepared. $^1$H NMR (CDCl$_3$): δ 2.50 (s, 3H), 7.41 (d, 1H), 7.71 (d, 2H), 7.93 (s, 1H), 7.98 (d, 1H), 8.05 (d, 2H), 8.78 (s, 1H), 12.52 (br s, 1H) ppm. Mass Spectrum m/e=481.0 (M−1)

Example 59

2-Chloro-N-[4-methyl-5-(naphthalen-2-ylsulfanyl)-pyrimidin-2-yl]-4-trifluoromethyl-benzenesulfonamide (59)

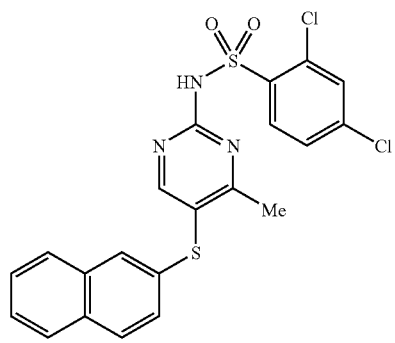

By a similar method using the appropriate starting materials the above compound was prepared. 1H NMR (CDCl$_3$): δ 2.41 (s, 3H), 7.25 (d, 1H), 7.50 (m, 2H), 7.67 (s, 1H), 7.72 (m, 5H), 8.54 (m, 2H), 10.58 (br s, 1H) ppm. Mass Spectrum m/e=509.8 (M+1)

Example 60

2,4-Dichloro-N-[5-(3,4-dichloro-phenoxy)-4-methyl-pyrimidin-2-yl]-benzenesulfonamide (60)

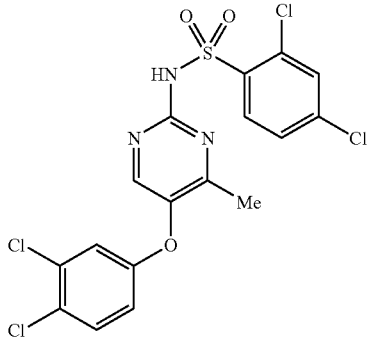

By a similar method using the appropriate starting materials the above compound was prepared. $^1$H NMR (DMSO): δ 2.29 (s, 3H), 6.74 (d, 1H), 6.99 (s, 1H), 7.40 (d, 1H), 7.47 (d, 1H), 7.52 (s, 1H), 8.29 (s, 1H), 8.35 (d, 1H) ppm. Mass Spectrum m/e=476.0 (M+1).

Example 61

2,4-Dichloro-5-methyl-N-{6-methyl-5-[4-(piperidine-1-sulfonyl)-phenylsulfanyl]-pyridin-2-yl}-benzenesulfonamide (61)

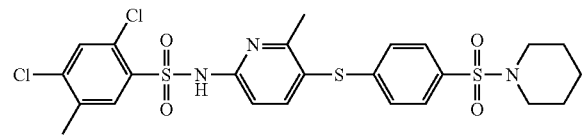

General Method 11

Step 1: Reaction of a 3-bromo- or 3-iodopyridine with a Substituted Thiophenol

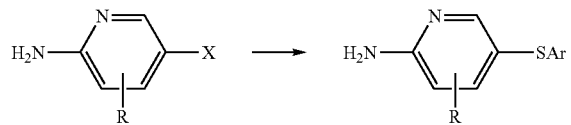

The relevant halopyridine (0.80 mmol), the thiophenol (1.00 mmol), potassium tert-butoxide (101 mg, 0.90 mmol), tris(dibenzylideneacetone)dipalladium (0) (70 mg, 76 μmol) and (oxydi-2,1-phenylene)bis-(diphenylphosphine) (82 mg, 0.15 mmol) were mixed and 1-methyl-2-pyrrolidinone (3 mL) was added. The mixture was stirred using a vortex stirrer until homogeneous, sealed under nitrogen, and heated at 100° C. (for iodopyridines) or 120° C. (for bromopyridines) for 5 minutes in a microwave reactor using powerMAX™. The reaction mixture was then added to ethyl acetate (50 mL), extracted with sodium bicarbonate (sat., aq., 3×25 mL)., dried over magnesium sulphate, and concentrated under reduced pressure to a dark brown oil. Flash chromatography (SiO$_2$, typical solvent mixture ethyl acetate:cyclohexane 1:1) affords coupled product (60-90%).

Step 2: Reaction of an Aminopyridine and an Aryl Sulfonyl Chloride

To the aminoheterocycle (0.50 mmol) in DCM (1 mL) was added the arylsulfonyl chloride (0.80 mmol), followed by pyridine (1 mL). The reaction flask was equipped with a drying tube and stirred vigorously for 16 hours. Hydrochloric acid (0.5N, aq., 30 mL) was then added and the mixture stirred for a further 5 minutes and then extracted with DCM (2×25 mL). The combined organic portions were concentrated under reduced pressure and purified by flash chromatography (SiO$_2$, typical solvent mixture ethyl acetate:cyclohexane 1:2) to afford the sulphonamide as a foam (50-80%).

Step 3: Conversion of an Alkoxycarbonylpyridine to an Alkanoylpyridine

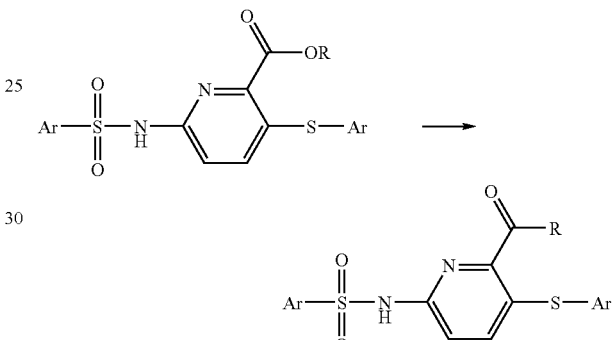

The alkoxycarbonylpyridine (1 mmol) was dissolved in THF (1 mL) and water (1 mL) added, followed by LiOH.H$_2$O (210 mg, 5.0 mmol). The reaction mixture was stirred vigorously until HPLC indicates complete consumption of starting material (10 mins-2 hours). The reaction mixture was then diluted with water (25 mL), acidified to pH 3 with hydrochloric acid (6N, aq.), and extracted with ethyl acetate (2×25 mL). The combined organic layers were dried over magnesium sulphate and concentrated under reduced pressure to afford the pyridinecarboxylic acid. This acid was then dissolved in DMF (2 mL), N,O-dimethylhydroxylamine hydrochloride (150 mg, 1.54 mmol) and O-(1H-benzotriazol-1-yl)-N,N,N', N'-tetramethyluronium tetrafluoroborate (TBTU)(500 mg, 1.56 mmol) were added, followed by N,N-diisopropylethylamine (400 mg, 3.09 mmol). The reaction mixture was allowed to stir at room temperature until HPLC indicates complete consumption of starting material (30 mins-4 hours), and was then diluted with ethyl acetate (50 mL), extracted with sodium bicarbonate (sat., aq., 3×25 mL), and concentrated under reduced pressure to a brown foam. This crude Weinreb amide was dissolved in THF (4 mL), cooled to 0° C., and a solution of Grignard reagent (3-10 equivalents, as a solution in Et$_2$O or THF) was added over 5 minutes. When HPLC shows the reaction had gone to completion (usually 20 mins-1 hour for $^n$Pr, $^c$Pr and Et Grignards, 18+ hours at room temperature for $^t$Bu), the reaction was quenched by the addition of ammonium chloride (sat. aq., 10 mL) and extracted with ethyl acetate (2×25 mL). The combined organic portions were dried over magnesium sulphate, evaporated, and purified by flash chromatography (SiO$_2$, typical solvent mixture ethyl acetate:cyclohexane 1:2) to afford the ketone as a white solid (yields 50-80% for $^nPr$, $^cPr$ and Et Grignards, 20-40% for $^iBu$).

2,4-Dichloro-5-methyl-N-{6-methyl-5-[4-(piperidine-1-sulfonyl)-phenylsulfanyl]-pyridin-2-yl}-benzenesulfonamide was prepared from 2-amino-5-bromo-6-methylpyridine and 4-(N-piperidinylsulfonyl)thiophenol according to General Method 11 step 1 followed by reaction with 2,4-dichloro-5-methylphenylsulfonyl chloride according to General Method 11 step 2. $^1$H NMR (CDCl$_3$): 9.58 (1H, br s, N$\underline{H}$), 8.09 (1H, s, A-ring C$\underline{H}$ ortho to 2×Cl), 7.67 & 6.97 (2×1H, 2×d, 2×J 11 Hz, pyridyl C$\underline{H}$'s), 7.62 & 7.12 (2×2H, 2×d, 2×J 10 Hz, Ar C$\underline{H}$'s of C-ring), 7.51 (1H, s, A-ring C$\underline{H}$ ortho to SO$_2$NH), 3.01-2.93 (4H, m, C$\underline{H}_2$NC$\underline{H}_2$), 2.50 & 2.41 (2×3H, 2×s, 2×C$\underline{H}_3$), 1.70-1.60 (4H, m, CH$_2$C$\underline{H}_2$CH$_2$C$\underline{H}_2$CH$_2$), 1.47-1.38 (2H, m, CH$_2$CH$_2$C$\underline{H}_2$CH$_2$CH$_2$). Hplc (Luna 2, Gradient 5): rt=6.72 minutes. LC/MS rt=7.34 minutes, 586/588 (MH$^+$).

Example 62

2,4-Dichloro-5-methyl-N-{4-methyl-5-[4-(piperidine-1-sulfonyl)-phenylsulfanyl]-pyridin-2-yl}-benzenesulfonamide (62)

62

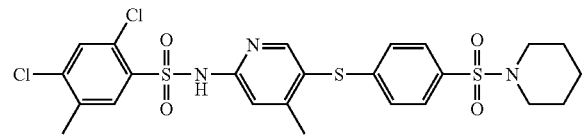

2,4-Dichloro-5-methyl-N-{4-methyl-5-[4-(piperidine-1-sulfonyl)-phenylsulfanyl]-pyridin-2-yl}-benzenesulfonamide was prepared from 2-amino-5-bromo-4-methylpyridine and 4-(N-piperidinylsulfonyl)thiophenol according to General Method 11 step 1 followed by reaction with 2,4-dichloro-5-methylphenylsulfonyl chloride according to General Method 11 step 2. $^1$H NMR (CDCl$_3$): 13.20 (1H, br s, N$\underline{H}$), 8.40 (1H, s, A-ring C$\underline{H}$ ortho to 2×Cl), 8.03 (1H, s, A-ring C$\underline{H}$ ortho to SO$_2$NH), 7.53 & 7.04 (2×2H, 2×d, 2×J 10 Hz, Ar C$\underline{H}$'s of C-ring), 7.41 & 7.15 (2×1H, 2×s, pyridyl C$\underline{H}$'s), 2.91-2.83 (4H, m, C$\underline{H}_2$NC$\underline{H}_2$), 2.38 & 2.23 (2×3H, 2×s, 2×C$\underline{H}_3$), 1.61-1.48 (4H, m, CH$_2$C$\underline{H}_2$CH$_2$C$\underline{H}_2$CH$_2$), 1.39-1.28 (2H, m, CH$_2$CH$_2$C$\underline{H}_2$CH$_2$CH$_2$). Hplc (Luna 2, Gradient 5): rt=6.73 minutes. LC/MS rt=7.43 minutes, 586/588 (MH$^+$).

Example 63

2,4-Dichloro-N-{4-methyl-5-[4-(piperidine-1-sulfonyl)-phenylsulfanyl]-pyridin-2-yl}-benzenesulfonamide (63)

63

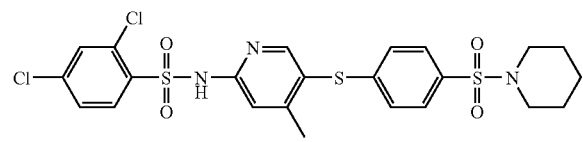

Prepared from 2-amino-5-bromo-4-methylpyridine and 4-(N-piperidinylsulfonyl)thiophenol according to General Method 11 step 1 followed by reaction with 2,4-dichlorophenylsulfonyl chloride according to General Method 11 step 2.

$^1$H NMR (CDCl$_3$): 13.00 (1H, br s, N$\underline{H}$), 8.38 (1H, s, A-ring C$\underline{H}$ ortho to 2×Cl), 8.13 (1H, d, J 11 Hz, A-ring C$\underline{H}$ ortho to SO$_2$NH), 7.53 & 7.05 (2×2H, 2×d, 2×J 10 Hz, Ar C$\underline{H}$'s of C-ring), 7.43 & 7.14 (2×1H, 2×s, pyridyl C$\underline{H}$'s), 7.34 (1H, d, J 11 Hz, A-ring C$\underline{H}$ ortho to Cl), 2.90-2.81 (4H, m, C$\underline{H}_2$NC$\underline{H}_2$), 2.21 (3H, s, C$\underline{H}_3$), 1.62-1.48 (4H, m, CH$_2$C$\underline{H}_2$CH$_2$C$\underline{H}_2$CH$_2$), 1.39-1.27 (2H, m, CH$_2$CH$_2$C$\underline{H}_2$CH$_2$CH$_2$). Hplc (Luna 2, Gradient 5): rt=6.43 minutes. LC/MS rt=7.43 minutes, 572/574 (MH$^+$).

Example 64

2-Chloro-N-{4-methyl-5-[4-(piperidine-1-sulfonyl)-phenylsulfanyl]-pyridin-2-yl}-4-trifluoromethyl-benzenesulfonamide (64)

64

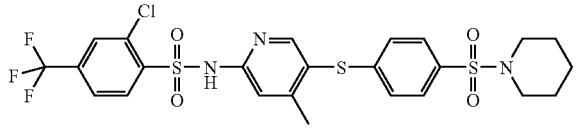

Prepared from 2-amino-5-bromo-4-methylpyridine and 4-(N-piperidinylsulfonyl)thiophenol according to General Method 11 step 1 followed by reaction with 2-chloro-4-trifluoromethylphenylsulfonyl chloride according to General Method 11 step 2. $^1$H NMR (CDCl$_3$): 13.39 (1H, br s, N$\underline{H}$), 8.39 (1H, s, A-ring C$\underline{H}$ ortho to Cl), 8.31 (1H, d, J 11 Hz, A-ring C$\underline{H}$ ortho to SO$_2$NH), 7.67 & 7.18 (2×1H, 2×s, pyridyl C$\underline{H}$'s), 7.61 (1H, d, J 11 Hz, A-ring C$\underline{H}$ ortho to CF$\underline{3}$), 7.53 & 7.04 (2×2H, 2×d, 2×J 10 Hz, Ar C$\underline{H}$'s of C-ring), 2.91-2.82 (4H, m, C$\underline{H}_2$NC$\underline{H}_2$), 2.22 (3H, s, C$\underline{H}_3$), 1.62-1.46 (4H, m, CH$_2$C$\underline{H}_2$CH$_2$C$\underline{H}_2$CH$_2$), 1.39-1.28 (2H, m, CH$_2$CH$_2$C$\underline{H}_2$CH$_2$CH$_2$). Hplc (Luna 2, Gradient 5): rt=6.47 minutes. LC/MS rt=7.13 minutes, 606 (MH$^+$).

Example 65

2,4-Dichloro-N-{6-methyl-5-[4-(piperidine-1-sulfonyl)-phenylsulfanyl]-pyridin-2-yl}-benzenesulfonamide (65)

65

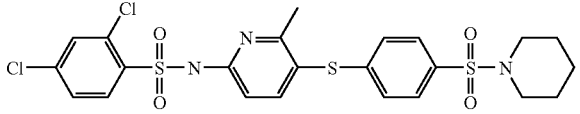

Prepared from 2-amino-5-bromo-6-methylpyridine and 4-(N-piperidinylsulfonyl)thiophenol according to General Method 11 step 1 followed by reaction with 2,4-dichlorophenylsulfonyl chloride according to General Method 11 step 2. $^1$H NMR (CDCl$_3$): 8.24, 7.76, 7.72, 7.51, 7.19, 7.05 (1H, 1H, 2H, 1H, 1H, 2H, 1H, 7×d, J 9, 11, 9, 11, 10, 9 Hz, Ar C$\underline{H}$'s), 7.63 (1H, s, A-ring C$\underline{H}$ ortho to 2×Cl), 3.10-3.01 (4H, m, C$\underline{H}_2$NC$\underline{H}_2$), 2.58 (3H, s, C$\underline{H}_3$), 1.76-1.68 (4H, m, CH$_2$C$\underline{H}_2$CH$_2$C$\underline{H}_2$CH$_2$), 1.58-1.47 (2H, m, CH$_2$CH$_2$C$\underline{H}_2$CH$_2$CH$_2$). Hplc (Luna 2, Gradient 5): rt=6.40 minutes. LC/MS rt=7.11 minutes, 572/574 (MH$^+$).

Example 66

2-Chloro-N-{6-methyl-5-[4-(piperidine-1-sulfonyl)-phenylsulfanyl]-pyridin-2-yl}-4-trifluoromethyl-benzenesulfonamide (66)

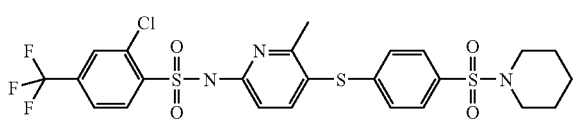

66

Prepared from 2-amino-5-bromo-6-methylpyridine and 4-(N-piperidinylsulfonyl)thiophenol according to General Method 11 step 1 followed by reaction with 2-chloro-4-trifluoromethylphenylsulfonyl chloride according to General Method 11 step 2. $^1$H NMR (CDCl$_3$): 8.21 (1H, d, J 10 Hz, Ar CH ortho to SO$_2$NH), 7.61-7.45 (5H, m, Ar CH's), 6.96 (2H, d, J 9 Hz, Ar CH's), 6.76 (1H, d, J 11 Hz, Ar CH), 2.86-2.78 (4H, m, CH$_2$NCH$_2$), 2.34 (3H, s, CH$_3$), 1.53-1.41 (4H, m, CH$_2$CH$_2$CH$_2$CH$_2$CH$_2$), 1.33-1.20 (2H, m, CH$_2$CH$_2$CH$_2$CH$_2$CH$_2$). Hplc (Luna 2, Gradient 5): rt=6.47 minutes. LC/MS rt=7.04 minutes, 606 (MH$^+$).

Example 67

2,4-Dichloro-5-methyl-N-{5-[4-(piperidine-1-sulfonyl)-phenylsulfanyl]-pyridin-2-yl}-benzenesulfonamide (67)

67

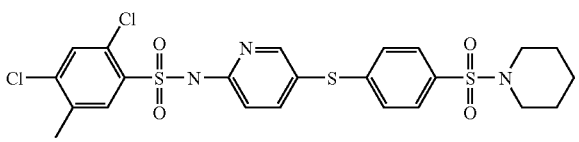

Prepared from 2-amino-5-bromopyridine and 4-(N-piperidinylsulfonyl)thiophenol according to General Method 11 step 1 followed by reaction with 2,4-dichloro-5-methylphenylsulfonyl chloride according to General Method 11 step 2. $^1$H NMR (CDCl$_3$): 8.35 & 8.02 (2×1H, 2×s, A-ring CH's), 7.63, 7.42 & 7.18 (3×1H, d, s & d, J 10 Hz, B-ring CH's) 7.55 & 7.11 (2×2H, 2×d, 2×J 10 Hz, Ar CH's of C-ring), 2.93-2.81 (4H, m, CH$_2$NCH$_2$), 2.34 (3H, s, CH$_3$), 1.60-1.48 (4H, m, CH$_2$CH$_2$CH$_2$CH$_2$CH$_2$), 1.39-1.27 (2H, m, CH$_2$CH$_2$CH$_2$CH$_2$CH$_2$). Hplc (Luna 2, Gradient 5): rt=6.77 minutes. LC/MS rt=7.44 minutes, 572/574 (MH$^+$).

Example 68

2,4-Dichloro-N-{5-[4-(piperidine-1-sulfonyl)-phenylsulfanyl]-pyridin-2-yl}-benzenesulfonamide (68)

68

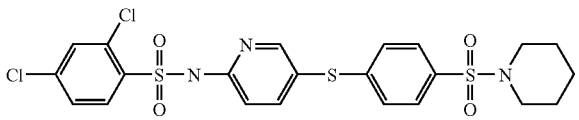

Prepared from 2-amino-5-bromopyridine and 4-(N-piperidinylsulfonyl)thiophenol according to General Method 11 step 1 followed by reaction with 2,4-dichlorophenylsulfonyl chloride according to General Method 11 step 2. $^1$H NMR (CDCl$_3$): 11.95 (1H, br s, NH), 8.55 (1H, s, Ar CH ortho to 2×Cl), 8.29 (1H, d, CH ortho to SO$_2$NH), 7.85, 7.61, 7.54 & 7.39 (4×1H, d, s, d & d, J 11, 10 & 11 Hz, A- & B-ring CH's) 7.73 & 7.30 (2×2H, 2×d, 2×J 10 Hz, Ar CH's of C-ring), 3.10-3.01 (4H, m, CH$_2$NCH$_2$), 2.18 (3H, s, CH$_3$), 1.79-1.68 (4H, m, CH$_2$CH$_2$CH$_2$CH$_2$CH$_2$), 1.60-1.48 (2H, m, CH$_2$CH$_2$CH$_2$CH$_2$CH$_2$). Hplc (Luna 2, Gradient 5): rt=6.48 minutes. LC/MS rt=7.19 minutes, 558/560 (MH$^+$).

Example 69

2-Chloro-N-{5-[4-(piperidine-1-sulfonyl)-phenylsulfanyl]-pyridin-2-yl}-4-trifluoromethyl-benzenesulfonamide (69)

69

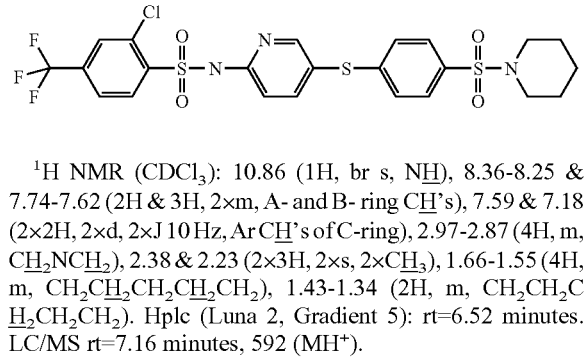

$^1$H NMR (CDCl$_3$): 10.86 (1H, br s, NH), 8.36-8.25 & 7.74-7.62 (2H & 3H, 2×m, A- and B- ring CH's), 7.59 & 7.18 (2×2H, 2×d, 2×J 10 Hz, Ar CH's of C-ring), 2.97-2.87 (4H, m, CH$_2$NCH$_2$), 2.38 & 2.23 (2×3H, 2×s, 2×CH$_3$), 1.66-1.55 (4H, m, CH$_2$CH$_2$CH$_2$CH$_2$CH$_2$), 1.43-1.34 (2H, m, CH$_2$CH$_2$CH$_2$CH$_2$CH$_2$). Hplc (Luna 2, Gradient 5): rt=6.52 minutes. LC/MS rt=7.16 minutes, 592 (MH$^+$).

Example 70

6-(2,4-Dichloro-benzenesulfonylamino)-3-[4-(piperidine-1-sulfonyl)-phenylsulfanyl]-pyridine-2-carboxylic acid methyl ester (70)

70

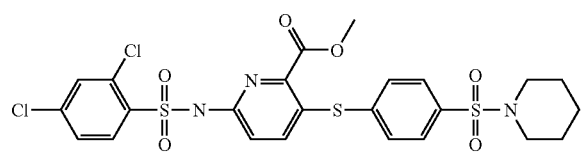

Prepared from 2-amino-5-bromo-6-methoxycarbonylpyridine and 4-(N-piperidinylsulfonyl)thiophenol according to General Method 11 step 1 followed by reaction with 2,4-dichlorophenylsulfonyl chloride according to General Method 11 step 2. $^1$H NMR (CDCl$_3$): 8.02 (1H, d, J 11 Hz, A-ring CH ortho to SO$_2$NH), 7.63 & 7.42 (2×2H, 2×d, 2×J 10 Hz, Ar CH's of C-ring), 7.43 (1H, s, A-ring CH ortho to 2×Cl) 7.32 (1H, d, J 11 Hz, Ar CH), 3.88 (3H, s, CH$_3$) 2.98-2.76 (4H, m, CH$_2$NCH$_2$),), 1.62-1.53 (4H, m, CH$_2$CH$_2$CH$_2$CH$_2$CH$_2$), 1.41-1.30 (2H, m, CH$_2$CH$_2$CH$_2$CH$_2$CH$_2$) further 2 aromatic protons were obscured by a solvent peak around 7.28 ppm. Hplc (Luna 2, Gradient 5): rt=6.55 minutes. LC/MS rt=7.23 minutes, 616/618 (MH$^+$).

Example 71

6-(2,4-Dichloro-benzenesulfonylamino)-3-[4-(piperidine-1-sulfonyl)-phenylsulfanyl]-pyridine-2-carboxylic acid (71)

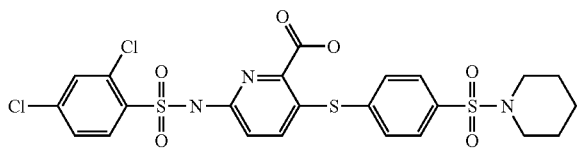

Synthesized from 6-(2,4-dichloro-benzenesulfonylamino)-3-[4-(piperidine-1-sulfonyl)-phenylsulfanyl]-pyridine-2-carboxylic acid methyl ester according to General Method 11 step 3, stopping at the carboxylic acid stage. $^1$H NMR (CDCl$_3$): 8.02 (1H, d, J 11 Hz, A-ring CH ortho to SO$_2$NH), 7.69 & 7.53 (2×2H, 2×d, 2×J 10 Hz, Ar CH's of C-ring), 7.44 (1H, s, A-ring CH ortho to 2×Cl) 7.33 (1H, d, J 11 Hz, A-ring CH ortho to Cl), 7.05 & 7.03 (2×1H, 2×d, 2×J 12 Hz, B-ring CH's), 2.96-2.88 (4H, m, CH$_2$NCH$_2$), 1.64-1.52 (4H, m, CH$_2$CH$_2$CH$_2$CH$_2$CH$_2$), 1.41-1.29 (2H, m, CH$_2$CH$_2$CH$_2$CH$_2$) Hplc (Luna 2, Gradient 5): rt=6.03 minutes. LC/MS rt=7.83 minutes, 602/604 (MH$^+$)

Example 72

6-(2,4-Dichloro-benzenesulfonylamino)-3-[4-(piperidine-1-sulfonyl)-phenylsulfanyl]-pyridine-2-carboxylic acid methoxy-methyl-amide (72)

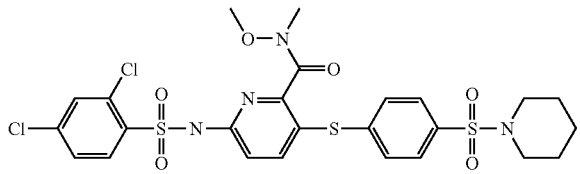

Synthesized from 6-(2,4-dichloro-benzenesulfonylamino)-3-[4-(piperidine-1-sulfonyl)-phenylsulfanyl]-pyridine-2-carboxylic acid methyl ester according to General Method 11 step 3, stopping at the amide stage. $^1$H NMR (CDCl$_3$): 8.01-7.15 (9H, m, Ar CH's), 3.41 & 3.22 (2×3H, 2×s, 2×CH$_3$), 2.90-2.78 (4H, m, CH$_2$NCH$_2$,), 1.60-1.48 (4H, m, CH$_2$CH$_2$CH$_2$CH$_2$CH$_2$), 1.32-1.27 (2H, m, CH$_2$CH$_2$CH$_2$CH$_2$CH$_2$) Hplc (Luna 2, Gradient 5): rt =6.15 minutes. LC/MS rt=6.80 minutes, 645/647(MH$^+$)

Example 73

N-{6-Butyryl-5-[4-(piperidine-1-sulfonyl)-phenylsulfanyl]-pyridin-2-yl}-2,4-dichloro-benzenesulfonamide (73)

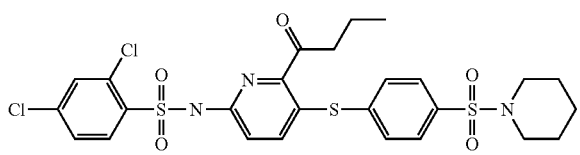

Prepared from 2-amino-5-bromo-6-methoxycarbonylpyridine and 4-(N-piperidinylsulfonyl)thiophenol according to General Method 11 step 1 followed by reaction with 2,4-dichlorophenylsulfonyl chloride according to General Method 11 step 2 and then General Method 11 step 3 employing $^n$propyl magnesium chloride. $^1$H NMR (CDCl$_3$): 7.99 (1H, d, J 11 Hz, A-ring CH ortho to SO$_2$NH), 7.70 & 7.52 (2×2H, 2×d, 2×J 10 Hz, Ar CH's of C-ring), 7.60 (1H, br s, NH), 7.47 (1H, s, A-ring CH ortho to 2×Cl) 7.30 (1H, d, J 11 Hz, A-ring CH ortho to Cl), 7.08 & 7.03 (2×1H, 2×d, 2×J 11 Hz, B-ring CH's), 2.98-2.90 (4H, m, CH$_2$NCH$_2$), 2.90 (2H, t, J 9 Hz, COCH$_2$), 1.68-1.53 (6H, m, CH$_2$CH$_2$CH$_2$CH$_2$CH$_2$ & CH$_2$CH$_3$), 1.43-1.31 (2H, m, CH$_2$CH$_2$CH$_2$CH$_2$CH$_2$), 0.91 (3H, t, J 9 Hz, CH$_2$CH$_3$). Hplc (Luna 2, Gradient 5): rt=7.24 minutes. LC/MS rt=7.92 minutes, 628/630 (MH$^+$).

Example 74

2-Chloro-N-{4-methyl-5-[4-(morpholine-4-sulfonyl)-phenylsulfanyl]-pyridin-2-yl}-4-trifluoromethyl-benzenesulfonamide (74)

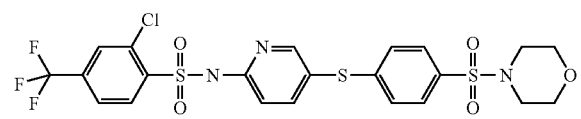

Prepared from 2-amino-5-bromo-4-methylpyridine and 4-(N-morpholinylsulfonyl)thiophenol according to General Method 11 step 1 followed by reaction with 2-chloro-4-trifluoromethylphenylsulfonyl chloride according to General Method 11 step 2. $^1$H NMR (CDCl$_3$): 13.25 (1H, br s, NH), 8.39 (1H, s, A-ring CH ortho to Cl), 8.32 (1H, d, J 11 Hz, A-ring CH ortho to SO$_2$NH), 7.65 & 7.15 (2×1H, 2×s, pyridyl CH's), 7.62 (1H, d, J 11 Hz, A-ring CH ortho to CF$_3$), 7.55 & 7.10 (2×2H, 2×d, 2×J 10 Hz, Ar CH's of C-ring), 3.70-3.60 (4H, m, CH$_2$OCH$_2$), 2.95-2.84 (4H, m, CH$_2$NCH$_2$), 2.23 (3H, s, CH$_3$) Hplc (Luna 2, Gradient 5): rt=6.01 minutes. LC/MS rt=6.75 minutes, 608 (MH$^+$).

Example 75

2,4-Dichloro-N-{4-methyl-5-[4-(morpholine-4-sulfonyl)-phenylsulfanyl]-pyridin-2-yl}-benzenesulfonamide (75)

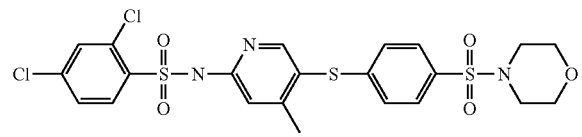

Prepared from 2-amino-5-bromo-4-methylpyridine and 4-(N-morpholinylsulfonyl)thiophenol according to General Method 11 step 1 followed by reaction with 2,4-chloro-methylphenylsulfonyl chloride according to General Method 11 step 2. $^1$H NMR (CDCl$_3$): 8.34 (1H, s, A-ring CH ortho to 2×Cl), 8.13 (1H, d, J 11 Hz, A-ring CH ortho to SO$_2$NH), 7.55 & 7.07 (2×2H, 2×d, 2×J 10 Hz, Ar CH's of C-ring), 7.43 & 7.11 (2×1H, 2×s, pyridyl CH's), 7.35 (1H, d, J 11 Hz, A-ring CH ortho to CF$_3$), 3.71-3.60 (4H, m, CH$_2$OCH$_2$), 2.93-2.81 (4H, m, CH$_2$NCH$_2$), 2.22 (3H, s, CH$_3$). Hplc (Luna 2, Gradient 5): rt=5.93 minutes. LC/MS rt=6.56 minutes, 574/576 (MH$^+$).

Example 76

6-(2,4-Dichloro-benzenesulfonylamino)-3-[4-(morpholine-4-sulfonyl)-phenylsulfanyl]-pyridine-2-carboxylic acid methyl ester (76)

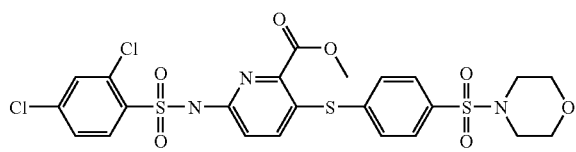

76

Prepared from 2-amino-5-bromo-6-methoxycarbonylpyridine and 4-(N-morpholinylsulfonyl)thiophenol according to General Method 11 step 1 followed by reaction with 2,4-dichlorophenylsulfonyl chloride according to General Method 11 step 2. $^1$H NMR (CDCl$_3$): 8.04 (1H, d, J 11 Hz, A-ring C$\underline{H}$ ortho to SO$_2$NH), 7.62 & 7.42 (2×2 H, 2×d, 2×J 10 Hz, C-ring C$\underline{H}$'s), 7.43 (1H, s, A-ring C$\underline{H}$ ortho to 2×Cl), 7.31 (1H, d, J 11 Hz, A ring C$\underline{H}$ ortho to Cl), 7.28 & 7.18(2×1H, 2×d, 2×J 10 Hz, pyridyl C$\underline{H}$'s), 3.89 (3H, s, C$\underline{H}_3$) 3.72-3.63 (4H, m, C$\underline{H}_2$OC$\underline{H}_2$), 2.98-2.88 (4H, m, C$\underline{H}_2$NC$\underline{H}_2$). Hplc (Luna 2, Gradient 5): rt=6.00 minutes. LC/MS rt=6.69 minutes, 618/620 (MH$^+$).

Example 77

2,4-Dichloro-N-{6-methyl-5-[4-(morpholine-4-sulfonyl)-phenylsulfanyl]-pyridin-2-yl}-benzenesulfonamide (77)

77

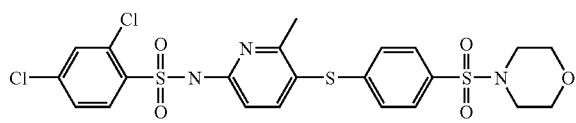

Prepared from 2-amino-5-bromo-6-methylpyridine and 4-(N-morpholinylsulfonyl)thiophenol according to General Method 11 step 1 followed by reaction with 2,4-dichlorophenylsulfonyl chloride according to General Method 11 step 2. $^1$H NMR (CDCl$_3$): 8.09 (1H, d, J 10 Hz, A-ring C$\underline{H}$ ortho to SO$_2$NH), 7.68, 7.35 & 7.12 (3×1H, 3×d, 3×J 10 Hz, pyridyl C$\underline{H}$'s & A-ring C$\underline{H}$ ortho to Cl), 7.58 & 7.08(2×2H, 2×d, 2×J 10 Hz, C-ring C$\underline{H}$'s), 7.46 (1H, s, A ring C$\underline{H}$ ortho to 2×Cl), 3.71-3.62 (4H, m, C$\underline{H}_2$OC$\underline{H}_2$), 2.94-2.85 (4H, m, C$\underline{H}_2$NC$\underline{H}_2$), 2.49 (3H, s, C$\underline{H}_3$). Hplc (Luna 2, Gradient 5): rt=5.81 minutes. LC/MS rt=6.58 minutes, 574/576 (MH$^+$).

Example 78

N-{6-Butyryl-5-[4-(morpholine-4-sulfonyl)-phenylsulfanyl]-pyridin-2-yl}-2,4-dichloro-benzenesulfonamide (78)

78

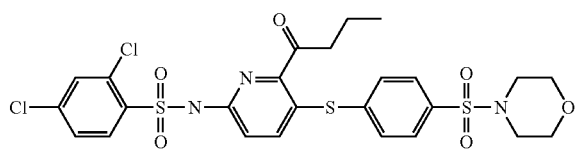

Prepared from 2-amino-5-iodo-6-n-pentoxycarbonylpyridine and 4-(N-morpholinylsulfonyl)thiophenol according to General Method 11 step 1 followed by reaction with 2,4-dichlorophenylsulfonyl chloride according to General Method 11 step 2 and then General Method 11 step 3 employing "propyl magnesium chloride. $^1$H NMR (CDCl$_3$): 7.95 (1H, d, J 11 Hz, A-ring C$\underline{H}$ ortho to SO$_2$NH), 7.62 & 7.50 (2×2H, 2×d, 2×J 10 Hz, Ar C$\underline{H}$'s of C-ring), 7.53 (1H, br s, N$\underline{H}$), 7.42 (1H, s, A-ring C$\underline{H}$ ortho to 2×Cl) 7.25 (1H, d, J 11 Hz, A-ring C$\underline{H}$ ortho to Cl), 7.05 & 7.02 (2×1H, 2×d, 2×J 11 Hz, B-ring C$\underline{H}$'s), 3.70-3.58 (4H, m, C$\underline{H}_2$OC$\underline{H}_2$), 2.98-2.88 (4H, m, C$\underline{H}_2$NC$\underline{H}_2$), 2.82 (2H, t, J 8 Hz, COC$\underline{H}_2$), 1.68-1.51 (2H, sextet, J 8 Hz, C$\underline{H}_2$CH$_3$), 0.86 (3H, t, J 9 Hz, CH$_2$C$\underline{H}_3$). Hplc (Luna 2, Gradient 5): rt=6.52 minutes. LC/MS rt=7.26 minutes, 630/632 (MH$^+$).

Example 79

2,4-Dichloro-N-{6-cyclopropanecarbonyl-5-[4-(morpholine-4-sulfonyl)-phenylsulfanyl]-pyridin-2-yl}-benzenesulfonamide (79)

79

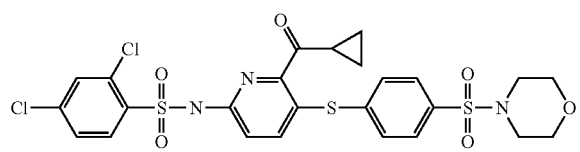

Prepared from 2-amino-5-iodo-6-"pentoxycarbonylpyridine and 4-(N-morpholinylsulfonyl)thiophenol according to General Method 11 step 1 followed by reaction with 2,4-dichlorophenylsulfonyl chloride according to General Method 11 step 2 and then General Method 11 step 3 employing cyclopropyl magnesium bromide. $^1$H NMR (CDCl$_3$): 8.01 (1H, d, J 11 Hz, A-ring C$\underline{H}$ ortho to SO$_2$NH), 7.68 & 7.53 (2×2H, 2×d, 2×J 10 Hz, Ar C$\underline{H}$'s of C-ring), 7.46 (1H, s, A-ring C$\underline{H}$ ortho to 2×Cl) 7.27 (1H, d, J 11 Hz, A-ring C$\underline{H}$ ortho to Cl), 7.06 & 7.04 (2×1H, 2×d, 2×J 11 Hz, B-ring C$\underline{H}$'s), 3.72-3.64 (4H, m, C$\underline{H}_2$OC$\underline{H}_2$), 3.10-3.02 (1H, m, C$\underline{H}$CO), 2.97-2.90 (4H, m, C$\underline{H}_2$NC$\underline{H}_2$), 1.21-1.11 & 1.05-0.96 (2×2H, 2×m, cyclopropyl C$\underline{H}_2$C$\underline{H}_2$). Hplc (Luna 2, Gradient 5): rt=6.34 minutes. LC/MS rt=7.05 minutes, 628/630 (MH$^+$).

Example 80

2,4-Dichloro-N-{6-(3-methyl-butyryl)-5-[4-(morpholine-4-sulfonyl)-phenylsulfanyl]-pyridin-2-yl}-benzenesulfonamide (80)

80

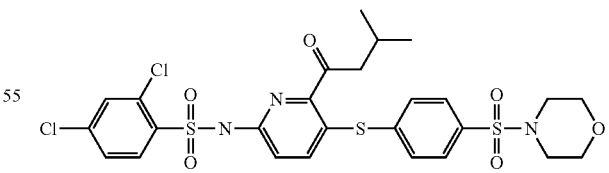

Prepared from 2-amino-5-iodo-6-"propoxycarbonylpyridine and 4-(N-morpholinylsulfonyl)thiophenol according to General Method 11 step 1 followed by reaction with 2,4-dichlorophenylsulfonyl chloride according to General Method 11 step 2 and then General Method 11 step 3 employing iso-butyl magnesium chloride. $^1$H NMR (CDCl$_3$): 7.99 (1H, d, J 11 Hz, A-ring C$\underline{H}$ ortho to SO$_2$NH), 7.66 & 7.53 (2×2H, 2×d, 2×J 10 Hz, Ar C$\underline{H}$'s of C-ring), 7.46 (1H, s, A-ring CH ortho to 2×Cl) 7.31 (1H, d, J 11 Hz, A-ring CH ortho to Cl), 7.09 & 7.07 (2×1H, 2×d, 2×J 11 Hz, B-ring C H's), 3.71-3.59 (4H, m, CH₂OCH₂), 2.99-2.89 (4H, m, CH₂NCH₂), 2.79 (2H, d, J 7 Hz, COCH₂), 2.14 (1H, nonet, J 7 Hz, CH₂CH₃), 0.89 (6H, d, J 7 Hz, CH₂CH₃). Hplc (Luna 2, Gradient 5): rt=6.75 minutes. LC/MS rt=7.51 minutes, 644/646 (MH⁺).

Example 81

N-{6-Butyryl-5-[4-(piperidine-1-sulfonyl)-phenylsulfanyl]-pyridin-2-yl}-2-chloro-4-trifluoromethyl-benzenesulfonamide (81)

81

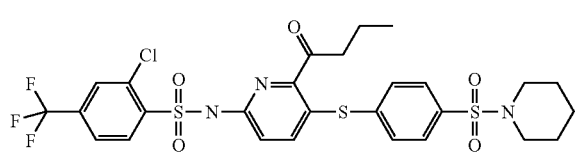

Prepared from 2-amino-5-iodo-6-ⁿpropoxycarbonylpyridine and 4-(N-piperidinylsulfonyl)thiophenol according to General Method 11 step 1 followed by reaction with 2-chloro-4-trifluoromethylphenylsulfonyl chloride according to General Method 11 step 2 and then General Method 11 step 3 employing ⁿpropyl magnesium chloride. ¹H NMR (CDCl₃): 8.21 (1H, d, J 11 Hz, A-ring CH ortho to SO₂NH), 7.72 (1H, s, A-ring CH ortho to CF₃ & Cl), 7.69 & 7.50 (2×2H, 2×d, 2×J 10 Hz, Ar CH's of C-ring), 7.60 (1H, d, J 11 Hz, A-ring CH ortho to Cl), 7.11 & 7.06 (2×1H, 2×d, 2×J 11 Hz, B-ring C H's), 2.97-2.90 (4H, m, CH₂NCH₂), 2.88 (2H, t, J 8 Hz, COC H₂), 1.68-1.52 (6H, m, CH₂CH₂CH₂CH₂CH₂ & CH₂CH₃), 1.41-1.30 (2H, m, CH₂CH₂CH₂CH₂CH₂), 0.90 (3H, t, J 8 Hz, CH₂CH₃). Hplc (Luna 2, Gradient 5): rt=7.17 minutes. LC/MS rt=7.95 minutes, 662 (MH⁺).

Example 82

2,4-Dichloro-N-{6-cyclopropanecarbonyl-5-[4-(piperidine-1-sulfonyl)-phenylsulfanyl]-pyridin-2-yl}-benzenesulfonamide (82)

82

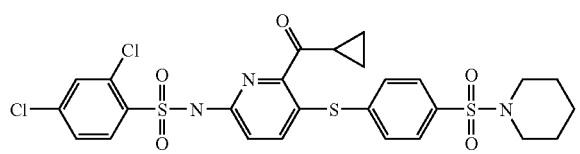

Prepared from 2-amino-5-iodo-6-ⁿpentoxycarbonylpyridine and 4-(N-piperidinylsulfonyl)thiophenol according to General Method 11 step 1 followed by reaction with 2,4-dichlorophenylsulfonyl chloride according to General Method 11 step 2 and then General Method 11 step 3 employing cyclopropyl magnesium bromide. ¹H NMR (CDCl₃): 8.00 (1H, d, J 11 Hz, A-ring CH ortho to SO₂NH), 7.62 & 7.52 (2×2H, 2×d, 2×J 10 Hz, Ar CH's of C-ring), 7.47 (1H, s, A-ring CH ortho to 2×Cl) 7.29 (1H, d, J 11 Hz, A-ring CH ortho to Cl), 7.10 & 7.05 (2×1H, 2×d, 2×J 11 Hz, B-ring C H's), 3.15-3.03 (1H, m, CHCO), 2.99-2.90 (4H, m, CH₂NC H₂), 1.65-1.52 (4H, m, CH₂CH₂CH₂CH₂CH₂), 1.40-1.30 (2H, m, CH₂CH₂CH₂CH₂CH₂), 1.23-1.11 & 1.06-0.98 (2×2H, 2×m, cyclopropyl CH₂CH₂). Hplc (Luna 2, Gradient 5): rt=6.90 minutes. LC/MS rt=7.61 minutes, 626/628 (MH⁺).

Example 83

2,4-Dichloro-N-{6-(3-methyl-butyryl)-5-[4-(piperidine-1-sulfonyl)-phenylsulfanyl]-pyridin-2-yl}-benzenesulfonamide (83)

83

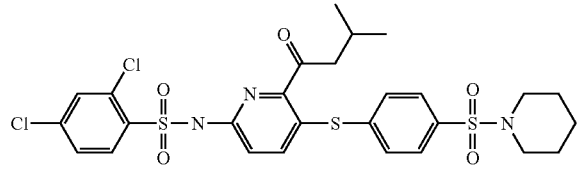

Prepared from 2-amino-5-iodo-6-ⁿpropoxycarbonylpyridine and 4-(N-piperidinylsulfonyl)thiophenol according to General Method 11I step 1 followed by reaction with 2,4-dichlorophenylsulfonyl chloride according to General Method 11 step 2 and then General Method 11 step 3 employing iso-butyl magnesium chloride. ¹H NMR (CDCl₃): 8.08 (1H, d, J 11 Hz, A-ring CH ortho to SO₂NH), 7.75 & 7.57 (2×2H, 2×d, 2×J 10 Hz, Ar CH's of C-ring), 7.53 (1H, s, A-ring CH ortho to 2×Cl) 7.39 (1H, d, J 11 Hz, A-ring CH ortho to Cl), 7.15 & 7.10 (2×1H, 2×d, 2×J 11 Hz, B-ring C H's), 3.04-2.96 (4H, m, CH₂NCH₂), 2.87 (2H, d, J 8 Hz, COC H₂), 2.23 (1H, nonet, J 8 Hz, CH₂CH₃), 0.97 (6H, d, J 8 Hz, CH₂CH₃), 1.69-1.56 (4H, m, CH₂CH₂CH₂CH₂CH₂), 1.45-1.31 (2H, m, CH₂CH₂CH₂CH₂CH₂). Hplc (Luna 2, Gradient 5): rt=7.37 minutes. LC/MS rt=8.14 minutes, 642/644 (MH⁺).

Example 84

2,4-Dichloro-N-{5-[4-(piperidine-1-sulfonyl)-phenylsulfanyl]-6-propionyl-pyridin-2-yl}-benzenesulfonamide (84)

84

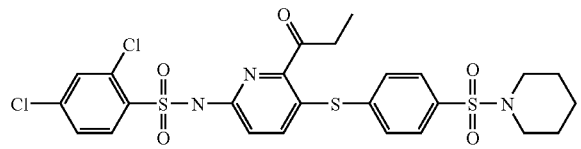

Prepared from 2-amino-5-iodo-6-ⁿpentoxycarbonylpyridine and 4-(N-piperidinylsulfonyl)thiophenol according to General Method 11 step 1 followed by reaction with 2,4-dichlorophenylsulfonyl chloride according to General Method 11 step 2 and then General Method 11 step 3 employing ⁿethyl magnesium bromide. ¹H NMR (CDCl₃): 8.02 (1H, d, J 11 Hz, A-ring CH ortho to SO₂NH), 7.83 (1H, br s, NH), 7.69 & 7.53 (2×2H, 2×d, 2×J 10 Hz, Ar CH's of C-ring), 7.46 (1H, s, A-ring CH ortho to 2×Cl) 7.31 (1H, d, J 11 Hz, A-ring CH ortho to Cl), 7.07 & 7.03 (2×1H, 2×d, 2×J 11 Hz, B-ring CH's), 2.97-2.85 (6H, m, CH₂NCH₂ & CH₂CO), 1.63-1.51 (4H, m, CH₂CH₂CH₂CH₂CH₃), 1.42-1.32 (2H, m, CH₂CH₂CH₂CH₂CH₂), 1.07 (3H, t, J 8 Hz, CH₂CH₃). Hplc (Luna 2, Gradient 5): rt=6.90 minutes. LC/MS rt=7.64 minutes, 614/616 (MH⁺).

Example 85

6-(2,4-Dichloro-benzenesulfonylamino)-3-[4-(piperidine-1-sulfonyl)-phenylsulfanyl]-pyridine-2-carboxylic acid isopropylamide (85)

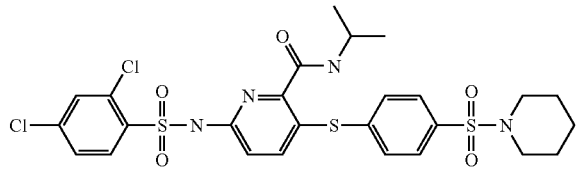

Prepared from 2-amino-5-iodo-6-″pentoxycarbonylpyridine and 4-(N-piperidinylsulfonyl)thiophenol according to General Method 11 step 1 followed by reaction with 2,4-dichlorophenylsulfonyl chloride according to General Method 11 step 2 and then a modification of General Method 11 step 3 where the procedure was stopped after the amide coupling, which employs isopropylamine as alternative nucleophile. ¹H NMR (CDCl₃): 7.98 (1H, d, J 11 Hz, A-ring CH ortho to SO₂NH), 7.68 & 7.56 (2×2H, 2×d, 2×J 10 Hz, Ar CH's of C-ring), 7.61 (1H, br s, NH), 7.44 (1H, s, A-ring CH ortho to 2×Cl), 7.38 (1H, d, J 9 Hz, NH), 7.31 (1H, d, J 11 Hz, A-ring CH ortho to Cl), 6.98 & 6.89 (2×1H, 2×d, 2×J 11 Hz, B-ring CH's), 4.22-4.09 (1H, m, NHCO), 2.97-2.84 (4H, m, CH₂NCH₂), 1.63-1.52 (4H, m, CH₂CH₂CH₂CH₂CH₃), 1.43-1.32 (2H, m, CH₂CH₂CH₂CH₂CH₃), 1.24-1.12 (6H, m, CH(CH₃)₂). Hplc (Luna 2, Gradient 5): rt=6.54 minutes. LC/MS rt=7.30 minutes, 643/645 (MH⁺).

Example 86

2,4-Dichloro-N-{5-[4-(morpholine-4-sulfonyl)-phenylsulfanyl]-6-propionyl-pyridin-2-yl}-benzenesulfonamide (86)

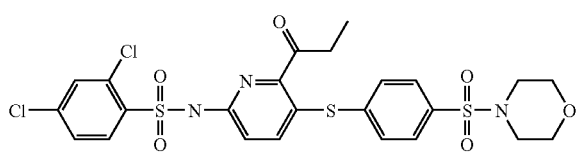

Prepared from 2-amino-5-iodo-6-″pentoxycarbonylpyridine and 4-(N-morpholinylsulfonyl)thiophenol according to General Method 11 step 1 followed by reaction with 2,4-dichlorophenylsulfonyl chloride according to General Method 11 step 2 and then General Method 11 step 3 employing ethyl magnesium chloride. ¹H NMR (CDCl₃): 8.01 (1H, d, J 11 Hz, A-ring CH ortho to SO₂NH), 7.72 (1H, br s, NH), 7.68 & 7.53 (2×2H, 2×d, 2×J 10 Hz, Ar CH's of C-ring), 7.47 (1H, s, A-ring CH ortho to 2×Cl) 7.31 (1H, d, J 11 Hz, A-ring CH ortho to Cl), 7.08 & 7.04 (2×1H, 2×d, 2×J 11 Hz, B-ring CH's), 3.72-3.61 (4H, m, CH₂OCH₂), 2.97-2.86 (6H, m, CH₂NCH₂ & COCH₂), 1.10 (3H, t, J 9 Hz, CH₂CH₃). Hplc (Luna 2, Gradient 5): rt=6.32 minutes. LC/MS rt=6.95 minutes, 616/618 (MH⁺).

Example 87

N-{6-Butyryl-5-[4-(morpholine-4-sulfonyl)-phenylsulfanyl]-pyridin-2-yl}-2-chloro-4-trifluoromethyl-benzenesulfonamide (87)

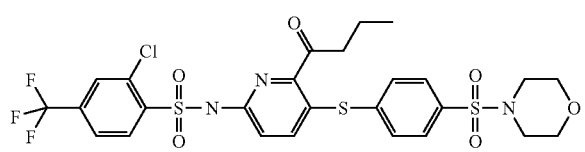

Prepared from 2-amino-5-iodo-6-″pentoxycarbonylpyridine and 4-(N-morpholinylsulfonyl)thiophenol according to General Method 11 step 1 followed by reaction with 2-chloro-4-trifluoromethylphenylsulfonyl chloride according to General Method 11 step 2 and then General Method 11 step 3 employing ″propyl magnesium chloride. ¹H NMR (CDCl₃): 8.22 (1H, d, J 11 Hz, A-ring CH ortho to SO₂NH), 7.72 (1H, s, A-ring CH ortho to CF₃ & Cl) 7.69 & 7.53 (2×2H, 2×d, 2×J 10 Hz, Ar CH's of C-ring), 7.61 (1H, d, J 11 Hz, A-ring CH ortho to Cl), 7.11 & 7.06 (2×1H, 2×d, 2×J 11 Hz, B-ring C H's), 3.71-3.62 (4H, m, CH₂OCH₂), 2.99-2.90 (4H, m, C H₂NCH₂), 2.86 (2H, t, J 8 Hz, COCH₂), 1.62 (2H, sextet, J 8 Hz, CH₂CH₃), 0.88 (3H, t, J 8 Hz, CH₂CH₃). Hplc (Luna 2, Gradient 5): rt=6.59 minutes. LC/MS rt=7.33 minutes, 664 (MH⁺).

Example 88

2-Chloro-N-{6-cyclopropanecarbonyl-5-[4-(morpholine-4-sulfonyl)-phenylsulfanyl]-pyridin-2-yl}-4-trifluoromethyl-benzenesulfonamide (88)

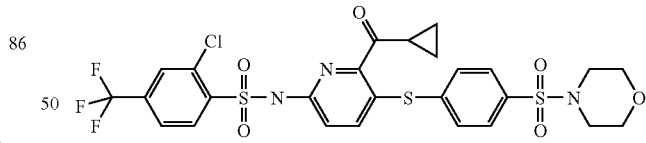

Prepared from 2-amino-5-iodo-6-″pentoxycarbonylpyridine and 4-(N-morpholinylsulfonyl)thiophenol according to General Method 11 step 1 followed by reaction with 2-chloro-4-trifluoromethylphenylsulfonyl chloride according to General Method 11 step 2 and then General Method 11 step 3 employing cyclopropyl magnesium bromide. ¹H NMR (CDCl₃): 8.22 (1H, d, J 11 Hz, A-ring CH ortho to SO₂NH), 7.71-7.41 (6H, m, A-ring & C-ring CH's), 7.11 & 7.05 (2×1H, 2×d, 2×J 11 Hz, B-ring CH's), 3.73-3.62 (4H, m, CH₂OCH₂), 3.06-2.90 (5H, m, CHCO & CH₂NCH₂), 2.86 (2H, t, J 8 Hz, COCH₂), 1.22-1 11 & 1.03-0.97 (2×2H, 2×m, cyclopropyl C H₂CH₂). Hplc (Luna 2, Gradient 5): rt=6.41 minutes. LC/MS rt=7.09 minutes, 662 (MH⁺).

Example 89

2-Chloro-N-{6-cyclopropanecarbonyl-5-[4-(piperidine-1-sulfonyl)-phenylsulfanyl]-pyridin-2-yl}-4-trifluoromethyl-benzenesulfonamide (89)

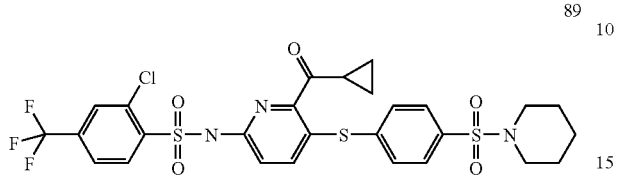

Prepared from 2-amino-5-iodo-6-″pentoxycarbonylpyridine and 4-(N-piperidinylsulfonyl)thiophenol according to General Method 11 step 1 followed by reaction with 2-chloro-4-trifluoromethylphenylsulfonyl chloride according to General Method 11 step 2 and then General Method 11 step 3 employing cyclopropyl magnesium bromide. $^1$H NMR (CDCl$_3$): 8.21 (1H, d, J 11 Hz, A-ring CH ortho to SO$_2$NH), 7.71 (1H, s, A-ring CH ortho to CF$_3$ & Cl) 7.68 & 7.50 (2×2H, 2×d, 2×J 10 Hz, Ar CH's of C-ring), 7.59 (1H, d, J 11 Hz, A-ring CH ortho to Cl), 7.10 & 7.05 (2×1H, 2×d, 2×J 11 Hz, B-ring CH's), 3.08-2.91 (5H, m, CHCO & CH$_2$NCH$_2$), 1.62-1.52 (4H, m, CH$_2$CH$_2$CH$_2$CH$_2$CH$_2$), 1.41-1.30 (2H, m, CH$_2$CH$_2$CH$_2$CH$_2$CH$_2$), 1.20-1.13 & 1.04-0.97 (2×2H, 2×m, cyclopropyl CH$_2$CH$_2$). Hplc (Luna 2, Gradient 5): rt=6.96 minutes. LC/MS rt=7.65 minutes, 660 (MH$^+$).

Example 90

N-[6-Butyryl-5-(4-diethylsulfamoyl-phenylsulfanyl)-pyridin-2-yl]-2,4-dichloro-benzenesulfonamide (90)

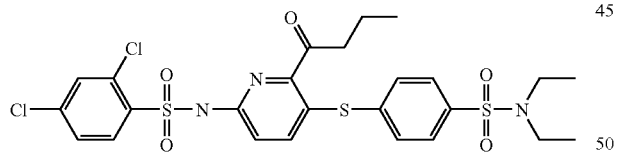

Prepared from 2-amino-5-iodo-6-″pentoxycarbonylpyridine and 4-(N,N-diethylaminosulfonyl)thiophenol according to General Method 11 step 1 followed by reaction with 2,4-dichlorophenylsulfonyl chloride according to General Method 11 step 2 and then General Method 11 step 3 employing ″propyl magnesium chloride. $^1$H NMR (CDCl$_3$): 8.14 (1H, d, J 11 Hz, A-ring CH ortho to SO$_2$NH), 7.91 & 7.75 (2×2H, 2×d, 2×J 10 Hz, Ar CH's of C-ring), 7.72 (1H, br s, NH), 7.67 (1H, s, A-ring CH ortho to 2×Cl) 7.43 (1H, d, J 11 Hz, A-ring CH ortho to Cl), 7.23 & 7.15 (2×1H, 2×d, 2×J 11 Hz, B-ring CH's), 3.35 (4H, q, J 8 Hz, CH$_2$NCH$_2$), 3.05 (2H, t, J 8 Hz, COCH$_2$), 1.79 (2H, sextet, J 8 Hz, CH$_2$CH$_3$), 1.23 (6H, t, J 8 Hz, N(CH$_2$CH$_3$)$_2$), 1.06 (3H, t, J 9 Hz, CH$_2$CH$_2$CH$_3$). Hplc (Luna 2, Gradient 5): rt=7.06 minutes. LC/MS rt=7.67 minutes, 616/618 (MH$^+$).

Example 91

2,4-Dichloro-N-[6-cyclopropanecarbonyl-5-(4-diethylsulfamoyl-phenylsulfanyl)-pyridin-2-yl]-benzenesulfonamide (91)

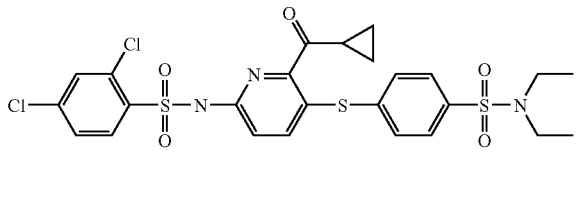

Prepared from 2-amino-5-iodo-6-″pentoxycarbonylpyridine and 4-(N,N-diethylaminosulfonyl)thiophenol according to General Method 11 step 1 followed by reaction with 2,4-dichlorophenylsulfonyl chloride according to General Method 11 step 2 and then General Method 11 step 3 employing cyclopropyl magnesium bromide. $^1$H NMR (CDCl$_3$): 8.12 (1H, d, J 11 Hz, A-ring CH ortho to SO$_2$NH), 7.87 & 7.61 (2×2H, 2×d, 2×J 10 Hz, Ar CH's of C-ring), 7.73 (1H, br s, NH), 7.56 (1H, s, A-ring CH ortho to 2×Cl) 7.42 (1H, d, J 11 Hz, A-ring CH ortho to Cl), 7.22 & 7.15 (2×1H, 2×d, 2×J 11 Hz, B-ring CH's), 3.34 (4H, q, J 8 Hz, CH$_2$NCH$_2$), 3.30-3.19 (1H, m, COCH), 1.36-1.28 & 1.21-1.12 (2×2H, 2×m, cyclopropyl CH$_2$CH$_2$), 1.21 (6H, t, J 8 Hz, N(CH$_2$CH$_3$)$_2$). Hplc (Luna 2, Gradient 5): rt=6.83 minutes. LC/MS rt=7.49 minutes, 614/616 (MH$^+$).

Example 92

2,4-Dichloro-N-[5-(4-diethylsulfamoyl-phenylsulfanyl)-6-propionyl-pyridin-2-yl]-benzenesulfonamide (92)

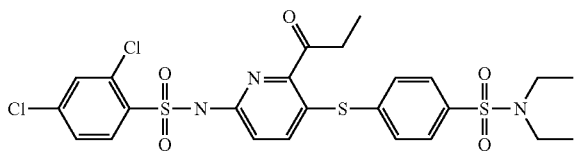

Prepared from 2-amino-5-iodo-6-″pentoxycarbonylpyridine and 4-(N,N-diethylaminosulfonyl)thiophenol according to General Method 11 step 1 followed by reaction with 2,4-dichlorophenylsulfonyl chloride according to General Method 11 step 2 and then General Method 11 step 3 employing ethyl magnesium chloride. $^1$H NMR (CDCl$_3$): 7.94 (1 H, d, J 11 Hz, A-ring CH ortho to SO$_2$NH), 7.71 & 7.44 (2×2H, 2×d, 2×J 10 Hz, Ar CH's of C-ring), 7.50 (1H, br s, NH), 7.40 (1H, s, A-ring CH ortho to 2×Cl) 7.25 (1H, d, J 11 Hz, A-ring CH ortho to Cl), 7.04 & 6.95 (2×1H, 2×d, 2×J 11 Hz, B-ring CH's), 3.15 (4H, q, J 8 Hz, CH$_2$NCH$_2$), 2.90 (2H, t, J 8 Hz, COCH$_2$), 1.11-1.00 (9H, m, 3×CH$_3$). Hplc (Luna 2, Gradient 5): rt=6.85 minutes. LC/MS rt=7.52 minutes, 602/604 (MH$^+$).

Example 93

2,4-Dichloro-N-[5-(4-diethylsulfamoyl-phenylsulfanyl)-6-(3-methyl-butyryl)-pyridin-2-yl]-benzenesulfonamide (93)

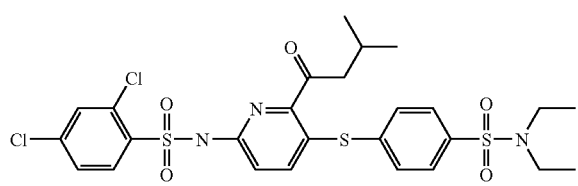

93

Prepared from 2-amino-5-iodo-6-″pentoxycarbonylpyridine and 4-(N,N-diethylaminosulfonyl)thiophenol according to General Method 11 step 1 followed by reaction with 2,4-dichlorophenylsulfonyl chloride according to General Method 11 step 2 and then General Method 11 step 3 employing iso-butyl magnesium chloride. $^1$H NMR (CDCl3): 8.00 (1H, d, J 11 Hz, A-ring CH ortho to SO$_2$NH), 7.74 & 7.48 (2×2H, 2×d, 2×J 10 Hz, Ar CH's of C-ring), 7.45 (1H, s, A-ring CH ortho to 2×Cl) 7.29 (1H, d, J 11 Hz, A-ring CH ortho to Cl), 7.08 & 7.01 (2×1H, 2×d, 2×J 11 Hz, B-ring CH's), 3.20 (4H, q, J 8 Hz, CH$_2$NCH$_2$), 2.79 (2H, d, J 8 Hz, COCH$_2$), 1.10 (6H, t, J 8 Hz, N(CH$_2$CH$_3$)$_2$), 0.89 (6H, d, J 8 Hz, CH(CH$_3$)$_3$). Hplc (Luna 2, Gradient 5): rt=7.24 minutes. LC/MS rt=8.00 minutes, 630/632 (MH$^+$).

Example 94

N-{6-Butyryl-5-[4-(pyrrolidine-1-sulfonyl)-phenylsulfanyl]-pyridin-2-yl}-2,4-dichloro-benzenesulfonamide (94)

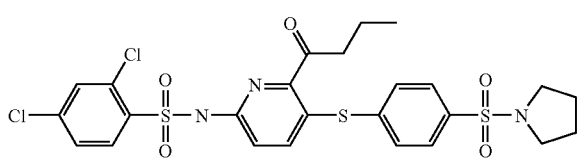

94

Prepared from 2-amino-5-iodo-6-″pentoxycarbonylpyridine and 4-(N-pyrollidylsulfonyl)thiophenol according to General Method 11 step 1 followed by reaction with 2,4-dichlorophenylsulfonyl chloride according to General Method 11 step 2 and then General Method 11 step 3 employing ″propyl magnesium chloride. $^1$H NMR (CDCl$_3$): 8.00 (1H, d, J 11 Hz, A-ring CH ortho to SO$_2$NH), 7.76 & 7.52 (2×2H, 2×d, 2×J 10 Hz, Ar CH's of C-ring), 7.61 (1H, br s, NH), 7.46 (1H, s, A-ring CH ortho to 2×Cl) 7.32 (1H, d, J 11 Hz, A-ring CH ortho to Cl), 7.07 & 7.03 (2×1H, 2×d, 2×J 11 Hz, B-ring CH's), 3.24-3.15 (4H, m, CH$_2$NCH$_2$), 2.89 (2H, t, J 8 Hz, COCH$_2$), 1.78-1.69 (4H, m, CH$_2$CH$_2$CH$_2$CH$_2$), 1.63 (2H, sextet, J 8 Hz, CH$_2$CH$_3$), 0.92 (3H, t, J 9 Hz, CH$_3$). Hplc (Luna 2, Gradient 5): rt=6.86 minutes. LC/MS rt=7.55 minutes, 614/616 (MH$^+$).

Example 95

2,4-Dichloro-N-{6-cyclopropanecarbonyl-5-[4-(pyrrolidine-1-sulfonyl)-phenylsulfanyl]-pyridin-2-yl}-benzenesulfonamide (95)

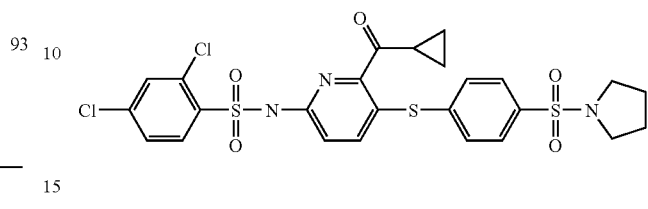

95

Prepared from 2-amino-5-iodo-6-″pentoxycarbonylpyridine and 4-(N-pyrollidylsulfonyl)thiophenol according to General Method 11 step 1 followed by reaction with 2,4-dichlorophenylsulfonyl chloride according to General Method 11 step 2 and then General Method 11 step 3 employing cyclopropyl magnesium bromide. $^1$H NMR (CDCl$_3$): 7.99 (1H, d, J 11 Hz, A-ring CH ortho to SO$_2$NH), 7.77 & 7.52 (2×2H, 2×d, 2×J 10 Hz, Ar CH's of C-ring), 7.62 (1H, br s, NH), 7.45 (1H, s, A-ring CH ortho to 2×Cl) 7.29 (1H, d, J 11 Hz, A-ring CH ortho to Cl), 7.06 & 7.03 (2×1H, 2×d, 2×J 11 Hz, B-ring CH's), 3.24-3.15 (4H, m, CH$_2$NCH$_2$), 3.15-3.03 (1H, m, COCH), 1.77-1.69 (4H, m, CH$_2$CH$_2$CH$_2$CH$_2$), 1.21-1.14 & 1.04-0.95 (2×2H, 2×m, cyclopropyl CH$_2$CH$_2$). Hplc (Luna 2, Gradient 5): rt=6.60 minutes. LC/MS rt=7.29 minutes, 612/614 (MH$^+$).

Example 96

2,4-Dichloro-N-{6-propionyl-5-[4-(pyrrolidine-1-sulfonyl)-phenylsulfanyl]-pyridin-2-yl}-benzenesulfonamide (96)

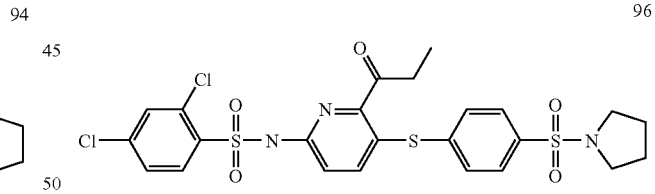

96

Prepared from 2-amino-5-iodo-6-″pentoxycarbonylpyridine and 4-(N-pyrollidylsulfonyl)thiophenol according to General Method 11 step 1 followed by reaction with 2,4-dichlorophenylsulfonyl chloride according to General Method 11 step 2 and then General Method 11 step 3 employing ethyl magnesium chloride. $^1$H NMR (CDCl$_3$): 8.01 (1 H, d, J 11 Hz, A-ring CH ortho to SO$_2$NH), 7.74 & 7.51 (2×2H, 2×d, 2×J 10 Hz, Ar CH's of C-ring), 7.63 (1H, br s, NH), 7.46 (1H, s, A-ring CH ortho to 2×Cl), 7.31 (1H, d, J 11 Hz, A-ring CH ortho to Cl), 7.05 & 7.02 (2×1H, 2×d, 2×J 11 Hz, B-ring CH's), 3.26-3.15 (4H, m, CH$_2$NCH$_2$), 2.95 (2H, q, J 8 Hz, COCH$_2$), 1.78-1.70 (4H, m, CH$_2$CH$_2$CH$_2$CH$_2$), 1.11 (3H, t, J 9 Hz, CH$_3$). Hplc (Luna 2, Gradient 5): rt=6.62 minutes. LC/MS rt=7.27 minutes, 600/602 (MH$^+$).

Example 97

N-{6-Butyryl-5-[4-(pyrrolidine-1-sulfonyl)-phenyl-sulfanyl]-pyridin-2-yl}-2-chloro-4-trifluoromethyl-benzenesulfonamide (97)

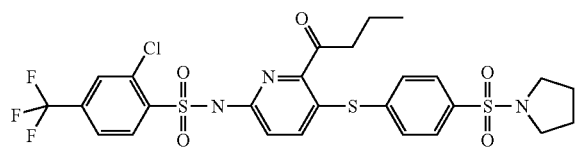

97

Prepared from 2-amino-5-iodo-6-"pentoxycarbonylpyridine and 4-(N-pyrollidylsulfonyl)thiophenol according to General Method 11 step 1 followed by reaction with 2-chloro-4-trifluoromethylphenylsulfonyl chloride according to General Method 11 step 2 and then General Method 11 step 3 employing "propyl magnesium chloride. $^1$H NMR (CDCl$_3$): 8.22 (1H, d, J 11 Hz, A-ring CH ortho to SO$_2$NH), 7.78 & 7.52 (2×2 H, 2d, 2×J 10 Hz, Ar CH's of C-ring), 7.70 (1H, s, A-ring CH ortho to CF$_3$ & Cl) 7.60 (1H, d, J 11 Hz, A-ring CH ortho to Cl), 7.08 & 7.04 (2×1H, 2×d, 2×J 11 Hz, B-ring CH's), 3.25-3.16 (4H, m, CH$_2$NCH$_2$), 2.86 (2H, t, J 8 Hz, COCH$_2$), 1.78-1.68 (4H, m, CH$_2$CH$_2$CH$_2$CH$_2$), 1.62 (2H, sextet, J 8 Hz, CH$_2$CH$_3$), 0.91 (3H, t, J 9 Hz, CH$_3$). Hplc (Luna 2, Gradient 5): rt=6.92 minutes. LC/MS rt=7.52 minutes, 648 (MH$^+$).

Example 98

2-Chloro-N-{6-cyclopropanecarbonyl-5-[4-(pyrrolidine-1-sulfonyl)-phenylsulfanyl]-pyridin-2-yl}-4-trifluoromethyl-benzenesulfonamide (98)

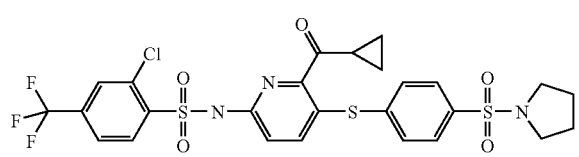

98

Prepared from 2-amino-5-iodo-6-"pentoxycarbonylpyridine and 4-(N-pyrollidylsulfonyl)thiophenol according to General Method 11 step 1 followed by reaction with 2-chloro-4-trifluoromethylphenylsulfonyl chloride according to General Method 11 step 2 and then General Method 11 step 3 employing cyclopropyl magnesium chloride. $^1$H NMR (CDCl$_3$): 8.21 (1H, d, J 11 Hz, A-ring CH ortho to SO$_2$NH), 7.77 & 7.51 (2×2 H, 2d, 2×J 10 Hz, Ar CH's of C-ring), 7.68 (1H, s, A-ring CH ortho to CF$_3$ & Cl) 7.58 (1H, d, J 11 Hz, A-ring CH ortho to Cl), 7.08 & 7.05 (2×1H, 2×d, 2×J 11 Hz, B-ring CH's), 3.24-3.13 (4H, m, CH$_2$NCH$_2$), 3.08-2.98 (1H, m, COCH), 1.78-1.66 (4H, m, CH$_2$CH$_2$CH$_2$CH$_2$), 1.21-1.13 & 1.03-0.94 (2×2H, 2×m, cyclopropyl CH$_2$CH$_2$). Hplc (Luna 2, Gradient 5): rt=6.67 minutes. LC/MS rt=7.29 minutes, 646 (MH$^+$).

Example 99

N-[6-Butyryl-5-(4-diethylsulfamoyl-phenylsulfanyl)-pyridin-2-yl]-2-chloro-4-trifluoromethyl-benzenesulfonamide (99)

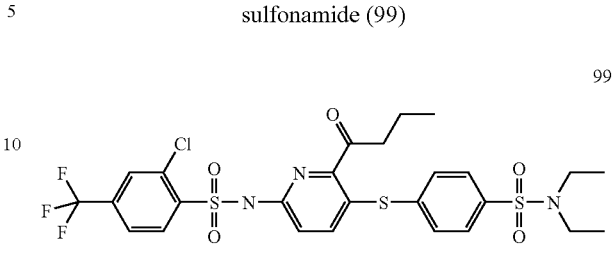

99

Prepared from 2-amino-5-iodo-6-"pentoxycarbonylpyridine and 4-(N,N-diethylaminosulfonyl)thiophenol according to General Method 11 step 1 followed by reaction with 2-chloro-4-trifluoromethylphenylsulfonyl chloride according to General Method 11 step 2 and then General Method 11 step 3 employing "propyl magnesium chloride. $^1$H NMR (CDCl$_3$): 8.21 (1H, d, J 11 Hz, A-ring CH ortho to SO$_2$NH), 7.74 & 7.48 (2×2 H, 2d, 2×J 10 Hz, Ar CH's of C-ring), 7.69 (1H, s, A-ring CH ortho to CF$_3$ & Cl) 7.60 (1H, d, J 11 Hz, A-ring CH ortho to Cl), 7.08 & 7.04 (2×1H, 2×d, 2×J 11 Hz, B-ring CH's), 3.21 (4H, q, J 8 Hz, CH$_2$NCH$_2$), 2.84 (2H, t, J 8 Hz, COCH$_2$), 1.61 (2H, sextet, J 8 Hz, CH$_2$CH$_3$), 1.09 (6H, t, J 8 Hz, N(CH$_2$CH$_3$)$_2$), 0.89 (3H, t, J 9 Hz, CH$_2$CH$_2$CH$_3$). Hplc (Luna 2, Gradient 5): rt=7.17 minutes. LC/MS rt=7.78 minutes, 650 (MH$^+$).

Example 100

2-Chloro-N-[6-cyclopropanecarbonyl-5-(4-diethylsulfamoyl-phenylsulfanyl)-pyridin-2-yl]-4-trifluoromethyl-benzenesulfonamide (100)

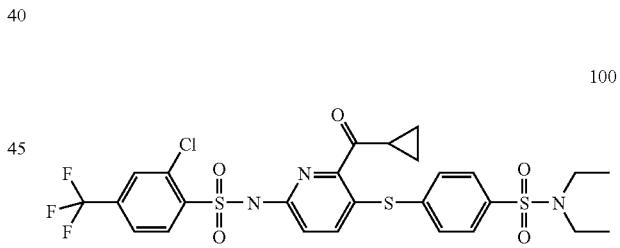

100

Prepared from 2-amino-5-iodo-6-"pentoxycarbonylpyridine and 4-(N,N-diethylaminosulfonyl)thiophenol according to General Method 11 step 1 followed by reaction with 2-chloro-4-trifluoromethylphenylsulfonyl chloride according to General Method 11 step 2 and then General Method 11 step 3 employing cyclopropyl magnesium bromide. $^1$H NMR (CDCl$_3$): 8.20 (1H, d, J 11 Hz, A-ring CH ortho to SO$_2$NH), 7.73 & 7.47 (2×2 H, 2×d, 2×J 10 Hz, Ar CH's of C-ring), 7.70 (1H, s, A-ring CH ortho to CF$_3$ & Cl) 7.58 (1 H, d, J 11 Hz, A-ring CH ortho to Cl), 7.09 & 7.04 (2×1H, 2×d, 2×J 11 Hz, B-ring CH's), 3.19 (4H, q, J 8 Hz, CH$_2$NCH$_2$), 3.08-2.97 (2H, t, J 8 Hz, COCH$_2$), 1.61 (2H, sextet, J 8 Hz, CH$_2$CH$_3$), 1.20-1.09 & 1.03-0.95 (2×2H, 2×m, cyclopropyl CH$_2$CH$_2$), 1.09 (6H, t, J 8 Hz, N(CH$_2$CH$_3$)$_2$). Hplc (Luna 2, Gradient 5): rt=6.94 minutes. LC/MS rt=7.42 minutes, 648 (MH$^+$).

Example 101

N-{6-Butyryl-5-[4-(tetrahydro-pyran-4-sulfonyl)-phenylsulfanyl]-pyridin-2-yl}-2-chloro-4-trifluoromethyl-benzenesulfonamide (101)

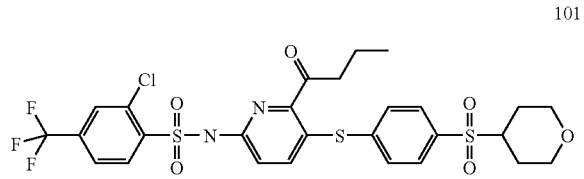

Prepared from 2-amino-5-iodo-6-"pentoxycarbonylpyridine and 4-(4-tetrahydropyranylsulfonyl)thiophenol according to General Method 11 step 1 followed by reaction with 2-chloro-4-trifluoromethylphenylsulfonyl chloride according to General General Method 11 step 2 and then General Method 11 step 3 employing "propyl magnesium chloride. $^1$H NMR (CDCl$_3$): 8.22 (1H, d, J 11 Hz, A-ring C$\underline{H}$ ortho to SO2NH), 7.78 & 7.53 (2×2H, 2×d, 2×J 10 Hz, Ar C$\underline{H}$'s of C-ring), 7.71 (1H, s, A-ring CH ortho to CF$_3$ & Cl) 7.61 (1H, d, J 11 Hz, A-ring C$\underline{H}$ ortho to Cl), 7.09 (2H, s, B-ring C$\underline{H}$'s), 4.05-3.95 & 3.32-3.20 (4H, m, C$\underline{H}_2$OC$\underline{H}_2$), 3.16-3.02 (1H, m, C$\underline{H}$SO$_2$), 2.84 (2H, t, J 8 Hz, COC$\underline{H}_2$), 1.88-1.53 (6H, m, 3×C$\underline{H}_2$), 0.89 (3H, t, J 9 Hz, CH$_2$CH$_2$C$\underline{H}_3$). Hplc (Luna 2, Gradient 5): rt=6.47 minutes. LC/MS rt=7.19 minutes, 663 (MH$^+$).

Example 102

2-Chloro-N-{6-cyclopropanecarbonyl-5-[4-(tetrahydro-pyran-4-sulfonyl)-phenylsulfanyl]-pyridin-2-yl}-4-trifluoromethyl-benzenesulfonamide (102)

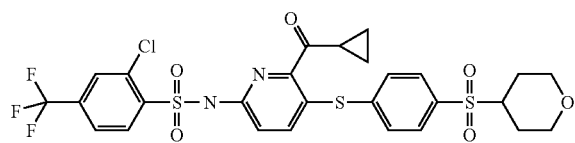

Prepared from 2-amino-5-iodo-6-"pentoxycarbonylpyridine and 4-(4-tetrahydropyranylsulfonyl)thiophenol according to General Method 11 step 1 followed by reaction with 2-chloro-4-trifluoromethylphenylsulfonyl chloride according to General Method 11 step 2 and then General Method 11 step 3 employing cyclopropyl magnesium bromide. $^1$H NMR (CDCl$_3$): 8.22 (1H, d, J 11 Hz, A-ring C$\underline{H}$ ortho to SO$_2$NH), 7.79 & 7.51 (2×2H, 2×d, 2×J 10 Hz, Ar C$\underline{H}$'s of C-ring), 7.70 (1H, s, A-ring C$\underline{H}$ ortho to CF$_3$ & Cl) 7.58 (1H, d, J 11 Hz, A-ring C$\underline{H}$ ortho to Cl), 7.11 (2H, s, B-ring C$\underline{H}$'s), 4.02-3.93 & 3.32-3.21 (4H, m, C$\underline{H}_2$OC$\underline{H}_2$), 3.18-2.97 (2H, m, C$\underline{H}$SO$_2$ & COC$\underline{H}$), 1.88-1.64 (4H, m, 2×C$\underline{H}_2$), 1.20-1.09 & 1.02-0.93 (2×2H, 2×m, cyclopropyl C$\underline{H}_2$C$\underline{H}_2$). Hplc (Luna 2, Gradient 5): rt=6.24 minutes. LC/MS rt=6.95 minutes, 661 (MH$^+$).

Example 103

2-Chloro-N-{6-methyl-5-[4-(morpholine-4-sulfonyl)-phenylsulfanyl]-pyridin-2-yl}-4-trifluoromethyl-benzenesulfonamide (103)

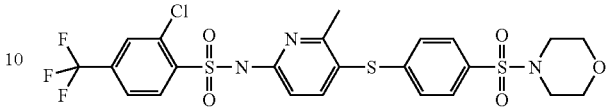

Prepared from 2-amino-5-bromo-6-methylpyridine and 4-(N-morpholinylsulfonyl)thiophenol according to General Method 11 step 1 followed by reaction with 2-chloro-4-trifluoromethylphenylsulfonyl chloride according to General Method 11 step 1. $^1$H NMR (CDCl$_3$): 8.24 (1H, d, J 10 Hz, Ar C$\underline{H}$ ortho to SO$_2$NH), 7.65 (1 H, s, A-ring C$\underline{H}$ ortho to Cl & CF$_3$), 7.61-7.48 (4H, m, Ar C$\underline{H}$'s), 7.03 (2H, d, J 9 Hz, Ar C$\underline{H}$'s), 6.81 (1H, d, J 11 Hz, Ar C$\underline{H}$), 3.66-3.58 (4H, m, C$\underline{H}_2$OC$\underline{H}_2$), 2.90-2.81 (4H, m, C$\underline{H}_2$NC$\underline{H}_2$), 2.41 (3H, s, C$\underline{H}_3$). Hplc (Luna 2, Gradient 5): rt=5.94 minutes. LC/MS rt=6.60 minutes, 608 (MH$^+$).

Example 104

2,4-Dichloro-N-{6-ethyl-5-[4-(morpholine-4-sulfonyl)-phenylsulfanyl]-pyridin-2-yl}-benzenesulfonamide (104)

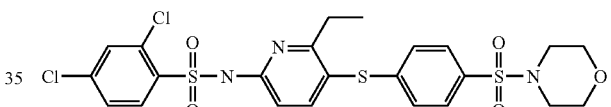

Prepared from 2-amino-5-bromo-6-ethylpyridine and 4-(N-morpholinylsulfonyl)thiophenol according to General Method 11 step 1 followed by reaction with 2,4-dichlorophenylsulfonyl chloride according to General Method 11 step 2. $^1$H NMR (CDCl$_3$): 8.00 (1H, d, J 10 Hz, A-ring C$\underline{H}$ ortho to SO$_2$NH), 7.50 & 6.98 (2×2 H, 2×d, C-ring C$\underline{H}$'s), 7.45 (1H, d, J 10 Hz, A-ring C$\underline{H}$ ortho to Cl), 7.35 (1H, s, A ring C$\underline{H}$ ortho to 2×Cl), 7.26 & 6.74 (2×1H, 2×d, 2×J 10 Hz, pyridyl C$\underline{H}$'s), 3.63-3.56 (4H, m, C$\underline{H}_2$OC$\underline{H}_2$), 2.88-2.79 (4H, m, C$\underline{H}_2$NC$\underline{H}_2$), 2.72 (3H, q, J 8 Hz, C$\underline{H}_2$CH$_3$), 1.09 (3H, t, J 8 Hz, CH$_2$C$\underline{H}_3$). Hplc (Luna 2, Gradient 5): rt=6.19 minutes. LC/MS rt=6.86 minutes, 588/590 (MH$^+$).

Example 105

2-Chloro-N-{6-ethyl-5-[4-(morpholine-4-sulfonyl)-phenylsulfanyl]-pyridin-2-yl}-4-trifluoromethyl-benzenesulfonamide (105)

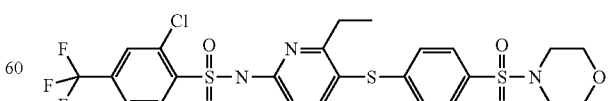

Prepared from 2-amino-5-bromo-6-ethylpyridine and 4-(N-morpholinylsulfonyl)thiophenol according to General Method 11 step 1 followed by reaction with 2-chloro-4-trifluoromethylphenylsulfonyl chloride according to General Method 11 step 2. $^1$H NMR (CDCl$_3$): 8.41 (1H, d, J 10 Hz, A-ring C$\underline{H}$ ortho to SO$_2$NH), 7.81-7.63 (5H, m, Ar C$\underline{H}$'s), 7.20 (2H, d, 2×C-ring C$\underline{H}$'s), 6.94 (1H, d, J 10 Hz, pyridyl C$\underline{H}$'s), 3.83-3.77 (4H, m, C$\underline{H}_2$OC$\underline{H}_2$), 3.09-2.98 (4H, m, C$\underline{H}_2$NC$\underline{H}_2$), 2.93 (3H, q, J 9 Hz, C$\underline{H}_2$CH$_3$), 1.31 (3H, t, J 9 Hz, CH$_2$C$\underline{H}_3$). Hplc (Luna 2, Gradient 5): rt=6.26 minutes. LC/MS rt=6.92 minutes, 622 (MH$^+$).

Example 106

N-{6-Butyryl-5-[4-(propane-2-sulfonyl)-phenylsulfanyl]-pyridin-2-yl}-2,4-dichloro-benzenesulfonamide (106)

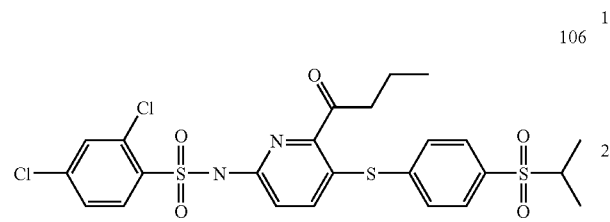

Prepared from 2-amino-5-iodo-6-"pentoxycarbonylpyridine and 4-(iso-propylsulfonyl)thiophenol according to General Method 11 step 1 followed by reaction with 2,4-dichlorophenylsulfonyl chloride according to General Method 11 step 2 and then General Method 11 step 3 employing "propyl magnesium chloride. $^1$H NMR (CDCl$_3$): 8.03 (1H, d, J 11 Hz, A-ring C$\underline{H}$ ortho to SO$_2$NH), 7.83 & 7.56 (2×2H, 2×d, 2×J 10 Hz, Ar C$\underline{H}$'s of C-ring), 7.65 (1H, br s, N$\underline{H}$), 7.48 (1H, s, A-ring C$\underline{H}$ ortho to 2×Cl) 7.33 (1H, d, J 11 Hz, A-ring C$\underline{H}$ ortho to Cl), 7.08 & 7.07 (2×1H, 2×d, 2×J 11 Hz, B-ring C$\underline{H}$'s), 3.22-3.08 (1H, m, C$\underline{H}$(CH$_3$)$_2$), 2.91 (2H, t, J 8 Hz, COC$\underline{H}_2$), 1.65 (2H, sextet, J 8 Hz, C$\underline{H}_2$CH$_3$), 1.31 (6H, d, J 7 Hz, CH(C$\underline{H}_3$)$_2$), 0.92 (3H, t, J 9 Hz, C$\underline{H}_3$). Hplc (Luna 2, Gradient 5): rt=6.60 minutes. LC/MS rt=7.30 minutes, 587/589 (MH$^+$).

Example 107

2,4-Dichloro-N-{6-cyclopropanecarbonyl-5-[4-(propane-2-sulfonyl)-phenylsulfanyl]-pyridin-2-yl}-benzenesulfonamide (107)

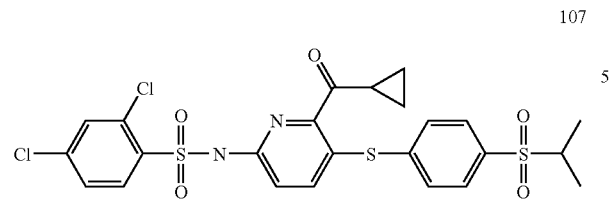

Prepared from 2-amino-5-iodo-6-"pentoxycarbonylpyridine and 4-(iso-propylsulfonyl)thiophenol according to General Method 11 step 1 followed by reaction with 2,4-dichlorophenylsulfonyl chloride according to General Method 11 step 2 and then General Method 11 step 3 employing cyclopropyl magnesium bromide. $^1$H NMR (CDCl$_3$): 8.01 (1H, d, J 11 Hz, A-ring C$\underline{H}$ ortho to SO$_2$NH), 7.79 & 7.53 (2×2H, 2×d, 2×J 10 Hz, Ar C$\underline{H}$'s of C-ring), 7.43 (1H, s, A-ring C$\underline{H}$ ortho to 2×Cl) 7.30 (1H, d, J 11 Hz, A-ring C$\underline{H}$ ortho to Cl), 7.07 (2H, s, B-ring C$\underline{H}$'s), 3.21-3.02 (2H, m, C$\underline{H}$(CH$_3$)$_2$ & COC$\underline{H}$), 1.28 (6H, d, J 7 Hz, CH(C$\underline{H}_3$)$_2$), 1.20-1.12 & 1.03-0.97 (2×2H, 2×m, cyclopropyl C$\underline{H}_2$C$\underline{H}_2$). Hplc (Luna 2, Gradient 5): rt=6.38 minutes. LC/MS rt=6.98 minutes, 585/587 (MH$^+$).

Example 108

2,4-Dichloro-N-{5-[4-(morpholine-4-sulfonyl)-phenylsulfanyl]-6-trifluoromethyl-pyridin-2-yl}-benzenesulfonamide (108)

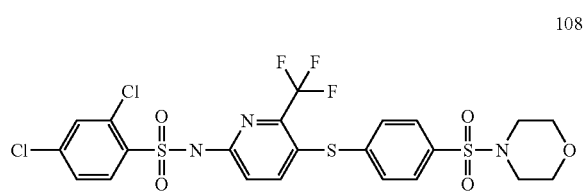

Prepared from 2-amino-5-bromo-6-trifluoromethylpyridine and 4-(N-morpholinylsulfonyl)thiophenol according to General Method 11 step 1 followed by reaction with 2,4-dichlorophenylsulfonyl chloride according to General Method 11 step 2. $^1$H NMR (CDCl$_3$): 8.10 (1H, d, J 10 Hz, A-ring C$\underline{H}$ ortho to SO$_2$NH), 7.62 & 7.35 (2×1 H, 2×d, 2×J 10 Hz, pyridyl C$\underline{H}$'s), 7.56 & 7.18 (2×2H, 2×d, 2×J 10 Hz, C-ring C$\underline{H}$'s), 7.45 (1H, s, A ring C$\underline{H}$ ortho to 2×Cl), 7.20 (1H, d, J 10 Hz, A-ring C$\underline{H}$ ortho to Cl), 3.71-3.63 (4H, m, C$\underline{H}_2$OC$\underline{H}_2$), 2.93-2.85 (4H, m, C$\underline{H}_2$NC$\underline{H}_2$). Hplc (Luna 2, Gradient 5): rt=6.39 minutes. LC/MS rt=7.06 minutes, 628/630 (MH$^+$).

Example 109

2-Chloro-N-{5-[4-(morpholine-4-sulfonyl)-phenylsulfanyl]-6-trifluoromethyl-pyridin-2-yl}-4-trifluoromethyl-benzenesulfonamide (109)

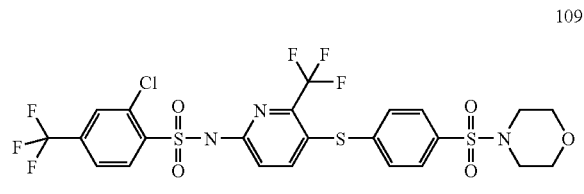

Prepared from 2-amino-5-bromo-6-trifluoromethylpyridine and 4-(N-morpholinylsulfonyl)thiophenol according to General Method 11 step 1 followed by reaction with 2-chloro-4-trifluoromethylphenylsulfonyl chloride according to General Method 11 step 2. $^1$H NMR (CDCl$_3$): 8.31 (1H, d, J 10 Hz, A-ring C$\underline{H}$ ortho to SO$_2$NH), 7.45 (1H, s, A ring C$\underline{H}$ ortho to CF$_3$ & Cl), 7.65-7.50 & 7.26-7.15 (4H & 3H, 2×m, Ar C$\underline{H}$'s), 3.71-3.61 (4H, m, C$\underline{H}_2$OC$\underline{H}_2$), 2.95-2.86 (4H, m, C$\underline{H}_2$NC$\underline{H}_2$). Hplc (Luna 2, Gradient 5): rt=6.53 minutes. LC/MS rt=7.06 minutes, 662 (MH$^+$).

Example 110

2-Chloro-N-{5-[4-(piperidine-1-sulfonyl)-phenylsulfanyl]-6-propoxy-pyridin-2-yl}-4-trifluoromethyl-benzenesulfonamide (110)

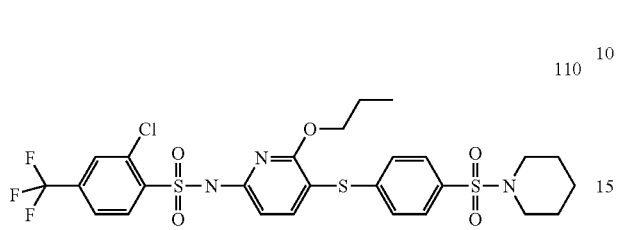

Prepared from 2-amino-5-iodo-6-"propoxypyridine and 4-(N-piperidinylsulfonyl)thiophenol according to General Method 11 step 1 followed by reaction with 2-chloro-4-trifluoromethylphenylsulfonyl chloride according to General Method 11 step 2. $^1$H NMR (CDCl$_3$): 8.46 (1H, d, J 10 Hz, Ar CH ortho to SO$_2$NH), 8.30 (1H, s, A ring CH ortho to CF$_3$ & Cl), 7.74-7.60 (4H, m, Ar CH's), 7.13 (2H, d, J 9 Hz, 2×C-ring CH's), 6.46 (1H, d, J 11 Hz, B-ring CH), 3.83 (2H, t, J 8 Hz, OCH$_2$), 3.04-2.92 (4H, m, CH$_2$NCH$_2$), 1.71-1.60 (4H, m, CH$_2$CH$_2$CH$_2$CH$_2$CH$_2$), 1.41-1.30 & 1.28-1.14 (2×2H, 2×m, CH$_2$CH$_2$CH$_2$CH$_2$CH$_2$ & OCH$_2$CH$_2$), 0.89 (3H, t, J 8 Hz, CH$_3$). Hplc (Luna 2, Gradient 5): rt=7.65 minutes. LC/MS rt=8.53 minutes, 650 (MH$^+$).

Example 111

2,4-Dichloro-N-{5-[4-(piperidine-1-sulfonyl)-phenylsulfanyl]-6-propoxy-pyridin-2-yl}-benzenesulfonamide (111)

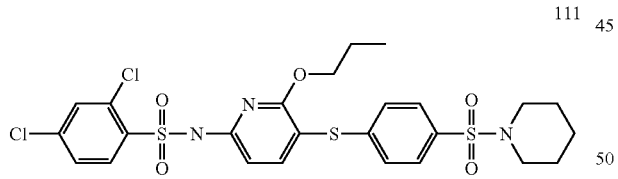

Prepared from 2-amino-5-iodo-6-"propoxypyridine and 4-(N-piperidinylsulfonyl)thiophenol according to General Method 11 step 1 followed by reaction with 2,4-dichlorophenylsulfonyl chloride according to General Method 11 step 2. $^1$H NMR (CDCl$_3$): 8.23-8.11 (2H, m, Ar CH ortho to SO$_2$NH & A ring CH ortho to 2×Cl), 7.64-7.50 & 7.41-7.29 (4H & 2H, 2×m, Ar CH's), 7.04 (2H, d, J 9 Hz, 2×C-ring CH's), 6.37 (1H, d, J 11 Hz, B-ring CH), 3.81 (2H, t, J 7 Hz, OCH$_2$), 2.95-2.82 (4H, m, CH$_2$NCH$_2$), 1.68-1.50 (4H, m, CH$_2$CH$_2$CH$_2$CH$_2$CH$_2$), 1.40-1.30 & 1.29-1.14 (2×2H, 2×m, CH$_2$CH$_2$CH$_2$CH$_2$CH$_2$ & OCH$_2$CH$_2$), 0.89 (3H, t, J 8 Hz, CH$_3$). Hplc (Luna 2, Gradient 5): rt=7.50 minutes. LC/MS rt=8.46 minutes, 616/618 (MH$^+$).

Example 112

N-[6-Butyryl-5-(4-cyclopentanesulfonyl-phenylsulfanyl)-pyridin-2-yl]-2,4-dichloro-benzenesulfonamide (112)

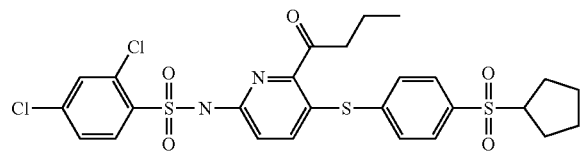

Prepared from 2-amino-5-iodo-6-"pentoxycarbonylpyridine and 4-(cyclopentylsulfonyl)thiophenol according to General Method 11 step 1 followed by reaction with 2,4-dichlorophenylsulfonyl chloride according to General Method 11 step 2 and then General Method 1-C employing "propyl magnesium chloride. $^1$H NMR (CDCl$_3$): 8.00 (1H, d, J 11 Hz, A-ring CH ortho to SO$_2$NH), 7.81 & 7.52 (2×2H, 2×d, 2×J 10 Hz, Ar CH's of C-ring), 7.70 (1H, br s, NH), 7.47 (1H, s, A-ring CH ortho to 2×Cl) 7.31 (1H, d, J 11 Hz, A-ring CH ortho to Cl), 7.05 & 7.04 (2×1H, 2×d, 2×J 11 Hz, B-ring CH's), 3.49-3.36 (1H, m, CH(CH$_3$)$_2$), 2.89 (2H, t, J 8 Hz, COCH$_2$), 2.04-1.50 (10H, m, 5×CH$_2$), 0.91 (3H, t, J 9 Hz, CH$_2$). Hplc (Luna 2, Gradient 5): rt=6.84 minutes. LC/MS rt=7.61 minutes, 613/615 (MH$^+$).

Example 113

2,4-Dichloro-N-[5-(4-cyclopentanesulfonyl-phenylsulfanyl)-6-cyclopropanecarbonyl-pyridin-2-yl]-benzenesulfonamide (113)

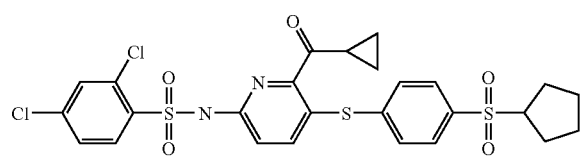

Prepared from 2-amino-5-iodo-6-"pentoxycarbonylpyridine and 4-(cyclopentylsulfonyl)thiophenol according to General Method 11 step 1 followed by reaction with 2,4-dichlorophenylsulfonyl chloride according to General Method 11 step 2 and then General Method 11 step 3 employing cyclopropyl magnesium bromide. $^1$H NMR (CDCl$_3$): 8.01 (1H, d, J 11 Hz, A-ring CH ortho to SO$_2$NH), 7.82 & 7.53 (2×2H, 2×d, 2×J 10 Hz, Ar CH's of C-ring), 7.79 (1H, br s, NH), 7.46 (1H, s, A-ring CH ortho to 2×Cl) 7.29 (1H, d, J 11 Hz, A-ring CH ortho to Cl), 7.05 & 7.04 (2×1H, 2×d, 2×J 11 Hz, B-ring CH's), 3.49-3.35 (1H, m, CH(CH$_3$)$_2$), 3.10-3.00 (1H, m, COCH), 2.03-1.48 (8H, m, 4×CH$_2$), 1.21-1.13 & 1.05-0.97 (2×2H, 2×m, cyclopropyl CH$_2$CH$_2$). Hplc (Luna 2, Gradient 5): rt=6.57 minutes. LC/MS rt=7.31 minutes, 611/613 (MH$^+$).

Example 114

N-[6-Butyryl-5-(4-cyclopentanesulfonyl-phenylsulfanyl)-pyridin-2-yl]-2-chloro-4-trifluoromethyl-benzenesulfonamide (114)

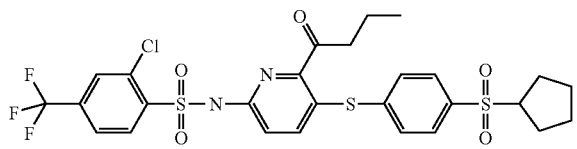

Prepared from 2-amino-5-iodo-6-"pentoxycarbonylpyridine and 4-(cyclopentylsulfonyl)thiophenol according to General Method 11 step 1 followed by reaction with 2-chloro-4-trifluoromethylphenylsulfonyl chloride according to General Method 11 step 2 and then General Method 11 step 3 employing "propyl magnesium chloride. $^1$H NMR (CDCl$_3$): 8.21 (1H, d, J 11 Hz, A-ring C$\underline{H}$ ortho to SO$_2$NH), 7.84 & 7.51 (2×2H, 2×d, 2×J 10 Hz, Ar C$\underline{H}$'s of C-ring), 7.68 (1H, s, A-ring C$\underline{H}$ ortho to 2×Cl) 7.59 (1H, d, J 11 Hz, A-ring C$\underline{H}$ ortho to Cl), 7.04 & 7.03 (2×1H, 2×d, 2×J 11 Hz, B-ring C$\underline{H}$'s), 3.48-3.36 (1H, m, C$\underline{H}$(CH$_3$)$_2$), 2.82 (2H, t, J 8 Hz, COC$\underline{H}_2$), 2.04-1.48(10H, m, 5×C$\underline{H}_2$), 0.88 (3H, t, J 9 Hz, C$\underline{H}_3$). Hplc (Luna 2, Gradient 5): rt=6.88 minutes. LC/MS rt=7.58 minutes, 647 (MH$^+$).

Example 115

2-Chloro-N-[5-(4-cyclopentanesulfonyl-phenylsulfanyl)-6-cyclopropanecarbonyl-pyridin-2-yl]-4-trifluoromethyl-benzenesulfonamide (115)

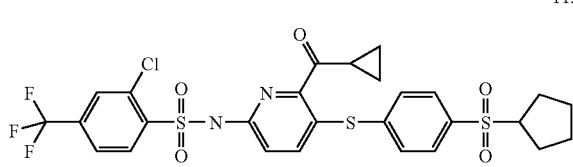

Prepared from 2-amino-5-iodo-6-"pentoxycarbonylpyridine and 4-(cyclopentylsulfonyl)thiophenol according to General Method 11 step 1 followed by reaction with 2-chloro-4-trifluoromethylphenylsulfonyl chloride according to General Method 11 step 2 and then General Method 11 step 3 employing cyclopropyl magnesium bromide. $^1$H NMR (CDCl$_3$): 8.22 (1H, d, J 11 Hz, A-ring C$\underline{H}$ ortho to SO$_2$NH), 7.82 & 7.52 (2×2H, 2×d, 2×J 10 Hz, Ar C$\underline{H}$'s of C-ring), 7.68 (1H, s, A-ring C$\underline{H}$ ortho to 2×Cl) 7.58 (1H, d, J 11 Hz, A-ring C$\underline{H}$ ortho to Cl), 7.06 & 7.05 (2×1H, 2×d, 2×J 11 Hz, B-ring C$\underline{H}$'s), 3.49-3.36 (1H, m, C$\underline{H}$(CH$_3$)$_2$), 3.02-2.90 (1H, m, COC$\underline{H}$), 2.04-1.49 (8H, m, 4×C$\underline{H}_2$), 1.20-1.11 & 1.03-0.94 (2×2H, 2×m, cyclopropyl C$\underline{H}_2$C$\underline{H}_2$). Hplc (Luna 2, Gradient 5): rt=6.65 minutes. LC/MS rt=7.34 minutes, 645 (1+).

Example 116

N-{6-Butyryl-5-[4-(pentane-3-sulfonyl)-phenylsulfanyl]-pyridin-2-yl}-2-chloro-4-trifluoromethyl-benzenesulfonamide (116)

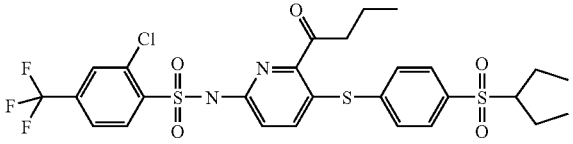

Prepared from 2-amino-5-iodo-6-"pentoxycarbonylpyridine and 4-(3-pentylsulfonyl)thiophenol according to General Method 11 step 1 followed by reaction with 2-chloro-4-trifluoromethylphenylsulfonyl chloride according to General Method 11 step 2 and then General Method 11 step 3 employing "propyl magnesium chloride. $^1$H NMR (CDCl$_3$): 8.22 (1H, d, J 11 Hz, A-ring C$\underline{H}$ ortho to SO$_2$NH), 7.80 & 7.51 (2×2H, 2×d, 2×J 10 Hz, Ar C$\underline{H}$'s of C-ring), 7.69 (1H, s, A-ring C$\underline{H}$ ortho to 2×Cl) 7.60 (1H, d, J 11 Hz, A-ring C$\underline{H}$0 ortho to Cl), 7.05 & 7.04 (2×1H, 2×d, 2×J 11 Hz, B-ring C$\underline{H}$'s), 2.86 (2H, t, J 8 Hz, COCH$_2$), 2.80-2.71 (1H, m, C$\underline{H}$(CH$_3$)$_2$), 1.88-1.50 (6H, m, 3×C$\underline{H}_2$) 0.99-0.84 (9H, m, 3×C$\underline{H}_2$). Hplc (Luna 2, Gradient 5): rt=7.00 minutes. LC/MS rt=7.83 minutes, 649 (MH$^+$).

Example 117

2-Chloro-N-{6-cyclopropanecarbonyl-5-[4-(pentane-3-sulfonyl)-phenylsulfanyl]-pyridin-2-yl}-4-trifluoromethyl-benzenesulfonamide (117)

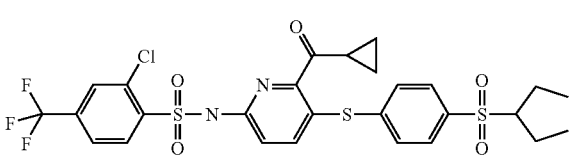

Prepared from 2-amino-5-iodo-6-"pentoxycarbonylpyridine and 4-(3-pentylsulfonyl)thiophenol according to General Method 11 step 1 followed by reaction with 2-chloro-4-trifluoromethylphenylsulfonyl chloride according to General Method 11 step 2 and then General Method 11 step 3 employing cyclopropyl magnesium bromide. $^1$H NMR (CDCl$_3$): 8.23 (1H, d, J 11 Hz, A-ring C$\underline{H}$ ortho to SO$_2$NH), 8.01 (1H, br s, NH), 7.80 & 7.52 (2×2H, 2×d, 2×J 10 Hz, Ar C$\underline{H}$'s of C-ring), 7.69 (1H, s, A-ring C$\underline{H}$ ortho to 2×Cl) 7.57 (1 $\underline{H}$, d, J 11 Hz, A-ring C$\underline{H}$ ortho to Cl), 7.06 (2H, s, B-ring C$\underline{H}$'s), 3.01-2.92 (1H, m, COC$\underline{H}$), 2.81-2.71 (1H, m, C$\underline{H}$(CH$_3$)$_2$), 1.88-1.52 (6H, m, 3×C$\underline{H}_2$), 1.20-1.09 (2H, m, 2×cyclopropyl C$\underline{H}$) 1.00-0.86 (8H, m, 2×C$\underline{H}_2$ & 2×cyclopropyl C$\underline{H}$). Hplc (Luna 2, Gradient 5): rt=6.80 minutes. LC/MS rt=7.55 minutes, 647 (MH$^+$).

Example 118

N-[6-Butyryl-5-(4-ethylsulfamoyl-phenylsulfanyl)-pyridin-2-yl]-2,4-dichloro-benzenesulfonamide (118)

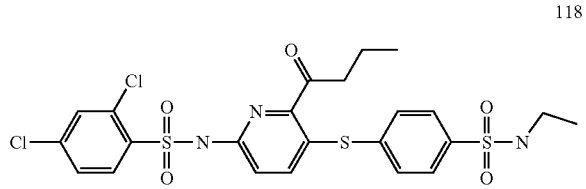

Prepared from 2-amino-5-iodo-6-″pentoxycarbonylpyridine and 4-(N-ethylaminosulfonyl)thiophenol according to General Method 11 step 1 followed by reaction with 2,4-dichlorophenylsulfonyl chloride according to General Method 11 step 2 and then General Method 11 step 3 employing ″propyl magnesium chloride. $^1$H NMR (CDCl$_3$): 8.00 (1H, d, J 11 Hz, A-ring CH ortho to SO$_2$NH), 7.80 & 7.50 (2×2H, 2×d, 2×J 10 Hz, Ar CH's of C-ring), 7.71 (1H, br s, NHAr), 7.45 (1H, s, A-ring CH ortho to 2×Cl) 7.30 (1H, d, J 11 Hz, A-ring CH ortho to Cl), 7.05 & 7.04 (2×1H, 2×d, 2×J 11 Hz, B-ring CH's), 4.43-4.36 (1H, m, NHEt), 2.99 (2H, pentet, J 8 Hz, NCH$_2$), 2.87 (2H, t, J 8 Hz, COCH$_2$), 1.62 (2H, sextet, J 8 Hz, CH$_2$CH$_3$), 1.07 & 0.90 (2×3H, 2×t, 2×J 8 Hz, 2×CH$_3$). Hplc (Luna 2, Gradient 5): rt=6.36 minutes. LC/MS rt=7.11 minutes, 588/590 (MH$^+$).

Example 119

2,4-Dichloro-N-[6-cyclopropanecarbonyl-5-(4-ethylsulfamoyl-phenylsulfanyl)-pyridin-2-yl]-benzenesulfonamide (119)

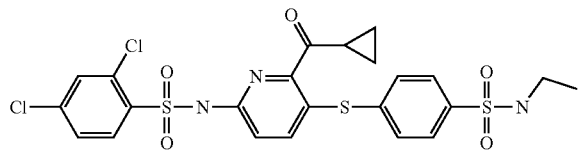

Prepared from 2-amino-5-iodo-6-″pentoxycarbonylpyridine and 4-(N-ethylaminosulfonyl)thiophenol according to General Method 11 step 1 followed by reaction with 2,4-dichlorophenylsulfonyl chloride according to General Method 11 step 2 and then General Method 11 step 3 employing cyclopropyl magnesium bromide. $^1$H NMR (CDCl$_3$): 8.02 (1H, d, J 11 Hz, A-ring CH ortho to SO$_2$NH), 7.88 (1H, br s, NHAr), 7.78 & 7.48 (2×2H, 2×d, 2×J 10 Hz, Ar CH's of C-ring), 7.43 (1H, s, A-ring CH ortho to 2×Cl) 7.29 (1 H, d, J 11 Hz, A-ring CH ortho to Cl), 7.05 (2H, s, B-ring CH's), 4.51-4.43 (1H, m, NHEt), 3.10-2.92 (3H, m, NCH$_2$ & COCH), 1.20-0.98 (7H, m, cyclopropyl CH$_2$CH$_2$ & CH$_3$). Hplc (Luna 2, Gradient 5): rt=6.12 minutes. LC/MS rt=6.85 minutes, 586/588 (MH$^+$).

Example 120

N-[6-Butyryl-5-(4-ethylsulfamoyl-phenylsulfanyl)-pyridin-2-yl]-2-chloro-4-trifluoromethyl-benzenesulfonamide (120)

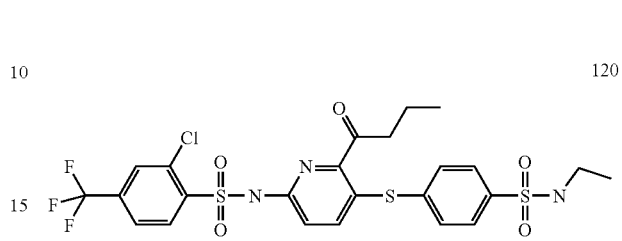

Prepared from 2-amino-5-iodo-6-″pentoxycarbonylpyridine and 4-(N-ethylaminosulfonyl)thiophenol according to General Method 11 step 1 followed by reaction with 2-chloro-4-trifluoromethylphenylsulfonyl chloride according to General Method 11 step 2 and then General Method 11 step 3 employing ″propyl magnesium chloride. $^1$H NMR (CDCl$_3$): 8.21 (1H, d, J 11 Hz, A-ring CH ortho to SO$_2$NH), 7.80 & 7.49 (2×2H, 2×d, 2×J 10 Hz, Ar CH's of C-ring), 7.72 (1H, s, A-ring CH ortho to 2×Cl) 7.59 (1H, d, J 11 Hz, A-ring CH ortho to Cl), 7.04 & 7.03 (2×1H, 2×d, 2×J 11 Hz, B-ring CH's), 4.40-4.31 (1H, m, NHEt), 2.99 (2H, pentet, J 8 Hz, NCH$_2$), 2.85 (2H, t, J 8 Hz, COCH$_2$), 1.61 (2H, sextet, J 8 Hz, CH$_2$CH$_3$), 1.08 & 0.90 (2×3H, 2×t, 2×J 8 Hz, 2×CH$_3$). Hplc (Luna 2, Gradient 5): rt=6.42 minutes. LC/MS rt=7.13 minutes, 622 (MH$^+$).

Example 121

2-Chloro-N-[6-cyclopropanecarbonyl-5-(4-ethylsulfamoyl-phenylsulfanyl)-pyridin-2-yl]-4-trifluoromethyl-benzenesulfonamide (121)

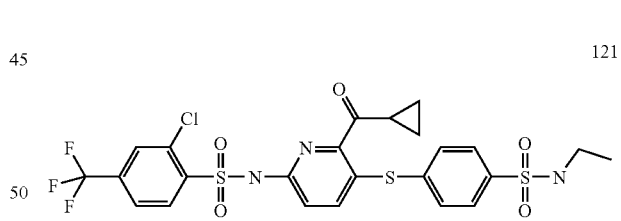

Prepared from 2-amino-5-iodo-6-″pentoxycarbonylpyridine and 4-(N-ethylaminosulfonyl)thiophenol according to General Method 11 step 1 followed by reaction with 2-chloro-4-trifluoromethylphenylsulfonyl chloride according to General Method 11 step 2 and then General Method 11 step 3 employing cyclopropyl magnesium bromide. $^1$H NMR (CDCl$_3$): 8.21 (1H, d, J 11 Hz, A-ring CH ortho to SO$_2$NH), 7.79 & 7.49 (2×2H, 2×d, 2×J 10 Hz, Ar CH's of C-ring), 7.70 (1H, s, A-ring CH ortho to 2×Cl) 7.59 (1H, d, J 11 Hz, A-ring CH ortho to Cl), 7.07 & 7.06 (2×1H, 2×d, 2×J 11 Hz, B-ring CH's), 4.42-4.35 (1H, m, NHEt), 3.05-2.91 (3H, m, NCH$_2$ & COCH), 1.21-0.92 (7H, m, cyclopropyl CH$_2$CH$_2$ & CH$_3$). Hplc (Luna 2, Gradient 5): rt=6.20 minutes. LC/MS rt=6.94 minutes, 620 (MH$^+$).

Example 122

N-{6-Butyl-5-[4-(piperidine-1-sulfonyl)-phenylsulfanyl]-pyridin-2-yl}-2,4-dichloro-benzenesulfonamide (122)

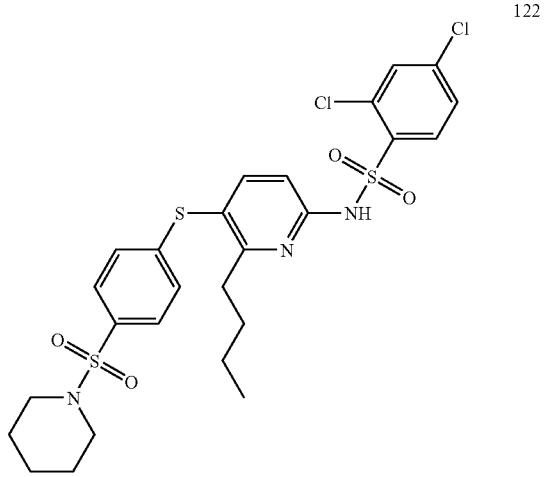

Step 1: 6-Amino-3-iodo-2-methylpyridine

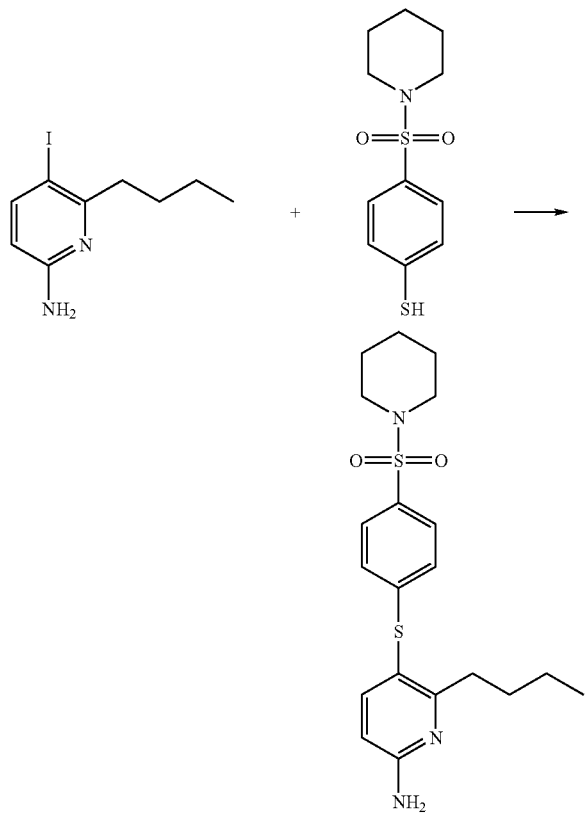

This compound was prepared by iodination of 6-methylpyridin-2-ylamine using the method described by A. Bouillon et al. Tetrahedron (2002) 2885-2890. $^1$H NMR CDCl$_3$ 7.64 (1H, d), 6.06 (1H, d), 4.31 (2H, bs), 2.73 (2H, m), 1.60 (2H, m), 1.49 (2H, m), 0.91 (3H, t)

Step 2: 6-Butyl-5-[4-(piperidine-1-sulfonyl)-phenylsulfanyl]-pyridin-2-ylamine

Prepared from 6-amino-3-iodo-2-methylpyridine and 4-(piperidine-1-sulfonyl) Benzenethiol using General Method 11 step 1 to give 6-butyl-5-[4-(piperidine-1-sulfonyl)-phenylsulfanyl]-pyridin-2-ylamine. $^1$HNMR CDCl$_3$ 7.49 (3H, m), 7.01 (2H, d), 6.37 (1H, d), 4.85 (2H, bs), 2.90 (4H, m), 2.76 (2H, m), 1.66 (6H, m), 1.2-1.4 (4H, m), 0.83 (3H, t)

Step 3: N-{6-Butyl-5-[4-(piperidine-1-sulfonyl)-phenylsulfanyl]-pyridin-2-yl}-2,4-dichloro-benzenesulfonamide

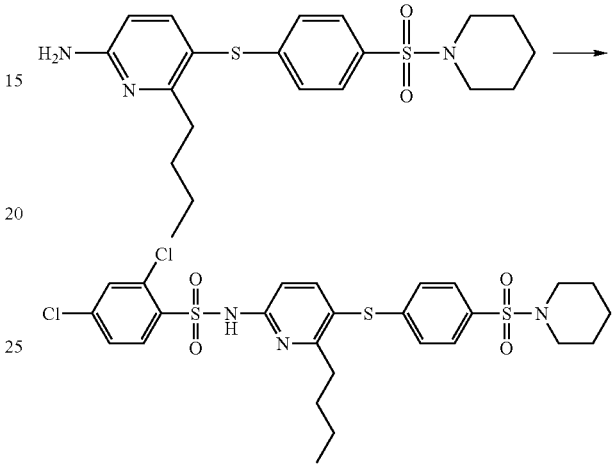

Prepared from 6-butyl-5-[4-(piperidine-1-sulfonyl)-phenylsulfanyl]-pyridin-2-ylamine and 2,4-dichlorobenzenesulfonyl chloride using General Method 11 step 2 to give N-{6-butyl-5-[4-(piperidine-1-sulfonyl)-phenylsulfanyl]-pyridin-2-yl}-2,4-dichloro-benzenesulfonamide. $^1$HNMR CDCl$_3$ 8.10 (1H, d), 7.58 (2H, d), 7.47 (1H, s), 7.36 (1H, d), 7.07 (2H, d), 6.81 (1H, d), 2.97 (4H, m), 2.80 (2H, t), 1.15-1.65 (10H, m), 0.81 (3H, t). LCMS (Luna 2, ): rt=8.11 minutes, 612 (M–H)$^-$.

Example 123

N-{6-Butyl-5-[4-(piperidine-1-sulfonyl)-phenylsulfanyl]-pyridin-2-yl}-2-chloro-4-trifluoromethyl-benzenesulfonamide (123)

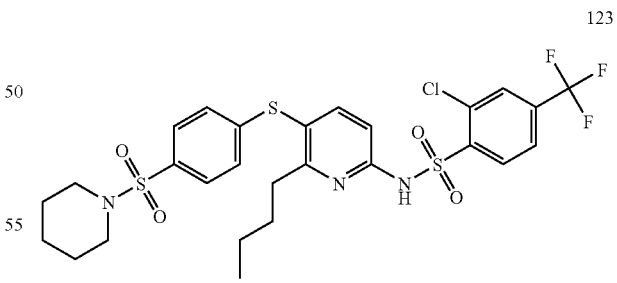

N-{6-Butyl-5-[4-(piperidine-1-sulfonyl)-phenylsulfanyl]-pyridin-2-yl}-2-chloro-4-trifluoromethyl-benzenesulfonamide was prepared from 6-amino-3-iodo-2-methylpyridine and 4-(piperidine-1-sulfonyl)benzenethiol using General Method 11 step 1 and 2-chloro-4-trifluoromethylbenzenesulfonyl chloride using General Method 11 step 2. $^1$HNMR CDCl$_3$ 8.31 (1H, d), 7.71 (1H, s), 7.56 (4H, m), 7.07 (2H, d), 6.79 (1H, d), 2.94 (4H, m), 2.80 (2H, t), 1.20-1.70 (10H, m), 0.83 (3H, t). LCMS (Luna 2, ): rt=8.10 minutes, 646 (M–H)$^-$.

Example 124

N-{6-Butyl-5-[4-(morpholine-4-sulfonyl)-phenylsulfanyl]-pyridin-2-yl}-2,4-dichloro-benzenesulfonamide (124)

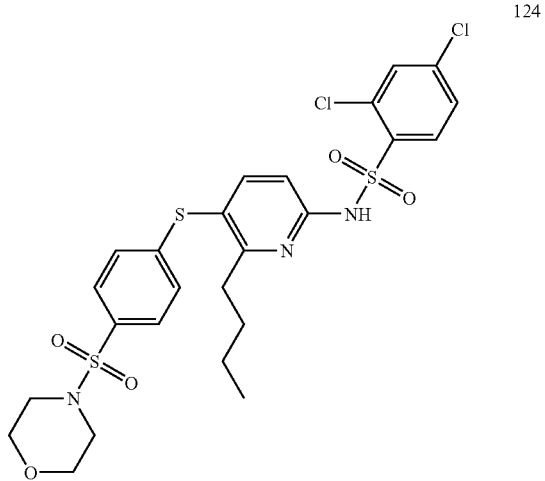

N-{6-Butyl-5-[4-(morpholine-4-sulfonyl)-phenylsulfanyl]-pyridin-2-yl}-2,4-dichloro-benzenesulfonamide was prepared from 6-amino-3-iodo-2-methylpyridine and 4-(morpholine-4-sulfonyl)benzenethiol using General Method 11 step 1 and 2,4-dichloro trifuoromethylbenzenesufonyl chloride using General Method 11 step 2. $^1$HNMR CDCl$_3$ 8.10 (1H, d), 7.71 (1H, s), 7.56 (3H, m), 7.33 (1H, s), 7.04 (2H, d), 6.70 (1H, d), 3.68 (4H, m), 2.90 (4H, m), 2.76 (2H, t), 1.52 (2H, m), 1.25 (2H, m) 0.83 (3H, t). LCMS (Luna 2,): rt=7.43 minutes, 614 (M−H)$^-$. HPLC MS8 5.47 min.

Example 125

N-{6-Butyl-5-[4-(morpholine-4-sulfonyl)-phenylsulfanyl]-pyridin-2-yl}-2-chloro-4-trifluoromethyl-benzenesulfonamide (125)

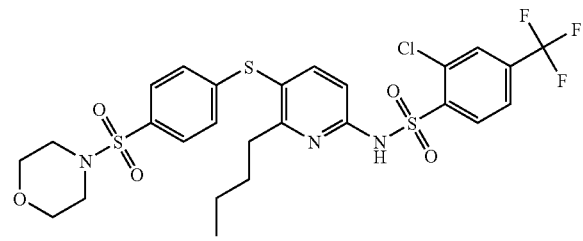

N-{6-Butyl-5-[4-(morpholine-4-sulfonyl)-phenylsulfanyl]-pyridin-2-yl}-2-chloro-4-trifluoromethyl-benzenesulfonamide was prepared from 6-amino-3-iodo-2-methylpyridine and 4-(morpholine-4-sulfonyl)benzenethiol using General Method 11 step 1 and 2-chloro-4-trifluoromethylbenzenesufonyl chloride using General Method 11 step 2. $^1$HNMR CDCl$_3$ 8.30 (1H, d), 7.69 (1H, s), 7.58 (4H, m), 7.09 (2H, d), 6.79 (1H, d), 3.67 (4H, m)2.88 (4H, m), 2.80 (2H, t), 1.50 (2H, m), 1.24 (2H, m) 0.81 (3H, t). LCMS (Luna 2, ): rt=7.34 minutes, 648 (M−H)$^-$. HPLC MS8 5.42 min.

Example 126

Method 12

2-(2,4-Dichloro-benzenesulfonylamino)-5-[4-(piperidine-1-sulfonyl)-phenylsulfanyl]-isonicotinic acid pentyl ester (126)

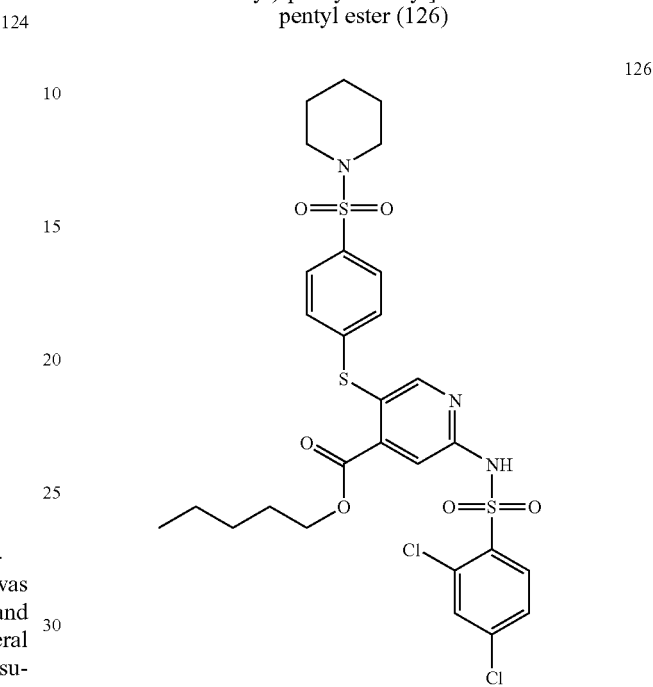

Step 1: 2-(2,4-Dichloro-benzenesulfonylamino)-5-iodo-isonicotinic acid pentyl ester

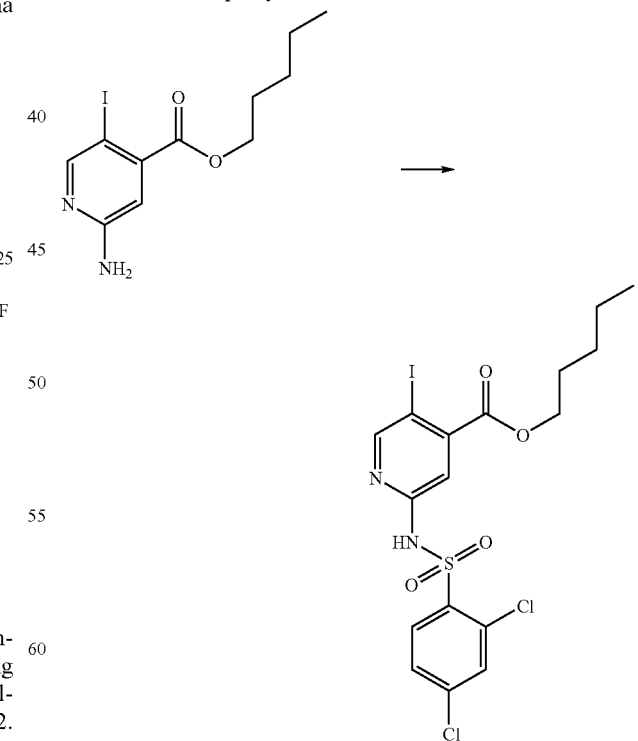

A solution of 2-amino-5-iodo-isonicotinic acid pentyl ester (1.51 g, 4.52 mmol) and sulfonyl chloride (1.17 g, 4.75 mmol) in pyridine (0.548 ml, 6.78 mmol) and dichloromethane (10 ml) was stirred overnight under nitrogen. The reaction was diluted with ethyl acetate (100 ml) and washed with NaHCO₃ solution (50 ml) and brine (50 ml), dried (MgSO₄) and concentrated under reduced pressure. The sulfonamide was purified by flash column chromatography using ethyl acetate 1/4 hexane as eluent to afford 2-(2,4-dichloro-benzenesulfonylamino)-5-iodo-isonicotinic acid pentyl ester as a yellow solid (502 mg, 20 %). $^1$H NMR (CDCl₃): 10.89 (1H, br s, NH); 8.77 (1H, s, Ar); 8.08 (1H, d, Ar); 7.52 (1H, s, py); 7.43 (1H, s, py); 7.32 (1H, d, Ar); 4.28 (2H, t, OCH₂); 1.75 (2H, m, OCH₂CH₂); 1.37 (4H, m, OCH₂CH₂C$\underline{H}_2$C$\underline{H}_2$CH₃); 0.91 (3H, t, CH₂C$\underline{H}_3$).

Step 2: 2-(2,4-Dichloro-benzenesulfonylamino)-5-[4-(piperidine-1-sulfonyl)-phenylsulfanyl]-isonicotinic acid pentyl ester

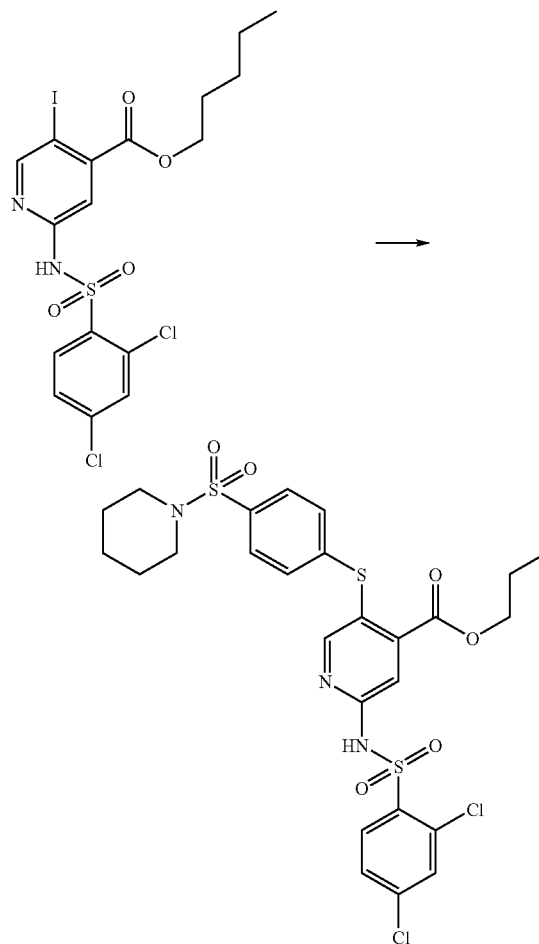

A solution of (oxydi-2,1-phenylene)bis-(diphenylphosphine) (DPEphos) (43 mg, 0.08 mmol) and tris(dibenzylideneacetone)dipalladium(0) (18 mg, 0.02 mmol) in N-methylpyrrolidinone (10 ml) was stirred at room temperature for 5 minutes under nitrogen. 4-(Piperidine-1-sulfonyl)-benzenethiol (121 mg, 0.4 mmol), 2-(2,4-dichloro-benzenesulfonylamino)-5-iodo-isonicotinic acid pentyl ester (218 mg, 0.4 mmol) and potassium t-butoxide (90 mg, 0.8 mmol) were added and the reaction stirred overnight at 100° C. The solvent was removed under reduced pressure and the residue taken up in chloroform. The chloroform solution was washed with brine (25 ml), dried (MgSO₄) and concentrated under reduced pressure. The residue was purified by flash column chromatography using ethyl acetate 2/3 hexane as eluent to afford 2-(2,4-dichloro-benzenesulfonylamino)-5-[4-(piperidine-1-sulfonyl)-phenylsulfanyl]-isonicotinic acid pentyl ester as a yellow foam (15 mg, 6%). $^1$H NMR (CDCl₃): 10.82 (1H, s, NH); 8.17 (1H, s, Ar); 8.09 (1H, d, Ar); 7.61 (2 H, m, Ar); 7.57 (1H, s, Ar); 7.38 (4H, m, py and Ar); 4.22 (2H, t, OCH₂); 2.90 (4H, m, 2×CH₂N pip); 1.66 (2H, m, OCH₂C$\underline{H}_2$); 1.54 (4H, m, 2×CH₂ pip); 1.33 (4H, m OCH₂CH₂C$\underline{H}_2$C$\underline{H}_2$CH₃); 1.19 (2H, m, CH₂ pip); 0.88 (3H, t, CH₂C$\underline{H}_3$). HPLC (Luna 2, Gradient 5): rt=7.82 minutes. LCMS rt=8.34 minutes, 673 (M+H)⁺.

Example 127

Alternative Method 13: N-{4-Butyryl-5-[4-(piperidine-1-sulfonyl)-phenylsulfanyl]-pyridin-2-yl}-2,4-dichloro-benzenesulfonamide (127)

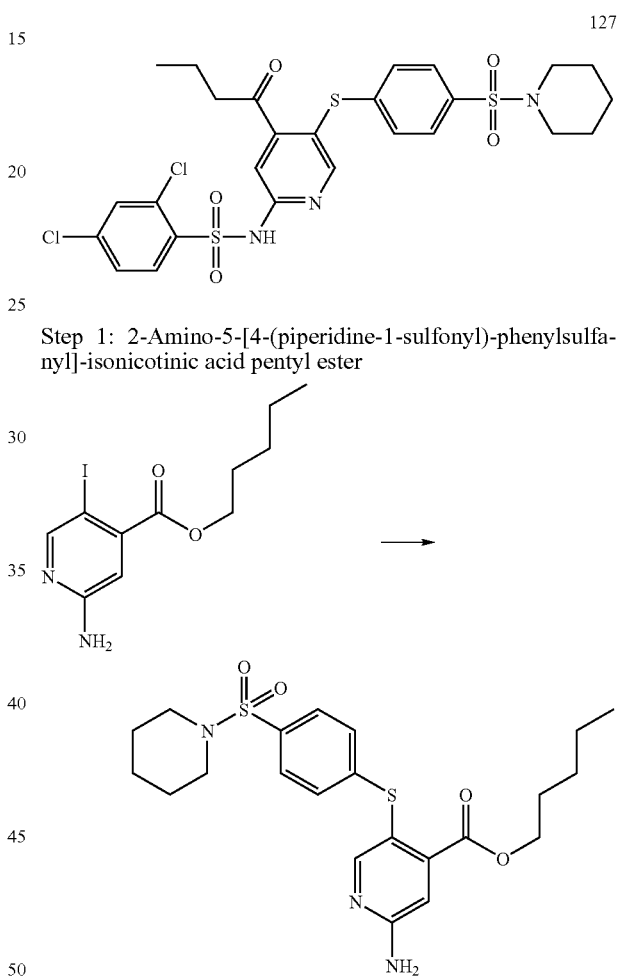

Step 1: 2-Amino-5-[4-(piperidine-1-sulfonyl)-phenylsulfanyl]-isonicotinic acid pentyl ester Copper iodide (26 mg, 0.14 mmol) and neocuproine (29 mg, 0.14 mmol) were added to a stirred mixture of 2-amino-5-iodo-isonicotinic acid pentyl ester (450 mg, 1.35 mmol), 4-(piperidine-1-sulfonyl)-benzenethiol (449 mg, 1.49 mmol) and sodium t-butoxide (195 mg, 2.025 mmol) in toluene (10 ml) and the reaction was heated to reflux overnight. The reaction was cooled to room temperature, solids filtered off through celite and the filtrate concentrated under reduced pressure onto silica. The residue was purified by flash column chromatography using ethyl acetate 2/3 hexane as eluent to afford 2-amino-5-[4-(piperidine-1-sulfonyl)-phenylsulfanyl]-isonicotinic acid pentyl ester as an orange solid (348 mg, 56%). $^1$H NMR (CDCl₃): (1H, s, py); 7.51 (2H, d, Ar); 7.10 (2H, d, Ar); 6.80 (1H, s, py); 4.92 (2H, br s, NH₂); 4.14 (2H, t, OCH₂); 2.90 (4H, m, 2×CH₂N pip); 1.53 (6H, m, OCH₂C$\underline{H}_2$, 2×CH₂ pip); 1.46 (2H, m, CH₂ pip); 1.24 (4H, m, OCH₂CH₂C$\underline{H}_2$C$\underline{H}_2$CH₃); 0.80 (3H, t, CH₂C$\underline{H}_3$).

Step 2: 2-(2, 4-Dichloro-benzenesulfonylamino)-5-[4-(piperidine-1-sulfonyl)-phenylsulfanyl]-isonicotinic acid pentyl ester

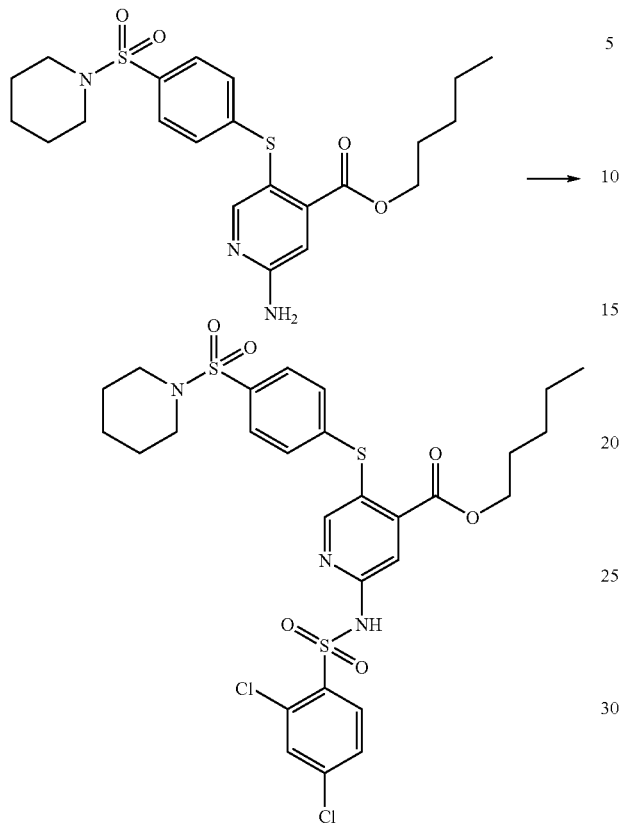

A solution of the 2-amino-5-[4-(piperidine-1-sulfonyl)-phenylsulfanyl]-isonicotinic acid pentyl ester (500 mg, 1.1 mmol), 2,4-dichlorobenzenesulfonylchloride (327 mg, 1.33 mmol) and 4-dimethylaminopyridine (134 mg, 1.1 mmol) in pyridine (10 ml) was stirred at 40° C. overnight. The pyridine was removed under reduced pressure and the residue purified by flash column chromatography using ethyl acetate 1/2 hexane as eluent to afford 2-(2,4-dichloro-benzenesulfonylamino)-5-[4-(piperidine-1-sulfonyl)-phenylsulfanyl]-isonicotinic acid pentyl ester as a yellow foam (217 mg, 29%).

Step 3: 2-(2,4-Dichloro-benzenesulfonylamino)-5-[4-(piperidine-1-sulfonyl)-phenylsulfanyl]-isonicotinic acid

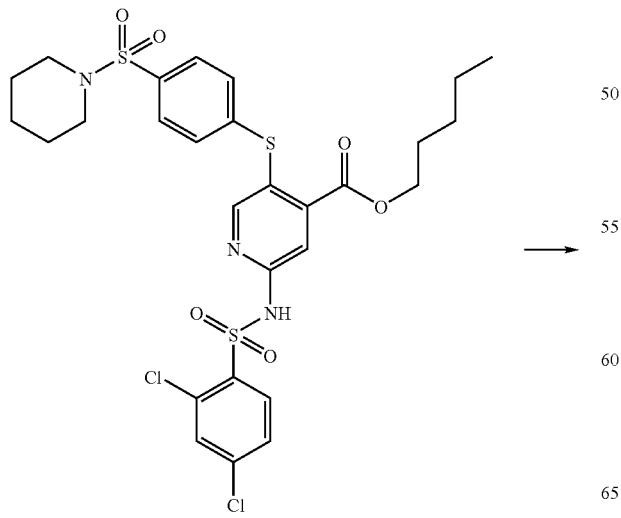

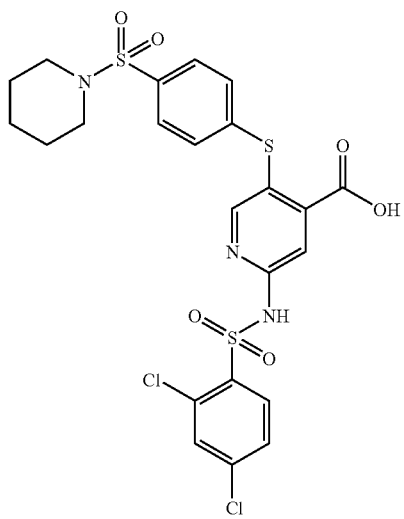

A solution of 2-(2,4-dichloro-benzenesulfonylamino)-5-[4-(piperidine-1-sulfonyl) -phenylsulfanyl]-isonicotinic acid pentyl ester (217 mg, 0.32 mmol) and lithium hydroxide monohydrate (54 mg, 1.3 mmol) in THF (15 ml) and water (15 ml) was stirred at 30° C. overnight. The reaction was diluted with water (25 ml), acidified to pH 1 with 1N HCl and extracted with ethyl acetate (2×30 ml). The combined extracts were dried (MgSO$_4$) and concentrated under reduced pressure to give 2-(2,4-dichloro-benzenesulfonylamino)-5-[4-(piperidine-1-sulfonyl)-phenylsulfanyl]-isonicotinic acid as a yellow solid (173 mg, 90%). $^1$H NMR (CDCl$_3$): 8.06 (1H, d, Ar); 7.96 (1H, s, Ar); 7.82 (1H, s, py); 7.67 (3H, m, py and Ar); 7.39 (3H, m, Ar); 2.94 (4H, m, 2×CH$_2$N pip); 1.56 (4H, m, 2×CH$_2$ pip); 1.39 (2H, m, CH$_2$ pip).

Step 4: 2-(2,4-Dichloro-benzenesulfonylamino)-N-methoxy-N-methyl-5-[4-piperidine-1-sulfonyl)-phenylsulfanyl]-isonicotinamide

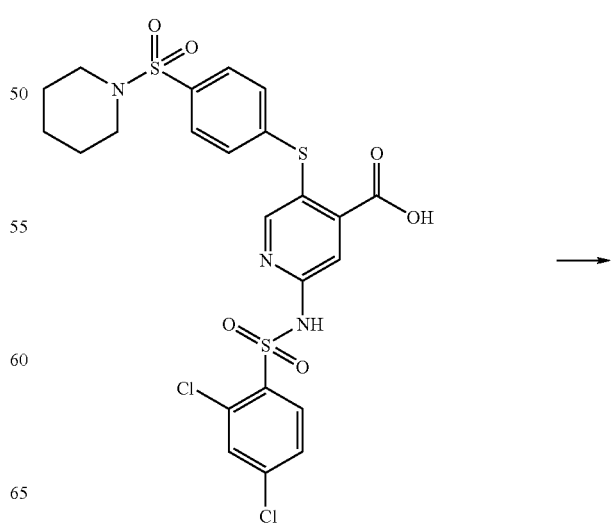

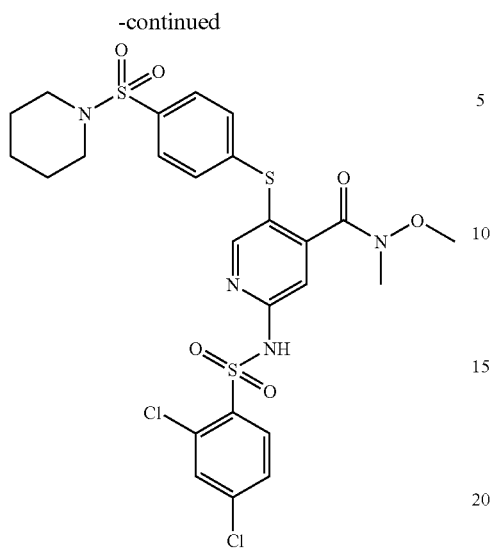

A solution of 2-(2,4-dichloro-benzenesulfonylamino)-5-[4-(piperidine-1-sulfonyl)-phenylsulfanyl]-isonicotinic acid (173 mg, 0.29 mmol), N,O-dimethylhydroxylamine hydrochloride (84 mg, 0.86 mmol), TBTU (276 mg, 0.86 mmol) and DIPEA (0.18 ml, 1 mmol) in DMF (10 ml) was stirred at room temperature overnight under nitrogen. The reaction was diluted with ethyl acetate (25 ml), washed with brine (3×25 ml), dried (MgSO4) and concentrated under reduced pressure. The residue was purified by flash column chromatography using methanol 1/9 chloroform as eluent to afford 2-(2,4-dichloro-benzenesulfonylamino)-N-methoxy-N-methyl-5-[4-(piperidine-1-sulfonyl)-phenylsulfanyl]-isonicotinamide as a yellow oil (153 mg, 82%). $^1$H NMR (CDCl$_3$): 8.40 (1H, s, Ar); 8.07 (1H, d, Ar); 7.53 (2H, d, Ar); 7.46 (1H, s, py); 7.34 (1H, d, Ar); 7.22 (3H, m, py and Ar); 3.34 (3H, s, CH$_3$O); 3.24 (3H, s, CH$_3$N); 2.88 (4H, m, 2×CH$_2$N pip); 1.55 (4H, m, 2×CH$_2$ pip); 1.33 (2H, m, CH$_2$ pip).

Step 5: N-{4-Butyryl-5-[4-(piperidine-1-sulfonyl)-phenylsulfanyl]-pyridin-2-yl}-2,4-dichloro-benzenesulfonamide

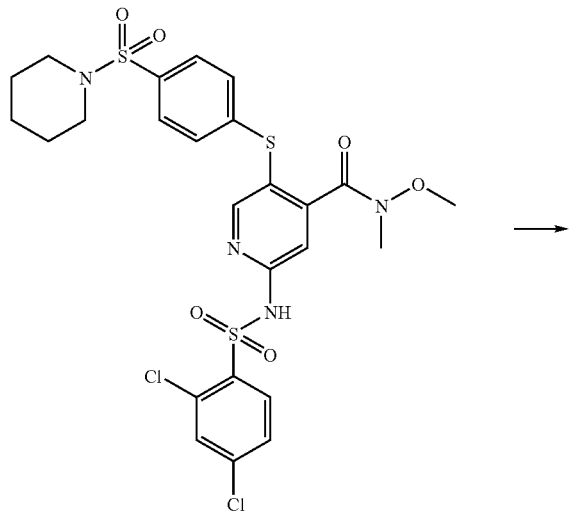

2-(2,4-Dichloro-benzenesulfonylamino)-N-methoxy-N-methyl-5-[4-(piperidine-1-sulfonyl)-phenylsulfanyl]-isonicotinamide (150 mg, 0.233 mmol) was stirred in THF (30 ml) under nitrogen at room temperature. 2M Propylmagnesium chloride (1.2 ml, 2.33 mmol) was added and the reaction stirred overnight. The reaction was quenched using 1N HCl solution partitioned between a mixture of NaHCO$_3$ solution (30 ml) and ethyl acetate (30 ml). The organic layer was dried (MgSO$_4$) and concentrated under reduced pressure. The residue was purified by flash column chromatography using ethyl acetate 2/3 hexane as eluent to give N-{4-butyryl-5-[4-(piperidine-1-sulfonyl)-phenylsulfanyl]-pyridin-2-yl}-2,4-dichloro-benzenesulfonamide as an off-white solid (10 mg, 6%). $^1$H NMR (CDCl$_3$): 8.21 (1H, s, Ar); 8.06 (1H, d, Ar); 7.60 (2H, d, Ar); 7.47 (1H, s, Ar); 7.38 (1H, d, Ar); 7.26 (3H, m, py and Ar); 2.89 (4H, m, 2×CH$_2$N pip); 2.70 (2H, t, COCH$_2$); 1.56 (6H, m, 2×CH$_2$ pip, COCH$_2$CH$_2$); 1.47 (2H, m, CH$_2$ pip); 0.90 (3H, t, COCH$_2$CH$_2$CH$_3$). HPLC (Luna 2, Gradient 1): rt=6.92 minutes. LCMS: rt=7.61 minutes, 629 (M+H)$^+$.

Example 128

Alternative Method 14:

2,4-dichloro-N-{4-cyclopropanecarbonyl-5-[4-(piperidine-1-sulfonyl)-phenylsulfanyl]-pyridin-2-yl}-benzenesulfonamide (128)

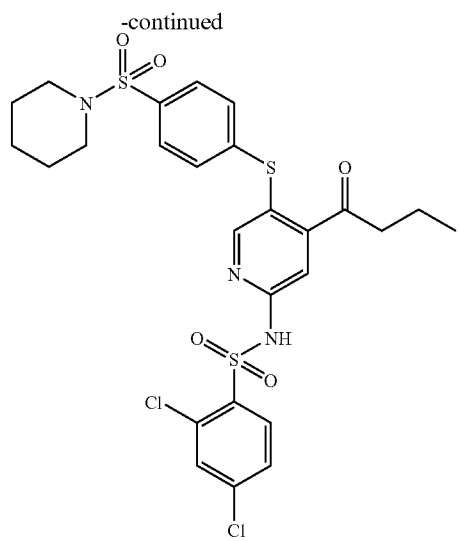

→

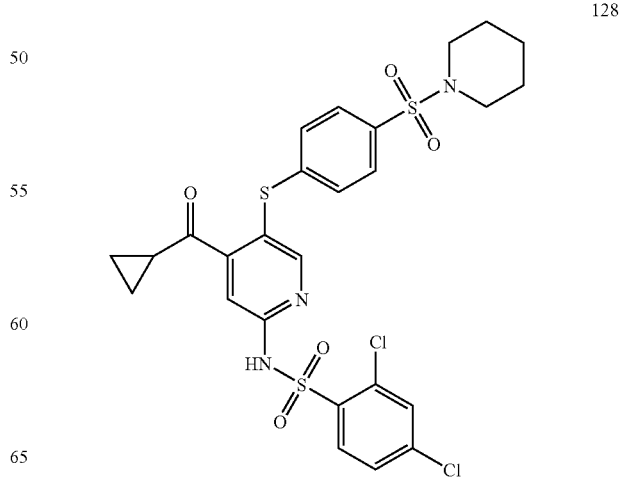

128

127

Step 1: 2,4-Dichloro-N-{4-formyl-5-[4-(piperidine-1-sulfonyl)-phenylsulfanyl]-pyridin-2-yl}-benzenesulfonamide

128

Step 2: 2,4-Dichloro-N-{4-(cyclopropyl-hydroxy-methyl)-5-[4-(piperidine-1-sulfonyl)-phenylsulfanyl]-pyridin-2-yl}-benzenesulfonamide

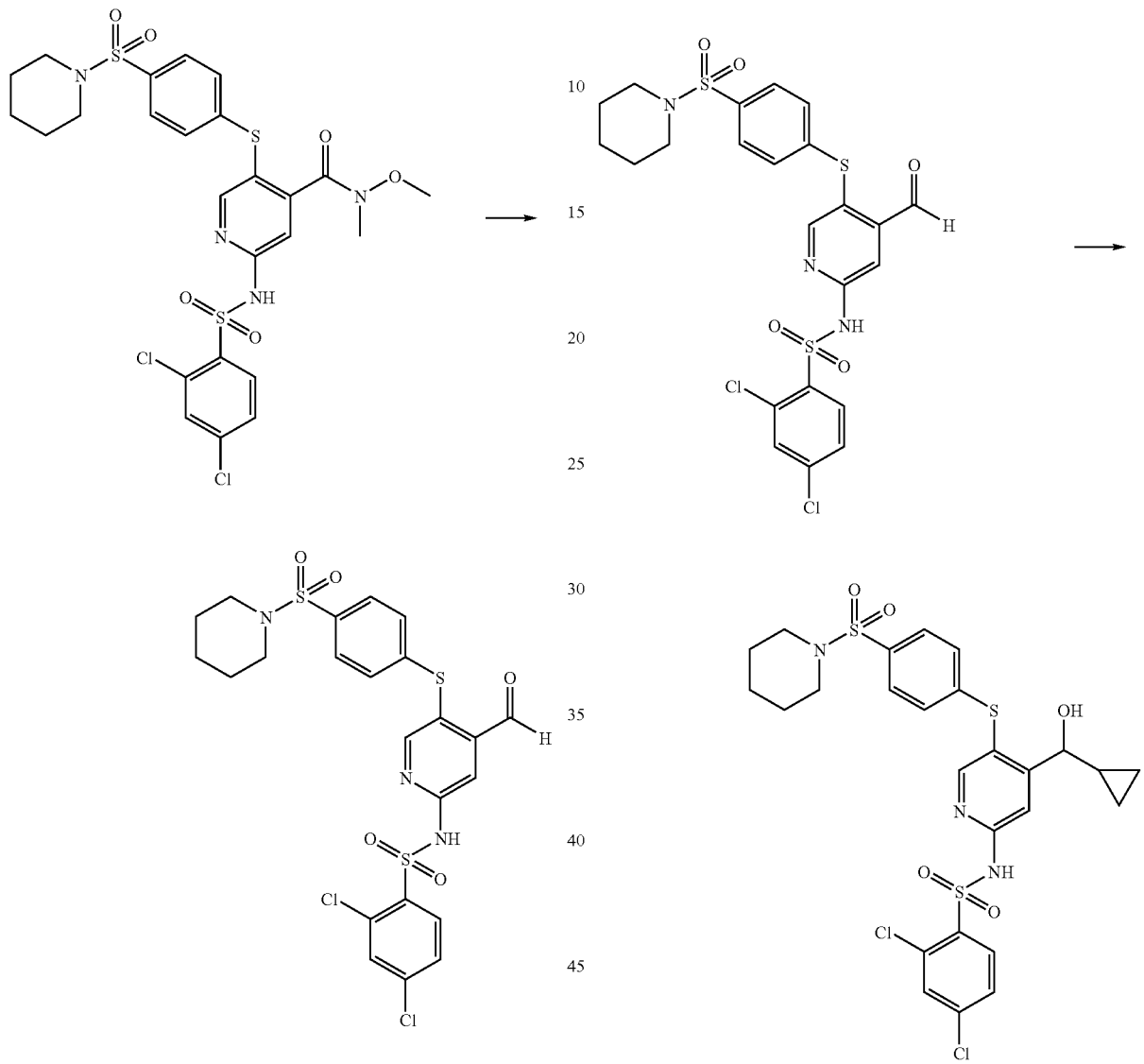

Lithium aluminium hydride (216 mg, 5.7 mmol) was added to a stirred solution of 2-(2,4-dichloro-benzenesulfonylamino)-N-methoxy-N-methyl-5-[4-(piperidine-1-sulfonyl)-phenylsulfanyl]-isonicotinamide (368 mg, 0.57 mmol) in THF (30 ml) and the reaction stirred for 90 minutes at room temperature. IN HCl solution (10 ml) was added cautiously and following 10 minutes of stirring NaHCO$_3$ solution (40 ml) was added. The aqueous solution was extracted with ethyl acetate (2×40 ml), the combined extracts dried (MgSO$_4$) and concentrated under reduced pressure. The residue was purified by flash column chromatography using ethyl acetate 2/3 hexane as eluent to afford 2,4-dichloro-N-{4-formyl-5-[4-(piperidine-1-sulfonyl)-phenylsulfanyl]-pyridin-2-yl}-benzenesulfonamide as a yellow oil (130 mg, 39%). $^1$H NMR (CDCl$_3$): 10.25 (1H, s, COH); 8.53 (1H, s, py); 8.17 (1H, d, Ar); 7.57 (2H, d, Ar); 7.51 (1H, s, Ar); 7.42 (2H, m, py and Ar); 7.21 (2H, d, Ar); 2.89 (4H, m, 2×CH$_2$N pip); 1.55 (4H, m, 2×CH$_2$ pip); 1.34 (2H, m, CH$_2$ pip).

A solution of cyclopropylmagnesium bromide (0.5 M, 1.55 ml, 0.78 mmol) was added to a stirred solution of 2,4-dichloro-N-{4-formyl-5-[4-(piperidine-1-sulfonyl)-phenylsulfanyl]-pyridin-2-yl}-benzenesulfonamide (130 mg, 0.22 mmol) in THF (15 ml) and the mixture stirred for 2 hours. The reaction was concentrated under reduced pressure onto silica and the residue purified by flash column chromatography using ethyl acetate 1/1 hexane as eluent to afford 2,4-dichloro-N-{4-(cyclopropyl-hydroxy-methyl)-5-[4-(piperidine-1-sulfonyl)-phenylsulfanyl]-pyridin-2-yl}-benzenesulfonamide as a green foam (74 mg, 54 %). $^1$H NMR (CDCl$_3$): 8.40 (1H, s, py); 8.18 (1H, d, Ar); 7.51 (3H, m, py and Ar); 7.39 (1H, s, py); 7.34 (1H, d, Ar); 7.06 (2H, d, Ar); 4.50 (1H, d, CHOH); 2.89 (4H, m, 2×CH$_2$N pip); 1.54 (4H, m, 2×CH$_2$ pip); 1.34 (2H, m, CH$_2$ pip); 0.97 (1H, m, CH cprop); 0.39 (4H, m, 2×CH$_2$ cprop).

129

Step 3: 2,4-Dichloro-N-{4-cyclopropanecarbonyl-5-[4-(piperidine-1-sulfonyl)-phenylsulfanyl]-pyridin-2-yl}-benzenesulfonamide

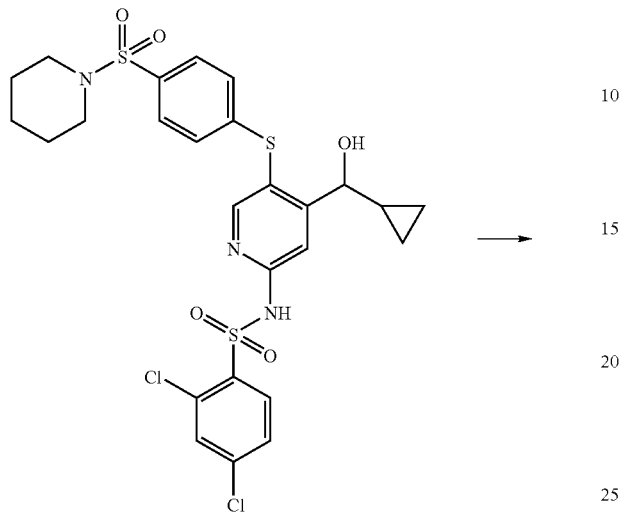

Dess Martin periodinane (60 mg, 0.14 mmol) was added to a stirred solution of 2,4-dichloro-N-{4-(cyclopropyl-hydroxy-methyl)-5-[4-(piperidine-1-sulfonyl)-phenylsulfanyl]-pyridin-2-yl}-benzenesulfonamide (74 mg, 0.12 mmol) in dichloromethane (5 ml) and the mixture stirred at room temperature overnight under nitrogen. The reaction was diluted with ethyl acetate (30 ml), washed with NaHCO$_3$ solution (20 ml), dried (MgSO$_4$) and concentrated under reduced pressure. The residue was purified by flash column chromatography using ethyl acetate 2/3 hexane as eluent to give 2,4-dichloro-N-{4-cyclopropanecarbonyl-5-[4-(piperidine-1-sulfonyl)-phenylsulfanyl]-pyridin-2-yl}-benzenesulfonamide as a yellow solid (38 mg, 51%). $^1$H NMR (CDCl$_3$): 8.32 (1H, s, py); 8.08 (1H, d, Ar); 7.57 (2H, d, Ar); 7.46 (1H, s, py); 7.36 (1H, d, Ar); 7.27 (2H, d, Ar); 2.89 (4H, m, 2×CH$_2$ pip); 2.17 (1H, m, COCH); 1.54 (4H, m, 2×CH$_2$ pip); 1.33 (2H, m, CH$_2$ pip); 0.82 (4H, m, 2×CH$_2$ cprop). HPLC (Luna 2, Gradient 5): rt=6.47 minutes. LCMS rt=7.24 minutes, 627 (M+H)$^+$. By a similar method using the appropriate starting materials the following can be prepared:

Example 129

2-Chloro-N-{4-cyclopropanecarbonyl-5-[4-(morpholine-4-sulfonyl)-phenylsulfanyl]-pyridin-2-yl}-4-trifluoromethyl-benzenesulfonamide (129)

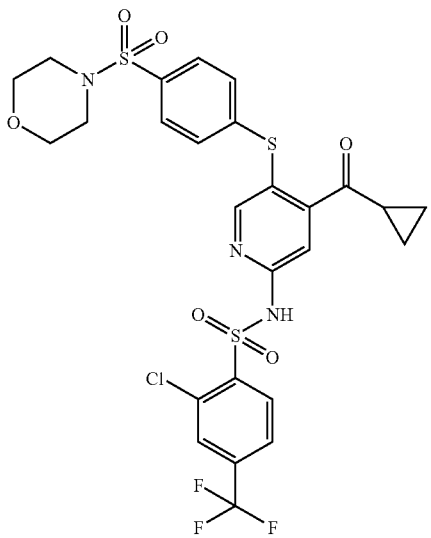

HPLC (Luna 2, Gradient 5): rt=6.00 minutes. LCMS: rt=6.72 minutes, 663 (M+H)$^+$

Example 130

Method 15

Preparation of 3-(2'-chloro-4'-trifluoromethyl)phenylsulfonylamino-5-n-butyl-6-(4''-N-morpholinesulfonyl)phenylthiopyridazine (130)

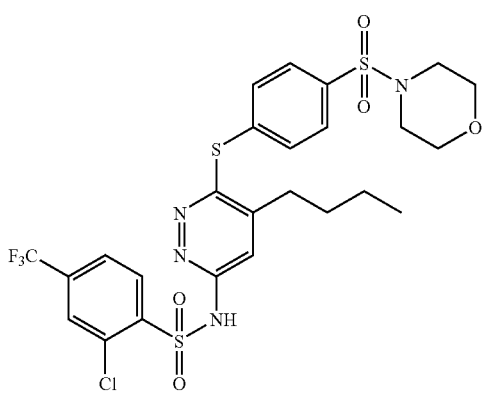

Step 1: 3,6-dichloro-4-n-butylpyridazine

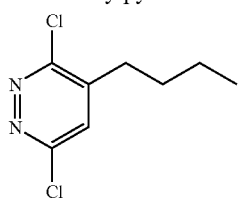

To a stirred suspension of 3,6-dichloropyridazine (22.5g, 0.151 mol), silver nitrate (12.7 g, 0.074 mol) and valeric acid (20.0 g, 0.195 mol) in water (250 ml) was added a solution of sulfuric acid (49.3 g, 0.50 mol) in water (250 ml) at 50 deg. A solution of ammonium persulfate (93 g, 0.40 mol) in water (200 ml) was then added over 30 minutes at 60 deg. The resulting mixture was then stirred at 80 deg for 40 minutes and then cooled to room temperature. The mixture was adjusted to pH8 with 25% aqueous ammonium hydroxide and extracted with diethyl ether (3×250 ml). The combined ether extracts were washed with water (200 ml), dried over magnesium sulfate and concentrated under reduced pressure. The residue was purified by flash column chromatography (5% ethyl acetate/hexane) to give 3,6-dichloro-4-n-butylpyridazine as a pale yellow oil (14.4 g, 47%). $^1$H-NMR (CDCl$_3$) 7.30 (1H, s, 5-H), 2.65 (2H, t, Bu), 1.58 (2H, m, Bu), 1.37 (2H, m, Bu), 0.91 (3H, t, Bu).

Step 2: 3-amino-5-n-butyl-6-chloropyridazine

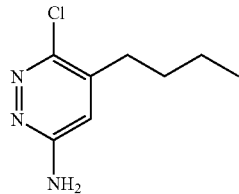

A mixture of 3,6-dichloro-4-n-butylpyridazine (7.1 g, 34 mmol), ethanol (70 ml) and 25% aqueous ammonium hydroxide (70 ml) was heated to 135 deg in a sealed pressure resistant reaction vessel (Parr: achieving a pressure of 90 psi) for 24 hours. After this time the mixture was cooled and concentrated under reduced pressure. The residue was partitioned between dichloromethane (250 ml) and water (250 ml) and the aqueous layer re-extracted with dichloromethane (200 ml). The combined organic extracts were dried over magnesium sulfate and concentrated under reduced pressure to give the crude product as a mixture of isomers. Purification by flash chromotography (10-100% ethyl acetate/hexane) gave 3-amino-5-n-butyl-6-chloropyridazine as a white solid (2.3 g, 36%). $^1$H-NMR (CDCl$_3$) 6.55 (1H, s, 4-H), 4.98 (2H, bs, NH$_2$), 2.57 (2H, t, Bu), 1.58 (2H, m, Bu), 1.37 (2H, m, Bu), 0.91 (3H, t, Bu)

Step 3: 3-Amino-5-n-butyl-6-(4'-morpholinesulfonyl)phenylthiopyridazine

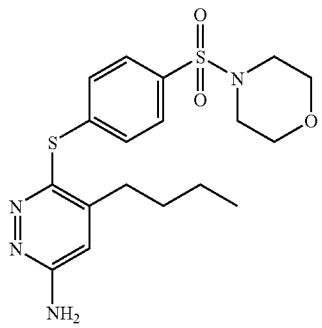

A mixture of 3-amino-5-n-butyl-6-chloropyridazine (0.5 g, 2.6 mmol), 4-N -morpholinesulfonylthiophenol (0.7 g, 2.7 mmol) and potassium t-butoxide (0.3 g, 2.6 mmol) in N-methylpyrollidinone (10 ml) was heated to 150 deg under nitrogen for 4 hours. After this time the mixture was cooled and partitioned between water (50 ml) and ethyl acetate (50 ml). The organic layer was washed with water (2×50 ml) and brine (50 ml), dried over magnesium sulfate and concentrated under reduced pressure. The residue was purified by flash column chromatography (1% methanol/dichloromethane) to give 3-amino-5-n-butyl-6-(4'-morpholinesulfonyl)phenylthiopyridazine as an oily solid (0.45 g, 42%). $^1$H-NMR (CDCl$_3$) 7.48 (2H, d, 6-Ph), 7.28 (2H, d, 6-Ph), 6.48 (1H, s, 4-H), 4.71 (2H, s, NH2), 3.60 (4H, t, morpholine), 2.85 (4H, t, morpholine), 2.50 (2H, t, Bu), 1.45 (2H, m, Bu), 1.23 (2H, m, Bu), 0.82 (3H, t, Bu).

Step 4: 3-(2'-Chloro-4'-trifluoromethyl)phenylsulfonylamino-5-n-butyl-6-(4"-morpholinesulfonyl)phenylthiopyridazine A mixture of 3-amino-5-n-butyl-6-(4'-morpholinosulfonyl)phenylthiopyridazine (0.2 g, 0.48 mmol) and 2-chloro-4-trifluoromethylbenzenesulfonyl chloride (0.15 g, 0.53 mmol) in pyridine (2 ml) was stirred overnight at room temperature. After this time the mixture was partitioned between ethyl acetate (50 ml) and 1N aqueous hydrochloric acid (50 ml). The organic layer was washed with 1N aqueous hydrochloric acid (50 ml), water (50 ml), brine (50 ml), dried over magnesium sulfate and concentrated under reduced pressure. The residue was purified by flash column chromatography (30% ethyl acetate/hexane) to give 3-(2'-chloro-4'-trifluoromethyl) phenylsulfonylamino-5-n-butyl-6-(4"-morpholinesulfonyl) phenylthiopyridazine (57 mg, 18%). $^1$H-NMR (CDCl$_3$) 12.41 (1H, bs, NHSO$_2$), 8.25 (1H, d, 3-Ph), 7.72 (2H, d, 6-Ph), 7.60 (4H, m, 3-Ph, 6-Ph), 6.91 (1H, s, 4-H), 3.71 (4H, t, morpholine), 3.07 (4H, t, morpholine), 2.58 (2H, t, Bu), 1.65 (2H, m, Bu), 1.42 (2H, m, Bu), 0.91 (3H, t, Bu). Hplc (Luna 2, Gradient 5): rt=6.51 minutes. LC/MS rt=7.36 minutes, 652 (MH$^+$).

Example 131

3-(2',4'-dichloro)phenylsulfonylamino-5-n-butyl-6-(4"-N- morpholinesulfonyl)phenylthiopyridazine (131)

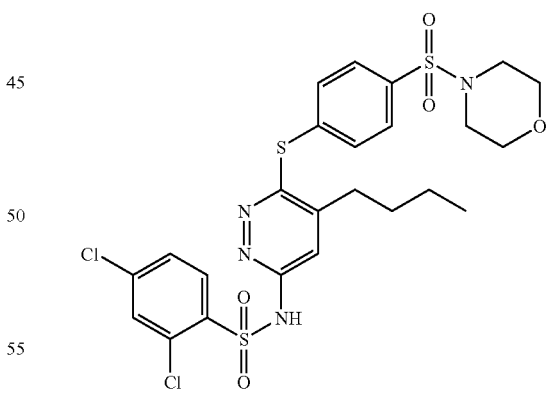

Using the methods described above and 3-amino-5-n-butyl-6-(4'- morpholinesulfonyl)phenylthiopyridazine and 2,4-dichlorobenzenesulfonyl chloride the above compound was prepared. $^1$H-NMR (CDCl$_3$) 8.09 (1H, d, 3-Ph), 7.75 (2H, d, 6-Ph), 7.54 (1H, d, 3-Ph), 7.30 (1H, dd, 3-Ph), 3.71 (4H, t, morpholine), 3.04 (4H, t, morpholine), 2.58 (2H, t, Bu), 1.60 (2H, m, Bu), 1.41 (2H, m, Bu), 0.92 (3H, t, Bu). Hplc (Luna 2, Gradient 5): rt=6.36 minutes. LC/MS rt -7.17 minutes, 619 (MH$^+$).

Example 132

3-(2',4'-dichloro)phenylsulfonylamino-5-n-butyl-6-(4"-N-piperidinesulfonyl)phenylthiopyridazine (132)

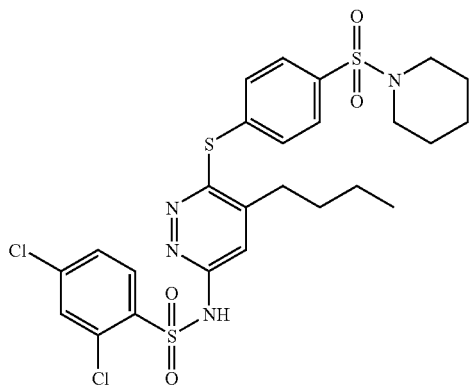

Using the methods described above with the appropriate starting materials the above compound was prepared. $^1$H-NMR (CDCl$_3$) 12.35 (1H, bs, NHSO$_2$), 8.05 (1H, d, 3-Ph), 7.75 (2H, d, 6-Ph), 7.60 (2H, d, 6-Ph), 7.41 (1H, d, 3-Ph), 7.30 (1H, dd, 3-Ph), 6.88 (1H, s, 4-H) 3.00 (4H, m, piperidine), 2.58 (2H, t, Bu), 1.67 (6H, m, piperidine, Bu), 1.50-1.10 (8H, m, piperidine, Bu), 0.92 (3H, t, Bu). Hplc (Luna 2, Gradient 5): rt=6.70 minutes. LC/MS rt=7.76 minutes, 617 (MH$^+$).

Example 133

Preparation of 3-(2',4'-dichloro)phenylsulfonylamino-5-n-butyl-6-(4"-cyclopentanesulfonyl)phenylthiopyridazine (133)

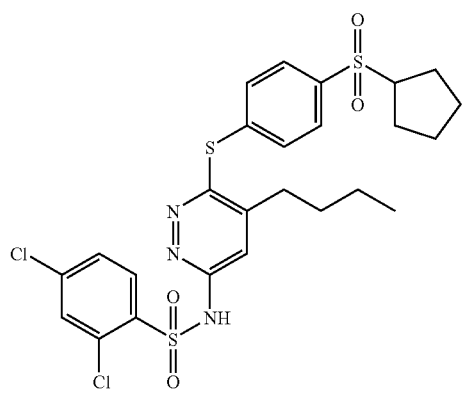

Using the methods described above with the appropriate starting materials the above compound was prepared. $^1$H-NMR (CDCl$_3$) 12.38 (1H, bs, NHSO$_2$), 8.07 (1H, d, 3-Ph), 7.90 (2H, d, 6-Ph), 7.60 (2H, d, 6-Ph), 7.43 (1H, d, 3-Ph), 7.30 (1H, dd, 3-Ph, 6.88 (1H, s, 4-H), 3.48 (1H, m, cyclopentyl), 2.59 (2H, t, Bu), 2.15-1.30 (12H, m, cyclopentyl, Bu), 0.92 (3H, t, Bu). Hplc (Luna 2, Gradient 5): rt=6.67 minutes. LC/MS rt=7.47 minutes, 602 (MH$^+$).

Example 134

Preparation of 3-(2'-chloro-4'-trifluoromethyl)phenylsulfonylamino-5-n-butyl-6-(4"-cyclopentanesulfonyl)phenylthiopyridazine (134)

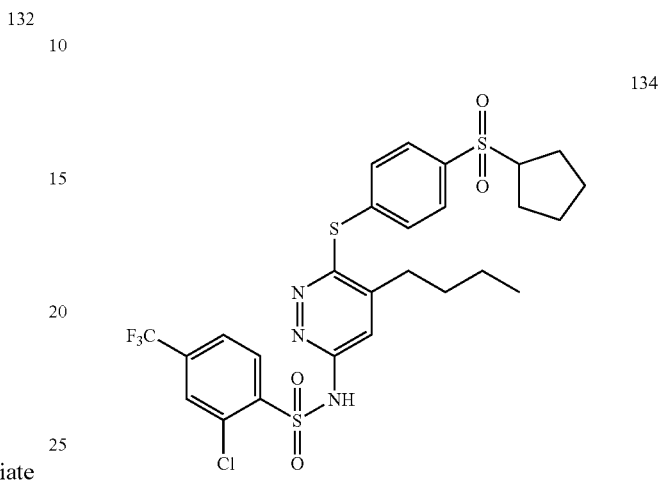

Using the methods described above with the appropriate starting materials the above compound was prepared. $^1$H-NMR (CDCl$_3$) 12.40 (1H, NHSO$_2$), 8.27 (1H, d, 3-Ph), 7.88 (2H, d, 6-Ph), 7.63 (4H, m, 3-Ph, 6-Ph), 6.91 (1H, s, 4-H), 3.48 (1H, m, cyclopentyl), 2.60 (2H, t, Bu), 2.15-1.10 (12H, m, cyclopentyl, Bu), 0.92 (3H, t, Bu). Hplc (Luna 2, Gradient 5): rt=6.80 minutes. LC/MS rt=7.69 minutes, 636 (MH$^+$).

Example 135

Preparation of 3-(2'-chloro-4'-trifluoromethyl)phenylsulfonylamino-5-iso-propyl-6-(4"-N-morpholinesulfonyl)phenylthiopyridazine (135)

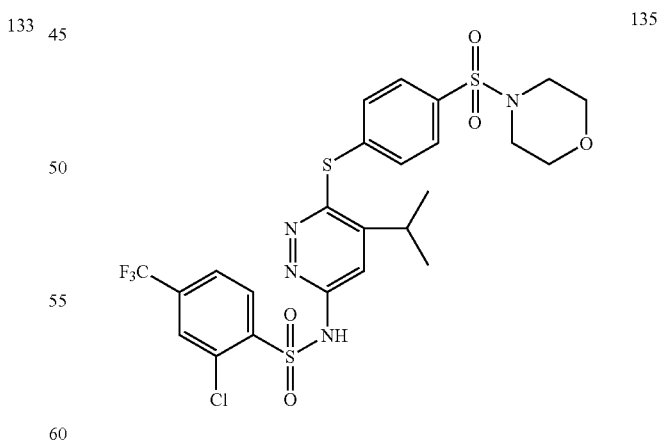

Using the methods described above with the appropriate starting materials the above compound was prepared. $^1$H-NMR (CDCl$_3$) 8.15 (1H, d, 3-Ph), 7.65 (2H, d, 6-Ph), 7.50 (4H, m, 3-Ph, 6-Ph), 6.82 (1H, s, 4-H), 3.67 (4H, t, morpholine), 2.92 (4H, t, morpholine), 2.85 (1H, m, iPr), 1.15 (6H, d, iPr). Hplc (Luna 2, Gradient 5): rt=6.23 minutes. LC/MS rt=6.98 minutes, 638 (MH$^+$).

Example 136

Alternative Method 16

2-Chloro-N-{5-methyl-6-[4-(piperidine-1-sulfonyl)-phenylsulfanyl]-pyridazin-3-yl}-4-trifluoromethyl-benzenesulfonamide (136)

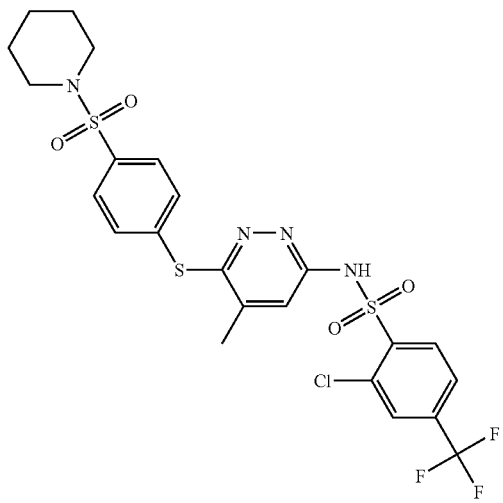

136

Step 1: 6-Chloro-5-methyl-pyridazin-3-ylamine and 6-chloro-4-methyl-pyridazin-3-ylamine

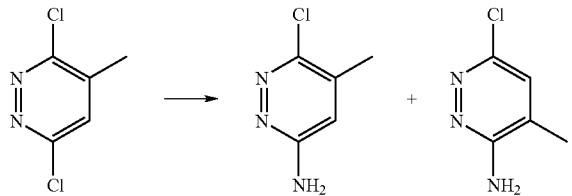

3,6-Dichloro-4-methylpyridazine (10 g) was mixed with ammonium hydroxide (62 mls) and heated at 135° C. in a sealed vessel at 12 Bar for 20 hours. The mixture was allowed to cool and all volatiles removed in vacuo. The crude material was pre-absorbed onto silica using methanol and purified by flash chromatography using methanol 0-5% in dichloromethane. Two fractions were isolated, Fraction 1 3.86g of a 1:0.66 Isomer A to Isomer B and Fraction 2-3.40g of a 1:2.5 mixture Isomer A to Isomer B. Fraction 1 $^1$H NMR (CDCl$_3$) 7.0 (1H, s) 6.6 (0.66H, s) 4.9 (broad) 2.25 (3H, s) 2.15 (~2H, s). Fraction 2 $^1$H NMR (CDCl$_3$) 7.0 (1H, s) 6.6 (2.5H, s) 4.7(broad) 2.25 (8H, s) 2.1(3H, s)

Step 2: 2-Chloro-N-5-methyl-6-[4-(piperidine-1-sulfonyl)-phenylsulfanyl]-pyridazin-3-yl)-4-trifluoromethyl-benzenesulfonamide

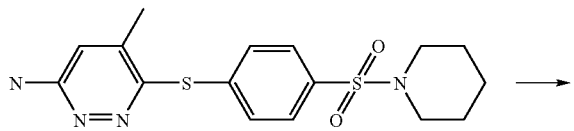

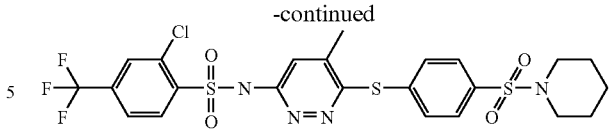

-continued

Step 2a: 4-Methyl-6-[4-(piperidine-1-sulfonyl)-phenylsulfanyl]-pyridazin-3-ylamine and 5-methyl-6-[4-(piperidine-1-sulfonyl)-phenylsulfanyl]-pyridazin-3-ylamine

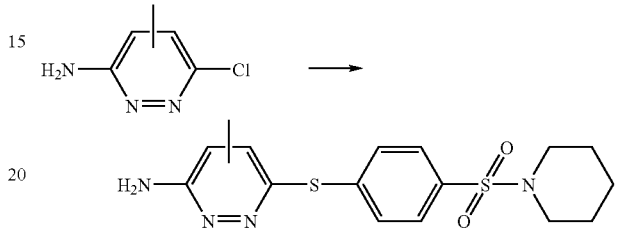

6-Chloro-4/5-methyl-pyridazin-3-ylamine from Fraction 2 above (0.5 g, a mixture of regioisomers 1:2.5), 4-(piperidine-1-sulfonyl)-benzenethiol (2g), potassium carbonate (1.1 g) and dimethylformamide (10 mls) were mixed and heated at 180° C. for 20 hours. All volatiles were removed in vacuo and the residue partitioned between ethylacetate and water. The organic solution was dried over magnesium sulphate and evaporated to dryness in vacuo. Purification by chromatography gave 0.53 g of a mixture still containing starting material. Further purification by Preparative HPLC gave a mixture of isomers 260 mgs as the trifluoroacetic acid (TFA) salt. Reaction of this TFA salt mixture with pyridine and 2-chloro-4-trifluoromethylbenzenesulphonylchloride gave a mixture of isomers of 2,2,2-trifluoro-N-{4/5-methyl-6-[4-(piperidine-1-sulfonyl)-phenylsulfanyl]-pyridazin-3-yl}-acetamides which can be separated by preparative hplc. The free amines were recovered by hydrolysis with aqueous sodium hydroxide to give: 5-Methyl-6-[4-(piperidine-1-sulfonyl)-phenylsulfanyl]-pyridazin-3-ylamine 120 mgs. $^1$H NMR (CDCl$_3$) 7.55 (2H, d) 7.3 (2H, d) 6.6(1H, s) 4.75(2H, broad) 2.9(4H, m) 2.2 (3H, s) 1.55 (4H, m) 1.35 (2H, m) and 4-Methyl-6-[4-(piperidine-1-sulfonyl)-phenylsulfanyl]-pyridazin-3-ylamine 20 mgs $^1$H NMR (CDCl$_3$) 7.60 (2H, d) 7.35 (2H, d) 7.1(1H, s) 5.0 (2H, broad) 2.95 (4H, m) 2.15 (3H, s) 1.60(4H, m) 1.40 (2H, m)

Step 2b: 2-Chloro-N-5-methyl-6-[4-(piperidine-1-sulfonyl)-phenylsulfanyl]-pyridazin-3-yl}-4-trifluoromethyl-benzenesulfonamide

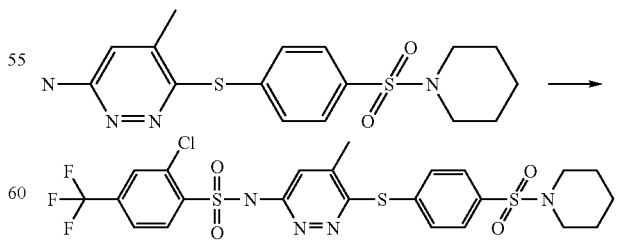

5-Methyl-6-[4-(piperidine-1-sulfonyl)-phenylsulfanyl]-pyridazin-3-ylamine (110 mgs), 2-chloro-4-trifluoromethyl-benzenesulfonyl chloride (160 mgs) and pyridine (1 ml) were heated at 50° C. under nitrogen for 72 hours. All volatiles were removed and the residue purified by Preparative HPLC to give 2-hloro-N-{5-methyl-6-[4-(piperidine-1-sulfonyl)-phenylsulfanyl]-pyridazin-3-yl}-4-trifluoromethyl-benzenesulfonamide 20 mg. $^1$H NMR (CDCl$_3$) 8.25 (1H, d) 7.75 (2H, m) 7.7 (1H, s) 7.6(3H, m) 6.95 (1H, s) 3.0 (4H, m) 2.3 (3H, s) 1.6(4H, m) 1.45 (2H, m). LCMS Polarity/Scan type: Negative Q1 Scan. M.wt.605(-H), 607(-H). Retention time 7.05 minutes. HPLC: -MS8. Retention time 4.99 minutes.

Example 137

2-Chloro-N-{4-methyl-6-[4-(piperidine-1-sulfonyl)-phenylsulfanyl]-pyridazin-3-yl}-4-trifluoromethyl-benzenesulfonamide (137)

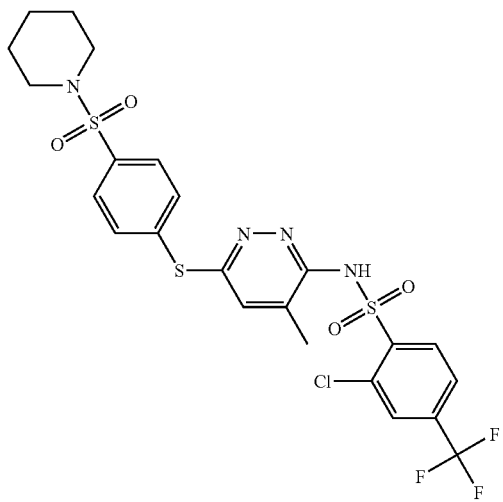

137

Can be prepared from 4-methyl-6-[4-(piperidine-1-sulfonyl)-phenylsulfanyl]-pyridazin-3-ylamine and 2-chloro-4-trifluoromethylbenzenesulfonyl chloride. $^1$H NMR (CDCl$_3$) 8.30 (1H, d) 7.75 (2H, m) 7.70(1H, s) 7.6(3H, m) 7.05(1H, s) 3.0(4H, m)2.1 (3H, s) 1.6(4H, m) 1.40(2H, m) LCMS Polarity/Scan type: Negative Q1 Scan. M.wt. 605(-H), 607(-H). Retention time 7.39 minutes. HPLC MS8 Retention time 5.36 minutes.

Example 138

2,4-Dichloro-5-methyl-N-{5-methyl-6-[4-(piperidine-1-sulfonyl)-phenylsulfanyl]-pyridazin-3-yl}-benzenesulfonamide (138) and 2,4-Dichloro-5-methyl-N-{4-methyl-6-[4-(piperidine-1-sulfonyl)-phenylsulfanyl]-pyridazin-3-yl}-benzenesulfonamide (139)

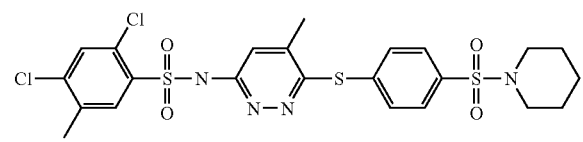

138

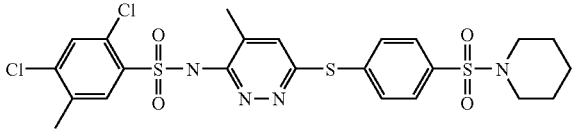

139

To a crude 1:1 mixture of 6-amino-3-chloro-4-methylpyridazine and 6-amino-3-chloro-5-methylpyridazine (100 mg, up to 0.70 mmol) in 1-methyl-2-pyrrolidinone (1 mL) was added 4-(N-piperidinylsulfonyl)thiophenol (258 mg, 1.00 mmol) followed by potassium tert-butoxide (112 mg, 1.00 mmol). The reaction mixture was then microwaved at 120° C. for 5 minutes using powerMAX™, cooled, poured onto ethyl acetate (50 mL), and extracted with water (3×25 mL). The organic portion was then dried over magnesium sulphate and evaporated. Flash chromatography (SiO$_2$, ethyl acetate:cyclohexane 1:1) afforded a mixture of two thiopyridazines. This mixture was dissolved in DCM and pyridine (50 mg, 0.63 mmol) was added, followed by 2,4-dichloro-5-methylphenylsulfonyl chloride. The reaction mixture was stirred overnight at room temperature, evaporated, and purified by flash chromatography (SiO$_2$, ethyl acetate:cyclohexane 1:2) to afford two isomeric pyridazines, 3.5 mg of isomer A, followed by 12 mg of isomer B. Isomer A: $^1$H NMR (CDCl$_3$): 8.00 & 7.39 (2×1H, 2×s, A-ring CH's), 7.71 & 7.56 (2×2H, 2×d, 2×J 10 Hz, Ar CH's of C-ring), 7.03 (1H, s, B-ring CH), 3.01-2.92 (4H, m, CH$_2$NCH$_2$), 2.32 & 2.11 (2×3H, 2×s, 2×CH$_3$) 1.65-1.54 (4H, m, CH$_2$CH$_2$CH$_2$CH$_2$CH$_2$), 1.39-1.28 (2H, m, CH$_2$CH$_2$CH$_2$CH$_2$CH$_2$). Hplc (Luna 2, Gradient 5): rt=6.93 minutes. LC/MS rt=7.70 minutes, 587/589 (MH$^+$). Isomer B: $^1$H NMR (CDCl$_3$): 12.38 (1H, br s, NH), 7.99 & 7.38 (2×1H, 2×s, A-ring CH's), 7.72 & 7.57 (2×2H, 2×d, 2×J 10 Hz, Ar CH's of C-ring), 6.86 (1H, s, B-ring CH), 3.03-2.92 (4H, m, CH$_2$NCH$_2$), 2.32 & 2.24 (2×3H, 2×s, 2×CH$_3$), 1.67-1.55 (4H, m, CH$_2$CH$_2$CH$_2$CH$_2$CH$_2$), 1.45-1.34 (2H, m, CH$_2$CH$_2$CH$_2$CH$_2$CH$_2$). Hplc (Luna 2, Gradient 5): rt=6.52 minutes. LC/MS rt=7.25 minutes, 587/589 (MH$^+$).

Example 140

2,4-Dichloro-5-methyl-N-{6-[4-(piperidine-1-sulfonyl)-phenylsulfanyl]-pyridazin-3-yl}-benzenesulfonamide (140)

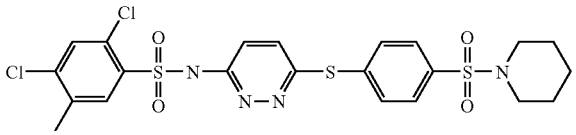

140

To a solution of 3-(2, 4-dichloro-5-methylphenylsulfonylamino)-6-chloropyridazine (by reaction of 3-amino-6-chloropyridazine and 2,4-dichloro-5-methylphenylsulfonyl chloride (100 mg, 0.28 mmol) in 1-methyl-2-pyrrolidinone (1 mL) was added 4-(N-piperidinylsulfonyl)thiophenol (80 mg, 0.31 mmol), potassium tert-butoxide (37 mg, 0.33 mmol), tris(dibenzylideneacetone)dipalladium (0) (25 mg, 27 µmol) and (oxydi-2,1-phenylene)bis-(diphenylphosphine) (30 mg, 56 µmol). The mixture was stirred using a vortex stirrer until homogeneous, sealed under nitrogen, and microwaved at 120° C. for 5 minutes using powerMAX™. The reaction mixture was then added to ethyl acetate (50 mL), extracted with sodium bicarbonate (sat., aq., 3×25 mL), dried over magnesium sulphate, and concentrated under reduced pressure to a dark brown oil. Flash chromatography (SiO$_2$, ethyl acetate:cyclohexane 1:2) afforded a pale yellow solid (32 mg, 20%). $^1$H NMR (CDCl3): 7.98 & 7.39(2×1H, 2×s, A-ring CH's), 7.73 & 7.5 (2×2H, 2×d, 2×J 10 Hz, Ar CH's of C-ring), 7.15.& 7.08 (2×1H, 2×d, 2×J 12 Hz, B-ring CH's), 2.99-2.92 (4H, m, CH$_2$NCH$_2$), 2.32 (3H, s, CH$_3$), 1.65-1.53 (4H, m, CH$_2$CH$_2$CH$_2$CH$_2$CH$_2$), 1.43-1.30 (2H, m, CH$_2$CH$_2$CH$_2$CH$_2$CH$_2$). Hplc (Luna 2, Gradient 5): rt=6.38 minutes. LC/MS rt=7.15 minutes, 573/575 (MH$^+$).

Example 141

Using methods similar to Lehmann, et al., ibid., selected compounds exhibited the following IC$_{50}$ values in a PPARγ ligand binding assay utilizing [$^3$H]-BRL 49653 as the radioligand. IC$_{50}$ values are defined as the concentration of test compounds required to reduce by 50% the specific binding of [$^3$H]-BRL 49653 and are represented by (+)<30 μM; (++)<10 μM; (+++)<1 μM.

TABLE 1

| Compound | PPARγ Binding IC$_{50}$ Filtration |
|---|---|
| 12 | +++ |
| 13 | +++ |
| 14 | +++ |
| 15 | +++ |
| 16 | +++ |
| 17 | ++ |
| 18 | + |
| 19 | +++ |
| 20 | +++ |
| 21 | ++ |
| 22 | +++ |
| 23 | ++ |
| 24 | ++ |
| 25 | + |
| 26 | + |
| 27 | ++ |
| 28 | +++ |
| 29 | ++ |
| 30 | ++ |
| 31 | ++ |
| 32 | +++ |
| 43 | +++ |
| 44 | +++ |
| 45 | +++ |
| 46 | +++ |
| 47 | +++ |
| 48 | +++ |
| 49 | ++ |
| 50 | ++ |
| 51 | ++ |
| 52 | ++ |
| 53 | ++ |
| 54 | + |
| 55 | ++ |
| 56 | + |
| 57 | ++ |
| 58 | ++ |
| 59 | ++ |
| 60 | ++ |
| 61 | +++ |
| 62 | +++ |
| 63 | +++ |
| 64 | +++ |
| 65 | +++ |
| 66 | +++ |
| 67 | +++ |
| 68 | +++ |
| 69 | +++ |
| 70 | +++ |
| 71 | ++ |
| 72 | +++ |

TABLE 1-continued

| Compound | PPARγ Binding IC$_{50}$ Filtration |
|---|---|
| 73 | +++ |
| 74 | +++ |
| 75 | +++ |
| 76 | +++ |
| 77 | +++ |
| 78 | +++ |
| 79 | +++ |
| 80 | +++ |
| 81 | +++ |
| 82 | +++ |
| 83 | +++ |
| 84 | +++ |
| 85 | +++ |
| 86 | +++ |
| 87 | +++ |
| 88 | +++ |
| 89 | +++ |
| 94 | +++ |
| 95 | +++ |
| 96 | +++ |
| 97 | +++ |
| 98 | +++ |
| 99 | +++ |
| 100 | +++ |
| 101 | +++ |
| 102 | +++ |
| 103 | +++ |
| 104 | ++ |
| 105 | ++ |
| 106 | +++ |
| 107 | +++ |
| 108 | ++ |
| 109 | ++ |
| 110 | ++ |
| 111 | ++ |
| 112 | +++ |
| 113 | +++ |
| 114 | +++ |
| 115 | +++ |
| 116 | +++ |
| 117 | ++ |
| 118 | +++ |
| 119 | +++ |
| 120 | +++ |
| 121 | +++ |
| 122 | +++ |
| 123 | +++ |
| 124 | +++ |
| 125 | +++ |
| 126 | +++ |
| 128 | +++ |
| 129 | +++ |
| 130 | +++ |
| 131 | +++ |
| 132 | +++ |
| 133 | +++ |
| 134 | +++ |
| 135 | ++ |
| 136 | +++ |
| 137 | ++ |
| 138 | +++ |
| 139 | +++ |
| 140 | +++ |
| 141 | ++ |
| 150 | ++ |
| 151 | ++ |
| 152 | +++ |
| 157 | ++ |
| 176 | ++ |
| 179 | ++ |
| 184 | ++ |
| 189 | ++ |
| 200 | +++ |
| 201 | +++ |
| 202 | +++ |
| 203 | +++ |

TABLE 1-continued

| Compound | PPARγ Binding IC$_{50}$ Filtration |
|---|---|
| 204 | +++ |
| 205 | +++ |
| 206 | +++ |
| 207 | +++ |
| 208 | +++ |
| 209 | +++ |
| 210 | +++ |
| 211 | +++ |
| 212 | +++ |
| 213 | +++ |
| 214 | +++ |
| 215 | +++ |
| 216 | +++ |
| 217 | +++ |
| 218 | +++ |
| 219 | +++ |
| 220 | +++ |
| 221 | +++ |
| 222 | +++ |
| 223 | +++ |
| 224 | +++ |
| 225 | +++ |
| 226 | +++ |
| 227 | +++ |
| 228 | +++ |
| 229 | +++ |
| 230 | +++ |
| 231 | +++ |
| 232 | +++ |
| 233 | +++ |
| 234 | +++ |
| 235 | +++ |
| 236 | +++ |
| 237 | +++ |
| 238 | +++ |
| 239 | +++ |
| 240 | +++ |
| 241 | +++ |
| 242 | +++ |
| 243 | +++ |
| 244 | +++ |
| 245 | +++ |
| 246 | +++ |
| 247 | +++ |
| 248 | +++ |
| 249 | +++ |
| 250 | +++ |
| 251 | +++ |
| 252 | +++ |
| 253 | +++ |
| 254 | +++ |
| 255 | +++ |
| 256 | +++ |
| 257 | +++ |
| 258 | +++ |
| 259 | +++ |
| 260 | +++ |
| 261 | +++ |
| 262 | +++ |
| 263 | +++ |
| 264 | +++ |
| 265 | +++ |
| 266 | +++ |
| 267 | +++ |
| 268 | +++ |
| 269 | +++ |
| 270 | +++ |
| 271 | +++ |
| 272 | +++ |
| 273 | +++ |
| 274 | +++ |
| 275 | +++ |
| 276 | +++ |
| 277 | +++ |
| 278 | +++ |
| 279 | +++ |
| 280 | +++ |
| 281 | +++ |
| 282 | +++ |
| 283 | +++ |
| 284 | +++ |
| 285 | +++ |
| 286 | +++ |
| 287 | +++ |
| 288 | +++ |
| 289 | +++ |
| 290 | +++ |
| 291 | +++ |
| 292 | +++ |
| 293 | +++ |
| 294 | +++ |
| 294 | ++ |
| 295 | +++ |
| 296 | +++ |
| 297 | +++ |
| 298 | +++ |
| 299 | +++ |
| 300 | +++ |
| 301 | +++ |
| 302 | +++ |
| 303 | +++ |
| 304 | +++ |
| 305 | +++ |
| 306 | +++ |
| 307 | +++ |
| 308 | +++ |
| 309 | +++ |
| 310 | +++ |
| 311 | +++ |
| 312 | +++ |
| 313 | +++ |
| 314 | +++ |
| 315 | +++ |
| 316 | +++ |
| 317 | +++ |
| 318 | +++ |
| 319 | +++ |
| 320 | +++ |
| 321 | +++ |
| 322 | +++ |
| 323 | +++ |
| 324 | +++ |
| 325 | +++ |
| 326 | +++ |
| 327 | +++ |
| 328 | +++ |
| 329 | +++ |
| 330 | +++ |
| 331 | +++ |
| 332 | +++ |
| 333 | +++ |
| 334 | +++ |
| 335 | +++ |
| 336 | +++ |
| 338 | +++ |
| 339 | +++ |
| 340 | +++ |
| 341 | +++ |
| 342 | +++ |
| 343 | +++ |
| 344 | +++ |
| 345 | +++ |
| 346 | +++ |
| 347 | +++ |
| 348 | +++ |
| 349 | +++ |
| 350 | +++ |
| 351 | +++ |
| 352 | +++ |
| 353 | +++ |
| 354 | +++ |
| 355 | +++ |

TABLE 1-continued

| Compound | PPARγ Binding IC$_{50}$ Filtration |
|---|---|
| 356 | +++ |
| 357 | +++ |
| 358 | +++ |
| 359 | +++ |
| 360 | +++ |
| 361 | +++ |
| 362 | +++ |
| 363 | +++ |
| 364 | +++ |
| 365 | +++ |
| 366 | +++ |
| 367 | +++ |
| 368 | +++ |
| 369 | ++ |
| 370 | + |
| 371 | ++ |
| 372 | ++ |
| 373 | ++ |
| 374 | ++ |
| 375 | ++ |
| 376 | ++ |
| 377 | ++ |
| 378 | ++ |
| 379 | ++ |
| 380 | ++ |
| 381 | ++ |
| 382 | ++ |
| 383 | ++ |
| 384 | ++ |
| 385 | ++ |
| 386 | ++ |
| 387 | ++ |
| 388 | ++ |
| 389 | ++ |
| 390 | ++ |
| 391 | ++ |
| 392 | ++ |
| 393 | ++ |
| 395 | ++ |
| 396 | ++ |
| 397 | ++ |
| 398 | ++ |
| 399 | ++ |
| 400 | ++ |
| 401 | ++ |
| 402 | ++ |
| 403 | ++ |
| 404 | ++ |
| 405 | ++ |
| 406 | ++ |
| 407 | ++ |
| 408 | ++ |
| 409 | ++ |
| 410 | ++ |
| 411 | ++ |
| 412 | ++ |
| 413 | ++ |
| 414 | + |
| 415 | ++ |
| 416 | ++ |
| 417 | ++ |
| 418 | ++ |
| 419 | ++ |
| 420 | ++ |
| 421 | ++ |
| 422 | ++ |
| 423 | ++ |
| 424 | ++ |
| 425 | ++ |
| 426 | ++ |
| 427 | ++ |
| 428 | ++ |
| 429 | ++ |
| 430 | + |
| 431 | + |
| 432 | + |

TABLE 1-continued

| Compound | PPARγ Binding IC$_{50}$ Filtration |
|---|---|
| 433 | + |
| 434 | + |
| 439 | +++ |
| 440 | +++ |
| 441 | +++ |
| 442 | +++ |
| 443 | ++ |
| 444 | ++ |
| 445 | +++ |
| 446 | ++ |
| 447 | +++ |
| 448 | +++ |
| 449 | ++ |
| 450 | +++ |
| 451 | +++ |
| 452 | +++ |
| 453 | +++ |
| 454 | +++ |
| 455 | ++ |
| 456 | +++ |
| 457 | +++ |
| 458 | ++ |
| 459 | +++ |
| 460 | ++ |
| 461 | +++ |
| 462 | +++ |
| 463 | +++ |
| 464 | +++ |
| 465 | +++ |
| 466 | +++ |
| 467 | +++ |
| 468 | +++ |
| 469 | +++ |
| 470 | +++ |
| 471 | +++ |
| 472 | +++ |
| 473 | +++ |
| 474 | +++ |
| 475 | +++ |
| 476 | +++ |
| 477 | +++ |
| 478 | +++ |
| 479 | +++ |
| 480 | +++ |

Examaple 142

This example describes in vitro assays that can be used to evaluate compounds of the invention.

Transient Transactivation Assay

In vitro PPAR activation activity can be measured using transient transactivation assay as described in U.S. Pat. No. 6,869,975, the contents of which is incorporated by reference in its entirety. CV-1 cells can be plated in DME medium supplemented with 10% charcoal stripped calf serum (Hy-Clone) at a density of 24,000 cells per well in a 96-well plate (Costar) 16-24 h before transfection. Approximately 16 ng of luciferase reporter plasmid, 8 ng of a control β-galactosidase expression vector (PCMVβ, Clontech), and 2-8 ng of PPAR expression plasmid can be mixed with carrier DNA (βBluescript, Stratagene) to a total of 80 ng per well in a volume of 10 μL of OptiME medium (GIBCO BRL). To this mixture can be added a second mix containing 10 μL of OptiME medium and 0.7 μL of LipoFectamine GIBCO BRL). After incubation for 30 min, an additional 80 μL of OptiME medium can be added and the resulting solution can be then applied to the cells. After 16 h the medium can be exchanged to DME medium supplemented with 10% dilipidated fetal calf serum (Sigma) and test compound (concentrations ranging from 10 μM to 0.1 nM). After incubation for an additional 24 h, the cells can be lysed and both luciferase and β-galactosidase activity can be measured. Luciferase activity can benormalized for transfection efficiency by using β-galactosidase derived from the cotransfected pCMVP plasmid as internal standard.

Plasmids

DR1$_{3X}$tk-luc reporter plasmids contain three copies of the consensus direct repeat 1 (DR1) PPAR response element (TATCA AGGTCA A AGGTCA TCTAG) (SEQ ID NO:1) inserted upstream of minimal herpes simplex thymidine kinase promoter in the pGL3 firefly luciferase reporter plasmid (Invitrogen).

G5 tk-luc contains 5 copies of the GAL4 binding site inserted upstream of minimal herpes simplex thymidine kinase promoter in the pGL3 firefly luciferase reporter plasmid.

pSG5huPPARδ and pSG5muPPARδ contain the nucleotide sequences for the human and murine PPARδ gene inserted into the expression vector pSG5 (Stratagene).

Plasmids containing nucleotide sequences encoding the ligand binding domains of human PPARα and human PPARγ inserted C-terminal to the GAL4 DNA binding domain of a suitable GAL4 DNA binding domain cloning vector can be prepared using conventional techniques.

The PPAR transient transactivation assays can also be carried out by transient transfection into human HEK 293 cells, as described, for example, in U.S. Pat. No. 6,602,901 and U.S. Pat No. 6,869,967, the contents of which are incorporated by reference in their entirety.

Binding Assay

Compounds can be tested for their ability to bind to PPARα, PPARγ or PPARδ by in vitro binding assays, such as used in U.S. Pat. No. 5,902,726, U.S. Pat. No. 6,762,171, and U.S. Pat No. 6,869,975, the contents of which are incorporated by reference in their entirety. For example, a Scintillation Proximity Assay (SPA) can be used to test the ability of the compounds to bind to PPARα, PPARγ or PPARδ. See, e.g., U.S. Pat No. 6,869,975. Polylysine coated yttrium silicate SPA beads (Amersham) can be reconstituted by adding 200 ng beads to 40 μL assay buffer [20 mM phosphate buffer pH 7.1, 50 mM sodium chloride, 2 mM EDTA, 10% (v/v) glycerol, and 2 mM 3-[(3-cholamidopropyl)-dimethylammonio]-1-propanesulfonate (CHAPS)]. To the bead slurry, 80-280 ng of GST-PPAR protein can be added and the mixture incubated for 2 h at 4° C. The 40 μL of bead slurry can be added to 10 μL of test compound solution (concentrations ranging from 10 μM to 0.1 nM). Following incubation for 1 h at room temperature, 50 μL of a 20-40 nM radioligand solution in assay buffer can be added. After incubation for an additional 1 h at room temperature the assay mix can be quantitated using a Topcount (Packard).

Radioligands

For PPARδ and PPARα binding assays, radiolabeled 2-(4-(3-(1-((2-chloro-6-fluoro-phenyl)ethyl)-3-(2,3-dichlorophenyl)ureido)propenyl)phenoxy)-2-methylpropionic acid (Brown et al. (1997) Chem. Biol. 12:909-918) can be used. For PPARγ binding assay radiolabeled 5-{4-[2-(methyl-pyridine-2-yl-amino)-ethoxy]-benzyl}-thiazolidine-2,4-dione (described in U.S. Pat. No. 5,902,726) can be used.

Proteins

For GST-PPARα and GST-PPARγ, cDNAs encoding amino acids 167-468 of PPARα and amino acids 175 to 475 of PPARγ, respectively, can be inserted into the bacterial expression vector pGEX 2T (Pharmacia). For GST-PPARδ, cDNA encoding amino acids 138-440 can be inserted into the bacterial expression vector pGEX 6P-1 (Pharmacia). GST-PPAR ligand binding domain protein can be expressed in BL21 (DE3) cells (Stratagene).

iNOS Inhibition Assay

Compounds can be tested for their ability to inhibit the activity and/or expression of iNOS using lipopolysaccharide (LPS) to induce iNOS expression in the mouse macrophage cell line, J 774. See, for example, U.S. Pat No. 6,869,975; International Publication No. WO 02/28434 to Buchan et al, the contents of which are incorporated by reference in their entirety.

Measurement of iNOS Activity

LPS-induced iNOS activity can be measured using the following assay conditions: J 774 cells are seeded at a density of 35000-50000 thousand cells per well, in a black, clear-bottomed, 96-well plate, 24 h prior to use. The cell culture and the drug dilutions are carried out in complete media, which consists of DMEM (Dulbecco's modification of Eagle's medium) containing fetal calf serum (10%), glutamine (2 mM), penicillin (100 u/mL) and streptomycin (100 μg/mL). The J 774 cells are pre-treated with PPARδ activators or vehicle, for 6 h prior to, and for 24 h subsequent to, the addition of LPS. Twenty-four hours after the addition of LPA, iNOS activity is measured using the following method: The cell culture media/drug dilutions are removed and the cells washed with D-PBS (Dulbecco's modification of phosphate-buffered saline). The D-PBS is then removed, and replaced with D-PBS containing DAF-2 (4,5-diaminofluorescein; 5 μM) and L-arginine (500 μM). After incubation at 37° C. for 3 h, fluorescence from each well is measured at an excitation wavelength of 485 nm and an emission wavelength of 530 nm. The ability of LPS to induce iNOS activity, in the presence and absence of a PPARδ or PPARγ activator, can then be calculated.

Measurement of Inhibition of iNOS mRNA

LPS-induced expression of iNOS mRNA can be measured using the following assay conditions: J 774 cells can be plated in 6-well plates (10$^6$ cells/well), 24 h prior to use. The cells can be pre-treated with PPARδ or PPARγ activator control media for 6 h, prior to addition of LPS, which can be co-incubated with the PPARδ or PPARγ activator/control for a further 24 h. At the end of this incubation period, the culture medium can be removed by aspirating and the cells washed with D-PBS. Following removal of the D-PBS, total cellular RNA can be isolated from each sample using a commercially available RNA isolation kit. First strand cDNA synthesis can be carried out as per instructions supplied with the AMV reverse transcription (RT) system. An aliquot (100 ng) of the RNA can be added to a mixture which contains (final concentrations) MgCl$_2$ (5 mM), Tris-HCl (10 mM; pH 8.8), KCl (50 mM), Triton X-100 (0.1%), dNTP (1 mM), rRNasin (1 U/μL), AMV reverse transcriptase (0.75 U/μL), oligo(dT)$_{15}$(25 ng/μL). The resulting mixture can be incubated in a thermal cycler at 42° C. for 30 min, followed by 95° C. for 15 min, and, finally, 4° C., until being transferred to a freezer (−20° C.) for storage.

For use in PCR, mouse iNOS sense, mouse iNOS anti-sense, mouse GAPDH sense and mouse GAPDH anti-sense primer sets, such as those used in International Publication No. WO 02/28434 to Buchan et al., can be used. PCR can be undertaken in a 50-μL reaction volume containing 5 μL of the RT reaction, sense and anti-sense primers for iNOS/GAPDH (0.4 pmol/μL), dNTPs (160 mM), KCl (50 mM), Tris-HCl (10 mM; pH 9.0), Triton X-100 (0.1%), MgCl$_2$ (2 mM) and Taq DNA polymerase (0.04 U/μL) (final concentrations). The PCR can be carried out in a thermal cycler using the following conditions: 95° C. for 60 s, followed by 28 cycles of 94° C. for 30 s, 55° C. for 60 s, 72° C. for 90 s. Following a final extension step of 72° C. for 5 min, the samples can be maintained at 4° C. until analyzed on an agarose gel. Analysis of sybr-green-stained gels, by densitometry, can be carried out using a Storm fluorimager system (Molecular Devices).

Measurement of Inhibition of TNF

LPS-induced iNOS activity and expresion of TNF can be measured using methods as described in U.S. Pat No. 6,869,975, the contents of which are incorporated by reference in its entirety. The following assay conditions can be used: J 774 cells can be seeded at a density of 35000-50000 thousand cells per well, in black, clear-bottomed, 96-well plates. The cell culture and the drug dilutions can be carried out in complete media, which consists of DMEM (Dulbecco's modification of Eagle's medium) containing fetal calf serum (10%), glutamine (2 mM), penicillin (100 u/mL) and streptomycin (100 μg/mL). The J 774 cells can be pre-treated with PPARδ or PPARγ activators, or vehicle, for 6 h prior to, and for 24 h subsequent to the addition of LPS. Twenty-four hours after the addition of LPS, iNOS activity can be measured by the following method: The cell culture media/drug dilutions can be removed for measurement of TNF concentrations, and quantified using a commercially available ELISA system. The cells can be washed with D-PBS. The D-PBS can then be removed, and replaced with D-PBS containing DAF-2 (4,5-diaminofluorescein; 5 μM) and L-arginine (500 μM). iNOS activity can then be measured as described above.

Adipocyte Differentiation Assay

The compounds of the invention can also be tested for their effect on cell growth and differentiation mediated by PPARδ or PPARγ, using methods such as used in U.S. Pat. No. 5,902,726, U.S. Pat. No. 6,506,781, U.S. Pat. No. 6,646,008, and U.S. Pat. No. 6,756,399, the contents of which are incorporated by reference in their entirety.

For example, adipocyte differentiation assay can be performed as described in U.S. Pat. No. 6,506,781, the contents of which are incorporated by reference in its entirety. C3H10T1/2 clone 8 murine fibroblasts (American Type Culture Collection) below passage 22 can be maintained in Dulbecco's modified Eagle's medium (Life Technologies, Inc.) supplemented with 10% fetal calf serum and 100 units/mL penicillin G and 100 microgram/mL streptomycin. One day after passage into 96-well microtiter plates ($12.5 \times 10^3$ cells/$cm_2$), the cells can be treated with 150 nM rosiglitazone plus 1 micromolar insulin and 1 micromolar 9-cis-retinoic acid (Sigma, St. Louis, Mo.). Vehicle or the compounds of the invention, which had been solublized to 10 mM in DMSO and then serially diluted from 1e-5 M to 1e-10 M into medium, can be added. After 7 days, cells can be lysed in 0.01% Digitonin (Sigma, St. Louis, Mo.) and the lipogenic activity determined by measuring total triglycerides using a Glycerol-Triglyceride (GPO-Trinder) kit (337-B, Sigma, St. Louis, Mo.). The mixture can be incubated at 37° C. for 2 h and the absorbance read at 550 nm. The % maximum inhibition of lipogenesis can be calculated relative to the vehicle treated cells.

Example 143

This example describes in vivo assays that can be used to evaluate the compounds of the invention.

HDL Cholesterol Assay in High Cholesterol Fed Rats

The compounds of the inventioin can be evaluted for their effect on PPAR functions, using animal models such as used in U.S. Pat No. 6,869,975, U.S. Pat. No. 6,506,781, and U.S. application Ser. No. 10/783,654, published as U.S. Pub. No. 2004/0209929, the contents of which are incorporated by reference in their entirety.

HDL cholesterol assay in high cholesterol fed rats can be carried out as described in U.S. Pat No. 6,869,975. Male Sprague-Dawley rats (BW: 100-120 g) can be fed a high cholesterol diet (1.25% cholesterol, 0.5% cholic acid and 10% coconut oil) for 14 days. The animals can be orally dosed with test compounds suspended to 0.5% methylcellulose solution once a day over the final 7 days. Typical doses of test compounds can be 1-30 mg/kg/day.

After 7 days of treatment, serum HDL cholesterol concentration can be determined from blood obtained by tail bleeds. HDL cholesterol determination can be performed on a Hitachi 7170 automatic analyzer.

Serum Gluclose and Insulin Level in Mice

The compounds prepared in accordance with the above examples may be evaluated for their effect on serum glucose and serum insulin in db/db mice (C578BL/KsJ-db/db Jcl), as described in U.S. applicaition Ser. No. 10/783,654, published as U.S. Pub. No. 2004/0209929, the contents of which are incorporated by reference in its entirety. The compounds may be dissolved in a vehicle consisting of 2% Tween80 in distilled water and administered orally. Dosage volume may be 10 ml/kg body weight. All aspects of the work including experimentation and disposal of the animals may be performed in general accordance with the International Guiding Principles for Biomedical Research Involving Animals (CIOMS Publication No. ISBN 92 90360194, 1985). Glucose-HA Assay kits (Wako, Japan) may be used for determination of serum glucose and ELISA Mouse Insulin Assay kits (SPI bio, France) may be utilized for determination of insulin. The positive control may be troglitazone (Helios Pharmaceutical, Louisville, Ky.).

The animals may be divided into twenty groups of four animals each. The animals may weigh 52±0.5 grams at age 8-10 weeks.

Prior to any treatment a blood sample (pretreatment blood) may be taken from each animal. Four groups of animals, the vehicle groups, may receive only doses of the vehicle. Each of the vehicle groups may receive 100, 30, 10 or 1 ml/kg body weight of the vehicle orally. A solution containing compounds of the invention (10 ml/kg body weight in tween 80/water) may be administered orally to the four positive control groups in doses of 100, 30, 10 and 1 ml/kg body weight respectively. The vehicle, positive control and test compound solutions may be administered to the groups immediately, 24 hours and 48 hours after drawing the pretreatment blood. Blood may be withdrawn (post treatment blood) 1.5 hours after administration of the last dose.

The serum glucose levels of the blood samples may be determined enzymatically (Mutaratose-GOD) and the insulin levels by ELISA (mouse insulin assay kit). The mean±SEM of each group may be calculated and the percent inhibition of serum glucose and insulin may be obtained by comparison between pretreatment blood and post treatment blood. The percentage of reduction of the serum glucose and insulin levels in the post treatment blood relative to the pretreatment blood may be determined and an unpaired students t test may be applied for the comparison between the control and test solution groups and the vehicle group. A significant difference may be considered at $P<0.05$.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications can be made thereto without departing from the spirit or scope of the appended Claims.

What is claimed is:

1. A compound having the formula (I):

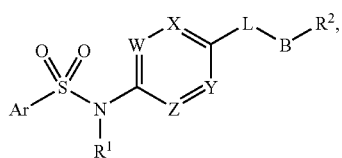

wherein

Ar is a member selected from the group consisting of phenyl, naphthyl and pyridyl; each of which is optionally substituted with from one to three $R^8$ substituents, wherein each $R^8$ is a member independently selected from the group consisting of halogen, cyano, nitro, $(C_1\text{-}C_8)$alkyl, $(C_1\text{-}C_8)$alkoxy, $(C_1\text{-}C_8)$haloalkyl, $(C_1\text{-}C_8)$haloalkoxy, $(C_2\text{-}C_8)$alkenyl, $(C_2\text{-}C_8)$alkynyl, hydroxyl and $NR^{12}R^{13}$;

B is aryl or heteroaryl; each of which is optionally substituted with from one to two $R^9$ substituents, wherein each $R^9$ is a member independently selected from the group consisting of halogen, nitro, $(C_1\text{-}C_8)$alkyl, $(C_1\text{-}C_8)$alkoxy and $NR^{12}R^{13}$;

L is selected from the group consisting of O, $S(O)_k$, $CR^aR^b$ and C(O);

each $R^a$ or $R^b$ is independently selected from the group consisting of hydrogen, cyano, nitro, and $(C_1\text{-}C_8)$alkyl;

W is independently $C(R^3)$ or N;

X is independently $C(R^4)$ or N;

Y is independently $C(R^5)$ or N;

Z is independently $C(R^6)$ or N, wherein one of W, X, Y and Z is N and three of W, X, Y and Z are other than N;

$R^1$ is selected from the group consisting of hydrogen, $(C_1\text{-}C_8)$alkyl, $(C_2\text{-}C_8)$heteroalkyl and aryl$(C_1\text{-}C_8)$alkyl;

$R^2$ is $S(O)_mR^7$;

each $R^3$, $R^4$, $R^5$, or $R^6$ is a member independently selected from the group consisting of hydrogen, hydroxy, halogen, cyano, nitro, $NR^{12}R^{13}$, $(C_1\text{-}C_8)$alkyl, halo$(C_1\text{-}C_8)$alkyl, hydroxy$(C_1\text{-}C_8)$alkyl, $(C_3\text{-}C_8)$cycloalkyl, $(C_1\text{-}C_8)$alkoxy, $(C_1\text{-}C_8)$thioalkoxy, $(C_2\text{-}C_8)$heteroalkyl, aryl, heteroaryl, —C(O)$R^{11}$, —CO$_2R^{11}$, —C(O)N $R^{12}R^{13}$, —C(O)CH$_2$CN, —X$^1Q^1$, X$^2OR^{11}$ and X$^2NR^{12}R^{13}$;

each $X^1$ is independently selected from the group consisting of $(C_1\text{-}C_2)$alkylene and C(O); and each $Q^1$ is independently selected from the group consisting of pyrrolidinyl, piperidinyl, and morpholinyl;

$R^7$ is selected from the group consisting of $(C_1\text{-}C_8)$alkyl, $(C_3\text{-}C_8)$cycloalkyl, $(C_1\text{-}C_8)$haloalkyl, aryl, $NR^{12}R^{13}$, $(C_3\text{-}C_8)$heterocycloalkyl, $X^2$—C(O)O$R^{15}$, $X^2$—C(O)N $(R^{15})_2$, and —$X^2$—$R^{12}R^{13}$;

each $X^2$ is $(C_1\text{-}C_8)$alkylene;

each $R^{11}$ is independently selected from the group consisting of hydrogen, $(C_1\text{-}C_8)$alkyl, $(C_2\text{-}C_8)$alkenyl, $(C_3\text{-}C_8)$cycloalkyl, $(C_2\text{-}C_8)$heteroalkyl, aryl, heteroaryl, heteroaryl$(C_1\text{-}C_8)$alkyl, $(C_3\text{-}C_8)$heterocycloalkyl and aryl$(C_1\text{-}C_8)$alkyl;

each $R^{12}$ and $R^{13}$ is independently selected from the group consisting of hydrogen, $(C_1\text{-}C_8)$alkyl, $(C_2\text{-}C_8)$alkenyl, $(C_3\text{-}C_8)$cycloalkyl, $(C_2\text{-}C_8)$heteroalkyl, $(C_1\text{-}C_8)$alkoxy, aryl and aryl$(C_1\text{-}C_8)$alkyl;

optionally, $R^{12}$ and $R^{13}$ are combined with the nitrogen to which each is attached to form a 3-, 4-, 5-, 6- or 7-membered ring which can be saturated or unsaturated and contain 0 to 2 additional heteroatoms selected from N, O and S; wherein said ring is optionally substituted with from one to four substituents selected from the group consisting of hydroxy, oxo, and $(C_1\text{-}C_8)$alkyl;

each $R^{15}$ is independently selected from the group consisting of H, $(C_1\text{-}C_8)$alkyl, $(C_2\text{-}C_8)$alkenyl and $(C_3\text{-}C_8)$cycloalkyl; and the subscripts k and m are independently an integer of 0 to 2.

2. The compound of claim 1, wherein Ar is phenyl, optionally substituted with from one to three $R^8$ substitutents, wherein each $R^8$ is independently selected from the group consisting of halogen, $(C_1\text{-}C_8)$alkyl, $(C_1\text{-}C_8)$alkoxy, and $(C_1\text{-}C_8)$haloalkyl.

3. The compound of claim 1, wherein $R^1$ is H.

4. The compound of claim 1, wherein W is N; X is $C(R^4)$; Y is $C(R^5)$; and Z is $C(R^6)$.

5. The compound of claim 1, wherein W is $C(R^3)$; Y is $C(R^5)$; Z is $C(R^6)$; and X is N.

6. The compound of claim 1, wherein each $R^3$, $R^4$, $R^5$, or $R^6$ is independently selected from the group consisting of hydrogen, hydroxy, halogen, $NR^{12}R^{13}$, $(C_1\text{-}C_8)$alkyl, $(C_3\text{-}C_8)$cycloalkyl, $(C_1\text{-}C_8)$alkoxy, $(C_1\text{-}C_8)$thioalkoxy, $(C_2\text{-}C_8)$heteroalkyl, $(C_2\text{-}C_8)$haloalkyl, CN, —C(O)$R^{11}$, —CO$_2R^{11}$ and —C(O)N$R^{12}R^{13}$.

7. The compound of claim 1, wherein L is O.

8. The compound of claim 1, wherein L is S.

9. The compound of claim 1, wherein B is aryl, which is optionally substituted with from one to two $R^9$ substituents.

10. The compound of claim 9, wherein B is phenyl or naphthyl, each of which is optionally substituted with from one to two $R^9$ substituents.

11. The compound of claim 10, wherein B is phenyl, which is optionally substituted with from one to two $R^9$ substituents.

12. The compound of claim 1, wherein B is heteroaryl, which is optionally substituted with from one to two $R^9$ substituents.

13. The compound of claim 1, wherein B is benzothiazolyl, which is optionally substituted with from one to two $R^9$ substituents.

14. The compound of claim 1 wherein $R^2$ is $SO_2R^7$.

15. The compound of claim 14, wherein $R^7$ is selected from the group consisting of $(C_1-C_8)$alkyl, $NR^{12}R^{13}$ and $(C_3-C_8)$heterocycloalkyl.

16. The compound of claim 15, wherein $R^7$ is selected from the group consisting of cyclopentyl, cyclohexyl, tetrahydropyranyl, pyrrolidinyl, piperidinyl, morpholinyl, piperazinyl, thiomorpholinyl, and azepinyl.

17. The compound of claim 15, wherein $R^7$ is selected from the group consisting of

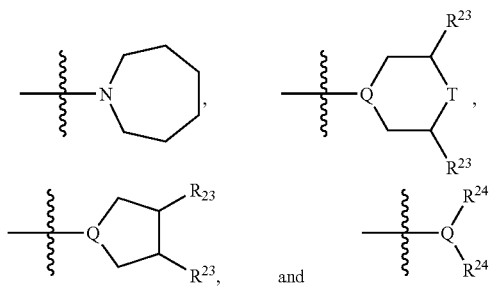

wherein
Q is N or CH;
T is $CHR^{16}$, $NR^{16}$, O, or $S(O)_1$;
$R^{16}$ is H or $(C_1-C_8)$alkyl;
each $R^{23}$ is a member independently selected from the group consisting of H and $(C_1-C_8)$alkyl;
each $R^{24}$ is selected from the group consisting of H, $(C_1-C_8)$alkyl and heteroalkyl; and
the subscript 1 is an integer of from 0 to 2.

18. The compound of claim 15, wherein $R^7$ is $X^2$—C(O)OR$^{15}$ or $X^2$—C(O)N(R$^{15}$)$_2$; and
each $R^{15}$ is H or $(C_1-C_8)$alkyl.

19. A compound having a formula selected from the group consisting of:

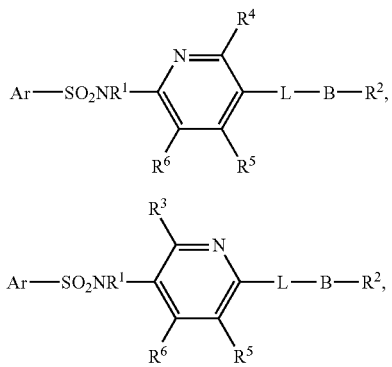

wherein
Ar is a member selected from the group consisting of phenyl, naphthyl and pyridyl; each of which is optionally substituted with from one to three $R^8$ substituents, wherein each $R^8$ is a member independently selected from the group consisting of halogen, cyano, nitro, $(C_1-C_8)$alkyl, $(C_1-C_8)$alkoxy, $(C_1-C_8)$haloalkyl, $(C_1-C_8)$haloalkoxy, $(C_2-C_8)$alkenyl, $(C_2-C_8)$alkynyl, hydroxyl and $NR^{12}R^{13}$;
B is aryl or heteroaryl; each of which is optionally substituted with from one to two $R^9$ substituents, wherein each $R^9$ is a member independently selected from the group consisting of halogen, nitro, $(C_1-C_8)$alkyl, $(C_1-C_8)$alkoxy and $NR^{12}R^{13}$;
L is selected from the group consisting of O, $S(O)_k$, $CR^aR^b$ and C(O);
each $R^a$ or $R^b$ is independently selected from the group consisting of hydrogen, cyano, nitro, and $(C_1-C_8)$alkyl;
$R^1$ is selected from the group consisting of hydrogen, $(C_1-C_8)$alkyl, $(C_2-C_{C8})$heteroalkyl and aryl$(C_1-C_8)$alkyl;
$R^2$ is $S(O)_mR^7$;
each $R^3$, $R^4$, $R^5$, or $R^6$ is a member independently selected from the group consisting of hydrogen, hydroxy, halogen, cyano, nitro, $NR^{12}R^{13}$, $(C_1-C_8)$alkyl, halo$(C_1-C_8)$alkyl, hydroxy$(C_1-C_8)$alkyl, $(C_3-C_8)$cycloalkyl, $(C_1-C_8)$alkoxy, $(C_1-C_8)$thioalkoxy, $(C_2-C_8)$heteroalkyl, aryl, heteroaryl, —C(O)R$^{11}$, —CO$_2$R$^{11}$, —C(O)N R$^{12}$R$^{13}$, —C(O)CH$_2$CN, —X$^1$Q$^1$, X$^2$OR$^{11}$ and X$^2$NR$^{12}$R$^{13}$;
each $X^1$ is independently selected from the group consisting of $(C_1-C_2)$alkylene and C(O); and
each $Q^1$ is independently selected from the group consisting of pyrrolidinyl, piperidinyl, and morpholinyl;
$R^7$ is selected from the group consisting of $(C_1-C_8)$alkyl, $(C_3-C_8)$cycloalkyl, $(C_1-C_8)$haloalkyl, aryl, $NR^{12}R^{13}$, $(C_3-C_8)$heterocycloalkyl, $X^2$—C(O)OR$^{15}$, $X^2$—C(O)N(R$^{15}$)$_2$, and —X$^2$—NR$^{12}$R$^{13}$;
each $X^2$ is $(C_1-C_8)$alkylene;
each $R^{11}$ is independently selected from the group consisting of hydrogen, $(C_1-C_8)$alkyl, $(C_2-C_8)$alkenyl, $(C_3-C_8)$cycloalkyl, $(C_2-C_8)$heteroalkyl, aryl, heteroaryl, heteroaryl$(C_1-C_8)$alkyl, $(C_3-C_8)$heterocycloalkyl and aryl$(C_1-C_8)$alkyl;
$R^{12}$ and $R^{13}$ are independently selected from the group consisting of hydrogen, $(C_1-C_8)$alkyl, $(C_2-C_8)$alkenyl, $(C_3-C_8)$cycloalkyl, $(C_2-C_8)$heteroalkyl, $(C_1-C_8)$alkoxy, aryl and aryl$(C_1-C_8)$alkyl;
optionally, $R^{12}$ and $R^{13}$ are combined with the nitrogen atom to which each is attached to form a 3-, 4-, 5-, 6- or 7-membered ring which can be saturated or unsaturated and contain 0 to 2 additional heteroatoms selected from N, O and S; wherein said ring is optionally substituted with from one to four substituents selected from the group consisting of hydroxy, oxo, and $(C_1-C_8)$alkyl;
each $R^{15}$ is selected from the group consisting of H, $(C_1-C_8)$alkyl, $(C_2-C_8)$alkenyl and $(C_3-C_8)$cycloalkyl; and
the subscripts k and m are independently an integer of 0 to 2.

20. The compound of claim 19, wherein Ar is phenyl, optionally substituted with from one to three $R^8$ substitutents, wherein each $R^8$ is independently selected from the group consisting of halogen, $(C_1-C_8)$alkyl, $(C_1-C_8)$alkoxy, and $(C_1-C_8)$haloalkyl.

21. The compound of claim 19, wherein $R^1$ is H.

22. The compound of claim 19, wherein each $R^3$, $R^4$, $R^5$, or $R^6$ is independently selected from the group consisting of hydrogen, hydroxy, halogen, $NR^{12}R^{13}$, $(C_1-C_8)$alkyl, $(C_3-C_8)$cycloalkyl, $(C_1-C_8)$alkoxy, $(C_1-C_8)$thioalkoxy, $(C_2-C_8)$heteroalkyl, $(C_1-C_8)$haloalkyl, CN, —C(O)$^{11}$, —CO$_2$R$^{11}$ and —C(O)NR$^{12}$R$^{13}$.

23. The compound of claim 19, wherein L is O.

24. The compound of claim 19, wherein L is S.

25. The compound of claim 19, wherein B is aryl; optionally substituted with from one to two $R^9$ substituents.

26. The compound of claim 25, wherein B is selected from the group consisting of phenyl and naphthyl; optionally substituted with from one to two $R^9$ substituents.

27. The compound of claim 26, wherein B is phenyl; optionally substituted with from one to two $R^9$ substituents.

28. The compound of claim 19, wherein B is heteroaryl; optionally substituted with from one to two $R^9$ substituents.

29. The compound of claim 28, wherein B is benzothiazolyl; optionally substituted with from one to two $R^9$ substituents.

30. The compound of claim 19, wherein $R^2$ is $SO_2R^7$.

31. The compound of claim 30, wherein $R^7$ is selected from the group consisting of $(C_1\text{-}C_8)$alkyl, $NR^{12}R^{13}$, and $(C_3\text{-}C_8)$heterocycloalkyl.

32. The compound of claim 31, wherein $R^7$ is selected from the group consisting of

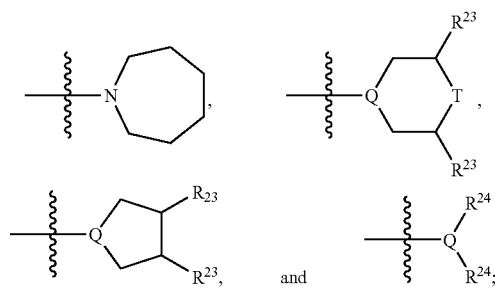

wherein
Q is N or CH;
T is $CHR^{16}$, $NR^{16}$, O, or $S(O)_l$;
$R^{16}$ is H or $(C_1\text{-}C_8)$alkyl;
each $R^{23}$ is a member independently selected from the group consisting of H and $(C_1\text{-}C_8)$alkyl;
each $R^{24}$ is selected from the group consisting of H, $(C_1\text{-}C_8)$alkyl and heteroalkyl; and
l is an integer of from 0 to 2.

33. The compound of claim 31, wherein $R^7$ is selected from the group consisting of cyclopentyl, cyclohexyl, tetrahydropyranyl, pyrrolidinyl, piperidinyl, morpholinyl, piperazinyl, thiomorpholinyl, and azepinyl.

34. The compound of claim 30, wherein $R^7$ is $X^2\text{—}C(O)OR^{15}$, $X^2\text{—}C(O)N(R^{15})_2$; and each $R^{15}$ is H or $(C_1\text{-}C_8)$alkyl.

35. A compound having the formula (VIII):

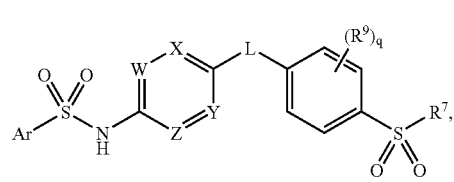

(VIII)

or a pharmaceutically acceptable salt thereof, wherein
Ar is a member selected from the group consisting of phenyl, naphthyl and pyridyl; each of which is optionally substituted with from one to three $R^8$ substituents, wherein each $R^8$ is a member independently selected from the group consisting of halogen, cyano, nitro, $(C_1\text{-}C_8)$alkyl, $(C_1\text{-}C_8)$alkoxy, $(C_1\text{-}C_8)$haloalkyl, $(C_1\text{-}C_8)$haloalkoxy, $(C_2\text{-}C_8)$alkenyl, $(C_2\text{-}C_8)$alkynyl, hydroxyl and $NR^{12}R^{13}$;
L is selected from the group consisting of O, $S(O)_k$, $CR^aR^b$ and C(O);
each $R^a$ or $R^b$ is independently selected from the group consisting of hydrogen, cyano, nitro, and $(C_1\text{-}C_8)$alkyl;
W is independently $C(R^3)$ or N;
X is independently $C(R^4)$ or N;
Y is independently $C(R^5)$ or N;
Z is independently $C(R^6)$ or N, wherein one of W, X, Y and Z is N and three of W, X, Y and Z are other than N;
each $R^3$, $R^4$, $R^5$, or $R^6$ is a member independently selected from the group consisting of hydrogen, hydroxy, halogen, cyano, nitro, $NR^{12}R^{13}$, $(C_1\text{-}C_8)$alkyl, halo$(C_1\text{-}C_8)$alkyl, hydroxy$(C_1\text{-}C_8)$alkyl, $(C_3\text{-}C_8)$cycloalkyl, $(C_1\text{-}C_8)$alkoxy, $(C_1\text{-}C_8)$thioalkoxy, $(C_2\text{-}C_8)$heteroalkyl, heteroaryl, $\text{—}C(O)R^{11}$, $\text{—}CO_2R^{11}$, $\text{—}C(O)NR^{12}R^{13}$, $\text{—}C(O)CH_2CN$, $\text{—}X^1Q^1$, $X^2OR^{11}$ and $X^2NR^{12}R^{13}$;
each $X^1$ is independently selected from the group consisting of $(C_1\text{-}C_2)$alkylene and C(O);
each $Q^1$ is independently selected from the group consisting of pyrrolidinyl, piperidinyl, and morpholinyl;
$R^7$ is selected from the group consisting of $(C_1\text{-}C_8)$alkyl, $(C_3\text{-}C_8)$cycloalkyl, $(C_1\text{-}C_8)$haloalkyl, aryl, $NR^{12}R^{13}$, $(C_3\text{-}C_8)$heterocycloalkyl, $X^2\text{—}C(O)OR^{15}$, $X^2\text{—}C(O)N(R^{15})_2$, and $\text{—}X^2\text{—}NR^{12}R^{13}$;
each $X^2$ is $(C_1\text{-}C_8)$alkylene;
each $R^9$ is a member independently selected from the group consisting of halogen, nitro, $(C_1\text{-}C_8)$alkyl, $(C_1\text{-}C_8)$alkoxy and $NR^{12}R^{13}$;
each $R^{11}$ is independently selected from the group consisting of hydrogen, $(C_1\text{-}C_8)$alkyl, $(C_2\text{-}C_8)$alkenyl, $(C_3\text{-}C_8)$cycloalkyl, $(C_2\text{-}C_8)$heteroalkyl, aryl, heteroaryl, heteroaryl$(C_1\text{-}C_8)$alkyl, $(C_3\text{-}C_8)$heterocycloalkyl and aryl$(C_1\text{-}C_8)$alkyl;
$R^{12}$ and $R^{13}$ are independently selected from the group consisting of hydrogen, $(C_1\text{-}C_8)$alkyl, $(C_2\text{-}C_8)$alkenyl, $(C_3\text{-}C_8)$cycloalkyl, $(C_2\text{-}C_8)$heteroalkyl, $(C_1\text{-}C_8)$alkoxy, aryl and aryl$(C_1\text{-}C_8)$alkyl;
optionally, $R^{12}$ and $R^{13}$ are combined with the nitrogen atom to which each is attached to form a 3-, 4-, 5-, 6- or 7-membered ring which can be saturated or unsaturated and contain 0 to 2 additional heteroatoms selected from N, O and S; wherein said ring is optionally substituted with from one to four substituents selected from the group consisting of hydroxy, oxo, and $(C_1\text{-}C_8)$alkyl;
each $R^{15}$ is selected from the group consisting of H, $(C_1\text{-}C_8)$alkyl, $(C_2\text{-}C_8)$alkenyl and $(C_3\text{-}C_8)$cycloalkyl; and
the subscripts k, l, m, and q are independently an integer of 0 to 2.

36. The compound of claim 35, wherein Ar is phenyl, which is optionally substituted with from one to three $R^8$ substituents, wherein each $R^8$ is independently selected from the group consisting of halogen, $(C_1\text{-}C_8)$alkyl, $(C_1\text{-}C_8)$alkoxy, and $(C_1\text{-}C_8)$haloalkyl.

37. The compound of claim 35, wherein $R^1$ is H.

38. The compound of claim 35, wherein each $R^3$, $R^4$, $R^5$, or $R^6$ is independently selected from the group consisting of hydrogen, hydroxy, halogen, $NR^{12}R^{13}$, $(C_1\text{-}C_8)$alkyl, $(C_3\text{-}C_8)$cycloalkyl, $(C_1\text{-}C_8)$alkoxy, $(C_1\text{-}C_8)$thioalkoxy, $(C_2\text{-}C_8)$heteroalkyl, $(C_1\text{-}C_8)$haloalkyl, CN, $\text{—}C(O)R^{11}$, $\text{—}CO_2R^{11}$ and $\text{—}C(O)NR^{12}R^{13}$.

39. The compound of claim 35, wherein L is O.

40. The compound of claim 35, wherein L is S.

41. The compound of claim 35, wherein each $R^9$ is hydrogen.

42. The compound of claim 35, wherein $R^7$ is selected from the group consisting of $(C_1\text{-}C_8)$alkyl, $NR^{12}R^{13}$, and $(C_3\text{-}C_8)$heterocycloalkyl.

43. The compound of claim 42, wherein $R^7$ is selected from the group consisting of

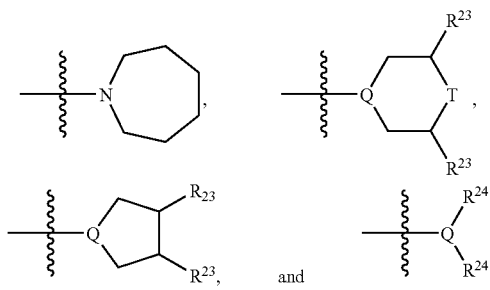

wherein
Q is N or CH;
T is $CHR^{16}$, $NR^{16}$, O, or $S(O)_l$;
$R^{16}$ is H or $(C_1-C_8)$alkyl;
each $R^{23}$ is a member independently selected from the group consisting of H and $(C_1-C_8)$alkyl;
each $R^{24}$ is selected from the group consisting of H, $(C_1-C_8)$alkyl;
and heteroalkyl;
the subscript l is an integer of from 0 to 2.

44. The compound of claim 42, wherein $R^7$ is selected from the group consisting of cyclopentyl, cyclohexyl, tetrahydropyranyl, pyrrolidinyl, piperidinyl, morpholinyl, piperazinyl, thiomorpholinyl, and azepinyl.

45. The compound of claim 35, wherein $R^7$ is $X^2$—C(O)$OR^{15}$ or $X^2$—C(O)N$(R^{15})_2$; and each $R^{15}$ is H or $(C_1-C_8)$alkyl.

46. A compound having the formula (IX):

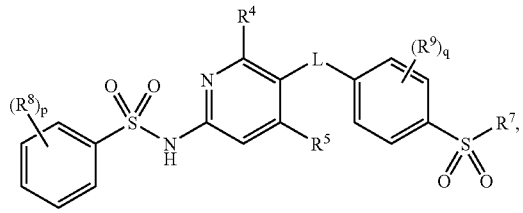

(IX)

wherein
$R^4$ is selected from the group consisting of H, $(C_1-C_8)$alkyl, halo$(C_1-C_8)$alkyl; $(C_1-C_8)$alkoxy, —$CO_2R^{11}$, —C(O)$NR^{12}R^{13}$, hydroxy$(C_1-C_8)$alkyl and C(O)$R^{11}$;
$R^5$ is selected from the group consisting of H, $(C_1-C_8)$alkyl, C(O)$R^{11}$ and —$CO_2R^{11}$;
L is selected from the group consisting of O, $S(O)_k$, $CR^aR^b$ and C(O);
each $R^a$ or $R^b$ is independently selected from the group consisting of hydrogen, cyano, nitro, and $(C_1-C_8)$alkyl;
$R^7$ is selected from the group consisting of $(C_1-C_8)$alkyl, $(C_3-C_8)$cycloalkyl, $(C_1-C_8)$haloalkyl, aryl, $NR^{12}R^{13}$, $(C_3-C_8)$heterocycloalkyl, $X^2$—C(O)$OR^{15}$, $X^2$—C(O)N$(R^{15})_2$, and —$X^2$—$NR^{12}R^{13}$;
each $X^2$ is $(C_1-C_8)$alkylene;
each $R^8$ is independently selected from the group consisting of halo, $(C_1-C_8)$alkyl, halo$(C_1-C_8)$alkyl;
each $R^9$ is a member independently selected from the group consisting of halogen, nitro, $(C_1-C_8)$alkyl, $(C_1-C_8)$alkoxy and $NR^{12}R^{13}$;
each $R^{11}$ is independently selected from the group consisting of hydrogen, $(C_1-C_8)$alkyl, $(C_2-C_8)$alkenyl, $(C_3-C_8)$cycloalkyl, $(C_2-C_8)$heteroalkyl, aryl, heteroaryl, heteroaryl$(C_1-C_8)$alkyl, $(C_3-C_8)$ heterocycloalkyl and aryl $(C_1-C_8)$alkyl;
each $R^{12}$ and $R^{13}$ are independently selected from the group consisting of hydrogen, $(C_1-C_8)$alkyl, $(C_2-C_8)$alkenyl, $(C_3-C_8)$cycloalkyl, $(C_2-C_8)$heteroalkyl, $(C_1-C_8)$alkoxy, aryl and aryl$(C_1-C_8)$alkyl;
optionally, $R^{12}$ and $R^{13}$ are combined with the nitrogen atom to which each is attached to form a 3-, 4-, 5-, 6- or 7-membered ring which can be saturated or unsaturated and contain 0 to 2 additional heteroatoms selected from N, O and S; wherein said ring is optionally substituted with from one to four substituents selected from the group consisting of hydroxy, oxo, and $(C_1-C_8)$alkyl;
each $R^{15}$ is selected from the group consisting of H, $(C_1-C_8)$alkyl, $(C_2-C_8)$alkenyl and $(C_3-C_8)$cycloalkyl; and
the subscript q is an integer of from 0 to 2; and
the subscript p is an integer of from 0 to 3.

47. The compound of claim 46, wherein L is S.

48. The compound of claim 46, wherein each $R^9$ is hydrogen.

49. The compound of claim 46, wherein $R^7$ is selected from the group consisting of $(C_1-C_8)$alkyl, $NR^{12}R^{13}$, and $(C_3-C_8)$heterocycloalkyl.

50. The compound of claim 49, wherein $R^7$ is selected from the group consisting of

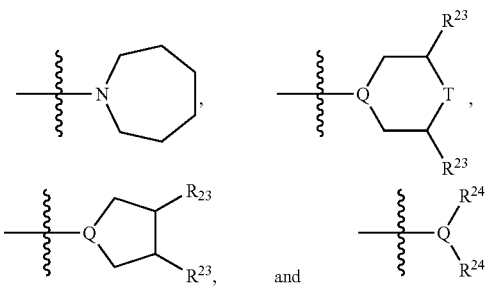

wherein
Q is N or CH;
T is $CHR^{16}$, $NR^{16}$, O or $S(O)_l$;
$R^{16}$ is H or $(C_1-C_8)$alkyl;
each $R^{23}$ is a member independently selected from the group consisting of H and $(C_1-C_8)$alkyl;
each $R^{24}$ is selected from the group consisting of H, $(C_1-C_8)$alkyl and heteroalkyl; and
the subscript l is an integer of from 0 to 2.

51. The compound of claim 49, wherein $R^7$ is selected from the group consisting of cyclopentyl, cyclohexyl, tetrahydropyranyl, pyrrolidinyl, piperidinyl, morpholinyl, piperazinyl, thiomorpholinyl, and azepinyl.

52. The compound of claim 46, wherein
$R^7$ is $X^2$—C(O)$OR^{15}$ or $X^2$—C(O)N$(R^{15})_2$; and
each $R^{15}$ is H or $(C_1-C_8)$alkyl.

53. A composition comprising a pharmaceutically acceptable carrier or excipient and a compound of claim 1.

54. A method for treating a condition or disorder, comprising administering to a subject in need thereof a therapeutically effective amount of a compound of claim 1, wherein the condition or disorder is selected from the group consisting of obesity, hypercholesterolemia, hyperlipidemia, dyslipidemia, hypertriglyceridemia, hyperglycemia, insulin resistance, hyperinsulinemia, syndrome X, atherosclerosis, rheumatoid arthritis, asthma, septic shock, ileus and migraine.

55. A method in accordance with claim 54, wherein said subject is a human.

56. A method in accordance with claim 54, wherein said administering is oral.

57. A method in accordance with claim 54, wherein said administering is parenteral.

58. A method in accordance with claim 54, wherein said administering is topical.

59. A method in accordance with claim 54, wherein said condition or disorder is selected from the group consisting of diabetes, obesity, hypercholesterolemia, hyperlipidemia, dyslipidemia, hypertriglylceridemia, hyperglycemia, insulin resistance, hyperinsulinemia, and syndrome X.

60. A method in accordance with claim 54, wherein said condition or disorder is rheumatoid arthritis.

61. A method in accordance with claim 54, wherein said condition or disorder is atherosclerosis.

62. A method in accordance with claim 54, wherein said condition or disorder is asthma.

63. A method in accordance with claim 54, wherein said condition or disorder is septic shock.

64. A method in accordance with claim 54, wherein said condition of disorder is ileus.

65. A method in accordance with claim 54, wherein condition or disorder is migraine.

66. A method in accordance with claim 54, wherein said compound is administered in combination with an anti-diabetic agent, an antiinflammatory agent, a cholesterol lowering agent, a chemotherapeutic agent or hormone therapy.

* * * * *

SEQUENCE LISTING

```
<160> NUMBER OF SEQ ID NOS: 1

<210> SEQ ID NO 1
<211> LENGTH: 23
<212> TYPE: DNA
<213> ORGANISM: Artificial Sequence
<220> FEATURE:
<223> OTHER INFORMATION: PPAR response element

<400> SEQUENCE: 1
tatcaaggtc aaaggtcatc tag                                         23
```